(12) United States Patent
Altamura et al.

(10) Patent No.: US 9,365,541 B2
(45) Date of Patent: Jun. 14, 2016

(54) COMPOUNDS FOR USE IN THE TREATMENT OF PARASITIC DISEASES

(71) Applicants: IRBM—SCIENCE PARK S.P.A., Pomezia (RM) (IT); C.N.C.C.S. SCARL COLLEZIONE NAZIONALE DEI COMPOSTI CHIMICI E CENTRO SCREENING, Pomezia (RM) (IT)

(72) Inventors: Sergio Altamura, Pomezia (IT); Ilaria Biancofiore, Pomezia (IT); Alberto Bresciani, Pomezia (IT); Federica Ferrigno, Pomezia (IT); Steven Harper, Pomezia (IT); Ralph Laufer, Pomezia (IT); Jesus Maria Ontoria Ontoria, Pomezia (IT); Savina Malancona, Pomezia (IT); Edith Monteagudo, Pomezia (IT); Emanuela Nizi, Pomezia (IT); Maria Vittoria Orsale, Pomezia (IT); Simona Ponzi, Pomezia (IT); Giacomo Paonessa, Pomezia (IT); Vincenzo Summa, Pomezia (IT); Maria Veneziano, Pomezia (IT)

(73) Assignee: IRBM—SCIENCE PARK S.P.A., Pomezia (RM) (IT)

( * ) Notice: Subject to any disclaimer, the term of this patent is extended or adjusted under 35 U.S.C. 154(b) by 0 days.

(21) Appl. No.: 14/437,890

(22) PCT Filed: Oct. 30, 2013

(86) PCT No.: PCT/EP2013/072688
§ 371 (c)(1),
(2) Date: Apr. 23, 2015

(87) PCT Pub. No.: WO2014/067985
PCT Pub. Date: May 8, 2014

(65) Prior Publication Data
US 2015/0299163 A1    Oct. 22, 2015

(30) Foreign Application Priority Data
Oct. 31, 2012  (IT) ............... RM2012A0530

(51) Int. Cl.
| C07D 233/64 | (2006.01) |
| A61K 31/427 | (2006.01) |
| C07D 401/04 | (2006.01) |
| C07D 403/12 | (2006.01) |
| C07D 401/14 | (2006.01) |
| C07D 405/14 | (2006.01) |
| C07D 413/14 | (2006.01) |
| C07D 401/12 | (2006.01) |
| C07D 403/10 | (2006.01) |
| C07D 403/14 | (2006.01) |
| C07D 405/12 | (2006.01) |
| C07D 413/12 | (2006.01) |
| C07D 417/12 | (2006.01) |
| C07D 417/14 | (2006.01) |
| C07D 453/02 | (2006.01) |
| C07D 471/04 | (2006.01) |
| C07D 487/04 | (2006.01) |
| C07D 513/04 | (2006.01) |
| A61K 45/06 | (2006.01) |
| A61K 31/439 | (2006.01) |
| A61K 31/4709 | (2006.01) |

(52) U.S. Cl.
CPC ............ *C07D 401/04* (2013.01); *A61K 31/427* (2013.01); *A61K 31/439* (2013.01); *A61K 31/4709* (2013.01); *A61K 45/06* (2013.01); *C07D 233/64* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01); *C07D 453/02* (2013.01); *C07D 471/04* (2013.01); *C07D 487/04* (2013.01); *C07D 513/04* (2013.01)

(58) Field of Classification Search
CPC ... A61K 45/06; A61K 31/427; A61K 31/439; A61K 31/4709; C07D 233/64; C07D 401/04; C07D 401/12; C07D 401/14; C07D 403/10; C07D 403/12; C07D 403/14; C07D 405/12; C07D 405/14; C07D 413/12; C07D 413/14; C07D 471/04; C07D 487/04; C07D 513/04
See application file for complete search history.

(56) References Cited

FOREIGN PATENT DOCUMENTS

| WO | 2006/061638 | * | 6/2006 |
| WO | 2006/061638 A2 | | 6/2006 |
| WO | 2009/042646 | * | 4/2009 |
| WO | 2009/042646 A1 | | 4/2009 |

OTHER PUBLICATIONS

Attenni, Bioorg & Med Chem Lett, vol. 19, 3081-3084, 2009.*
Sumanadasa, Antimicrobial Agengs & Chemo, 56(7), 3849-3856, Jul. 2012.*
Andrews, abstract only,Curr Top Med Chem, vol. 9(3), 292-308, 2009.*
Andrews, Immunology and Cell Biology, vol. 90, 66-77, 2012, published online Nov. 2011.*

(Continued)

*Primary Examiner* — D M Seaman
(74) *Attorney, Agent, or Firm* — Lucas & Mercanti, LLP

(57) ABSTRACT

The present invention relates to compounds useful for treating parasitic diseases, which are infectious diseases caused or transmitted by a parasite. Compounds of the invention are particularly active against the causative pathogens in malaria. Such compounds are selective inhibitors of parasitic histone deacetylase (PfHDAC) and suppress the growth of parasites, such as *Plasmodium falciparum*, at a lower concentration than the concentration required for the inhibition of the growth of mammalian cells.

9 Claims, 2 Drawing Sheets

(56) References Cited

OTHER PUBLICATIONS

Pescatore, G., et al: "Optimization of a series of potent and selective ketone histone deacetylase inhibitors", Bioorganic & Medicinal Chemistry Letters, Pergamon, Elsevier Science, GB, vol. 18. No. 20, Oct. 15, 2008, pp. 5528-5532, [retrieved on Sep. 6, 2008].

Attenni, B., et al: "Histone deacetylase inhibitors with a primary amide zinc binding group display antitumor activity in xenograft model", Bioorganic & Medicinal Chemistry Letters, Pergamon, Elsevier Science, GB, vol. 19, No. 11, Jun. 1, 2009, pp. 3081-3084, [retrieved on Apr. 9, 2009].

* cited by examiner

(A)

(B)

COMPOUNDS FOR USE IN THE TREATMENT OF PARASITIC DISEASES

CROSS-REFERENCE TO RELATED APPLICATIONS

This application is a 371 of PCT/EP2013/072688, filed Oct. 30, 2013, which claims the benefit of Italian Patent Application No. RM2012A000530, filed Oct. 31, 2012.

FIELD OF THE INVENTION

Compounds of the present invention are useful for treating parasitic diseases, which are infectious diseases caused or transmitted by a parasite. Compounds of the invention are particularly active against the causative pathogens in malaria. Such compounds are selective inhibitors of parasitic histone deacetylase (PfHDAC) and suppress the growth of parasites, such as *Plasmodium falciparum* at a lower concentration than the concentration required for the inhibition of the growth of mammalian cells.

BACKGROUND OF THE INVENTION

Parasitic diseases are among the leading causes of death globally, collectively second only to cardiovascular diseases. Malaria is one of the most significant parasitic diseases resulting in an estimated 500 million new infections and 2 millions deaths annually, predominantly in sub-Saharan Africa and Asia. It is caused by members of the genus *Plasmodium*, in particular by *Plasmodium falciparum*, which is the principal malarial protozoan parasite in humans. Similarly, leishmaniasis is a tropical/sub-tropical parasitic disease, caused by members of the genus *Leishmania*, which infects over two million people annually. *Toxoplasma* parasites, the causative agents of toxoplasmosis, can cause serious opportunistic infections in immune-compromised individuals such as those with AIDS, or in people undergoing chemotherapy or organ transplants. Trypanosomiasis is another widespread parasitic infection, caused by *Trypanosoma cruzi* and *Trypanosoma brucei* which are transmitted by insect vectors. Likewise, schistosomiasis is a parasitic disease caused by several species of trematodes, a parasitic worm of the genus *Schistosoma*. Together parasitic diseases pose a significant health and economic burdens, particularly in underdeveloped regions. There is currently no effective vaccine targeted to any human parasitic disease, therefore anti-parasitic drugs continue to be crucial for the treatment of the diseases. Unfortunately, where drugs are available, they are under increasing threat of failure owing to drug-resistant parasites. Intense research efforts are underway to discover and develop new drugs to treat neglected diseases and to address the growing problem of parasite resistance (Dondorp A M et al, *N. Engl. J. Med.* 2009, 361, 455-467).

Histone deacetylase (HDAC) inhibitor drugs, originally targeted for cancer use, are now being investigated to target a range of parasitic diseases (Andrews K T et al, *Immunology and Cell Biology* 2012, 90, 66-77).

Histone-modifying enzymes are crucial for modulating cell chromatin structure and gene expression in eukaryotic organisms. Histone deacetylases (HDACs) and histone acetyl transferases (HATs) determine the pattern of histone acetylation, which together with other dynamic sequential post-translational modifications might represent a 'code' that can be recognised by non-histone proteins forming complexes involved in the regulation of gene expression. This and the ability of histone deacetylases (HDACs) to also modify non-histonic substrates and participate in multi-protein complexes contributes to the regulation of gene transcription, cell cycle progression and differentiation, genome stability and stress responses.

HDAC inhibitors cause the induction of differentiation, growth arrest and/or apoptosis in a broad spectrum of transformed cells in culture and tumours in animals, including both haematological cancers and solid tumours. These inhibitory effects are believed to be caused, in part, by accumulation of acetylated proteins, such as nucleosomal histones, which appear to play a major role in regulation of gene transcription.

HDACs have been identified in all the major human parasitic pathogens. The potential of HDAC inhibitors as anti-parasitic agents was first realized over a decade ago when the cyclic tetrapeptide apicidin was found to have broad spectrum anti-parasitic activity (Darkin-Rattray S J et al, *Proc Natl Acad Sci USA* 1996, 93, 13143-13147). Pan inhibitors of both class I and II HDACs, such as the cyclic tetrapeptide apicidin and the hydroxamate tricostatin A (TSA), have potent anti-malarial activity in vitro (Darkin-Rattray S J et al). These compounds cause hyperacetylation of *P. falciparum* histones, indicating inhibition of one or more PfHDACs. However, both apicidin and TSA suffer from metabolic instability and neither is parasite-selective, so without modifications that overcome these problems, both are unsuitable as antiparasitic drugs. In contrast to TSA, SAHA has less potent activity against *P. falciparum* ($IC_{50}$~100-300 nM), but somewhat improved parasite-specific selectivity (Dow G S et al, *Antimicrob Agents Chemother* 2008, 52, 3467-3477). Despite its clinical use for cancer, the in vivo efficacy of SAHA against *Plasmodium* parasites in murine malaria models has not yet been reported.

Several hydroxamic acid-based HDAC inhibitor analogues have been described with better potency against *P. falciparum* parasites in vitro than SAHA and in some case much better selectivity. HDAC inhibitor analogues screened in those studies included compounds based on L-cysteine, 2-amino-suberic acid (Andrews K T et al, *Antimicrob Agents Chemother* 2008, 52, 1454-1461), triazolylphenyl (Chen Y et al, *J Med Chem* 2008, 51, 3437-3448), compounds with cinnamate or non-steroidal antinflammatory components (Wheatley N C et al, *Bioorg Med Chem Lett* 2010, 20, 7080-7084), and a panel of 50 phenyl-thiazolyl hydroxamate based HDAC inhibitor analogues (Dow G S et al, *Antimicrob Agents Chemother* 2008, 52, 3467-3477). The latter study identified compound WR301801 which was found to hyperacetylate *P. falciparum* histones and inhibit *P. falciparum* deacetylase activity in nuclear extracts. However, orally administered WR301801 was not able to cure mice unless co-administered with sub-curative doses of the anti-malarial drug chloroquinine SB939, a hydroxamic acid that is a pan inhibitor of mammalian HDACs and shows antitumoral activity, was reported to be a potent inhibitor of the growth of *P. falciparum* in vitro causing hyperacetylation of parasite histone and non-histone proteins (Sumanadasa S D M et al, *Antimicrob. Agents Chemother.* 2012, 56, 3849-3856). When SB939 was administered orally in an in vivo murine model of cerebral malaria it significantly inhibited *P. Berghei* ANKA parasite growth, preventing development of cerebral malaria-like symptoms.

WO2006/017214 describes hydroxamic acid derivatives that are inhibitors of histone deacetylases, useful for treating cellular proliferative diseases and also having antiprotozoal properties. WO2008/019025 relates to isoform-selective HDAC inhibitors useful for treating cancer, neurological diseases and malaria. WO2009/042646 relates to multifunctional molecules wherein one pharmacophore is capable of inhibiting zinc-binding enzymes (e.g. HDAC) and one pharmacophore is capable of inhibiting a different cellular function involved in aberrant proliferation, differentiation or survival of cells. Such molecules are disclosed for the treatment of many disorders, including protozoal infections. However, all these compounds have low specificity.

These findings demonstrate the potential of HDAC inhibitors as potential anti-parasitic drugs. However, to progress HDAC inhibitors as drugs for parasitic diseases, a high level of potency and selectivity for parasites versus host cells is essential. Further, improved pharmacokinetic profiles are needed to accommodate the unique challenges facing the application of drugs for developing-world diseases, such as oral efficacy and complementary profiles with combination drugs, for single infections (as in the case of malaria), or poly-parasitism and polymicrobial infections (for example, HIV and parasite co-infection).

WO 2006/061638 describes HDAC inhibitors useful for treating cellular proliferative disease, with improved pharmacokinetic properties.

In the present invention, further investigation of this class of compounds lead to the identification and selection of amides as a zinc binding moiety and substitution patterns that enhanced the selective anti-parasite activities. These features allow for highly selective killing action against parasites rather than normal host cells. In particular, compounds of the invention are HDAC inhibitors that incorporate an amide as zinc-binding group and selectively suppress the growth of *Plasmodium falciparum* at a lower concentration than the concentration required for the inhibition of the growth of mammalian cells in culture.

SUMMARY OF THE INVENTION

The compounds of this invention are HDAC inhibitors that are several fold selectively toxic to parasites, namely *plasmodium* parasites.

It is therefore an object of the invention a compound of general formula (I):

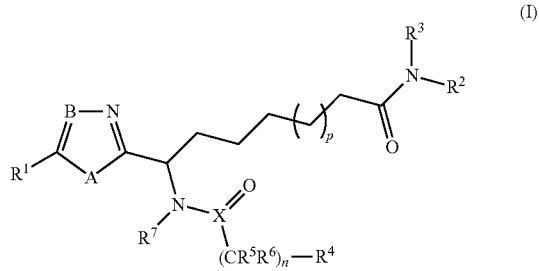

wherein:
X is C or S=O;
A is selected from NH, O or S;
B represents CH or N;
n is 0, 1, 2 or 3;
p is 0, 1 or 2;
$R^1$ is $C_{6-10}$aryl, 5 membered unsaturated heterocycle containing 1, 2, 3, or 4 heteroatoms independently selected from O, N or S, but not more than one of which is O or S, 6 membered unsaturated heterocycle containing 1, 2 or 3 nitrogen atoms, 8-13 membered unsaturated or partially saturated heterocycle containing heteroatoms independently selected from O, N and S; any of which rings being optionally substituted by one or more groups independently chosen from cyano, halogen, nitro, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl $C_{6-10}$aryl, $C_{6-10}$aryloxy, $C_{6-10}$arylcarbonyl, $N(R^a)_2$, $C_{1-6}$alkyl-$N(R^a)_2$, $SO_2N(R^a)_2$, $N(R^a)SO_2R^a$, 5 or 6 membered saturated or unsaturated heterocycle optionally substituted by one or more groups independently chosen from halogen, $C_{1-6}$alkyl, halo$C_{1-6}$alkyl, $C_{1-6}$alkoxy;

$R^2$ represents H, $C_{1-6}$alkyl, $C_{6-10}$aryl, 5 or 6 membered saturated or unsaturated heterocycle, $C_{6-10}$aryl-$C_{1-6}$ alkyl, heteroaryl-$C_{1-6}$alkyl; any of which rings being optionally substituted by one or more groups independently chosen from halogen, hydroxy, amino, $N(R^a)_2$, $C_{1-6}$alkyl, halo$C_{1-6}$alkyl, $C_{1-6}$alkoxy and halo$C_{1-6}$alkoxy;

$R^3$ represents hydrogen or $C_{1-6}$alkyl;

$R^4$ is hydrogen, sulphonylamino, $C_{1-6}$alkyl, halo$C_{1-6}$alkyl, hydroxy$C_{1-6}$alkyl, $SO_2C_{1-6}$alkyl, $C_{1-6}$alkoxy, halo$C_{1-6}$alkoxy, $C_{3-10}$cycloalkyl, halo$C_{3-10}$cycloalkyl, $C_{2-6}$alkenyl, $C_{2-6}$ alkynyl, $N(R^a)_2$, $C_{6-10}$aryl, $C_{6-10}$aryl$C_{1-6}$alkyl, $C_{6-10}$aryl$C_{1-6}$alkoxy, $C_{6-10}$aryl$C_{1-6}$alkylamino; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-15 membered saturated, partially saturated or unsaturated heterocycle containing heteroatoms independently selected from N, O or S; any of which rings being optionally substituted by one or more groups independently chosen from halogen, hydroxy, $N(R^a)_2$, $C_{1-6}$alkyl, halo$C_{1-6}$alkyl, $C_{1-6}$alkoxy, halo$C_{1-6}$ alkoxy, $C_{1-6}$alkyl-$N(R^a)_2$, nitro, phenyl, 5 or 6 membered saturated, partially saturated or unsaturated heterocycle containing 1, 2 or 3 heteroatoms independently selected from N, O and S, said rings being optionally substituted by one or more group independently chosen from halogen, $C_{1-6}$alkyl, halo$C_{1-6}$alkyl or $C_{1-6}$alkoxy; each $R^a$ is independently selected from hydrogen, $C_{1-6}$alkyl, $C_{6-10}$aryl, $C_{1-6}$alkylcarbonyl and $C_{6-10}$arylcarbonyl, or $N(R^a)_2$ is a cyclic amine selected from pyrrolidine, pyperidine, pyperazine ad morpholine;

$R^5$ and $R^6$ are independently hydrogen, $C_{1-6}$alkyl, or $CR^5R^6$ represents a carbonyl or $CR^5R^6$ represents a cyclopropyl;

$R^7$ represents hydrogen or $C_{1-6}$alkyl;

and pharmaceutically acceptable salts, tautomers, stereoisomers thereof, for use in the treatment of parasitic diseases. In the instant invention "parasitic disease" refers also to a "parasitic infection".

Preferably A is NH and B is CH; more preferably p is 1; even more preferably $R^2$ represents methyl and $R^3$ represents hydrogen.

In a preferred embodiment $R^1$ is naphthyl, 6-methoxynaphthyl, quinolinyl, 2-methoxyquinolinyl, 3-methoxyquinolinyl, 2-(trifluoromethyl)quinolinyl, 2-chloroquinolinyl, isoquinolinyl, 3-methoxyisoquinolinyl, (1H-pyrazol-1-yl)phenyl, (1H-pyrazol-5-yl)phenyl, (1-methyl-1H-pyrazol-3-yl)phenyl, 2-oxo-1,2-dihydroquinolinyl, 1H-indolyl, 1-ethoxynaphthyl, trifluoromethylphenyl, (pyridin-4-yl)phenyl, (pyridin-3-yl)phenyl, (pyridin-2-yl)phenyl, 1H-indazolyl, aminomethylphenyl, cyanophenyl, acetamidophenyl, 1-chloro-3-methoxyphenyl, 1,2-dichlorophenyl, 1-chloro-2-methylphenyl, benzo[b]thiophenyl, 5-methoxy-1H-indolyl, (5-methyl-1H-pyrazol-3-yl)phenyl, (3,5-dimethyl-1H-pyrazol-1-yl)phenyl, (dimethylamino)methylphenyl, 2,3-dihydrobenzo[b][1,4]dioxinyl, 1,1'-biphenyl, (thiophen-2-yl) phenyl, 1H-benzo[d][1,2,3]triazolyl, [1,2,4]triazolo[1,5-a] pyridinyl, 1-methyl-1H-indolyl, benzo furanyl, 6-fluoronaphthyl, 1-methyl-2-oxo-1,2-dihydroquinolinyl, 1H-pyrazolo[3,4-b]pyridinyl, 1-methyl-1H-indazolyl, 2-methoxy-6-phenylpyridinyl, 2-phenylthiophenyl, 1-methoxyisoquinolinyl, 7-(trifluoromethyl)isoquinolinyl, (thiazol-2-yl)phenyl, (thiazol-4-yl)phenyl.

In a further preferred embodiment $R^4$ is phenyl, pyperidine, pyrrolidine, morpholine, piperazine, 5,6,7,8-tetrahydro-1,8-naphthyridine, 1,2,3-triazole, 1,2,4-triazole, benzo[d][1,2,3]triazole, benzo[d]imidazole, pyrazole, thiazole, isothiazole, pyrimidine, quinoxaline, quinoline, isoquinoline, imidazo[1,2-a]pyridine, azetidine, tetrazole, [1,2,4]triazolo[1,5-a]pyrimidine, imidazole, 1,3,4-thiadiazole, 1,2,5-thiadiazole, 6,7-dihydro-5H-thiazolo[3,2-a]pyrimidine, tetrahydro-2H-pyrane, pyridine, quinuclidine, 2-oxo-1,2,3,4-tetrahydroquinoline, indole, 2-oxobenzo[d]oxazole, pyrazine, 1,3,4-oxadiazole, difluorocyclobutane, 2-(5-oxo-4,5-dihydro-1H-1,2,4-triazole, tetrahydrofurane, tetrahydropyrane, benzo[d]thiazole, imidazo[2,1-b]thiazole, 2-oxoquinazoline, 2-oxopyrrolidine, 2H-indazole, octahydro-1H-quinolizine; any of which rings being optionally substituted by one or more groups independently chosen from halogen, hydroxy, $N(R^a)_2$, $C_{1-6}$alkyl, halo$C_{1-6}$alkyl, $C_{1-6}$alkoxy, halo$C_{1-6}$alkoxy, $C_{1-6}$alkyl-$N(R^a)_2$, nitro, phenyl, 5 or 6 membered saturated, partially saturated or unsaturated heterocycle containing 1, 2 or 3 heteroatoms independently selected from N, O and S, said rings being optionally substituted by one or more group independently chosen from halogen, $C_{1-6}$alkyl;

each $R^a$ is independently selected from hydrogen, $C_{1-6}$alkyl, or $N(R^a)_2$ is a cyclic amine selected from pyrrolidine, pyperidine, and morpholine.

It is an object of the invention the compound (S)-N-(7-(methylamino)-1-(5-(naphthalen-2 yl)-1H-imidazol-2-yl)-7-oxoheptyl)quinuclidine-4-carboxamide for use in the treatment of parasitic diseases.

It is a further object of the invention a compound of general formula (I) selected from the following list:

(S)-N-(1-(5-(6-methoxynaphthalen-2-yl)-1H-imidazol-2-yl)-7-(methylamino)-7-oxoheptyl)quinuclidine-4-carboxamide;

(S)-N-(1-(5-(6-fluoronaphthalen-2-yl)-1H-imidazol-2-yl)-7-(methylamino)-7-oxoheptyl)quinuclidine-4-carboxamide;

(S)-N-(1-(5-(3-(aminomethyl)phenyl)-1H-imidazol-2-yl)-7-(methylamino)-7-oxoheptyl)thiazole-5-carboxamide;

(S)-N-(1-(5-(2-methoxyquinolin-3-yl)-1H-imidazol-2-yl)-7-(methylamino)-7-oxoheptyl)quinuclidine-4-carboxamide;

(S)-N-(1-(5-(2-methoxyquinolin-3-yl)-1H-imidazol-2-yl)-7-(methylamino)-7-oxoheptyl)thiazole-5-carboxamide;

(S)-7-(5-(2-methoxyquinolin-3-yl)-1H-imidazol-2-yl)-N-methyl-7-(4-cyanophenylsulfonamido)heptanamide;

(S)-N-(1-(5-(4-(1H-pyrazol-5-yl)phenyl)-1H-imidazol-2-yl)-7-(methylamino)-7-oxoheptyl)thiazole-5-carboxamide;

(S)-N-(7-(methylamino)-7-oxo-1-(5-(quinolin-6-yl)-1H-imidazol-2-yl)heptyl)thiazole-5-carboxamide;

(S)-N-(1-(5-(1H-indol-5-yl)-1H-imidazol-2-yl)-7-(methylamino)-7-oxoheptyl)thiazole-5-carboxamide;

(S)-N-(7-(methylamino)-7-oxo-1-(5-(2-oxo-1,2-dihydroquinolin-3-yl)-1H-imidazol-2-yl)heptyl)thiazole-5-carboxamide;

(S)-N-(7-(methylamino)-7-oxo-1-(5-(quinolin-3-yl)-1H-imidazol-2-yl)heptyl)thiazole-5-carboxamide;

(S)-N-(1-(5-(4-(1H-pyrazol-1-yl)phenyl)-1H-imidazol-2-yl)-7-(methylamino)-7-oxoheptyl)thiazole-5-carboxamide;

(S)-N-(1-(5-(1H-indazol-5-yl)-1H-imidazol-2-yl)-7-(methylamino)-7-oxoheptyl)thiazole-5-carboxamide;

(S)-N-(1-(5-(isoquinolin-7-yl)-1H-imidazol-2-yl)-7-(methylamino)-7-oxoheptyl)thiazole-5-carboxamide;

(S)-N-(1-(5-(4-(1-methyl-1H-pyrazol-3-yl)phenyl)-1H-imidazol-2-yl)-7-(methylamino)-7-oxoheptyl)thiazole-5-carboxamide;

(S)-N-(1-(5-(isoquinolin-7-yl)-1H-imidazol-2-yl)-7-(methylamino)-7-oxoheptyl)isothiazole-4-carboxamide;

(S)-N-(7-(methylamino)-7-oxo-1-(5-(3-(trifluoromethyl)isoquinolin-7-yl)-1H-imidazol-2-yl)heptyl)thiazole-5-carboxamide;

(S)-N-(1-(5-(3-methoxyisoquinolin-7-yl)-1H-imidazol-2-yl)-7-(methylamino)-7-oxoheptyl)thiazole-5-carboxamide;

(S)-N-(1-(5-(isoquinolin-7-yl)-1H-imidazol-2-yl)-7-(methylamino)-7-oxoheptyl)isothiazole-5-carboxamide;

(S)-1-isopropyl-N-(1-(5-(isoquinolin-7-yl)-1H-imidazol-2-yl)-7-(methylamino)-7-oxoheptyl)-1H-pyrazole-4-carboxamide;

(S)-N-(1-(5-(isoquinolin-7-yl)-1H-imidazol-2-yl)-7-(methylamino)-7-oxoheptyl)-2-methylthiazole-5-carboxamide;

(S)-N-(1-(5-(4-(1-methyl-1H-pyrazol-3-yl)phenyl)-1H-imidazol-2-yl)-7-(methylamino)-7-oxoheptyl)isothiazole-5-carboxamide;

(S)-1-isopropyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide;

(S)-2-methyl-N-(1-(5-(4-(1-methyl-1H-pyrazol-3-yl)phenyl)-1H-imidazol-2-yl)-7-(methylamino)-7-oxoheptyl)thiazole-5-carboxamide;

(S)-N-(1-(5-(4-(1-methyl-1H-pyrazol-3-yl)phenyl)-1H-imidazol-2-yl)-7-(methylamino)-7-oxoheptyl)isothiazole-4-carboxamide;

(S)-N-(1-(5-(4-(1-methyl-1H-pyrazol-3-yl)phenyl)-1H-imidazol-2-yl)-7-(methylamino)-7-oxoheptyl)-2-(pyrrolidin-1-ylmethyl)thiazole-5-carboxamide;

(S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide;

(S)-1-isopropyl-N-(1-(5-(3-methoxyisoquinolin-7-yl)-1H-imidazol-2-yl)-7-(methylamino)-7-oxoheptyl)-1H-pyrazole-4-carboxamide;

(S)-N-(7-(methylamino)-7-oxo-1-(5-(4-(thiazol-2-yl)phenyl)-1H-imidazol-2-yl)heptyl)thiazole-5-carboxamide;

(S)-N-(7-(methylamino)-7-oxo-1-(5-(4-(thiazol-4-yl)phenyl)-1H-imidazol-2-yl)heptyl)thiazole-5-carboxamide;

and pharmaceutically acceptable salts, tautomers, stereoisomers thereof.

Preferably, the compound selected from the previous list is for medical use, more preferably for use in the treatment of parasitic diseases.

In a preferred embodiment the parasitic disease is selected from malaria, leishmaniasis, trypanosomiasis, toxoplasmosis and schistosomiasis, more preferably the parasitic disease is malaria, still preferably malaria is caused by parasites as *Plasmodium falciparum* or by *Plasmodium vivax*.

In preferred embodiment the technical effect of compounds of the invention is to exert a selective toxicity for said parasites with respect to host cells, namely a selective killing and/or growth-inhibiting activity of said parasites with respect to a host mammal.

It is a further object of the invention a pharmaceutical composition comprising an effective amount of one or more compounds as defined above or a pharmaceutically acceptable prodrug thereof, alone or in combination with other active compounds, and at least one pharmaceutically acceptable excipient.

The skilled person shall select suitable dosages and regimens to have compounds of the invention to exert their selective toxicity and/or killing and/growth inhibiting activity on parasites.

The present invention includes within its scope prodrugs of the compounds of formula (I). In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

When any variable (e.g. $R^5$ and $R^6$, etc.) occurs more than one time in any constituent, its definition on each occurrence is independent at every other occurrence. Also, combinations of substituents and variables are permissible only if such combinations result in stable compounds.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_1$-$C_6$ alkyl" is defined to include groups having 1, 2, 3, 4, 5 or 6 carbons in a linear or branched arrangement. For example, "$C_1$-$C_6$ alkyl" specifically includes methyl, ethyl, n-propyl, i-propyl, n-butyl, t-butyl, i-butyl, pentyl, hexyl, and so on. The term "cycloalkyl" means a monocyclic, bicyclic or polycyclic saturated aliphatic hydrocarbon group having the specified number of carbon atoms. For example, "$C_{3-10}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl. "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy group is methoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

The term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. The straight or branched portion of the alkenyl group may contain double bonds and may be substituted if a substituted alkenyl group is indicated. Preferred alkenyl groups include ethenyl and propenyl.

The term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. The straight or branched portion of the alkynyl group may contain triple bonds and may be substituted if a substituted alkynyl group is indicated. Preferred alkynyl groups include ethynyl and propynyl.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furanyl, furazanyl, imidazolyl, imidazothiazolyl, indolinyl, indolyl, indolizinyl, isoindolinyl, indazolyl, isobenzofuranyl, isoindolyl, isoquinolyl, isothiazolinyl, isoxazolyl, naphthpyridinyl, oxadiazolyl, oxazolyl, oxazolinyl, oxoquinazolinyl isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolidinyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, pyrazolinyl, pyrrolinyl, morpholinyl, thiomorpholinyl, dihydrobenzoimidazolyl, dihydrobenzo furanyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl and N-oxides thereof. Further particular heterocycles include dihydroquinazolinyl, dihydrophthalazinyl, dihydroisoindolyl, tetrahydronaphthyridinyl, tetrahydrobetacarbolinyl and N-oxides thereof. Attachment of a heterocyclyl substituent can occur via a carbon atom or via a heteroatom.

A preferred 4 membered saturated heterocycle is azetidinyl.

Preferred 5 or 6 membered saturated or partially saturated hetereocycles are pyrrolidinyl, piperidyl, piperazinyl, morpholinyl, azoniabicyclo[2.2.1]heptanyl, azoniabicyclo[2.2.2] octanyl, thiomorpholinyl and thiazolidinyl.

Preferred 5 membered unsaturated heterocycles are thienyl, thiazolyl, pyrazolyl, isoxazolyl, imidazolyl, thiadiazolyl, oxazolyl, triazolyl, tetrazolyl, furyl and oxadiazolyl.

A preferred 6 membered unsaturated heterocycle is pyridinyl.

Preferred 8-10 membered saturated, partially saturated or unsaturated heterocycles are benzothienyl, indolyl, benzothiadiazolyl, benzoxadiazolyl, thiazolotriazolyl, dihydrobenzodioxinyl, dihydrothiazolopyrimidinyl, dihydrobenzoxazinyl, dihydrobenzofuranyl, benzothiazolyl, quinolinyl, isoquinolinyl, benzimidazolyl, benzofuranyl, dihydrobenzoxazolyl, dihydroindolyl, dihydroquinazolinyl, dihydrophthalazinyl, indazolyl, benzisoxazolyl, benzotriazolyl, dihydroisoindolyl, tetrahydronaphthyridinyl, triazolopyrimidinyl and tetrahydroquinoliny.

A preferred 13 membered partially saturated heterocycle is tetrahydrobetacarbolinyl.

As used herein, the term 'halogen' refers to fluorine, chlorine, bromine and iodine, of which fluorine, chlorine and bromine are preferred.

Included in the instant invention is the free base of compounds of formula (I), as well as the pharmaceutically acceptable salts and stereoisomers thereof. Some of the specific compounds exemplified herein are the protonated salts of amine compounds. Compounds of formula (I) containing one or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of formula (I). The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reaction of the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reaction of a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferably, a pharmaceutically acceptable salt of this invention contains one equivalent of a compound of formula (I) and 1, 2 or 3 equivalent of an inorganic or organic acid. More particularly, pharmaceutically acceptable salts of this invention are the tartrate, trifluoroacetate or the chloride salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylamino ethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention find use in a variety of applications for human and animal health. The compounds of the invention are histone deacetylase (HDAC) inhibitors. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See *J. Med. Chem.* 2003, 46, 5097 and *Curr. Med. Chem.* 2003, 10, 2343. In particular, compounds of the invention have anti-parasite activities allowing for highly selective killing action against parasites rather than normal host cells. Such compounds incorporate an amide as zinc-binding group and suppress the growth of *Plasmodium falciparum* at a lower concentration than the concentration required for the inhibition of the growth of mammalian cells.

The present invention relates to compounds that are capable of treating mammalian parasitic diseases. Examples of parasitic diseases include malaria, toxoplasmosis, trypanosomiasis, leishmaniasis, schistosomiasis. As a matter of facts all of above parasitic agents have specific parasitic HDAC.

The compounds of the invention inhibit the activity of HDAC enzymes and are several folds selectively cytotoxic to the *plasmodium* parasites. HDACs are expressed/transcribed across multiple lifecycle stages of the parasite *Plasmodium falciparum*, compounds of the invention are useful for killing or inhibiting the growth and/or survival of *Plasmodium falciparum*.

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution may be then introduced into a water and glycerol mixture and processed to form a microemulstion. The injectable solutions or microemulsions may be introduced into a patient's blood stream by local bolus injection.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of formula (I) are employed. The compounds of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage regimen will normally be determined by the prescribing physician with the dosage generally varying according to the age, weight, sex and response of the individual patient, as well as the severity of the patient's symptoms.

The instant compounds are also useful in combination with known therapeutic agents for simultaneous, separate or sequential administration.

In an embodiment, the compounds of the present invention may be used in combination with known agents useful for treating or preventing parasitic diseases, including malaria, toxoplasmosis, trypanosomiasis, Chagas disease, leishmaniasis, schistosomiasis, amebiasis, giardiasis, clonorchiasis, fasciolopsiasis, lymphatic filariasis, onchocerciasis, thricomoniasis and cestodiasis. Combinations of the presently disclosed compounds with other agents useful for treating or preventing parasitic disease are within the scope of the invention. A person of ordinary skill in the art would be able to discern which combinations of agents would be useful based on the particular characteristics of the drugs and the disease involved.

In particular, existing therapies for malaria include, but are not limited to cloroquine, proguanil, mefloquine, quinine, pyrimethamine-sulphadoxine, doxocycline, berberine, halofantrine, primaquine, atovaquone, pyrimethamine-dapsone, artemisinin and quinhaosu.

Existing therapies for leishmaniasis include, but are not limited to meglumine antimonite, sodium stibogluconate and amphotericin B.

Existing therapies for schistosomiasis include, but are not limited to praziquantel and oxamniquine.

The term "administration" and variants thereof (e.g., "administering" a compound) in reference to a compound of the invention means introducing the compound or a prodrug of the compound into the system of the subject in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

When a compound of the present invention is administered into a human subject, the daily dosage regimen will normally be determined by the prescribing physician, with the dosage generally varying according to the age, weight, and response of the individual patient, as well as the severity of the patient's symptoms. In one exemplary application, oral dosages of the present invention will range between about 0.01 mg per kg of body weight per day (mg/kg/day) to about 100 mg/kg/day, preferably 0.01 to 10 mg/kg/day, and most preferably 0.1 to 5.0 mg/kg/day.

These and other aspects of the invention will be apparent from the teachings contained herein.

Abbreviations used in the description of the chemistry and in the Examples that follow are: DMF: dimethylformamide; DMSO: dimethylsulfoxide; MeOH: methanol; EtOH: ethanol; EtOAc: ethyl acetate; DCM: dichloromethane; THF: tetrahydrofurane; DME: dimethoxyethane; AcOH: acetic acid; TFA: trifluoroacetic acid; (g): gas; min: minutes; h: hour(s); eq.: equivalent(s); M: molar; RT: room temperature; RP-HPLC: reversed phase high-pressure liquid chromatography; DIPEA: N,N-diisopropylethylamine; DMAP: 4-(dimethylamino)pyridine; NMM: 4-methylmorpholine; EDCI: 1-(3-dimethylaminopropyl)-3-ethylcarbodiimide hydrochloride; HOBt: 1-hydroxybenzotriazole; HATU: O-(7-azabenzotriazol-1-yl)-N,N,N',N'-tetramethyluronium hexafluorophosphate; HBTU: O-(benzotriazol-1-yl)-N,N,N',N'-tetramethyluronium hexafluorophosphate; TBTU: O-(benzotriazol-1-yl)-N,N,N',N'-tetramethyluronium tetrafluoroborate; and NIS: N-iodosuccinimide.

BRIEF DESCRIPTION OF THE DRAWINGS

The present invention will be described by means of non limiting examples referring to the following figures.

DETAILED DESCRIPTION OF THE INVENTION

Figure 1:
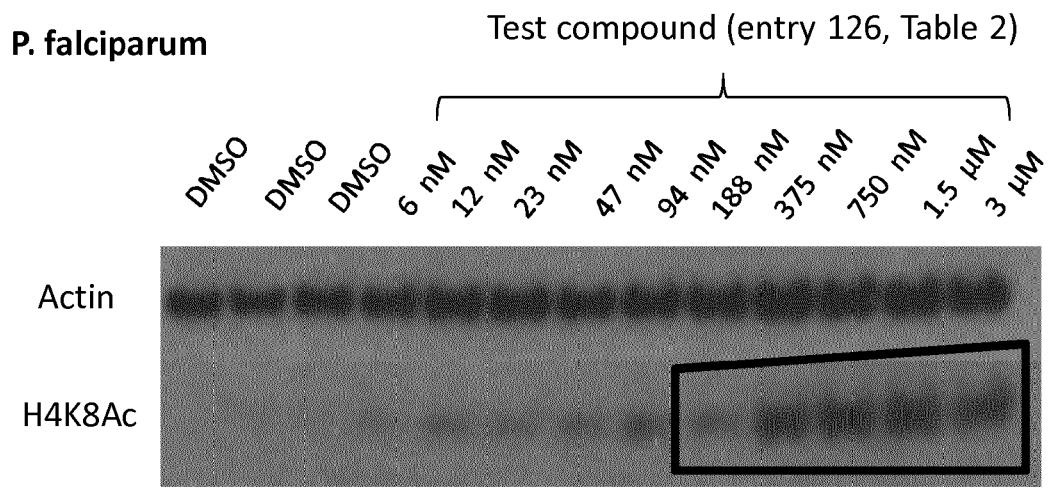
FIG. 1. Hyperacetylation of *P. falciparum* histones. *Plasmodium falciparum* 3D7 infected erythrocytes (5-7% parasitemia) were cultured for 14-16 hours in vitro with increasing concentrations (6 nM to 3 uM) of (A): compound (S)-N-(7-(methylamino)-1-(5-(naphthalen-2-yl)-1H-imidazol-2-yl)-7-oxoheptyl)quinuclidine-4-carboxamide (Table 2, entry 126) or with vehicle (0.01% DMSO); increasing concentrations (20 nM to 10 uM) of (B): compound (S)-N-(1-(5-(4-(1H-pyrazol-5-yl)phenyl)-1H-imidazol-2-yl)-7-(methylamino)-7-oxoheptyl)thiazole-5-carboxamide (Table 2, entry 221; Example 4, D9). Beta-actin was used as loading control (see materials and methods). H4K8Ac: antibody directed against acetylated lysine 8 of histone 4.
Figure 1:
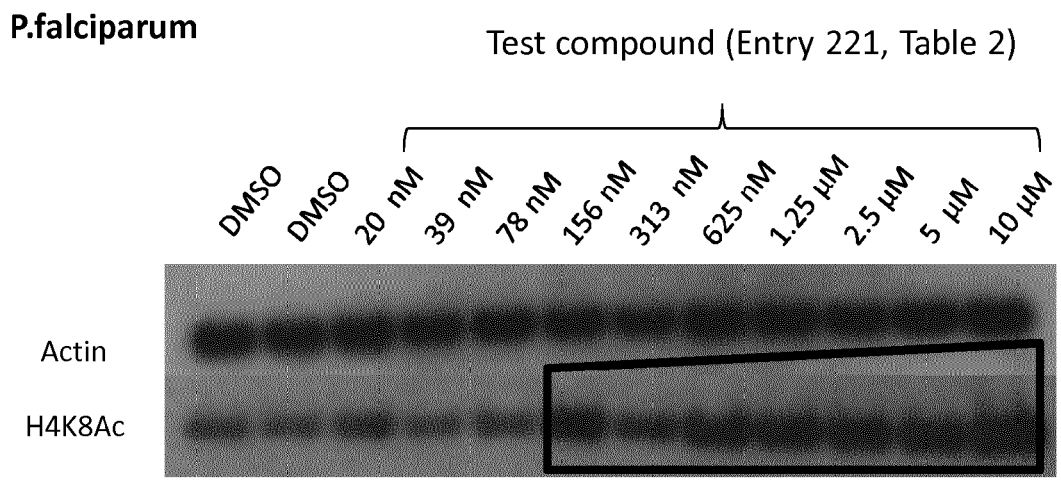

Materials and Methods
Chemistry
a) General Procedures.

Compounds of this invention can be prepared as described in Scheme 1 from a suitably elaborated alkyl chain functionalised in the α-position with an amino derivative. These derivatives can be prepared by those skilled in the art and methods to synthesise such heterocycles are described in Alan Katritzky, Comprehensive Heterocyclic Chemistry. (Pergamon Press, New York, 1984) and Comprehensive Heterocylic Chemistry IL (Pergamon Press, New York, 1996) amongst other texts. The free amino group can be coupled with an acid derivative to form amides as described in Scheme 1, methods for coupling carboxylic acids (and acid derivatives) with amines to form carboxamides are well known in the art. Suitable methods are described, for example, in Jerry March, Advanced Organic Chemistry, 3rd edition, John Wiley & Sons, 1985, 370-376. Likewise reaction with a sulfonyl chloride in the presence of base gives the corresponding sulfonamide, see Jerry March, Advanced Organic Chemistry. 4th edition, John Wiley & Sons, 1992, 496-499.

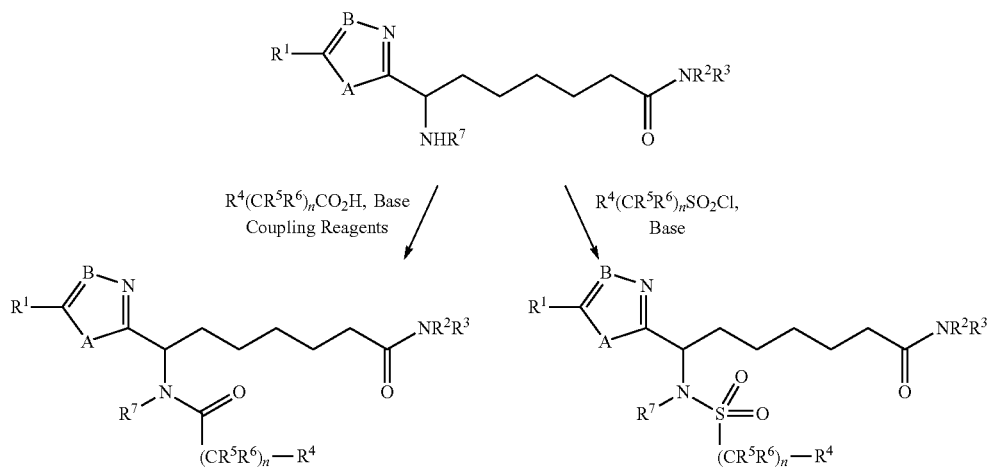

Scheme 1

A route to pendant imidazoles is shown in Scheme 2 from the key protected amino ester (these amino acid derivatives can be prepared by those skilled in the art using standard chemistry, such as described in Williams, R. M. *Synthesis of Optically Active α-Amino Acids*, Pergamon Press, 1989).

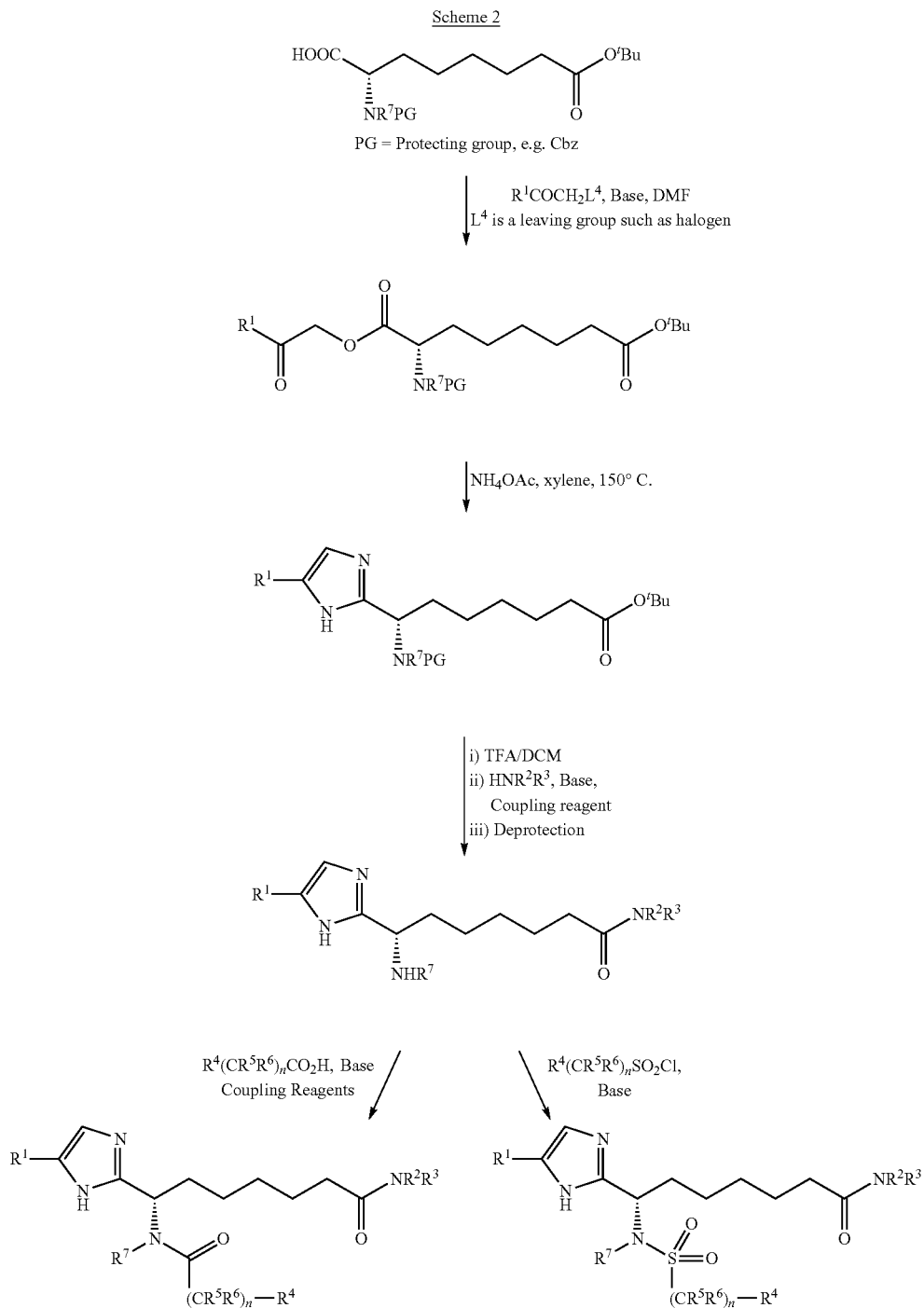

The amino esters can be reacted with a halomethyl ketone in the presence of base, for example Cs$_2$CO$_3$, and the resulting intermediate is treated with an excess of ammonium acetate and heated at 150° C. to yield the desired imidazole, and such conditions are described in *Bioorg. Med. Chem. Lett.* 1996, 6; 1601, *Tetrahedron* 1996, 52, 10131 and *J. Am. Chem. Soc.* 1981, 103, 3446. Selective removal of the protecting groups enables further functionalisation. For instance, treatment with an acid such as TFA in a solvent such a DCM led to the deprotection of the tert-butyl ester. Coupling of the resulting carboxylic acid with an amine in the presence of coupling reagent such as HATU, and a base such as DIPEA in a solvent such as DMF led to the formation of the terminal carboxamide. Appropriate deprotection of the amino group using procedures described in Protecting Groups in Organic Synthesis (3$^{rd}$ Edition, Greene, T. W. and Wuts, P. G. M., Wiley Interscience, 1999) led to an intermediate that could be transformed using the procedures described in Scheme 1.

An alternative route for the preparation of imidazoles is shown in Scheme 3, where the chiral α-amino acid is reduced to the corresponding aldehyde, via formation of the Weinreb amide.

Scheme 3

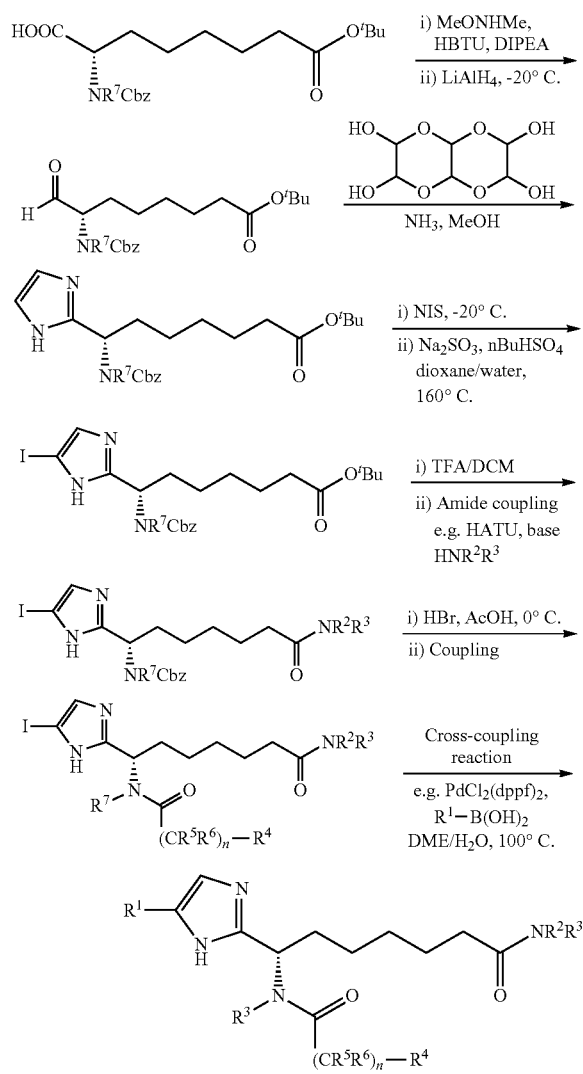

Scheme 4

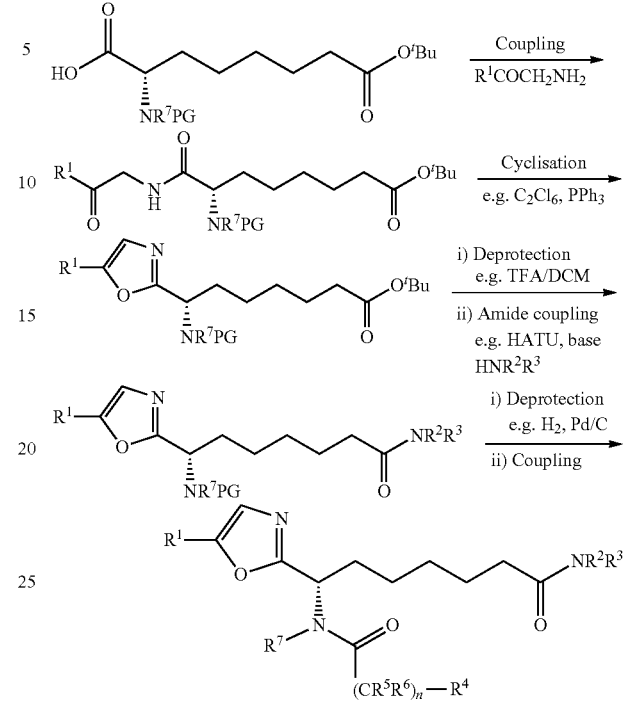

The aldehyde can readily be converted to the required imidazole by literature procedures as described in WO2009/026701. Double iodination with NIS, followed by selective reduction with $Na_2SO_3$, affords the key iodo-imidazole intermediate. Selective deprotection and amide coupling leads to an advanced fully functionalized iodoimidazole analog, which can be used in Pd catalysed cross-coupling reactions for the introduction of a substituent onto the imidazole ring as described in WO2010/138791. The Pd catalyzed cross-coupling reaction can be performed on earlier intermediates possessing the iodoimidazole fragment, allowing late stage elaboration of either the terminal carboxylic acid or the amino group as described previously. A synthetic route for the preparation of oxazoles, is shown in Scheme 4. An α-aminoketone is coupled with a carboxylic acid, and the resulting amide formed can then be cyclised under dehydrative conditions to yield the desired heterocycle. One method for performing the cyclisation is to use hexachloroethane and triphenylphosphine as described by Nicolaou et al. *J. Am. Chem. Soc.* 2004, 126, 10162-10173. This intermediate can be further elaborated as described in Scheme 2 for the imidazole analogs.

Where the synthesis of intermediates and starting materials is not described, these compounds are commercially available or can be made from commercially available compounds by standard methods or by extension of the Examples herein. Non commercially available aryl- and heteroaryl boronic acids or esters where prepared by reacting the corresponding aryl and heteroaryl halides with bis(pinacolato)diboron in the presence of palladium catalyst, as described, for example, in *J. Org. Chem.* (2006), 71(20), 7899 or in *J. Org. Chem.* (2011), 76(15), 6394. Compounds of formula (I) may be converted to other compounds of formula (I) by known methods or by methods described in the Examples.

During any of the synthetic sequences described herein it may be necessary and/or desirable to protect sensitive or reactive groups on any of the molecules concerned. This may be achieved by means of conventional protecting groups, such as those described in Protecting Groups in Organic Synthesis ($3^{rd}$ Edition, Greene, T. W. and Wuts, P. G. M.; Wiley Interscience, 1999) and Protecting Groups (Kocienski, P. J.; Thieme, 1994). The protecting groups may be removed at a convenient subsequent stage using methods known from the art. For example, when the Boc protecting group is present, it may be removed by the addition of solvents such as TFA and DCM. The compound may also be hydrogenated using standard methods, such as treating with a catalyst such as Pd/C, in a solvent such as methanol in a hydrogen atmosphere. As described previously the heterocyclic group may be protected by protecting groups such as SEM during the synthesis of the compounds of Formula (I), which can subsequently be removed under standard conditions as described above. Further examples of protecting groups on the heterocyclic ring include tert-butyl(dimethyl)silylmethyl and BOM. The BOM group may subsequently be removed using standard methods, for example by the addition of a reagent such as $BBr_3$ and a solvent such as toluene at about room temperature.

a) EXAMPLES

The following Examples illustrate the present invention.

Example 1

(S)-4-((1-(5-(2-methoxyquinolin-1-ium-3-yl)-1H-imidazol-2-yl)-7-(methylamino)-7-oxoheptyl)carbamoyl)quinuclidin-1-ium mono L-tartrate salt (A5)

Step 1: (S)-tert-butyl 7-(((benzyloxy)carbonyl)amino)-7-(5-(2-methoxyquinolin-3-yl)-1H-imidazol-2-yl)heptanoate (A1)

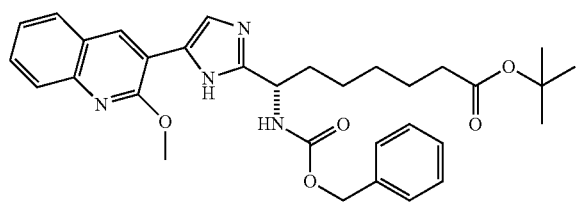 [SMILES: COc1nc2ccccc2cc1-c1cnc([C@H](CCCCCC(=O)OC(C)(C)C)NC(=O)OCc2ccccc2)[nH]1]

A solution of (S)-2-(((benzyloxy)carbonyl)amino)-8-(tert-butoxy)-8-oxooctanoic acid (prepared as described in WO2006/061638), N-ethyl-N'-(3-dimethylaminopropyl)-carbo diimide hydrochloride (1.3 eq.) and HOBt (1.3 eq.) were dissolved in anhydrous DMF and stirred for 15 min. The resulting solution was added to a mixture of 2-hydroxy-1-(2-methoxyquinolin-3-yl)ethanone (1 eq.) (prepared as described in *J. Med. Chem.* 2009, 59, 3453-3456) and DMAP (0.3 eq.) in anhydrous DMF (0.7 M). After stirring at room temperature for 16 h the mixture was partitioned between DCM and water. The organic phase was washed with water and brine and dried over $Na_2SO_4$. Concentration under reduced pressure gave an oily crude which was used as such. A solution of the resulting oil and ammonium acetate (20 eq.) in xylene was heated under Dean-Stark conditions for 1.5 h. After cooling to room temperature the mixture was diluted with EtOAc and water. The organic phase was separated and washed with sat. aq. $NaHCO_3$, brine, dried over $Na_2SO_4$ and concentrated under reduced pressure to give a crude that was purified by column chromatography (eluent: petroleum ether/EtOAc from 7:3 to 2:3) to give the title compound as a yellow powder. MS (ES$^+$) $C_{32}H_{38}N_4O_5$: 559 (M+H)$^+$.

Step 2: (S)-3-(2-(1-(((benzyloxy)carbonyl)amino)-6-carboxyhexyl)-1H-imidazol-3-ium-5-yl)-2-methoxyquinolin-1-ium bis trifluoroacetate (A2)

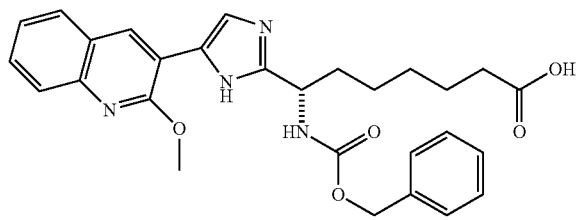 [SMILES: COc1nc2ccccc2cc1-c1cnc([C@H](CCCCCC(=O)O)NC(=O)OCc2ccccc2)[nH]1]

To a solution of A1 in DCM (0.11 M) cooled to 0° C. was slowly added TFA (1 M). Reaction mixture was stirred at 4° C. for 24 h. Volatiles were removed under reduced pressure, the resulting oily residue was co-evaporated first with toluene then with $Et_2O$ to give the title compound which was used as such in the next step. MS (ES$^+$) $C_{28}H_{36}N_4O_5$: 503 (M+H)$^+$.

Step 3: (S)-benzyl (1-(5-(2-methoxyquinolin-3-yl)-1H-imidazol-2-yl)-7-(methylamino)-7-oxoheptyl)carbamate (A3)

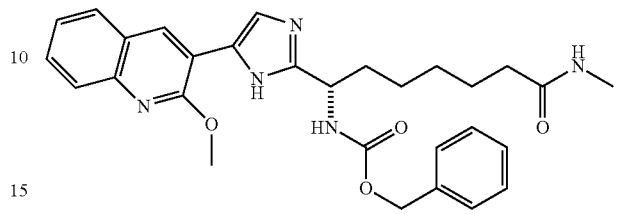

To a solution of A2 in DMF (0.14 M) was added methylamine (2.0 M solution in THF, 5 eq.) followed by HATU (2 eq.) and DIPEA (3 eq.). Reaction mixture was stirred at RT for 1 h. Then solvent was concentrated in vacuo and the resulting residue was diluted with EtOAc, washed with sat. aq. $NaHCO_3$, brine, dried over $Na_2SO_4$ and concentrated under reduced pressure. The resulting crude was purified by column chromatography (eluent: DCM/MeOH from 100:0 to 9:1) to get the title compound as a solid. MS (ES$^+$) $C_{29}H_{33}N_5O_4$: 516 (M+H)$^+$.

Step 4: (S)-7-amino-7-(5-(2-methoxyquinolin-3-yl)-1H-imidazol-2-yl)-N-methylheptanamide (A4)

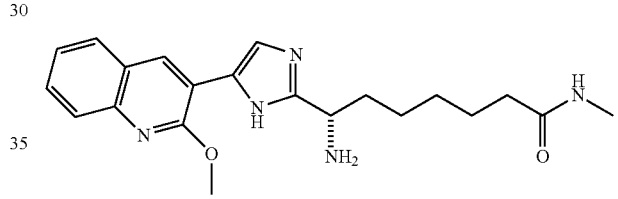

A3 was dissolved in EtOAc/MeOH (1:1) (0.01 M) and treated with Pd/C. Mixture was purged with $N_2$ and stirred under $H_2$ atmosphere at room temperature for 24 h. Then, reaction mixture was filtered through a pad of silica and filtrate was concentrated under vacuum to give the title compound which was used as such in the next step. MS (ES$^+$) $C_{21}H_{27}N_5O_2$: 382 (M+H)$^+$.

Step 5: (S)-4-((1-(5-(2-methoxyquinolin-1-ium-3-yl)-1H-imidazol-2-yl)-7-(methylamino)-7-oxoheptyl)carbamoyl)quinuclidin-1-ium mono L-tartrate salt (A5)

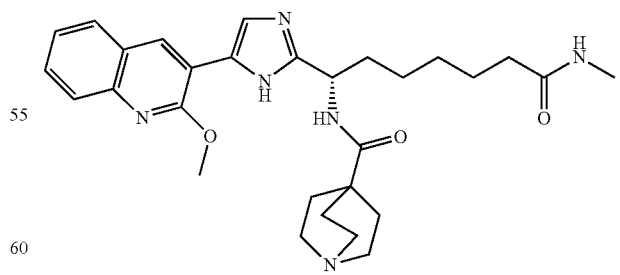

A solution of 4-carboxyquinuclidin-1-ium chlorhydrate (1.3 eq.) in DMF (0.2 M) was treated with TBTU (1.3 eq.) and NMM (2.6 eq.). The reaction mixture was stirred at room temperature for 10 minutes and then added to a solution of A4 in DMF (0.2 M). The reaction was stirred at RT for 2 h and subsequently was purified by RP-HPLC (Acetonitrile/$H_2O$+

0.1% TFA). The product was obtained as TFA salt which was partitioned between DCM and sat. aq. NaHCO$_3$. The organic phase was separated, dried over Na$_2$SO$_4$ and concentrated under reduced pressure. The resulting syrup was dissolved in acetonitrile/H$_2$O (2:3) and treated with L-tartaric acid (1 eq.). The resulting solution was lyophilized to obtain the title compound. $^1$H-NMR (400 MHz, 300 K, DMSO-d$_6$) δ 8.73 (br s, 1H), 7.94 (t, 2H, J 9.6 Hz), 7.76 (d, 1H, J 8.0 Hz), 7.67 (br s, 1H), 7.60 (m, 2H), 7.42 (t, 1H, J 8.0 Hz), 5.02 (m, 1H), 4.13 (s, 3H), 3.93 (s, 2H), 3.18 (t, 6H, J 7.2 Hz), 2.54 (d, 3H, J 4.4 Hz), 2.05-1.91 (m, 8H), 1.51-1.23 (m, 8H). MS (ES$^+$) C$_{29}$H$_{38}$N$_6$O$_3$: 519 (M+H)$^+$.

Example 2

(S)-N-(1-(5-(2-methoxyquinolin-3-yl)-1H-imidazol-2-yl)-7-(methylamino)-7-oxoheptyl)thiazole-5-carboxamide (B1)

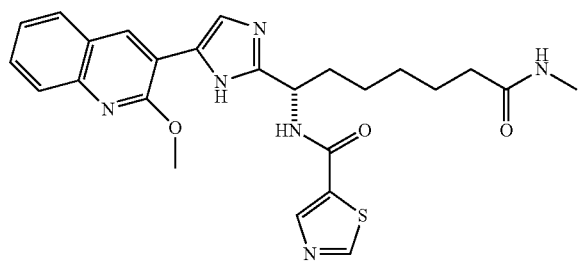 [SMILES: CNC(=O)CCCCC[C@H](NC(=O)c1cncs1)c1ncc(-c2cc3ccccc3nc2OC)[nH]1]

A glass tube was charged with thiazole-5-carboxylic acid (1.5 eq.), PS-carbodiimide resin (2 eq.), HOBt (1.7 eq.) and diluted with DCM (0.04 M). The tube was capped and stirred on a rotor for 10 min. Then, a solution of A4 in DMF (0.06 M) was added and the reaction mixture was stirred in a rotor for 24 h. After addition of MP-Trisamine resin (10 eq.) the reaction was stirred for additional 24 h. The resulting reaction mixture was filtered through a fritted syringe and washed with DCM. The combined organic solutions were concentrated under reduced pressure to give the title compound. MS (ES$^+$) C$_{25}$H$_{28}$N$_6$O$_3$S: 493 (M+H)$^+$.

Example 3

(S)-7-(4-cyanophenylsulfonamido)-7-(5-(2-methoxyquinolin-3-yl)-1H-imidazol-2-yl)-N-methylheptanamide (C1)

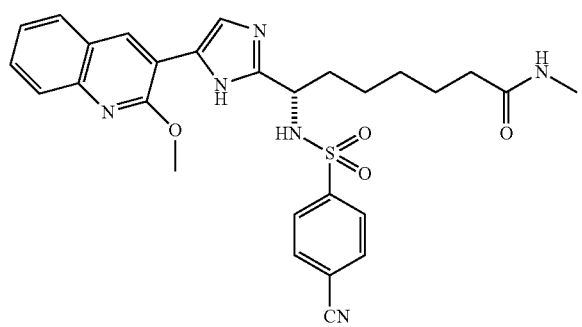 [SMILES: CNC(=O)CCCCC[C@H](NS(=O)(=O)c1ccc(C#N)cc1)c1ncc(-c2cc3ccccc3nc2OC)[nH]1]

To a solution of A4 and Et$_3$N (1.1 eq.) in DCM (0.1 M) was added 4-cyanobenzene sulfonyl chloride (1.1 eq.). The reaction mixture was stirred at room temperature for 2 h. Volatiles were removed under reduced pressure to give a residue that was dissolved in acetonitrile and purified by RP-HPLC (Acetonitrile/H$_2$O+0.1% TFA) to give the trifluoroacetate salt of title compound a white solid. $^1$H-NMR (400 MHz, 300 K, DMSO-d$_6$) δ 8.68 (br s, 1H), 8.44 (s, 1H), 7.95-7.74 (m, 6H), 7.60-7.55 (m, 3H), 7.46 (m, 1H), 4.43 (m, 1H), 4.11 (s, 3H), 2.51 (d, 3H, J 4.4 Hz), 1.96 (t, 2H, J 7.4 Hz), 1.85-1.75 (m, 2H), 1.45-1.30 (m, 2H), 1.30-0.95 (m, 4H). MS (ES$^+$) C$_{28}$H$_{33}$N$_5$O$_4$S: 547 (M+H)$^+$.

Example 4

(S)-N-(1-(5-(4-(1H-pyrazol-5-yl)phenyl)-1H-imidazol-2-yl)-7-(methylamino)-7-oxoheptyl)thiazole-5-carboxamide (D9)

Step 1: (S)-tert-butyl 7-(((benzyloxy)carbonyl)amino)-8-(methoxy(methyl)amino)-8-oxooctanoate (D1)

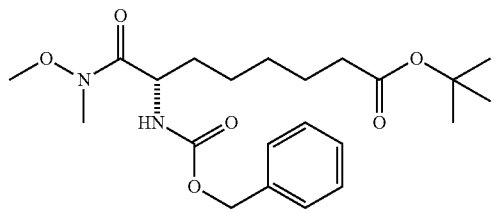 [SMILES: CON(C)C(=O)[C@H](CCCCCC(=O)OC(C)(C)C)NC(=O)OCc1ccccc1]

A solution of (S)-2-(((benzyloxy)carbonyl)amino)-8-(tert-butoxy)-8-oxooctanoic acid (prepared as described in WO2006/061638), HBTU (1.1 eq.) and DIPEA (2 eq.) in DMF (0.7 M) was stirred at room temperature for 10 min. Then, dimethylhydroxylamine hydrochloride (1.1 eq.) was added. The reaction mixture was stirred at room temperature for a further 16 h then diluted with EtOAc. Organic phase was washed with sat. aq. NaHCO$_3$, brine, dried over Na$_2$SO$_4$ and concentrated under reduced pressure to give a residue that was purified by column chromatography (eluent: petroleum ether/EtOAc from 85:15 to 1:4) to give the title compound as a pale yellow oil. MS (ES$^+$) C$_{22}$H$_{34}$N$_2$O$_6$: 423 (M+H)$^+$.

Step 2: (S)-tert-butyl 7-(((benzyloxy)carbonyl)amino)-8-oxooctanoate (D2)

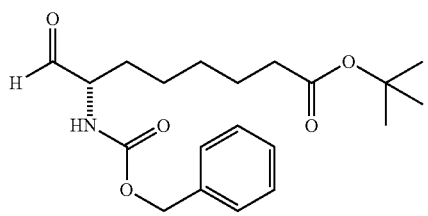 [SMILES: CC(C)(C)OC(=O)CCCCC[C@@H](C=O)NC(=O)OCc1ccccc1]

To a stirred solution of D1 in THF (0.15 M) cooled to −20° C., was added dropwise a 1.0 M solution of LiAlH$_4$ in THF (1.25 eq.). Reaction mixture was stirred at −20° C. for 30 min before quenching with EtOAc and partitioning between EtOAc and 0.1 M HCl. The organic phase was separated and the aqueous phase extracted into EtOAc. The combined organic extracts were washed with H$_2$O, brine, dried over Na$_2$SO$_4$ and concentrated under reduced pressure to give the title compound as pale yellow oil which was used in the next step without further purification. MS (ES$^+$) C$_{20}$H$_{29}$NO$_5$: 364 (M+H)$^+$.

Step 3: (S)-tert-butyl 7-(((benzyloxy)carbonyl)amino)-7-(1H-imidazol-2-yl)heptanoate (D3)

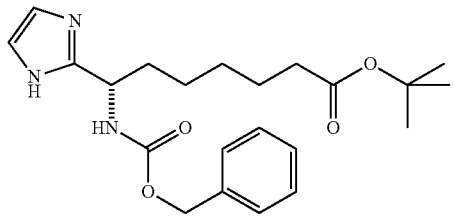 [SMILES: CC(C)(C)OC(=O)CCCCC[C@H](NC(=O)OCc1ccccc1)c1ncc[nH]1]

To a stirred solution of D2 in MeOH (0.4 M) at room temperature was added glyoxal trimer dihydrated (1.0 eq.) followed by slowly addition of ammonia (7.0 M in MeOH, 5.0 eq.). The reaction mixture was stirred in a sealed tube at room temperature for 72 h performing 3 subsequent additions of both glyoxal trimer dihydrated and ammonia until no more progress of the reaction was observed. Evaporation of the solvent under reduced pressure gave a crude that was purified by column chromatography (eluent: petroleum ether/EtOAc from 4:1 to EtOAc) to give the title compound as a yellow solid. MS (ES$^+$) C$_{22}$H$_{31}$N$_3$O$_4$: 402 (M+H)$^+$.

Step 4: (S)-tert-butyl 7-(((benzyloxy)carbonyl)amino)-7-(4,5-diiodo-1H-imidazol-2-yl)heptanoate (D4)

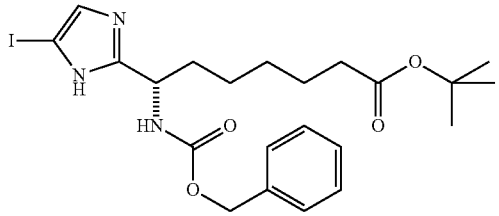 [SMILES: CC(C)(C)OC(=O)CCCCC[C@H](NC(=O)OCc1ccccc1)c1ncc(I)[nH]1]

To a stirred solution of D3 in CH$_3$CN (0.05 M) cooled to −10° C. was added, portionwise, NIS (3.0 eq.). Reaction mixture was stirred at −10° C. for 1 h then 2 subsequent additions of NIS (1 eq.) after 30 min each were performed until completion of reaction was observed. The reaction mixture was allowed to warm up to room temperature and then, CH$_3$CN was removed under reduced pressure. The resulting residue was dissolved in EtOAc and washed with sat. aq. NaHCO$_3$, sat. aq. Na$_2$S$_2$O$_3$, sat. aq. NaCl, dried over Na$_2$SO$_4$ and concentrated under reduced pressure to give the crude diiodo-analog as brown oil which was used without further purification. MS (ES$^+$) C$_{22}$H$_{29}$I$_2$N$_3$O$_4$: 654 (M+H)$^+$. This crude was dissolved in 1,4-dioxane/H$_2$O (4:1, 0.1 M) and Na$_2$SO$_3$ (10 eq.) and tetrabuthylammonium hydrogen phosphate (2.0 eq.) were added. The reaction mixture was heated under microwave irradiation at 160° C. for 30 min. Then, the organic solvent was removed under reduced pressure and the aqueous phase was extracted with EtOAc. The combined organic extracts were washed with sat. aq. NaHCO$_3$, sat. aq. NaCl, dried over Na$_2$SO$_4$ and concentrated under reduced pressure to give an oily residue which was purified by column chromatography (eluent: petroleum ether/EtOAc from 4:1 to 1:4) to give the title compound as a yellow oil. MS (ES$^+$) C$_{22}$H$_{30}$IN$_3$O$_4$: 528 (M+H)$^+$.

Step 5: (S)-2-(1-(((benzyloxy)carbonyl)amino)-6-carboxyhexyl)-5-iodo-1H-imidazol-3-ium trifluoro-acetate (D5)

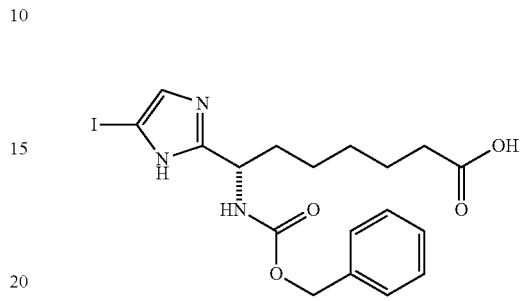

To a stirred solution of D4 in DCM (0.19 M) cooled to 0° C. was slowly added TFA (35 eq.). The reaction mixture was stirred at 0° C. for 30 min then allowed to warm up to room temperature and stirred for another 2 h. Solvent was evaporated under reduced pressure affording an oily residue was co-evaporated first with toluene then with Et$_2$O to give the title compound as a pale brown solid which was used as such in the next step. MS (ES$^+$) C$_{18}$H$_{22}$IN$_3$O$_4$: 472 (M+H)$^+$.

Step 6: (S)-benzyl (1-(5-iodo-1H-imidazol-2-yl)-7-(methylamino)-7-oxoheptyl)carbamate (D6)

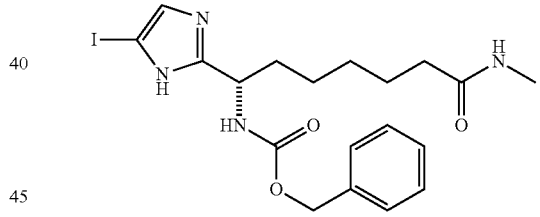

To a stirred solution of D5 in DMF (0.3 M) was added methylamine (2.0 M solution in THF, 5.0 eq.) followed by HBTU (2.0 eq.). Solution pH was adjusted to basic value by addition of methylamine (2.0 M solution in THF, 2.5 eq.). Reaction mixture was stirred at room temperature for 1 h, then two more addition of HBTU (4.47 g, 28.5 mmol, 1.0 eq.) and methylamine (2.0 M solution in THF, 2.5 eq.) every 30 min were performed to reach completion of reaction. Solvent was concentrated under reduced pressure and the resulting residue was diluted with EtOAc, washed with sat. aq. NaHCO$_3$, Brine, dried over Na$_2$SO$_4$ and concentrated under reduced pressure. The resulting crude was purified by column chromatography (eluent: petroleum ether/EtOAc from 4:1 to EtOAc) to give the title compound as a white solid. $^1$H-NMR (400 MHz, 300K, CDCl$_3$) δ 12.11 (br s, 1H), 7.69-7.59 (m, 2H), 7.41-7.27 (m, 4H), 7.19 (s, 1H), 5.06 (d, 1H, J 12.8 Hz), 5.00 (d, 1H, J 12.8 Hz), 4.57 (m, 1H), 2.54 (d, 3H, J 4.8 Hz), 2.01 (t, 2H, J 7.4 Hz), 1.85-1.60 (m, 2H), 1.50-1.38 (m, 2H), 1.32-1.12 (m, 4H). MS (ES$^+$) C$_{19}$H$_{25}$IN$_4$O$_3$: 485 (M+H)$^+$.

Step 7: (S)-7-amino-7-(5-iodo-1H-imidazol-2-yl)-N-methylheptanamide (D7)

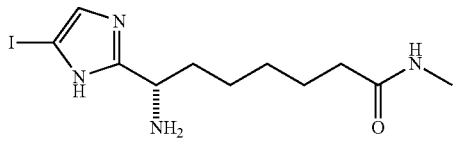 [SMILES: CNC(=O)CCCCC[C@H](N)c1ncc(I)[nH]1]

A solution of D6 in DCM (0.2 M) was treated with an excess of HBr solution in AcOH at 0° C. and the reaction mixture was stirred at this temperature for 1 h. Then solvents were removed under reduced pressure and excess reagents were removed by repeated addition of toluene and evaporation of the solvent. The residue obtained was dissolved in MeOH, passed through a SCX resin cartridge and the cartridge washed with MeOH. Then, the cartridge was treated with a 7N solution of $NH_3$ in MeOH and the organic solution was concentrated under reduced pressure to give the title compound as a white powder. MS (ES$^+$) $C_{11}H_{19}IN_4O$: 351 (M+H)$^+$.

Step 8: (S)-N-(1-(5-iodo-1H-imidazol-2-yl)-7-(methylamino)-7-oxoheptyl)thiazole-5-carboxamide (D8)

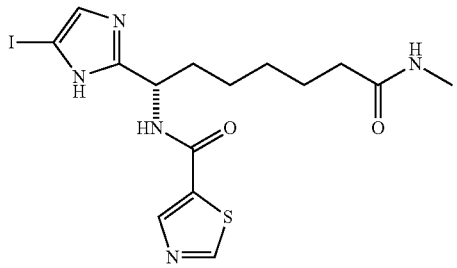 [SMILES: CNC(=O)CCCCC[C@H](NC(=O)c1cncs1)c1ncc(I)[nH]1]

A solution of thiazole-5-carboxylic acid (1.5 eq.) in DMF (1 M) was treated with EDC.HCl (1.5 eq.), HOBt (1.5 eq.) and DIPEA (1.5 eq.), Reaction mixture was stirred at room temperature for 10 min and then added to a solution of D7 in DMF (0.33 M). The reaction mixture was stirred at room temperature for 1 h and subsequently partitioned between DCM and sat. aq. NaHCO$_3$. The organic phase was separated and the aqueous phase extracted with DCM. The combined organic extracts were washed with brine, dried over Na$_2$SO$_4$ and concentrated under reduced pressure to give a crude that was purified by flash chromatography (Biotage; 25M; DCM/MeOH) to afford the title compound as a white powder. $^1$H-NMR (400 MHz, 300K, DMSO-d$_6$) δ 12.25 (br s, 1H), 9.23 (s, 1H), 9.02 (d, 1H, J 8.0 Hz), 8.58 (s, 1H), 7.65 (br s, 1H), 7.23 (s, 1H), 5.05 (m, 1H), 2.55 (d, 3H, J 5.2 Hz), 2.02 (t, 2H, J 7.6 Hz), 1.97 (m, 1H), 1.82 (m, 1H), 1.47 (m, 2H), 1.25 (m, 4H); MS (ES$^+$) $C_{15}H_{20}IN_5O_2S$: 462 (M+H)$^+$.

Step 9: (S)-N-(1-(5-(4-(1H-pyrazol-5-yl)phenyl)-1H-imidazol-2-yl)-7-(methylamino)-7-oxoheptyl)thiazole-5-carboxamide (D9)

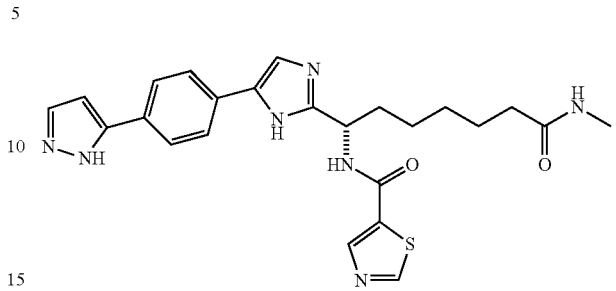

A degassed microwave vial was charged with D8, (4-(1H-pyrazol-5-yl)phenyl)boronic acid (2 eq.), PdCl$_2$(dppf)$_2$ (0.2 eq.) and potassium carbonate (3 eq.). A degassed solution of DME/H$_2$O (1:1, 0.05 M) was added and the suspension was degassed for further 10 minutes and then heated at 110° C. for 1 h. After cooling, solvents were removed under reduced pressure and the resulting residue dissolved in DMF and filtered. The crude material was purified by preparative RP-HPLC (Acetonitrile/H$_2$O+0.1% TFA). The product was obtained as TFA salt which was partitioned between DCM and sat. aq. NaHCO$_3$. The organic phase was separated, dried over Na$_2$SO$_4$ and concentrated under reduced pressure. The resulting white solid was dissolved in acetonitrile/H$_2$O (1:1) and treated with L-tartaric acid (1 eq.). The resulting solution was lyophilized to obtain the title compound as tartrate salt. $^1$H-NMR (400 MHz, 300K, DMSO-d$_6$) δ: 13.50-12.50 (br s, 4H), 9.23 (s, 1H), 9.03 (d, 1H, J 8 Hz), 8.61 (s, 1H), 7.85-7.45 (m, 7H), 6.69 (d, 1H J 2 Hz), 5.11 (m, 1H), 4.30 (s, 2H), 2.53 (d, J 4.4 Hz), 3H), 2.15-2.00 (m, 3H), 2.00-1.80 (m, 1H), 1.55-1.42 (m, 2H), 1.42, 1.20 (m, 4H). MS (ES$^+$) $C_{24}H_{27}N_7O_2S$: 478 (M+H)$^+$.

Example 5

(S)-4-((1-(5-(6-methoxynaphthalen-2-yl)-1H-imidazol-3-ium-2-yl)-7-(methylamino)-7-oxoheptyl)carbamoyl)quinuclidin-1-ium mono L-tartrate salt (E5)

Step 1: (S)-tert-butyl 7-(((benzyloxy)carbonyl)amino)-7-(5-(6-methoxynaphthalen-2-yl)-1H-imidazol-2-yl)heptanoate (E1)

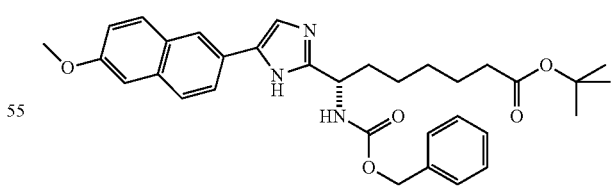

A degassed microwave vial was charged with D4, (6-methoxy-2-naphthyl)boronic acid (2 eq.), PdCl$_2$(dppf)$_2$ (0.2 eq.) and K$_2$CO$_3$ (3 eq.). A degassed solution of DME/H$_2$O (1:1, 0.05 M) was added and the suspension was degassed for further 10 minutes and then heated at 110° C. for 30 min. After cooling, reaction mixture was diluted with EtOAc and filtered through a pad of Solka-Floc®. The filtrate was washed with sat. aq. NaHCO$_3$ sol., brine, dried over Na$_2$SO$_4$, filtered and concentrated to give a dark red residue. The resulting crude was purified by column chromatography (eluent: petroleum ether/EtOAc from 95:5 to 1:1) to give the title compound as a pale yellow solid. MS (ES+) C33H39N3O5: 558 (M+H)+.

Step 2: (S)-2-(1-(((benzyloxy)carbonyl)amino)-6-carboxyhexyl)-5-(6-methoxynaphthalen-2-yl)-1H-imidazol-3-ium trifluoroacetate (E2)

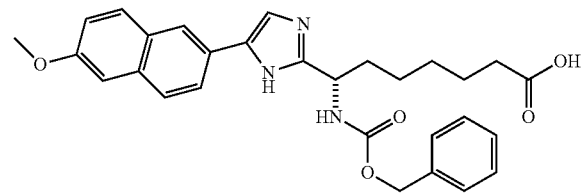 [SMILES: COc1ccc2cc(-c3cnc([C@H](CCCCCC(=O)O)NC(=O)OCc4ccccc4)[nH]3)ccc2c1]

To a stirred solution of E1 in DCM (0.2 M) cooled to 0° C. TFA (70 eq.) was slowly added. The reaction mixture was stirred at room temperature for 2 h. Then, solvent was evaporated under reduced pressure to afford an oily residue that was co-evaporated first with toluene then with Et2O to give the title compound as a pale red solid which was used as such in the next step. MS (ES+) C29H31N3O5: 502 (M+H)+.

Step 3: (S)-benzyl (1-(5-(6-methoxynaphthalen-2-yl)-1H-imidazol-2-yl)-7-(methylamino)-7-oxoheptyl)carbamate (E3)

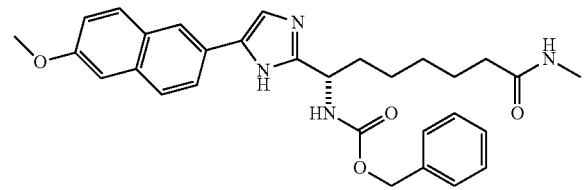

To a stirred solution of E2 in DMF (0.1 M) were added HATU (1.5 eq.) and DIPEA (2.0 eq.) followed after 10 min by methylamine (2.0 M solution in THF, 5 eq.). Reaction mixture was stirred at room temperature for 16 h, then it was diluted with EtOAc, washed with sat. aq. NaHCO3 sol., brine, dried over Na2SO4, filtered and concentrated to give a dark brown residue. The resulting crude was purified by column chromatography (eluent: petroleum ether/EtOAc from 9:1 to 100% EtOAc, then EtOAc/MeOH=95:5) to give the title compound as a colorless oil. MS (ES+) C30H34N4O4: 515 (M+H)+.

Step 4: (S)-7-amino-7-(5-(6-methoxynaphthalen-2-yl)-1H-imidazol-2-yl)-N-methylheptanamide (E4)

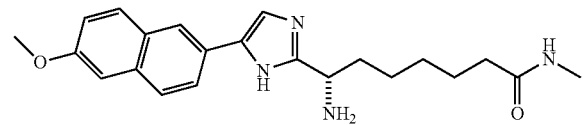

E3 was dissolved in EtOAc/MeOH (1:1, 0.1 M) and treated with Pd/C (10% w/w). Mixture was purged with N2 and stirred under H2 atmosphere at room temperature for 16 h. Then, reaction mixture was filtered through a pad of Solka-Floc® and filtrate was concentrated under reduced pressure to give the title compound as pale yellow oil which was used as such in the next step. MS (ES+) C22H28N4O2: 381 (M+H)+.

Step 5: (S)-4-((1-(5-(6-methoxynaphthalen-2-yl)-1H-imidazol-3-ium-2-yl)-7-(methylamino)-7-oxoheptyl)carbamoyl)quinuclidin-1-ium mono L-tartrate salt (E5)

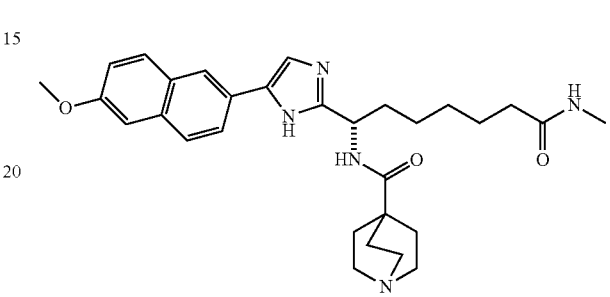

A solution of 4-carboxyquinuclidin-1-ium chlorhydrate (1.3 eq.) in DMF (0.2 M) was treated with TBTU (1.3 eq.) and NMM (2.6 eq.). The reaction mixture was stirred at room temperature for 10 min and then added to a solution of E4 in DMF (0.2 M). The reaction was stirred at RT for 2 h, then filtered and purified by RP-HPLC (CH3CN/H2O+0.1% TFA). The product was obtained as TFA salt which was partitioned between EtOAc and sat. aq. NaHCO3. The organic phase was separated, dried (Na2SO4) and concentrated under reduced pressure. The resulting pale yellow solid was dissolved in acetonitrile/H2O (1:1) and treated with L-tartaric acid (1 eq.). The resulting solution was lyophilized to obtain the title compound. (400 MHz, 300K, DMSO-d6) δ: 11.5 (br s, 1H), 8.14 (br s, 1H), 7.95-7.73 (m, 4H), 7.66 (m, 1H), 7.54 (m, 1H), 7.27 (d, 1H, J 2 Hz), 7.12 (dd, 1H, J 8.8 and 2.4 Hz), 4.99 (m, 1H), 3.89 (s, 2H), 3.86 (s, 3H), 3.16 (m, 6H), 2.54 (d, J 4.4 Hz), 3H), 2.02 (t, 2H, J 7.4 Hz), 2.01 (m, 6H), 1.83 (m, 2H), 1.48 (m, 2H), 1.35-1.15 (m, 4H). MS (ES+) C30H39N5O3: 518 (M+H)+.

Example 6

(S)-4-((1-(5-(2-methoxyquinolin-1-ium-3-yl)oxazol-2-yl)-7-(methylamino)-7-oxoheptyl)carbamoyl)quinuclidin-1-ium mono L-tartrate salt (F8)

Step 1: tert-butyl (2-(2-methoxyquinolin-3-yl)-2-oxoethyl)carbamate (F1)

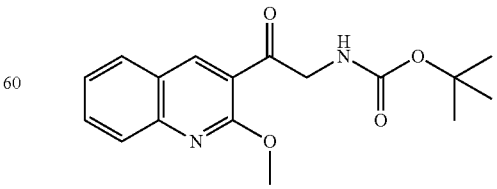

To a solution of mesityl bromide (4 eq.) in THF (1.7 M) cooled to −78° C. was added a solution of tBuLi in THF (8 eq., 1.7 M) dropwise. The mixture was left stirring at −78° C. for 1 h. Mixture was then allowed to reach 0° C. and a solution of 2-methoxyquinoline (3 eq.) in THF (0.32 M) was added dropwise over 10 min. The resulting mixture was aged at 0° C. for 1 h, then cooled to −78° C. and added dropwise with a solution of tert-butyl (2-(methoxy(methyl)amino)-2-oxoethyl) carbamate (1 eq.) in THF (0.22 M). The reaction mixture was stirred at −78° C. for 30 min, then left at room temperature overnight. The reaction mixture was diluted with dichloromethane and washed with sat. aq. NaHCO$_3$, dried over Na$_2$SO$_4$, and concentrated under reduced pressure. The resulting crude product was purified by flash chromatography (SiO$_2$, Petroleum ether/EtOAc, from 5% to 40% EtOAc). Pooled fractions were concentrated under vacuum to give the title compound. MS (ES$^+$) C$_{17}$H$_{20}$N$_2$O$_4$: 317 (M+H)$^+$.

Step 2:
2-amino-1-(2-methoxyquinolin-3-yl)ethanone (F2)

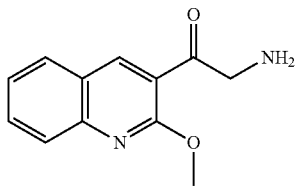 [SMILES: COc1nc2ccccc2cc1C(=O)CN]

F1 was solubilized in dioxane (30 mL) and treated with 16 mL of 4N HCl in dioxane at 0° C. Mixture was stirred for 1 h at room temperature, poured in sat. aq. NaHCO$_3$ and extracted with dichloromethane. The organic phase was dried over Na$_2$SO$_4$, filtered and concentrated to give the title compound which was used as such in the next step. MS (ES$^+$) C$_{12}$H$_{12}$N$_2$O$_2$: 217 (M+H)$^+$.

Step 3: (S)-tert-butyl 7-(((benzyloxy)carbonyl) amino)-8-((2-(2-methoxyquinolin-3-yl)-2-oxoethyl) amino)-8-oxooctanoate (F3)

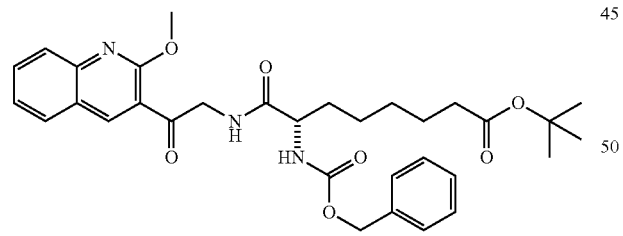

A solution of (S)-2-((benzyloxy)carbonyl)amino)-8-(tert-butoxy)-8-oxooctanoic acid (prepared as described in WO2006/061638), EDC.HCl (1.3 eq.), HOBt (1.3 eq.) in DMF (0.3 M) was stirred at room temperature for 10 min. Then F2 and DIPEA (3.0 eq.) were added and the resulting mixture was stirred at room temperature for 1 h 30 min. The reaction mixture was diluted with EtOAc, washed with sat. aq. NaHCO$_3$ sol., brine, dried (Na$_2$SO$_4$), filtered and concentrated under reduced pressure to give a crude that was purified by column chromatography (eluent: Petroleum ether/EtOAc from 97:3 to 3:7) to give the title compound as yellow oil. MS (ES$^+$) C$_{32}$H$_{39}$N$_3$O$_7$: 578 (M+H)$^+$.

Step 4 (S)-tert-butyl 7-(((benzyloxy)carbonyl) amino)-7-(5-(2-methoxyquinolin-3-yl)oxazol-2-yl) heptanoate (F4)

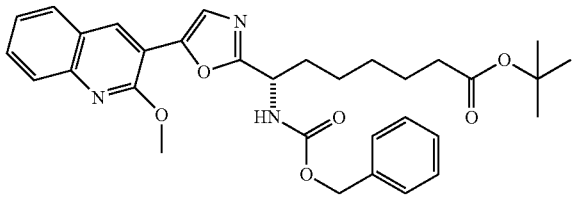

PPh$_3$ (2.0 eq.) and C$_2$Cl$_6$ (2.0 eq.) were dissolved in DCM (0.72 M) at room temperature and Et$_3$N (4.0 eq.) was added, followed after 5 min of stirring by dropwise addition of a solution of F3 in DCM (0.36 M). The mixture was stirred at room temperature for 1 h and then was diluted with DCM, washed with brine, dried (Na$_2$SO$_4$), filtered and concentrated under reduced pressure. Crude was purified by column chromatography (eluent: Petroleum ether/EtOAc from 94:6 to 2:3) to give the title compound as orange oil. MS (ES$^+$) C$_{32}$H$_{37}$N$_3$O$_6$: 560 (M+H)$^+$.

Step 5: (S)-7-(((benzyloxy)carbonyl)amino)-7-(5-(2-methoxyquinolin-3-yl)oxazol-2-yl)heptanoic acid (F5)

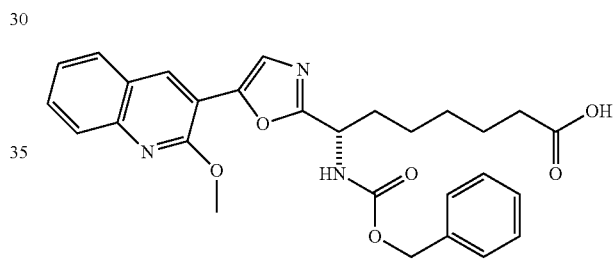

To a stirred solution of F4 in DCM (0.11 M) cooled to 0° C. TFA (15 eq.) was slowly added. The reaction mixture was stirred at 0° C. for 3 days. The solvent was evaporated to afford an oily residue that was co-evaporated first with toluene then with Et$_2$O to give the title compound as a pale yellow solid which was used directly in the next step. MS (ES$^+$) C$_{28}$H$_{29}$N$_3$O$_6$: 504 (M+H)$^+$.

Step 6: (S)-benzyl (1-(5-(2-methoxyquinolin-3-yl) oxazol-2-yl)-7-(methylamino)-7-oxoheptyl)carbamate (F6)

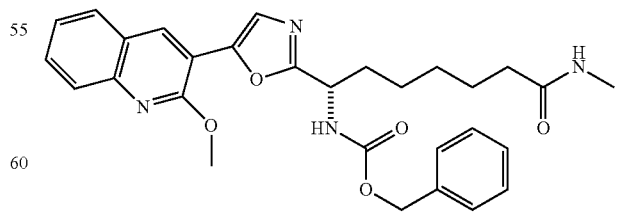

To a stirred solution of F5 in DMF (0.1 M) were added HATU (2.0 eq.) and DIPEA (3.0 eq.) followed after 10 min by methylamine (2.0 M solution in THF, 5.0 eq.). Reaction mixture was stirred at room temperature for 16 h. Then, reaction mixture was diluted with EtOAc, washed with sat. aq. NaHCO₃, brine, dried over Na₂SO₄, filtered and concentrated under reduced pressure. The resulting crude was purified by column chromatography (eluent: Petroleum ether/EtOAc from 1:1 to 100% EtOAc, then EtOAc/MeOH=95:5) to give the title compound as pale yellow solid. MS (ES⁺) $C_{29}H_{32}N_4O_5$: 517 (M+H)⁺.

Step 7: (S)-7-amino-7-(5-(2-methoxyquinolin-3-yl) oxazol-2-yl)-N-methylheptanamide (F7)

F6 was dissolved in EtOAc/MeOH (1:1, 0.025 M) and treated with Pd/C (10% w/w). Mixture was purged with N₂ and stirred under H₂ atmosphere at room temperature for 48 h. Then, reaction mixture was filtered through a pad of Solka-Floc® and filtrate was concentrated under vacuum to give the title compound as pale yellow solid which was used as such in the next step. MS (ES⁺) $C_{21}H_{26}N_4O_3$: 383 (M+H)⁺.

Step 8: (S)-4-((1-(5-(2-methoxyquinolin-1-ium-3-yl) oxazol-2-yl)-7-(methylamino)-7-oxoheptyl)carbamoyl)quinuclidin-1-ium mono L-tartrate salt (F8)

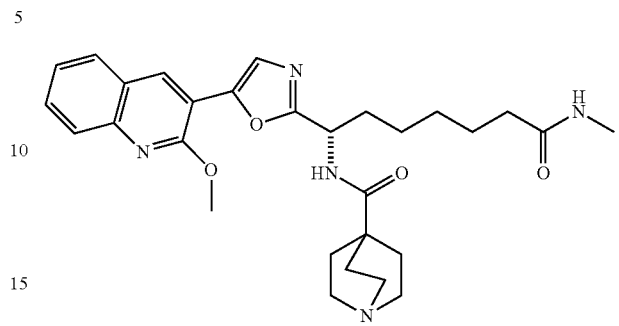

A solution of 4-carboxyquinuclidin-1-ium chlorhydrate (1.3 eq.) in DMF (0.1 M) was treated with HOBt (1.3 eq.), EDC HCl (1.3 eq.) and DIPEA (1.3 eq.). The reaction mixture was stirred at room temperature for 10 minutes and then added to F7. The reaction was stirred for at RT for 48 h, filtered and directly purified by RP-HPLC (Acetonitrile/H₂O+0.1% TFA). The product was obtained as TFA salt which was partitioned between DCM and sat. aq. NaHCO₃. The organic phase was separated dried over Na₂SO₄ and concentrated under reduced pressure. The resulting solid was dissolved in acetonitrile/H₂O (1:1) and treated with L-tartaric acid (1 eq.). The resulting solution was lyophilized to obtain the title compound. MS (ES⁺) $C_{29}H_{37}N_5O_4$: 520 (M+H)⁺.

The following compounds (Table 1) were prepared according to the procedures described in Examples 1 to 6.

TABLE 1

| Entry | Compound Name | Structure | Molecular Ion [M + H]⁺ | Procedure |
|---|---|---|---|---|
| 1 | (S)-N-methyl-7-(5-(naphthalen-2-yl)-1H-imidazol-2-yl)-7-(2-(piperidin-1-yl)acetamido)heptanamide | 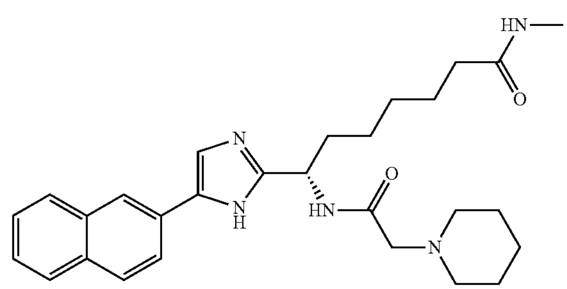 [SMILES: CNC(=O)CCCCC[C@H](NC(=O)CN1CCCCC1)c1ncc(-c2ccc3ccccc3c2)[nH]1] | 476 | Example 1 |
| 2 | (S)-N-(7-(methylamino)-1-(5-(naphthalen-2-yl)-1H-imidazol-2-yl)-7-oxoheptyl)-5,6,7,8-tetrahydro-1,8-naphthyridine-4-carboxamide | 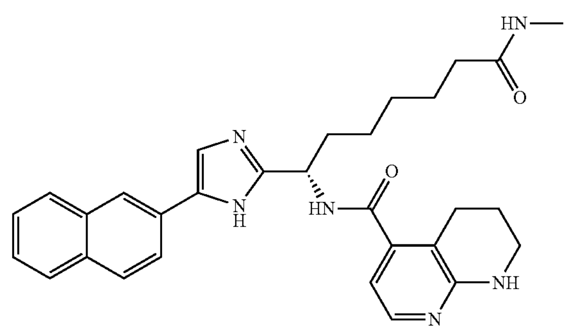 [SMILES: CNC(=O)CCCCC[C@H](NC(=O)c1ccnc2c1CCCN2)c1ncc(-c2ccc3ccccc3c2)[nH]1] | 511 | Example 1 |

TABLE 1-continued

| Entry | Compound Name | Structure | Molecular Ion [M + H]⁺ | Procedure |
|---|---|---|---|---|
| 3 | (S)-N-methyl-7-(5-(naphthalen-2-yl)-1H-imidazol-2-yl)-7-(3-nitrophenyl-sulfonamido)heptanamide | 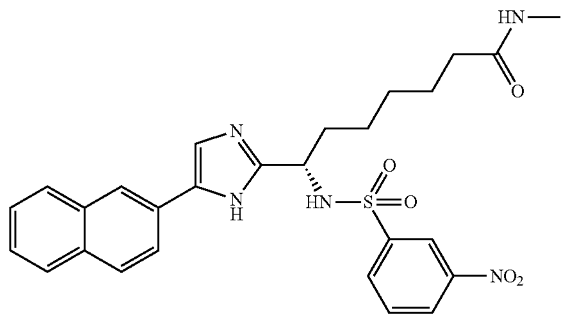 [SMILES: CNC(=O)CCCCC[C@H](NS(=O)(=O)c1cccc([N+](=O)[O-])c1)c1ncc(-c2ccc3ccccc3c2)[nH]1] | 536 | Example 3 |
| 4 | (S)-1-methyl-N-((S)-7-(methylamino)-1-(5-(naphthalen-2-yl)-1H-imidazol-2-yl)-7-oxoheptyl)pyrrolidine-3-carboxamide | 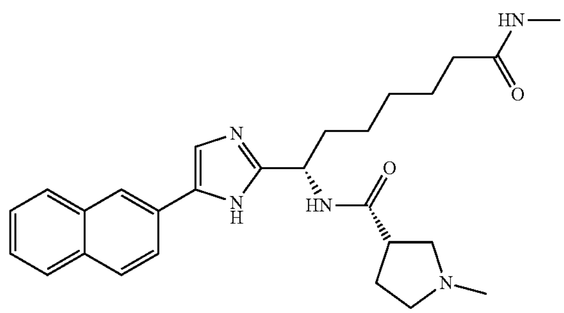 | 462 | Example 1 |
| 5 | (S)-1-methyl-N-(7-(methylamino)-1-(5-(naphthalen-2-yl)-1H-imidazol-2-yl)-7-oxoheptyl)piperidine-4-carboxamide | 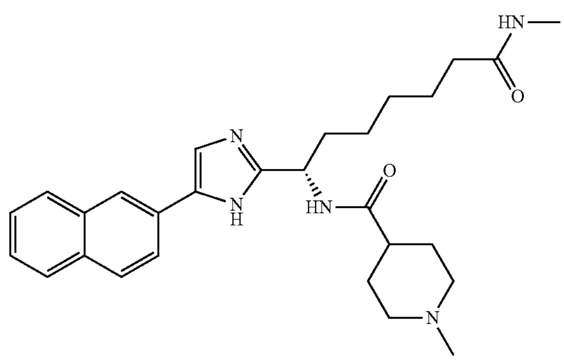 [SMILES: CNC(=O)CCCCC[C@H](NC(=O)C1CCN(C)CC1)c1ncc(-c2ccc3ccccc3c2)[nH]1] | 476 | Example 1 |
| 6 | (S)-7-(2-(1H-1,2,3-triazol-1-yl)acetamido)-7-(5-(2-methoxyquinolin-3-yl)-1H-imidazol-2-yl)-N-methylheptanamide | 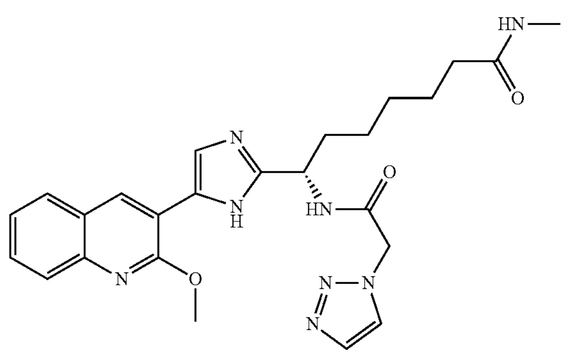 [SMILES: CNC(=O)CCCCC[C@H](NC(=O)Cn1ccnn1)c1ncc(-c2cc3ccccc3nc2OC)[nH]1] | 491 | Example 1 |

TABLE 1-continued

| Entry | Compound Name | Structure | Molecular Ion [M + H]+ | Procedure |
|---|---|---|---|---|
| 7 | (S)-7-(2-(1H-benzo[d][1,2,3]triazol-1-yl)acetamido)-7-(5-(2-methoxyquinolin-3-yl)-1H-imidazol-2-yl)-N-methylheptanamide | 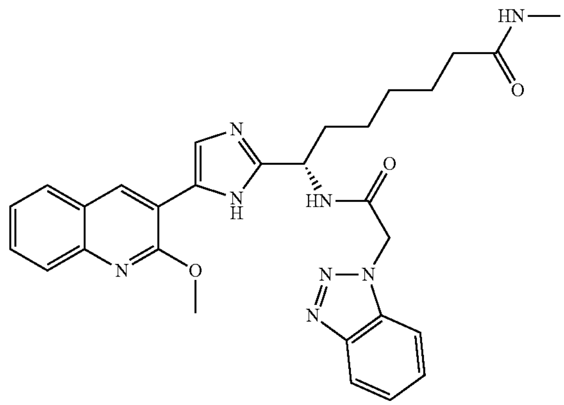 [SMILES: CNC(=O)CCCCC[C@H](NC(=O)Cn1nnc2ccccc21)c1ncc(-c2cc3ccccc3nc2OC)[nH]1] | 541 | Example 1 |
| 8 | (S)-7-(3-(2-ethyl-1H-benzo[d]imidazol-1-yl)propanamido)-7-(5-(2-methoxyquinolin-3-yl)-1H-imidazol-2-yl)-N-methylheptanamide | 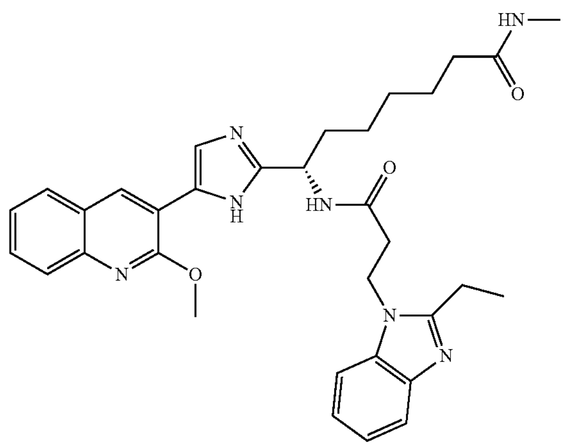 [SMILES: CCc1nc2ccccc2n1CCC(=O)N[C@@H](CCCCCC(=O)NC)c1ncc(-c2cc3ccccc3nc2OC)[nH]1] | 582 | Example 1 |
| 9 | (S)-N-(1-(5-(2-methoxyquinolin-3-yl)-1H-imidazol-2-yl)-7-(methylamino)-7-oxoheptyl)-1,3-dimethyl-1H-pyrazole-5-carboxamide | 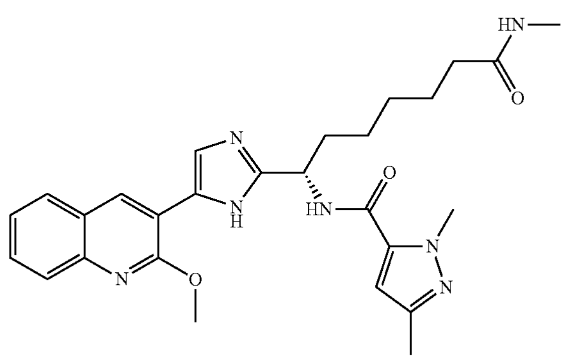 [SMILES: CNC(=O)CCCCC[C@H](NC(=O)c1cc(C)nn1C)c1ncc(-c2cc3ccccc3nc2OC)[nH]1] | 504 | Example 1 |
| 10 | (S)-N-(7-(methylamino)-7-oxo-1-(5-(quinolin-7-yl)-1H-imidazol-2-yl)heptyl)thiazole-5-carboxamide | 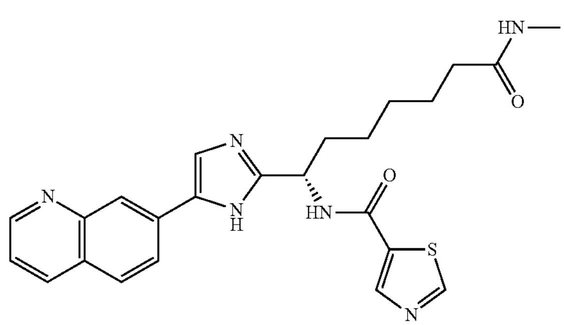 [SMILES: CNC(=O)CCCCC[C@H](NC(=O)c1cncs1)c1ncc(-c2ccc3cccnc3c2)[nH]1] | 463 | Example 4 |

TABLE 1-continued

| Entry | Compound Name | Structure | Molecular Ion [M + H]+ | Procedure |
|---|---|---|---|---|
| 11 | (S)-7-(2-(1H-1,2,4-triazol-1-yl)acetamido)-7-(5-(4-(1H-pyrazol-1-yl)phenyl)-1H-imidazol-2-yl)-N-methylheptanamide | 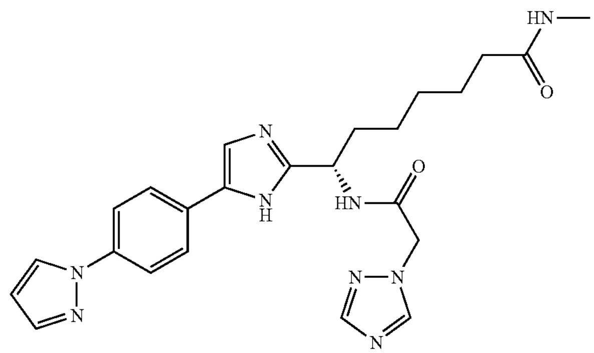 [SMILES: CNC(=O)CCCCC[C@H](NC(=O)Cn1cncn1)c1ncc(-c2ccc(-n3cccn3)cc2)[nH]1] | 476 | Example 1 |
| 12 | (S)-N-(1-(5-(4-(1H-pyrazol-1-yl)phenyl)-1H-imidazol-2-yl)-7-(methylamino)-7-oxoheptyl)isothiazole-4-carboxamide | 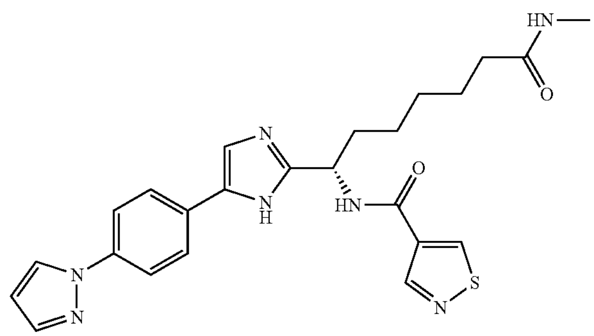 [SMILES: CNC(=O)CCCCC[C@H](NC(=O)c1cnsc1)c1ncc(-c2ccc(-n3cccn3)cc2)[nH]1] | 478 | Example 1 |
| 13 | (S)-2,3-dimethyl-N-(7-(methylamino)-1-(5-(naphthalen-2-yl)-1H-imidazol-2-yl)-7-oxoheptyl)quinoxaline-5-carboxamide | 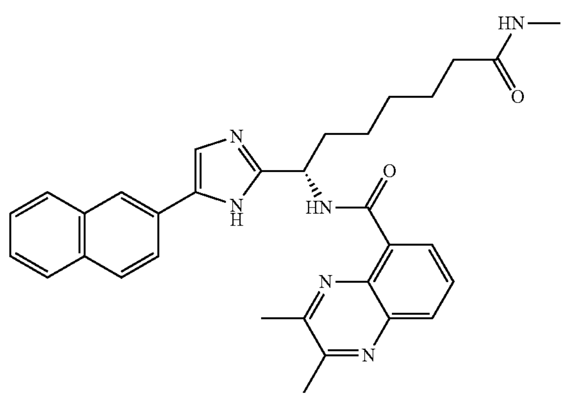 [SMILES: CNC(=O)CCCCC[C@H](NC(=O)c1cccc2nc(C)c(C)nc12)c1ncc(-c2ccc3ccccc3c2)[nH]1] | 535 | Example 1 |
| 14 | (S)-N-(1-(5-(3-methoxyquinolin-7-yl)-1H-imidazol-2-yl)-7-(methylamino)-7-oxoheptyl)thiazole-5-carboxamide | 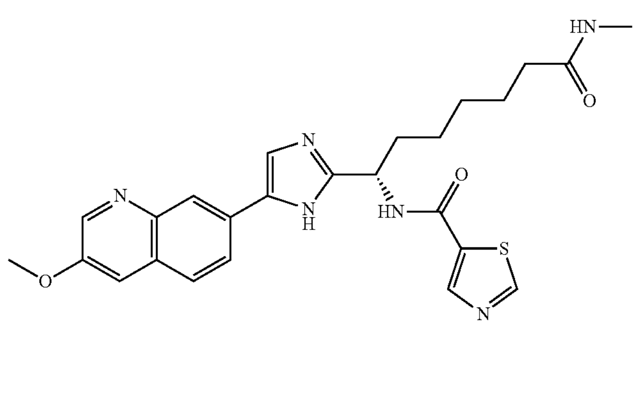 | 493 | Example 4 |

TABLE 1-continued

| Entry | Compound Name | Structure | Molecular Ion [M + H]+ | Procedure |
|---|---|---|---|---|
| 15 | (S)-7-(2-(imidazo[1,2-a]pyridin-3-yl)acetamido)-7-(5-(isoquinolin-7-yl)-1H-imidazol-2-yl)-N-methylheptanamide | 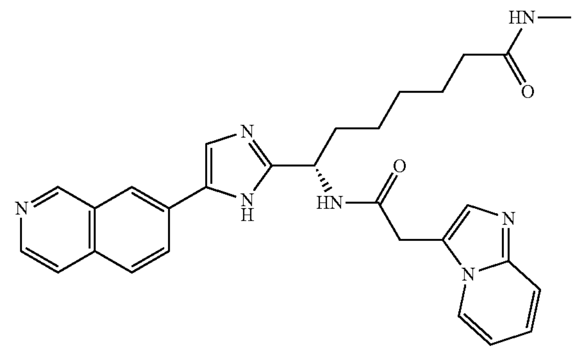 [SMILES: CNC(=O)CCCCC[C@H](NC(=O)Cc1cnc2ccccn12)c1ncc(-c2ccc3ccncc3c2)[nH]1] | 510 | Example 1 |
| 16 | (S)-N-(1-(5-(4-(1-methyl-1H-pyrazol-3-yl)phenyl)-1H-imidazol-2-yl)-7-(methylamino)-7-oxoheptyl)isothiazole-5-carboxamide | 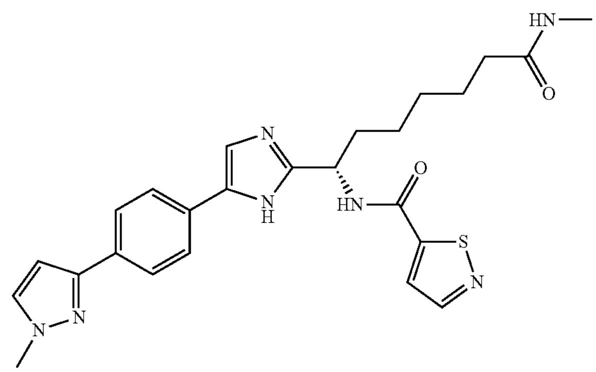 [SMILES: CNC(=O)CCCCC[C@H](NC(=O)c1ccns1)c1ncc(-c2ccc(-c3ccn(C)n3)cc2)[nH]1] | 492 | Example 1 |
| 17 | (S)-2-methyl-N-(1-(5-(4-(1-methyl-1H-pyrazol-3-yl)phenyl)-1H-imidazol-2-yl)-7-(methylamino)-7-oxoheptyl)thiazole-5-carboxamide | 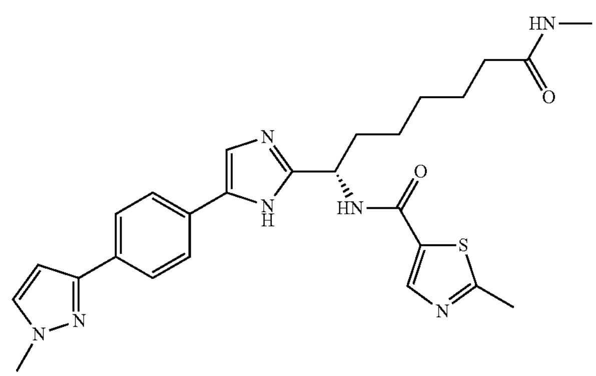 [SMILES: CNC(=O)CCCCC[C@H](NC(=O)c1cnc(C)s1)c1ncc(-c2ccc(-c3ccn(C)n3)cc2)[nH]1] | 506 | Example 1 |
| 18 | (S)-1-methyl-N-(7-(methylamino)-7-oxo-1-(5-(2-oxo-1,2-dihydroquinolin-3-yl)-1H-imidazol-2-yl)heptyl)azetidine-3-carboxamide | 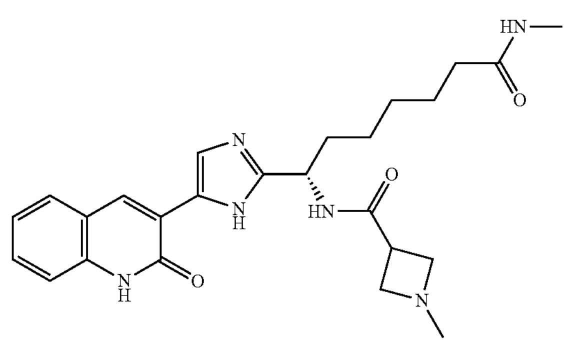 [SMILES: CNC(=O)CCCCC[C@H](NC(=O)C1CN(C)C1)c1ncc(-c2cc3ccccc3[nH]c2=O)[nH]1] | 465 | Example 4 |

TABLE 1-continued

| Entry | Compound Name | Structure | Molecular Ion [M + H]+ | Procedure |
|---|---|---|---|---|
| 19 | (S)-N-(7-(methylamino)-7-oxo-1-(5-(2-(trifluoromethyl)quinolin-6-yl)-1H-imidazol-2-yl)heptyl)thiazole-5-carboxamide | 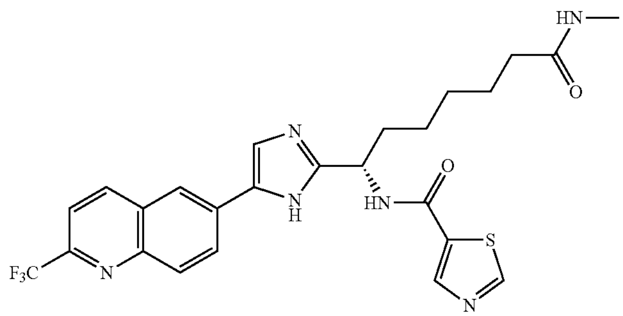 [SMILES: CNC(=O)CCCCC[C@H](NC(=O)c1cncs1)c1ncc(-c2ccc3nc(C(F)(F)F)ccc3c2)[nH]1] | 531 | Example 4 |
| 20 | (S)-N-methyl-7-(5-(naphthalen-2-yl)-1H-imidazol-2-yl)-7-(2-(5-(pyrrolidin-1-yl)-2H-tetrazol-2-yl)acetamido)heptanamide | 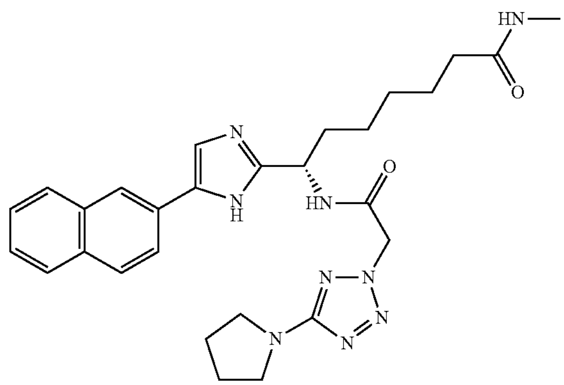 [SMILES: CNC(=O)CCCCC[C@H](NC(=O)Cn1nnc(N2CCCC2)n1)c1ncc(-c2ccc3ccccc3c2)[nH]1] | 530 | Example 1 |
| 21 | (S)-N-methyl-7-(5-(naphthalen-2-yl)-1H-imidazol-2-yl)-7-(2-phenylacetamido)heptanamide | 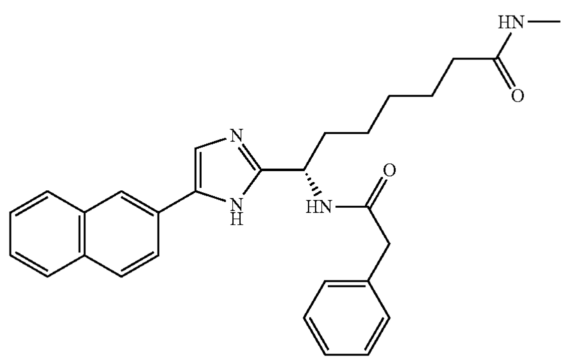 [SMILES: CNC(=O)CCCCC[C@H](NC(=O)Cc1ccccc1)c1ncc(-c2ccc3ccccc3c2)[nH]1] | 469 | Example 1 |
| 22 | (S)-7-(2-([1,2,4]triazolo[1,5-a]pyrimidin-6-yl)acetamido)-N-methyl-7-(5-(naphthalen-2-yl)-1H-imidazol-2-yl)heptanamide | 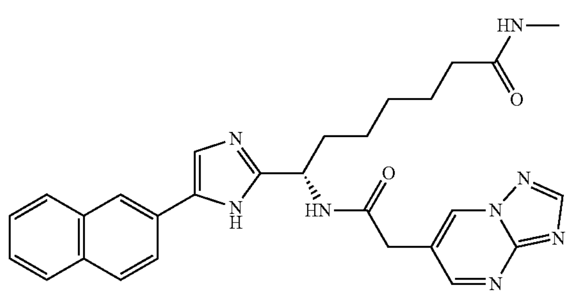 [SMILES: CNC(=O)CCCCC[C@H](NC(=O)Cc1cnc2ncnn2c1)c1ncc(-c2ccc3ccccc3c2)[nH]1] | 511 | Example 1 |

TABLE 1-continued

| Entry | Compound Name | Structure | Molecular Ion [M + H]+ | Procedure |
|---|---|---|---|---|
| 23 | (S)-N-methyl-7-(2-morpholinoacetamido)-7-(5-(naphthalen-2-yl)-1H-imidazol-2-yl)heptanamide | 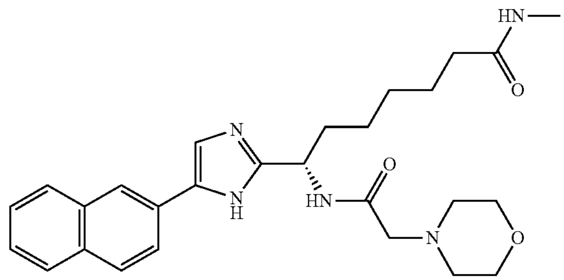 [SMILES: CNC(=O)CCCCC[C@H](NC(=O)CN1CCOCC1)c1ncc(-c2ccc3ccccc3c2)[nH]1] | 478 | Example 1 |
| 24 | (S)-N-(1-(5-(1H-indol-5-yl)-1H-imidazol-2-yl)-7-(methylamino)-7-oxoheptyl)thiazole-5-carboxamide | 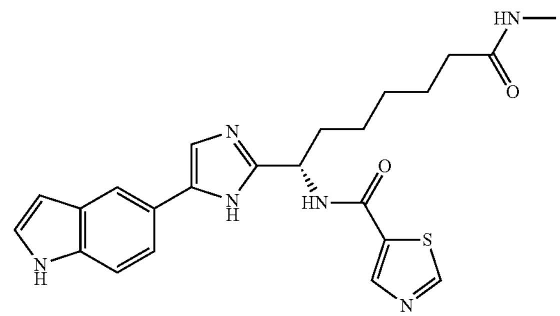 [SMILES: CNC(=O)CCCCC[C@H](NC(=O)c1cncs1)c1ncc(-c2ccc3[nH]ccc3c2)[nH]1] | 451 | Example 4 |
| 25 | (S)-N-(1-(5-(5-ethoxynaphthalen-2-yl)-1H-imidazol-2-yl)-7-(methylamino)-7-oxoheptyl)thiazole-5-carboxamide | 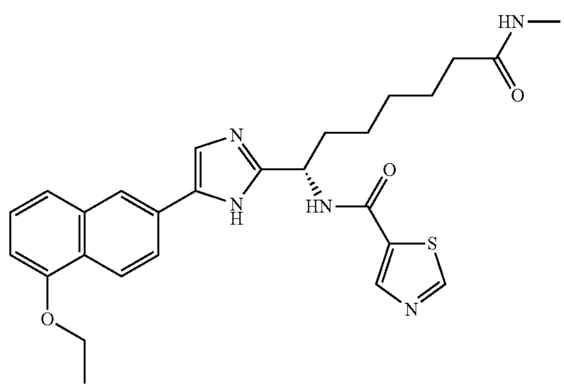 [SMILES: CCOc1cccc2cc(-c3cnc([C@H](CCCCCC(=O)NC)NC(=O)c4cncs4)[nH]3)ccc12] | 506 | Example 5 |
| 26 | S)-1-methyl-N-(7-(methylamino)-1-(5-(naphthalen-2-yl)-1H-imidazol-2-yl)-7-oxoheptyl)azetidine-3-carboxamide | 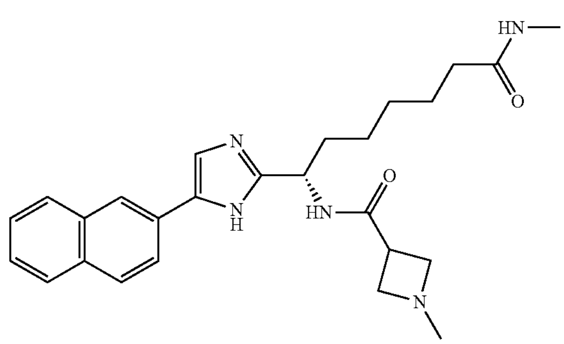 [SMILES: CNC(=O)CCCCC[C@H](NC(=O)C1CN(C)C1)c1ncc(-c2ccc3ccccc3c2)[nH]1] | 448 | Example 1 |

TABLE 1-continued

| Entry | Compound Name | Structure | Molecular Ion [M + H]+ | Procedure |
|---|---|---|---|---|
| 27 | (S)-7-(3-(1H-imidazol-1-yl)propanamido)-7-(5-(2-methoxyquinolin-3-yl)-1H-imidazol-2-yl)-N-methylheptanamide | 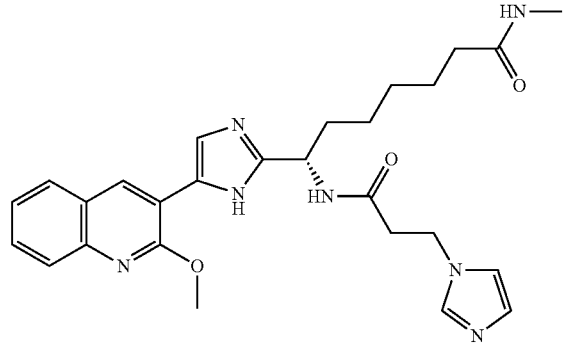 [SMILES: CNC(=O)CCCCC[C@H](NC(=O)CCn1ccnc1)c1ncc(-c2cc3ccccc3nc2OC)[nH]1] | 504 | Example 1 |
| 28 | (S)-7-(3-(2-ethyl-1H-benzo[d]imidazol-1-yl)propanamido)-N-methyl-7-(5-(4-(trifluoromethyl)phenyl)-1H-imidazol-2-yl)heptanamide | 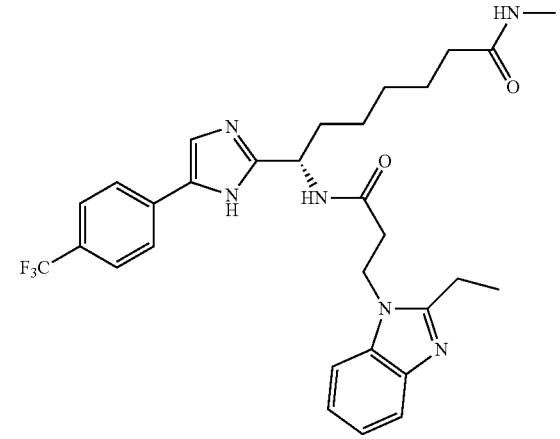 [SMILES: CCc1nc2ccccc2n1CCC(=O)N[C@@H](CCCCCC(=O)NC)c1ncc(-c2ccc(C(F)(F)F)cc2)[nH]1] | 569 | Example 1 |
| 29 | (S)-N-(7-(methylamino)-7-oxo-1-(5-(4-(pyridin-4-yl)phenyl)-1H-imidazol-2-yl)heptyl)thiazole-5-carboxamide | 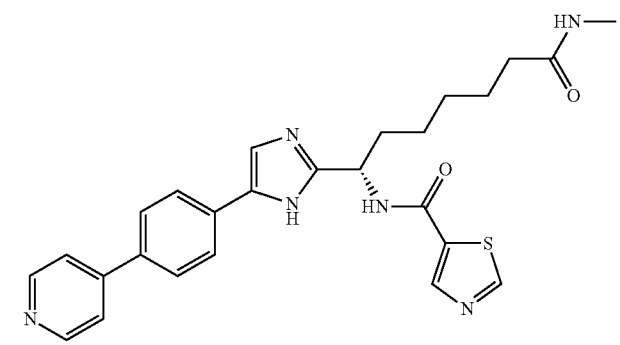 [SMILES: CNC(=O)CCCCC[C@H](NC(=O)c1cncs1)c1ncc(-c2ccc(-c3ccncc3)cc2)[nH]1] | 489 | Example 4 |
| 30 | (S)-N-(1-(5-(2-methoxyquinolin-3-yl)-1H-imidazol-2-yl)-7-(methylamino)-7-oxoheptyl)-2-(pyridin-3-yl)thiazole-4-carboxamide | 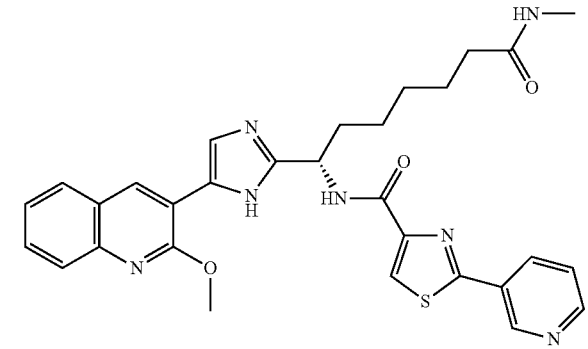 [SMILES: CNC(=O)CCCCC[C@H](NC(=O)c1csc(-c2cccnc2)n1)c1ncc(-c2cc3ccccc3nc2OC)[nH]1] | 570 | Example 2 |

TABLE 1-continued

| Entry | Compound Name | Structure | Molecular Ion [M + H]+ | Procedure |
|---|---|---|---|---|
| 31 | (S)-N-(1-(5-(2-methoxyquinolin-3-yl)-1H-imidazol-2-yl)-7-(methylamino)-7-oxoheptyl)-5-methyl-1,3,4-thiadiazole-2-carboxamide | 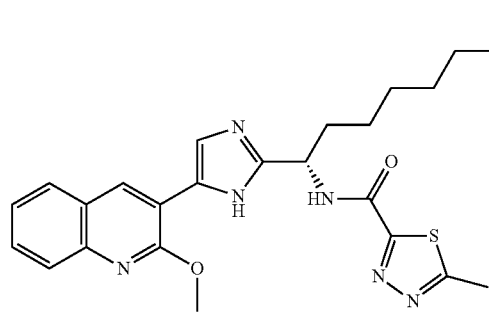 | 508 | Example 2 |
| 32 | (7S)-7-(2-(3-(dimethylamino)pyrrolidin-1-yl)acetamido)-7-(5-(2-methoxyquinolin-3-yl)-1H-imidazol-2-yl)-N-methylheptanamide | 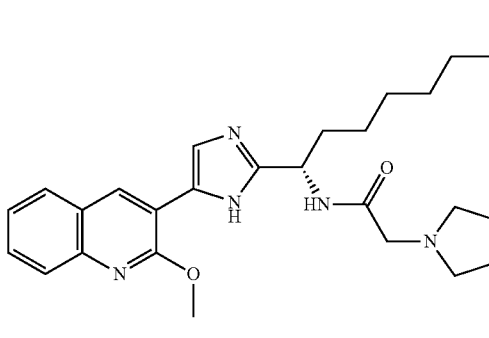 | 536 | Example 2 |
| 33 | N-((S)-1-(5-(2-methoxyquinolin-3-yl)-1H-imidazol-2-yl)-7-(methylamino)-7-oxoheptyl)-1-methylpiperidine-3-carboxamide | 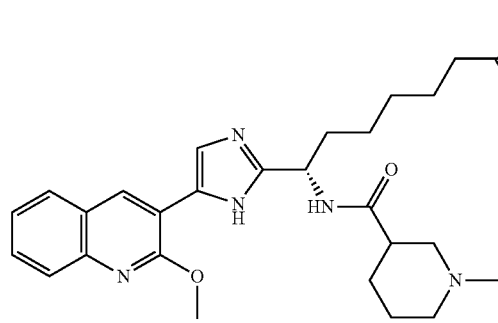 | 507 | Example 2 |
| 34 | (S)-N-(1-(5-(1H-indazol-5-yl)-1H-imidazol-2-yl)-7-(methylamino)-7-oxoheptyl)isothiazole-4-carboxamide | 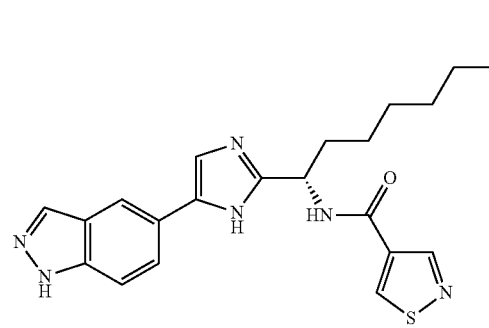 | 452 | Example 4 |

TABLE 1-continued

| Entry | Compound Name | Structure | Molecular Ion [M + H]+ | Procedure |
|---|---|---|---|---|
| 35 | (S)-N-(1-(5-(3-(aminomethyl)phenyl)-1H-imidazol-2-yl)-7-(methylamino)-7-oxoheptyl)thiazole-5-carboxamide | 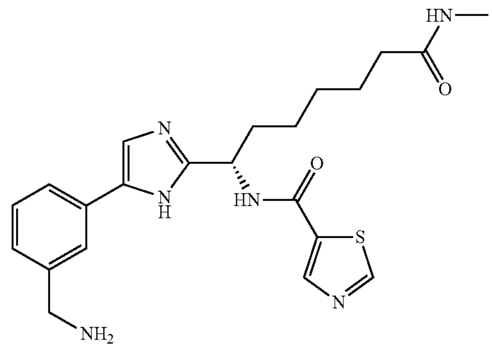 [SMILES: CNC(=O)CCCCC[C@H](NC(=O)c1cncs1)c1ncc(-c2cccc(CN)c2)[nH]1] | 441 | Example 4 |
| 36 | (S)-N-(7-(methylamino)-7-oxo-1-(5-(quinolin-8-yl)-1H-imidazol-2-yl)heptyl)thiazole-5-carboxamide | 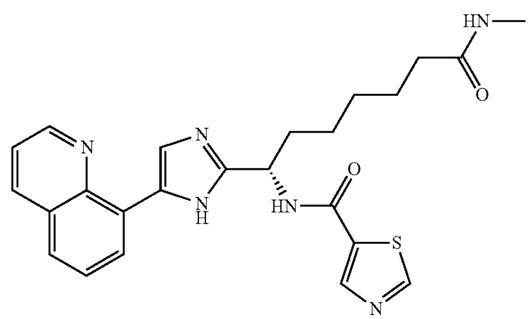 [SMILES: CNC(=O)CCCCC[C@H](NC(=O)c1cncs1)c1ncc(-c2cccc3cccnc23)[nH]1] | 463 | Example 4 |
| 37 | (S)-N-(7-(methylamino)-7-oxo-1-(5-(quinolin-3-yl)-1H-imidazol-2-yl)heptyl)thiazole-5-carboxamide | 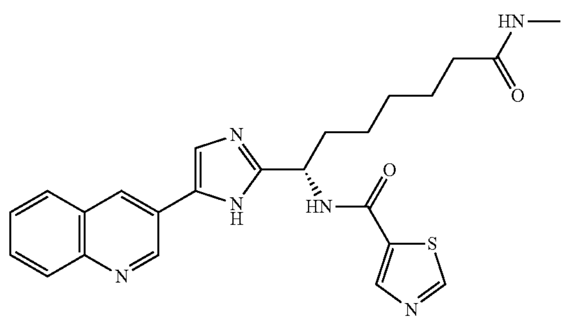 [SMILES: CNC(=O)CCCCC[C@H](NC(=O)c1cncs1)c1ncc(-c2cnc3ccccc3c2)[nH]1] | 463 | Example 4 |
| 38 | (S)-benzyl (1-(5-(4-(1H-pyrazol-3-yl)phenyl)-1H-imidazol-2-yl)-7-(methylamino)-7-oxoheptyl)carbamate | 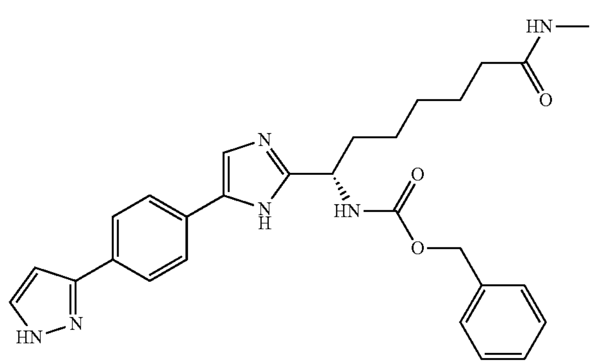 [SMILES: CNC(=O)CCCCC[C@H](NC(=O)OCc1ccccc1)c1ncc(-c2ccc(-c3cc[nH]n3)cc2)[nH]1] | 501 | Example 5 |

TABLE 1-continued

| Entry | Compound Name | Structure | Molecular Ion [M + H]+ | Procedure |
|---|---|---|---|---|
| 39 | (S)-7-(5-(4-(1H-pyrazol-1-yl)phenyl)-1H-imidazol-2-yl)-7-(3-(5,7-dimethyl-[1,2,4]triazolo[1,5-a]pyrimidin-6-yl)propanamido)-N-methylheptanamide | 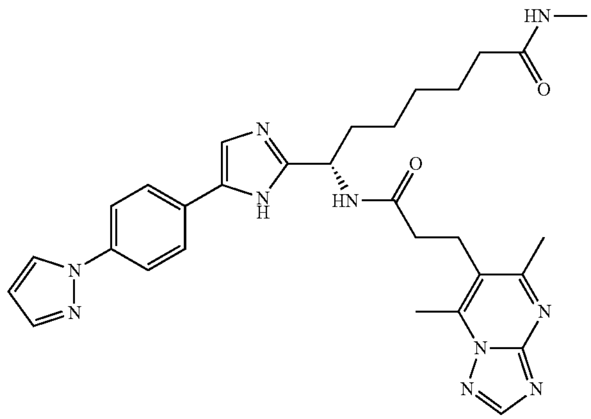 [SMILES: CNC(=O)CCCCC[C@H](NC(=O)CCc1c(C)nc2ncnn2c1C)c1ncc(-c2ccc(-n3cccn3)cc2)[nH]1] | 569 | Example 1 |
| 40 | (S)-7-(5-(4-(1H-pyrazol-1-yl)phenyl)-1H-imidazol-2-yl)-7-(2-(6,7-dihydro-5H-thiazolo[3,2-a]pyrimidin-3-yl)acetamido)-N-methylheptanamide | 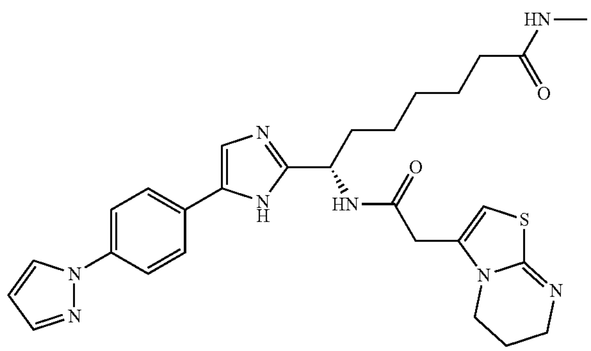 [SMILES: CNC(=O)CCCCC[C@H](NC(=O)CC1=CSC2=NCCCN12)c1ncc(-c2ccc(-n3cccn3)cc2)[nH]1] | 547 | Example 1 |
| 41 | (S)-4-methyl-N-(7-(methylamino)-1-(5-(naphthalen-2-yl)-1H-imidazol-2-yl)-7-oxoheptyl)tetrahydro-2H-pyran-4-carboxamide | 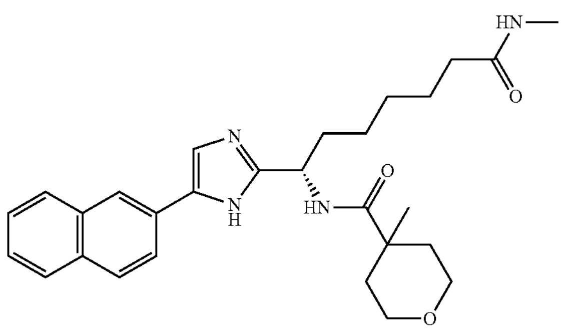 [SMILES: CNC(=O)CCCCC[C@H](NC(=O)C1(C)CCOCC1)c1ncc(-c2ccc3ccccc3c2)[nH]1] | 477 | Example 1 |
| 42 | (S)-4-(2,4-dioxoimidazolidin-1-yl)-N-(7-(methylamino)-1-(5-(naphthalen-2-yl)-1H-imidazol-2-yl)-7-oxoheptyl)benzamide | 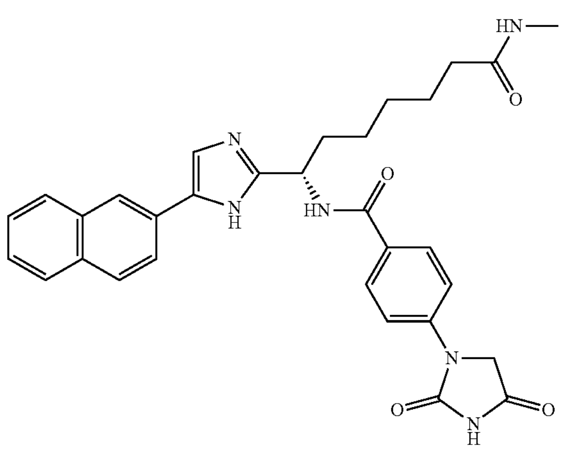 [SMILES: CNC(=O)CCCCC[C@H](NC(=O)c1ccc(N2CC(=O)NC2=O)cc1)c1ncc(-c2ccc3ccccc3c2)[nH]1] | 553 | Example 1 |

TABLE 1-continued

| Entry | Compound Name | Structure | Molecular Ion [M + H]+ | Procedure |
|---|---|---|---|---|
| 43 | (S)-3-(3,5-dimethyl-1H-pyrazol-1-yl)-N-(7-(methylamino)-1-(5-(naphthalen-2-yl)-1H-imidazol-2-yl)-7-oxoheptyl)benzamide | 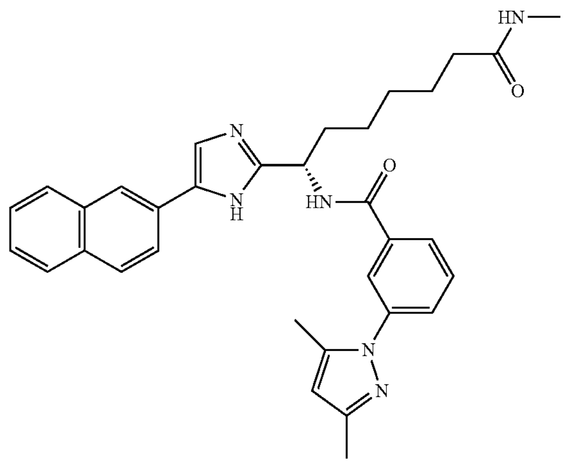 [SMILES: CNC(=O)CCCCC[C@H](NC(=O)c1cccc(-n2nc(C)cc2C)c1)c1ncc(-c2ccc3ccccc3c2)[nH]1] | 549 | Example 1 |
| 44 | (S)-N-(7-(methylamino)-1-(5-(naphthalen-2-yl)-1H-imidazol-2-yl)-7-oxoheptyl)-[1,2,4]triazolo[1,5-a]pyrimidine-2-carboxamide | 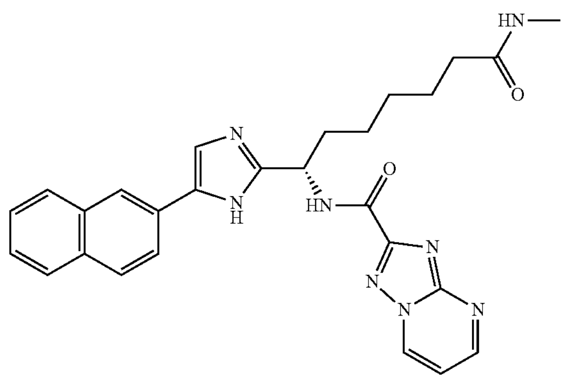 [SMILES: CNC(=O)CCCCC[C@H](NC(=O)c1nc2ncccn2n1)c1ncc(-c2ccc3ccccc3c2)[nH]1] | 497 | Example 1 |
| 45 | (S)-7-(2-(1H-benzo[d]imidazol-1-yl)acetamido)-N-methyl-7-(5-(naphthalen-2-yl)-1H-imidazol-2-yl)heptanamide | 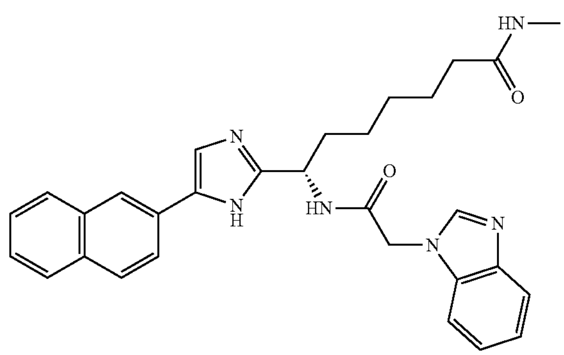 [SMILES: CNC(=O)CCCCC[C@H](NC(=O)Cn1cnc2ccccc21)c1ncc(-c2ccc3ccccc3c2)[nH]1] | 509 | Example 1 |
| 46 | (S)-N-(7-(methylamino)-1-(5-(naphthalen-2-yl)-1H-imidazol-2-yl)-7-oxoheptyl)-1,2,5-thiadiazole-3-carboxamide | 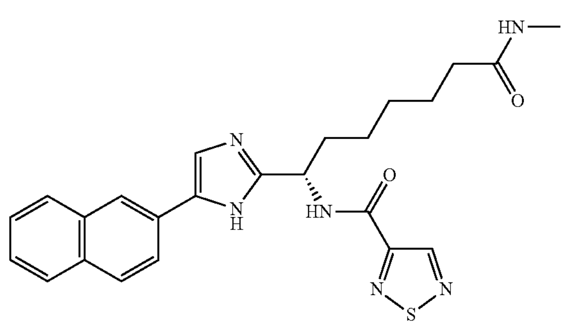 [SMILES: CNC(=O)CCCCC[C@H](NC(=O)c1cnsn1)c1ncc(-c2ccc3ccccc3c2)[nH]1] | 463 | Example 1 |

TABLE 1-continued

| Entry | Compound Name | Structure | Molecular Ion [M + H]+ | Procedure |
|---|---|---|---|---|
| 47 | (S)-N-(1-(5-(isoquinolin-7-yl)-1H-imidazol-2-yl)-7-(methylamino)-7-oxoheptyl)isothiazole-4-carboxamide | 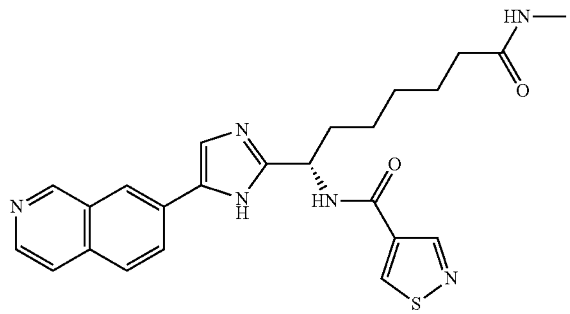 [SMILES: CNC(=O)CCCCC[C@H](NC(=O)c1cnsc1)c1ncc(-c2ccc3ccncc3c2)[nH]1] | 463 | Example 1 |
| 48 | (S)-N-(1-(5-(isoquinolin-7-yl)-1H-imidazol-2-yl)-7-(methylamino)-7-oxoheptyl)thiazole-4-carboxamide | 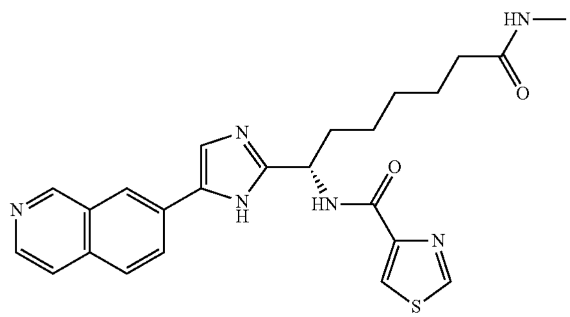 [SMILES: CNC(=O)CCCCC[C@H](NC(=O)c1cscn1)c1ncc(-c2ccc3ccncc3c2)[nH]1] | 463 | Example 1 |
| 49 | N-((S)-1-(5-(isoquinolin-7-yl)-1H-imidazol-2-yl)-7-(methylamino)-7-oxoheptyl)-2-(pyridin-4-yl)cyclopropanecarboxamide | 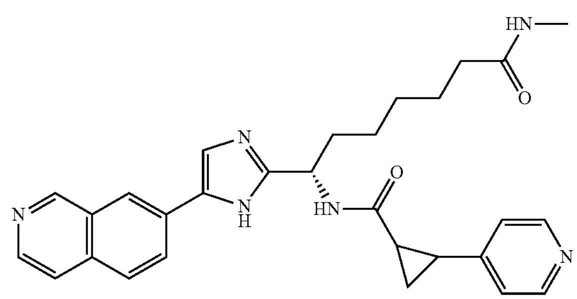 [SMILES: CNC(=O)CCCCC[C@H](NC(=O)C1CC1c1ccncc1)c1ncc(-c2ccc3ccncc3c2)[nH]1] | 497 | Example 1 |
| 50 | (S)-N-(1-(5-(isoquinolin-7-yl)-1H-imidazol-2-yl)-7-(methylamino)-7-oxoheptyl)-2-methylthiazole-5-carboxamide | 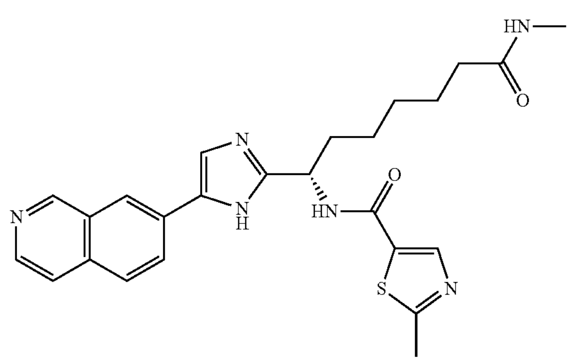 [SMILES: CNC(=O)CCCCC[C@H](NC(=O)c1cnc(C)s1)c1ncc(-c2ccc3ccncc3c2)[nH]1] | 477 | Example 1 |

TABLE 1-continued

| Entry | Compound Name | Structure | Molecular Ion [M + H]+ | Procedure |
|---|---|---|---|---|
| 51 | (S)-1-isopropyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide | 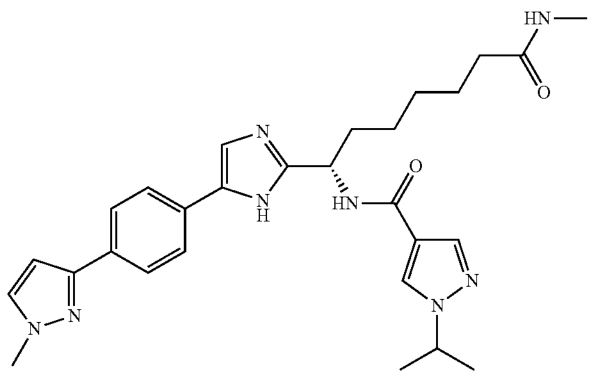 [SMILES: CNC(=O)CCCCC[C@H](NC(=O)c1cnn(C(C)C)c1)c1ncc(-c2ccc(-c3ccn(C)n3)cc2)[nH]1] | 517 | Example 1 |
| 52 | (S)-N-(1-(5-(benzo[b]thiophen-2-yl)-1H-imidazol-2-yl)-7-(methylamino)-7-oxoheptyl)thiazole-5-carboxamide | 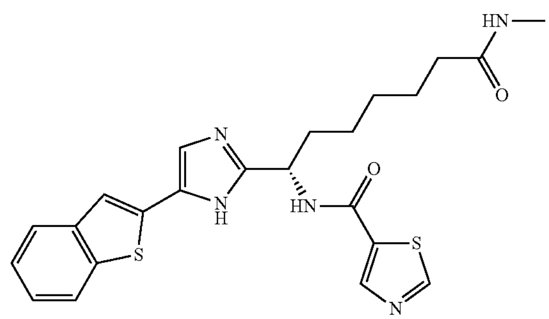 [SMILES: CNC(=O)CCCCC[C@H](NC(=O)c1cncs1)c1ncc(-c2cc3ccccc3s2)[nH]1] | 468 | Example 4 |
| 53 | (S)-7-(3-benzylureido)-N-methyl-7-(5-(naphthalen-2-yl)-1H-imidazol-2-yl)heptanamide | 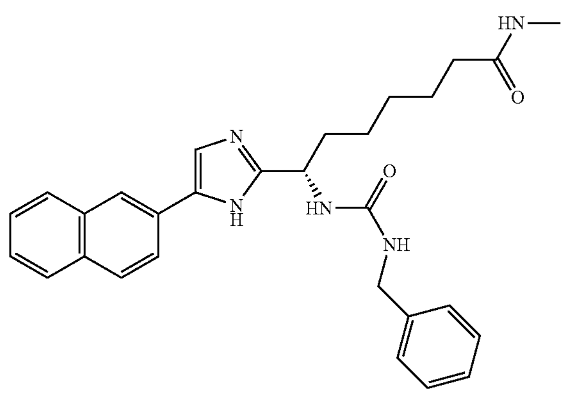 [SMILES: CNC(=O)CCCCC[C@H](NC(=O)NCc1ccccc1)c1ncc(-c2ccc3ccccc3c2)[nH]1] | 484 | Example 1 |
| 54 | (S)-N-(1-(5-(4-cyanophenyl)-1H-imidazol-2-yl)-7-(methylamino)-7-oxoheptyl)thiazole-5-carboxamide | 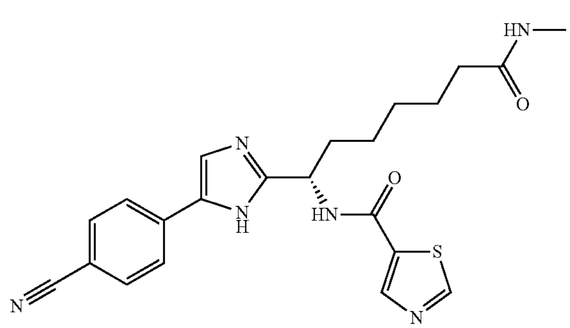 [SMILES: CNC(=O)CCCCC[C@H](NC(=O)c1cncs1)c1ncc(-c2ccc(C#N)cc2)[nH]1] | 437 | Example 4 |

TABLE 1-continued

| Entry | Compound Name | Structure | Molecular Ion [M + H]+ | Procedure |
|---|---|---|---|---|
| 55 | (S)-N-(1-(5-(4-acetamidophenyl)-1H-imidazol-2-yl)-7-(methylamino)-7-oxoheptyl)thiazole-5-carboxamide | 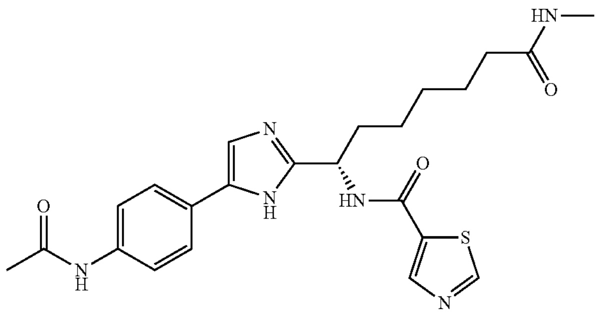 [SMILES: CNC(=O)CCCCC[C@H](NC(=O)c1cncs1)c1ncc(-c2ccc(NC(C)=O)cc2)[nH]1] | 469 | Example 4 |
| 56 | (S)-N-(1-(5-(5-methoxy-1H-indol-2-yl)-1H-imidazol-2-yl)-7-(methylamino)-7-oxoheptyl)thiazole-5-carboxamide | 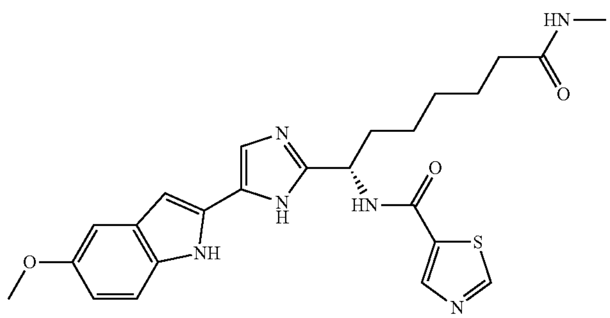 | 481 | Example 4 |
| 57 | (S)-7-amino-1-(5-(2-methoxyquinolin-3-yl)oxazol-2-yl)-7-oxoheptyl quinuclidine-4-carboxamide | 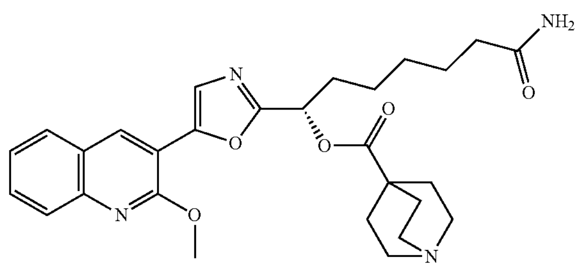 [SMILES: COc1nc2ccccc2cc1-c1cnc([C@H](CCCCCC(N)=O)OC(=O)C23CCN(CC2)CC3)o1] | 506 | Example 6 |
| 58 | (S)-N-(1-(5-(2-methoxyquinolin-3-yl)oxazol-2-yl)-7-(methylamino)-7-oxoheptyl)-1-methylazetidine-3-carboxamide | 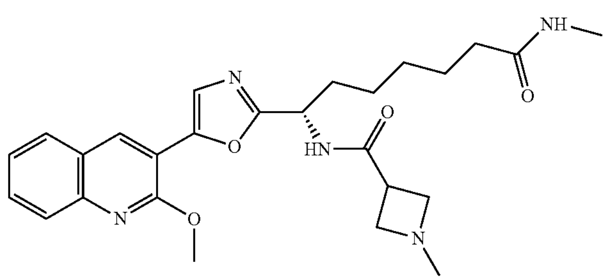 [SMILES: CNC(=O)CCCCC[C@H](NC(=O)C1CN(C)C1)c1ncc(-c2cc3ccccc3nc2OC)o1] | 480 | Example 6 |
| 59 | (S)-N-(1-(5-(4-chloro-2-methoxyphenyl)-1H-imidazol-2-yl)-7-(methylamino)-7-oxoheptyl)thiazole-5-carboxamide | 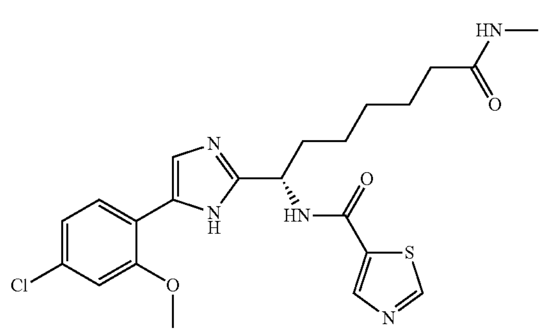 [SMILES: CNC(=O)CCCCC[C@H](NC(=O)c1cncs1)c1ncc(-c2ccc(Cl)cc2OC)[nH]1] | 476, 478 | Example 5 |

TABLE 1-continued

| Entry | Compound Name | Structure | Molecular Ion [M + H]+ | Procedure |
|---|---|---|---|---|
| 60 | (S)-7-(2-(1H-1,2,3-triazol-1-yl)acetamido)-7-(5-(isoquinolin-7-yl)-1H-imidazol-2-yl)-N-methylheptanamide | 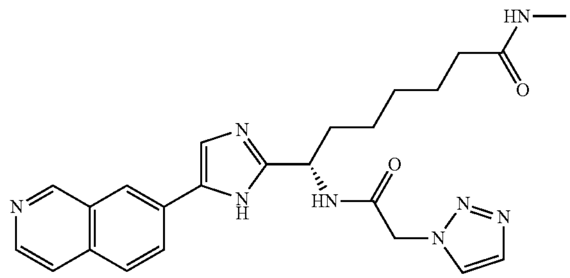 [SMILES: CNC(=O)CCCCC[C@H](NC(=O)Cn1ccnn1)c1ncc(-c2ccc3ccncc3c2)[nH]1] | 461 | Example 1 |
| 61 | (S)-N-(1-(5-(4-(5-methyl-1H-pyrazol-3-yl)phenyl)-1H-imidazol-2-yl)-7-(methylamino)-7-oxoheptyl)thiazole-5-carboxamide | 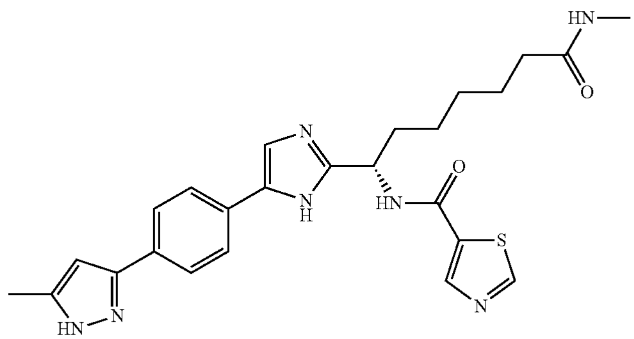 | 492 | Example 4 |
| 62 | (S)-N-(1-(5-(4-(aminomethyl)phenyl)-1H-imidazol-2-yl)-7-(methylamino)-7-oxoheptyl)thiazole-5-carboxamide | 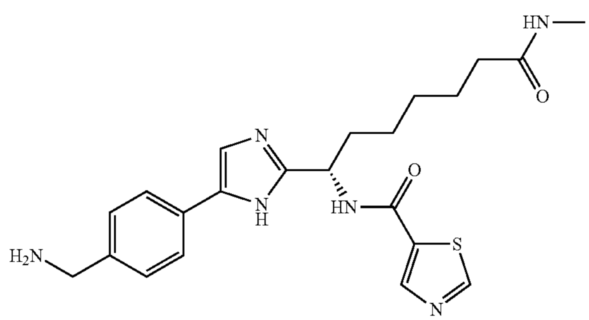 [SMILES: CNC(=O)CCCCC[C@H](NC(=O)c1cncs1)c1ncc(-c2ccc(CN)cc2)[nH]1] | 441 | Example 4 |
| 63 | N-((S)-1-(5-(4-(1H-pyrazol-1-yl)phenyl)-1H-imidazol-2-yl)-7-(methylamino)-7-oxoheptyl)-2-oxo-1,2,3,4-tetrahydroquinoline-4-carboxamide | 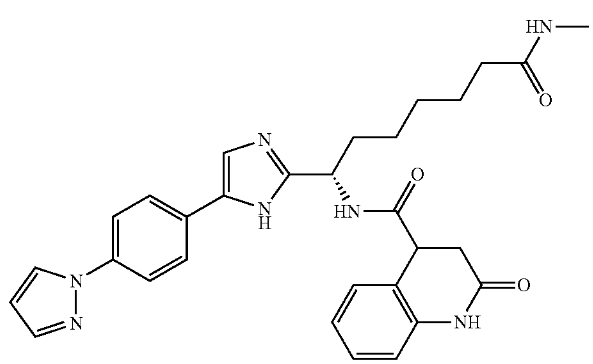 [SMILES: CNC(=O)CCCCC[C@H](NC(=O)C1CC(=O)Nc2ccccc21)c1ncc(-c2ccc(-n3cccn3)cc2)[nH]1] | 540 | Example 1 |

TABLE 1-continued

| Entry | Compound Name | Structure | Molecular Ion [M + H]⁺ | Procedure |
|---|---|---|---|---|
| 64 | (S)-7-(2-(1H-1,2,3-triazol-1-yl)acetamido)-7-(5-(4-(1H-pyrazol-1-yl)phenyl)-1H-imidazol-2-yl)-N-methylheptanamide | 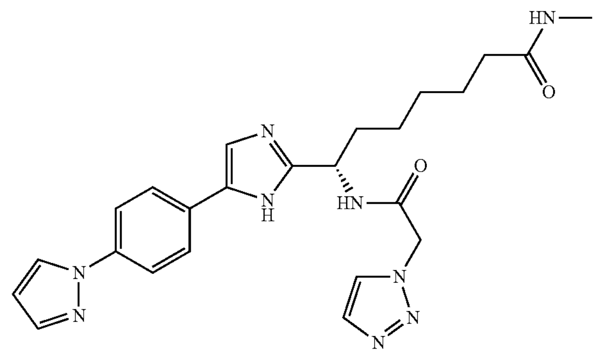 [SMILES: CNC(=O)CCCCC[C@H](NC(=O)Cn1ccnn1)c1ncc(-c2ccc(-n3cccn3)cc2)[nH]1] | 476 | Example 1 |
| 65 | (S)-N-methyl-7-(5-(naphthalen-2-yl)-1H-imidazol-2-yl)-7-(2-(4-phenylthiazol-2-yl)acetamido)heptanamide | 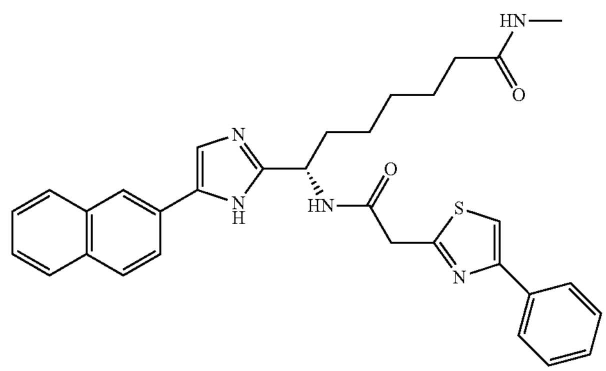 [SMILES: CNC(=O)CCCCC[C@H](NC(=O)Cc1nc(-c2ccccc2)cs1)c1ncc(-c2ccc3ccccc3c2)[nH]1] | 552 | Example 1 |
| 66 | (S)-N-(7-(methylamino)-1-(5-(naphthalen-2-yl)-1H-imidazol-2-yl)-7-oxoheptyl)-3-morpholinobenzamide | 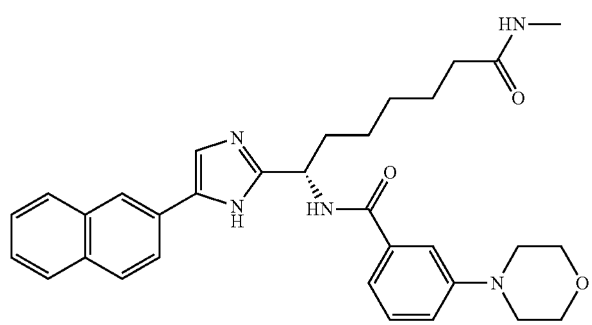 [SMILES: CNC(=O)CCCCC[C@H](NC(=O)c1cccc(N2CCOCC2)c1)c1ncc(-c2ccc3ccccc3c2)[nH]1] | 540 | Example 1 |
| 67 | (S)-N-(1-(5-(isoquinolin-7-yl)-1H-imidazol-2-yl)-7-(methylamino)-7-oxoheptyl)-2-(pyrrolidin-1-ylmethyl)thiazole-5-carboxamide | 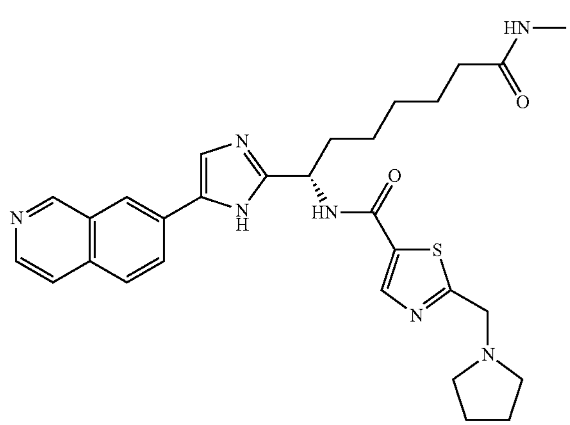 [SMILES: CNC(=O)CCCCC[C@H](NC(=O)c1cnc(CN2CCCC2)s1)c1ncc(-c2ccc3ccncc3c2)[nH]1] | 546 | Example 1 |

TABLE 1-continued

| Entry | Compound Name | Structure | Molecular Ion [M + H]+ | Procedure |
|---|---|---|---|---|
| 68 | (S)-7-(5-(isoquinolin-7-yl)-1H-imidazol-2-yl)-N-methyl-7-(2-(pyrrolidin-1-yl)acetamido)heptanamide | 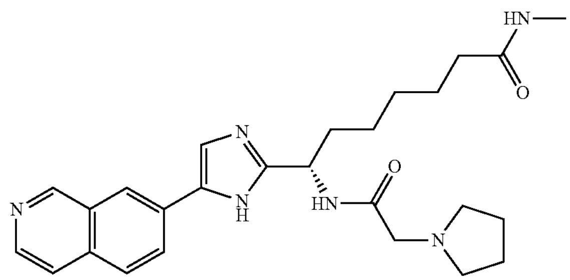 [SMILES: CNC(=O)CCCCC[C@H](NC(=O)CN1CCCC1)c1ncc(-c2ccc3ccncc3c2)[nH]1] | 463 | Example 1 |
| 69 | (S)-N-(1-(5-(isoquinolin-7-yl)-1H-imidazol-2-yl)-7-(methylamino)-7-oxoheptyl)isothiazole-5-carboxamide | 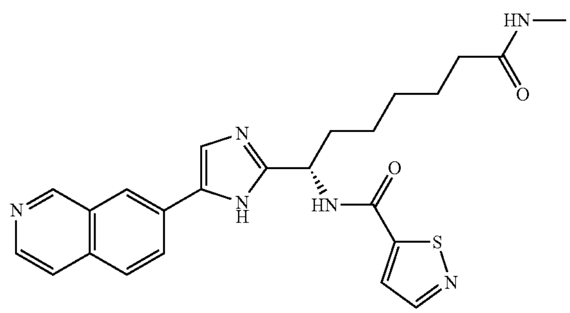 [SMILES: CNC(=O)CCCCC[C@H](NC(=O)c1ccns1)c1ncc(-c2ccc3ccncc3c2)[nH]1] | 463 | Example 1 |
| 70 | (S)-7-(5-(isoquinolin-7-yl)-1H-imidazol-2-yl)-N-methyl-7-(2-(4-methylthiazol-2-yl)acetamido)heptanamide | 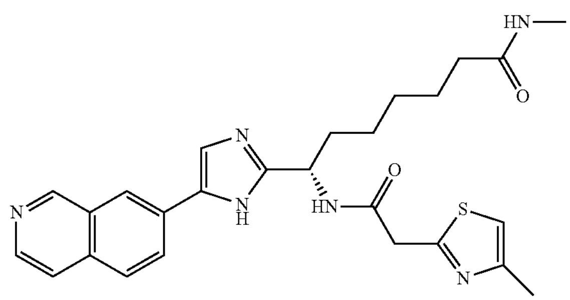 [SMILES: CNC(=O)CCCCC[C@H](NC(=O)Cc1nc(C)cs1)c1ncc(-c2ccc3ccncc3c2)[nH]1] | 491 | Example 1 |
| 71 | (S)-7-(2-(1H-1,2,3-triazol-1-yl)acetamido)-N-methyl-7-(5-(4-(1-methyl-1H-pyrazol-3-yl)phenyl)-1H-imidazol-2-yl)heptanamide | 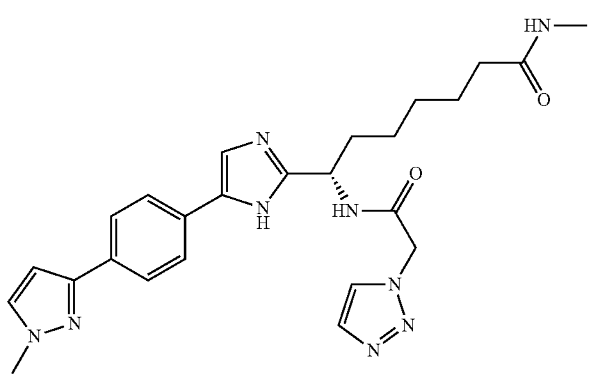 [SMILES: CNC(=O)CCCCC[C@H](NC(=O)Cn1ccnn1)c1ncc(-c2ccc(-c3ccn(C)n3)cc2)[nH]1] | 490 | Example 1 |
| 72 | (S)-N-(7-(ethylamino)-1-(5-(2-methoxyquinolin-3-yl)-1H-imidazol-2-yl)-7-oxoheptyl)thiazole-5-carboxamide | 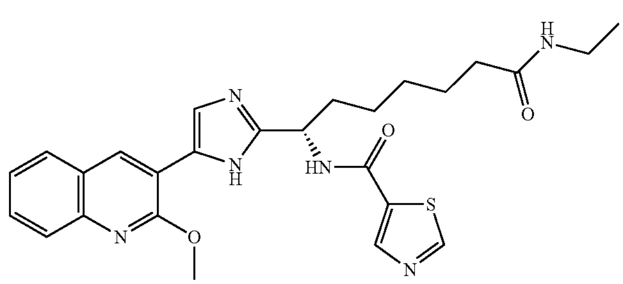 [SMILES: CCNC(=O)CCCCC[C@H](NC(=O)c1cncs1)c1ncc(-c2cc3ccccc3nc2OC)[nH]1] | 507 | Example 1 |

TABLE 1-continued

| Entry | Compound Name | Structure | Molecular Ion [M + H]+ | Procedure |
|---|---|---|---|---|
| 73 | (S)-benzyl (7-(methylamino)-1-(5-(naphthalen-2-yl)-1H-imidazol-2-yl)-7-oxoheptyl)carbamate | 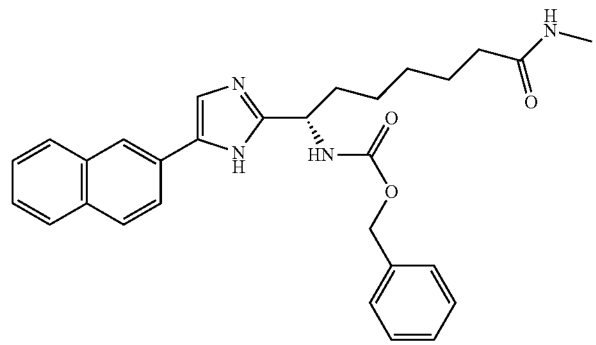 [SMILES: CNC(=O)CCCCC[C@H](NC(=O)OCc1ccccc1)c1ncc(-c2ccc3ccccc3c2)[nH]1] | 485 | Example 1 |
| 74 | (S)-5-methoxy-N-(7-(methylamino)-1-(5-(naphthalen-2-yl)-1H-imidazol-2-yl)-7-oxoheptyl)-1H-indole-2-carboxamide | 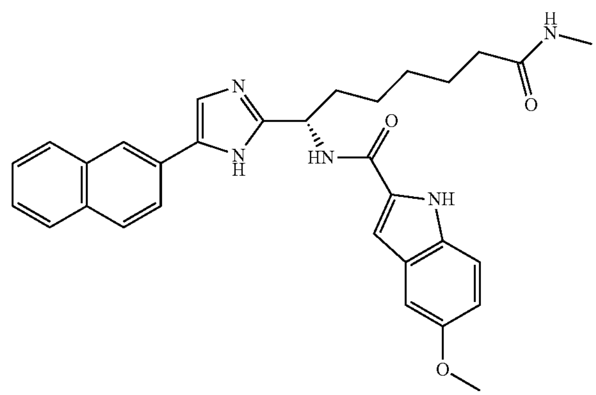 [SMILES: CNC(=O)CCCCC[C@H](NC(=O)c1cc2cc(OC)ccc2[nH]1)c1ncc(-c2ccc3ccccc3c2)[nH]1] | 524 | Example 1 |
| 75 | (S)-N-methyl-7-(5-(naphthalen-2-yl)-1H-imidazol-2-yl)-7-(2-(2-oxobenzo[d]oxazol-3(2H)-yl)acetamido)heptanamide | 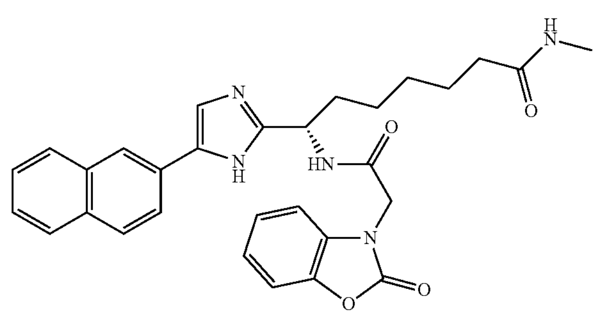 [SMILES: CNC(=O)CCCCC[C@H](NC(=O)Cn1c(=O)oc2ccccc21)c1ncc(-c2ccc3ccccc3c2)[nH]1] | 526 | Example 1 |
| 76 | (S)-7-(2-(5-methoxy-2-methyl-1H-indol-3-yl)acetamido)-N-methyl-7-(5-(naphthalen-2-yl)-1H-imidazol-2-yl)heptanamide | 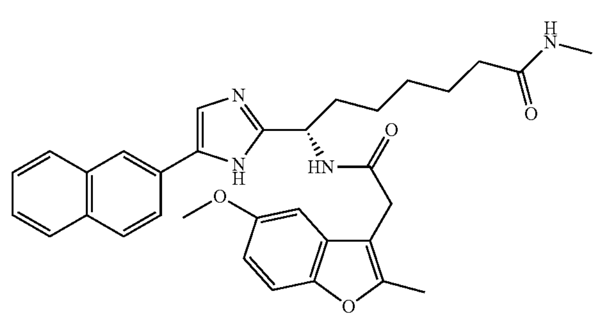 [SMILES: CNC(=O)CCCCC[C@H](NC(=O)Cc1c(C)oc2ccc(OC)cc12)c1ncc(-c2ccc3ccccc3c2)[nH]1] | 552 | Example 1 |

TABLE 1-continued

| Entry | Compound Name | Structure | Molecular Ion [M + H]+ | Procedure |
|---|---|---|---|---|
| 77 | (S)-7-(5-(2-methoxyquinolin-3-yl)-1H-imidazol-2-yl)-N-methyl-7-(2-(pyrazin-2-yl)acetamido)heptanamide | 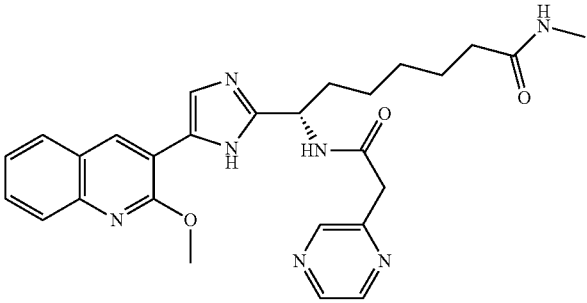 [SMILES: CNC(=O)CCCCC[C@H](NC(=O)Cc1cnccn1)c1ncc(-c2cc3ccccc3nc2OC)[nH]1] | 502 | Example 2 |
| 78 | (S)-N-(1-(5-(2-methoxyquinolin-3-yl)-1H-imidazol-2-yl)-7-(methylamino)-7-oxoheptyl)-5-methyl-1,3,4-oxadiazole-2-carboxamide | 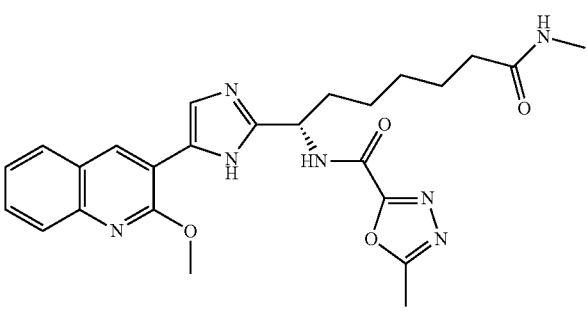 [SMILES: CNC(=O)CCCCC[C@H](NC(=O)c1nnc(C)o1)c1ncc(-c2cc3ccccc3nc2OC)[nH]1] | 492 | Example 2 |
| 79 | (S)-N-(1-(5-(4-((dimethylamino)methyl)phenyl)-1H-imidazol-2-yl)-7-(methylamino)-7-oxoheptyl)thiazole-5-carboxamide | 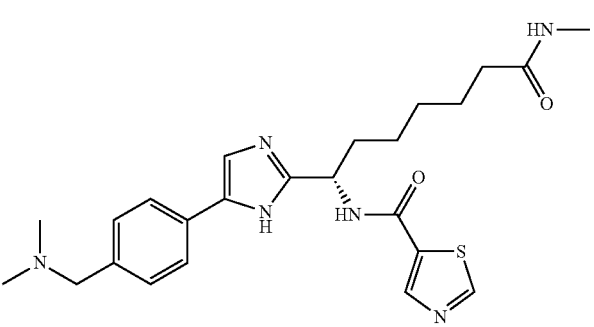 | 469 | Example 4 |
| 80 | (S)-N-(1-(5-(2,3-dihydrobenzo[b][1,4]dioxin-5-yl)-1H-imidazol-2-yl)-7-(methylamino)-7-oxoheptyl)thiazole-5-carboxamide | 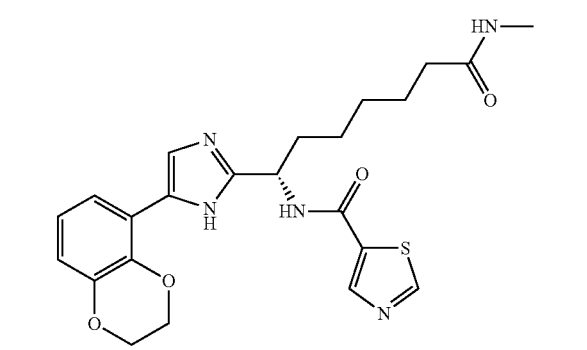 [SMILES: CNC(=O)CCCCC[C@H](NC(=O)c1cncs1)c1ncc(-c2cccc3c2OCCO3)[nH]1] | 470 | Example 4 |
| 81 | (S)-N-(1-(5-(2-chloroquinolin-3-yl)-1H-imidazol-2-yl)-7-(methylamino)-7-oxoheptyl)thiazole-5-carboxamide | 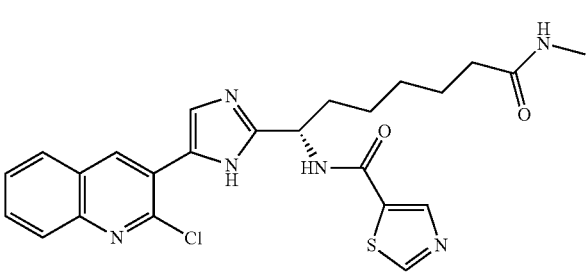 [SMILES: CNC(=O)CCCCC[C@H](NC(=O)c1cncs1)c1ncc(-c2cc3ccccc3nc2Cl)[nH]1] | 497, 499 | Example 4 |

TABLE 1-continued

| Entry | Compound Name | Structure | Molecular Ion [M + H]+ | Procedure |
|---|---|---|---|---|
| 82 | (S)-N-(1-(5-(4-(3,5-dimethyl-1H-pyrazol-1-yl)phenyl)-1H-imidazol-2-yl)-7-(methylamino)-7-oxoheptyl)thiazole-5-carboxamide | 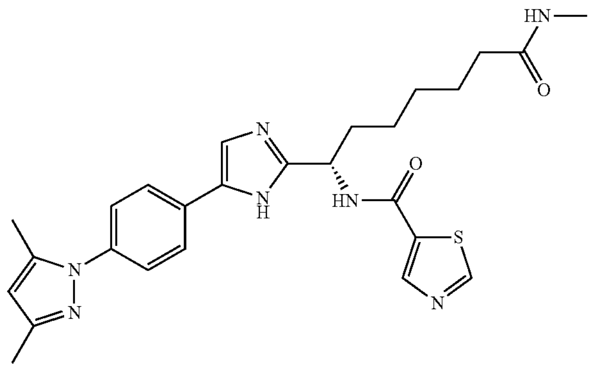 [SMILES: CNC(=O)CCCCC[C@H](NC(=O)c1cncs1)c1ncc(-c2ccc(-n3nc(C)cc3C)cc2)[nH]1] | 506 | Example 4 |
| 83 | (S)-5-methyl-N-(7-(methylamino)-1-(5-(naphthalen-2-yl)-1H-imidazol-2-yl)-7-oxoheptyl)-1-phenyl-1H-pyrazole-3-carboxamide | 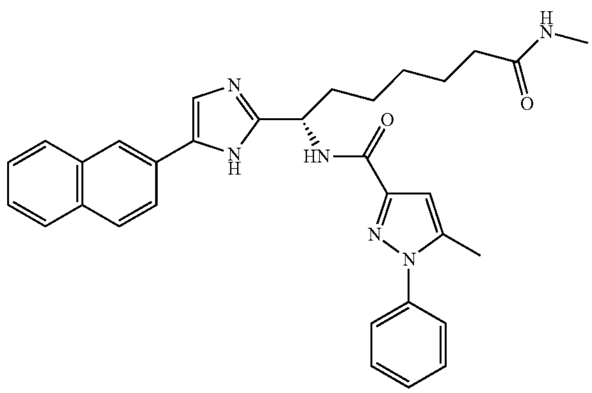 [SMILES: CNC(=O)CCCCC[C@H](NC(=O)c1cc(C)n(-c2ccccc2)n1)c1ncc(-c2ccc3ccccc3c2)[nH]1] | 535 | Example 1 |
| 84 | (S)-N-(7-(methylamino)-1-(5-(naphthalen-2-yl)-1H-imidazol-2-yl)-7-oxoheptyl)-6-(1H-pyrrol-1-yl)nicotinamide | 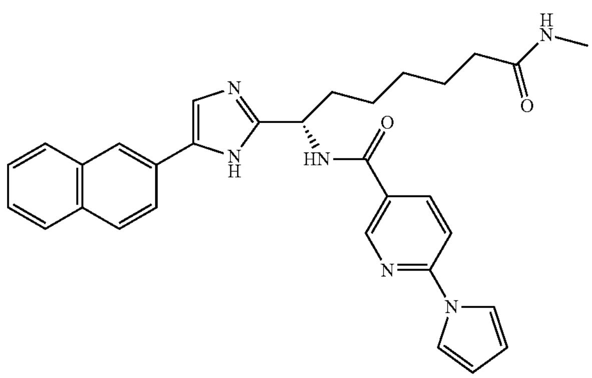 [SMILES: CNC(=O)CCCCC[C@H](NC(=O)c1ccc(-n2cccc2)nc1)c1ncc(-c2ccc3ccccc3c2)[nH]1] | 521 | Example 1 |
| 85 | (S)-5-methyl-N-(7-(methylamino)-1-(5-(naphthalen-2-yl)-1H-imidazol-2-yl)-7-oxoheptyl)-1,3,4-thiadiazole-2-carboxamide | 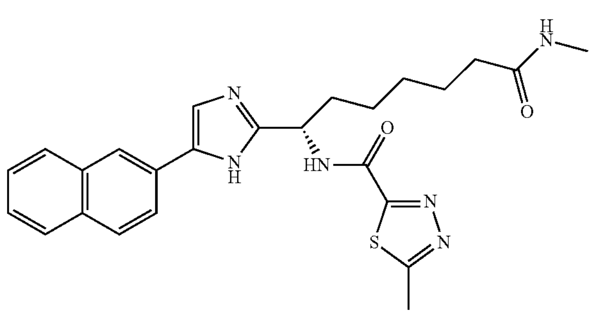 [SMILES: CNC(=O)CCCCC[C@H](NC(=O)c1nnc(C)s1)c1ncc(-c2ccc3ccccc3c2)[nH]1] | 477 | Example 1 |

TABLE 1-continued

| Entry | Compound Name | Structure | Molecular Ion [M + H]+ | Procedure |
|---|---|---|---|---|
| 86 | (7S)-7-(2-(1H-pyrazol-1-yl)propanamido)-N-methyl-7-(5-(naphthalen-2-yl)-1H-imidazol-2-yl)heptanamide | 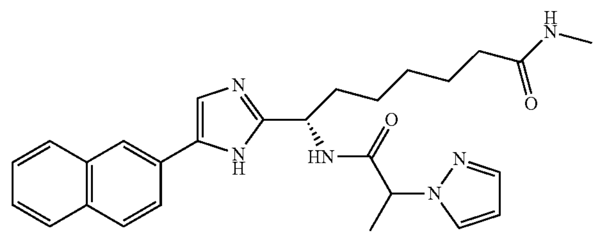 [SMILES: CNC(=O)CCCCC[C@H](NC(=O)C(C)n1cccn1)c1ncc(-c2ccc3ccccc3c2)[nH]1] | 473 | Example 1 |
| 87 | (S)-3-(furan-2-yl)-N-(7-(methylamino)-1-(5-(naphthalen-2-yl)-1H-imidazol-2-yl)-7-oxoheptyl)-1H-pyrazole-5-carboxamide | 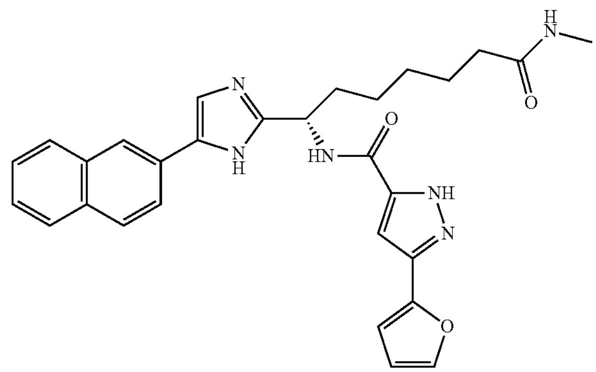 [SMILES: CNC(=O)CCCCC[C@H](NC(=O)c1cc(-c2ccco2)n[nH]1)c1ncc(-c2ccc3ccccc3c2)[nH]1] | 511 | Example 1 |
| 88 | (S)-N-(7-(methylamino)-1-(5-(naphthalen-2-yl)-1H-imidazol-2-yl)-7-oxoheptyl)-2-(1H-tetrazol-1-yl)benzamide | 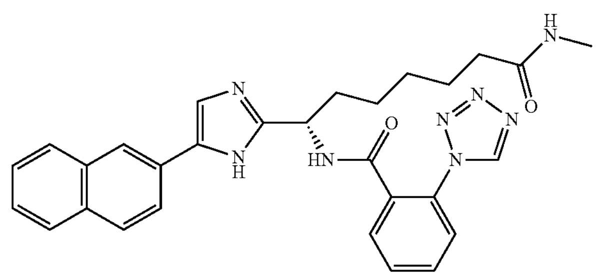 [SMILES: CNC(=O)CCCCC[C@H](NC(=O)c1ccccc1-n1cnnn1)c1ncc(-c2ccc3ccccc3c2)[nH]1] | 523 | Example 1 |
| 89 | (S)-N-(7-(methylamino)-1-(5-(naphthalen-2-yl)-1H-imidazol-2-yl)-7-oxoheptyl)quinoxaline-5-carboxamide | 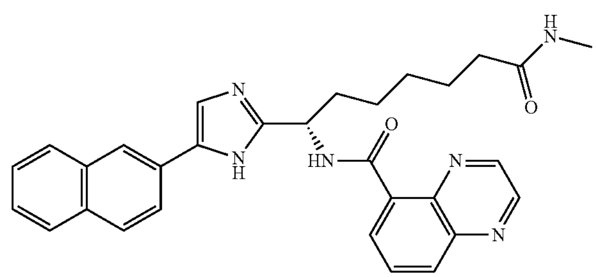 [SMILES: CNC(=O)CCCCC[C@H](NC(=O)c1cccc2nccnc12)c1ncc(-c2ccc3ccccc3c2)[nH]1] | 507 | Example 1 |
| 90 | (S)-7-(2-(1H-1,2,4-triazol-1-yl)acetamido)-7-(5-(isoquinolin-7-yl)-1H-imidazol-2-yl)-N-methylheptanamide | 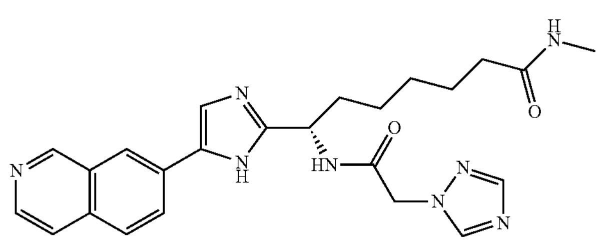 [SMILES: CNC(=O)CCCCC[C@H](NC(=O)Cn1cncn1)c1ncc(-c2ccc3ccncc3c2)[nH]1] | 461 | Example 1 |

TABLE 1-continued

| Entry | Compound Name | Structure | Molecular Ion [M + H]+ | Procedure |
|---|---|---|---|---|
| 91 | (S)-1-isopropyl-N-(1-(5-(isoquinolin-7-yl)-1H-imidazol-2-yl)-7-(methylamino)-7-oxoheptyl)-1H-pyrazole-4-carboxamide | 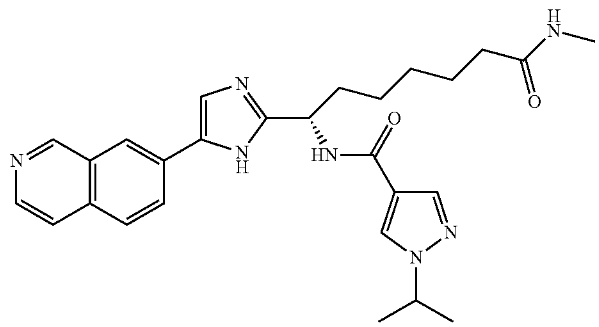 [SMILES: CNC(=O)CCCCC[C@H](NC(=O)c1cnn(C(C)C)c1)c1ncc(-c2ccc3ccncc3c2)[nH]1] | 488 | Example 1 |
| 92 | 2,2-difluoro-N-((S)-1-(5-(4-(1-methyl-1H-pyrazol-3-yl)phenyl)-1H-imidazol-2-yl)-7-(methylamino)-7-oxoheptyl)cyclobutane carboxamide | 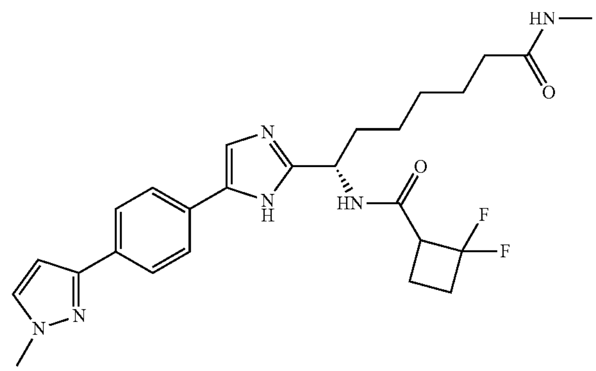 [SMILES: CNC(=O)CCCCC[C@H](NC(=O)C1CCC1(F)F)c1ncc(-c2ccc(-c3ccn(C)n3)cc2)[nH]1] | 499 | Example 1 |
| 93 | (S)-7-(2-(6,7-dihydro-5H-thiazolo[3,2-a]pyrimidin-3-yl)acetamido)-N-methyl-7-(5-(4-(1-methyl-1H-pyrazol-3-yl)phenyl)-1H-imidazol-2-yl)heptanamide | 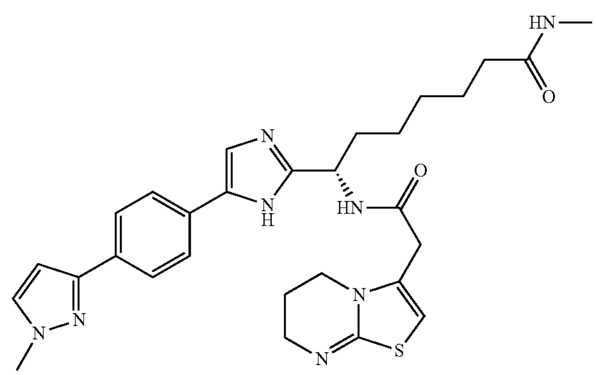 [SMILES: CNC(=O)CCCCC[C@H](NC(=O)CC1=CSC2=NCCCN12)c1ncc(-c2ccc(-c3ccn(C)n3)cc2)[nH]1] | 561 | Example 1 |
| 94 | (S)-benzyl (1-(5-(isoquinolin-7-yl)-1H-imidazol-2-yl)-7-(methylamino)-7-oxoheptyl)carbamate | 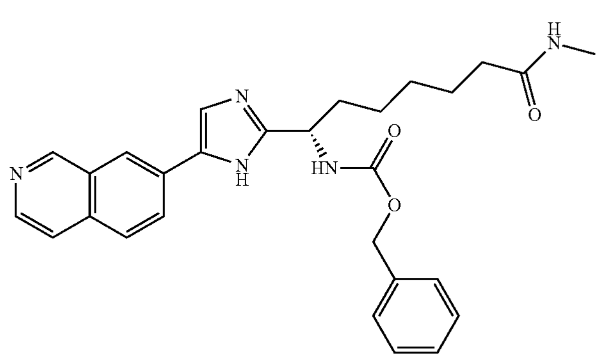 [SMILES: CNC(=O)CCCCC[C@H](NC(=O)OCc1ccccc1)c1ncc(-c2ccc3ccncc3c2)[nH]1] | 486 | Example 5 |

TABLE 1-continued

| Entry | Compound Name | Structure | Molecular Ion [M + H]+ | Procedure |
|---|---|---|---|---|
| 95 | (S)-N-(7-(methylamino)-1-(5-(naphthalen-2-yl)-1H-imidazol-2-yl)-7-oxoheptyl)thiazole-5-carboxamide | 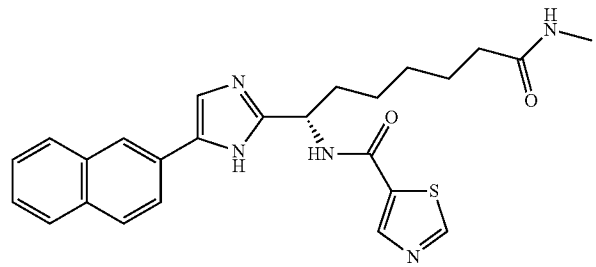 [SMILES: CNC(=O)CCCCC[C@H](NC(=O)c1cncs1)c1ncc(-c2ccc3ccccc3c2)[nH]1] | 462 | Example 1 |
| 96 | (S)-7-(2-(5-methoxy-2-methyl-1H-indol-3-yl)acetamido)-7-(5-(naphthalen-2-yl)-1H-imidazol-2-yl)heptanamide | 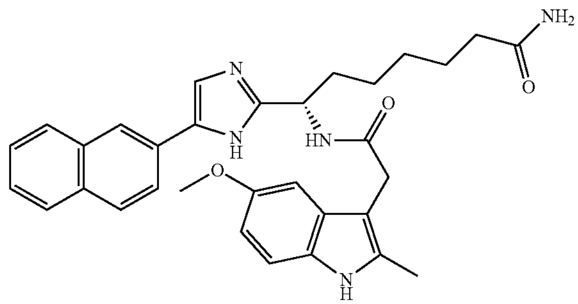 [SMILES: COc1ccc2[nH]c(C)c(CC(=O)N[C@@H](CCCCCC(N)=O)c3ncc(-c4ccc5ccccc5c4)[nH]3)c2c1] | 538 | Example 1 |
| 97 | (S)-N-(1-(5-(3-methoxynaphthalen-2-yl)-1H-imidazol-2-yl)-7-(methylamino)-7-oxoheptyl)thiazole-5-carboxamide | 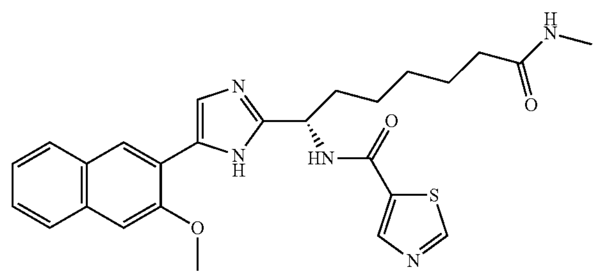 [SMILES: CNC(=O)CCCCC[C@H](NC(=O)c1cncs1)c1ncc(-c2cc3ccccc3cc2OC)[nH]1] | 492 | Example 5 |
| 98 | (S)-N-(1-(5-(2-methoxyquinolin-3-yl)-1H-imidazol-2-yl)-7-(methylamino)-7-oxoheptyl)-1-methylazetidine-3-carboxamide | 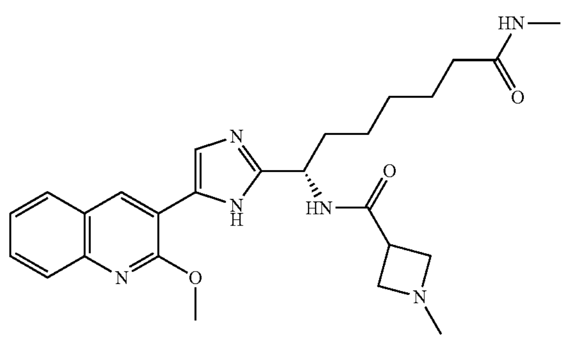 [SMILES: CNC(=O)CCCCC[C@H](NC(=O)C1CN(C)C1)c1ncc(-c2cc3ccccc3nc2OC)[nH]1] | 479 | Example 1 |
| 99 | (S)-7-(5-(2-methoxyquinolin-3-yl)-1H-imidazol-2-yl)-N-methyl-7-(3-(piperidin-1-yl)propanamido)heptanamide | 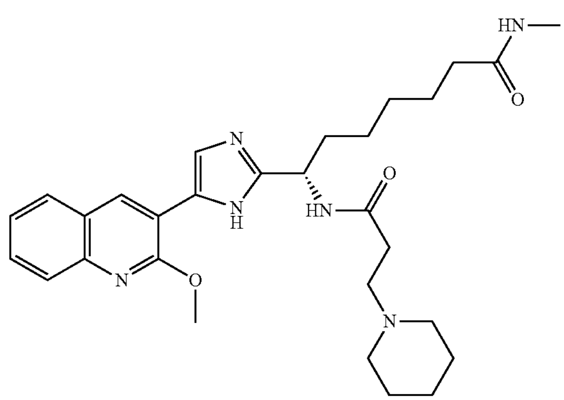 [SMILES: CNC(=O)CCCCC[C@H](NC(=O)CCN1CCCCC1)c1ncc(-c2cc3ccccc3nc2OC)[nH]1] | 521 | Example 1 |

TABLE 1-continued

| Entry | Compound Name | Structure | Molecular Ion [M + H]+ | Procedure |
|---|---|---|---|---|
| 100 | (1r,3R,5S)-N-((S)-7-(methylamino)-7-oxo-1-(5-(4-(trifluoromethyl)phenyl)-1H-imidazol-2-yl)heptyl)adamantane-1-carboxamide | 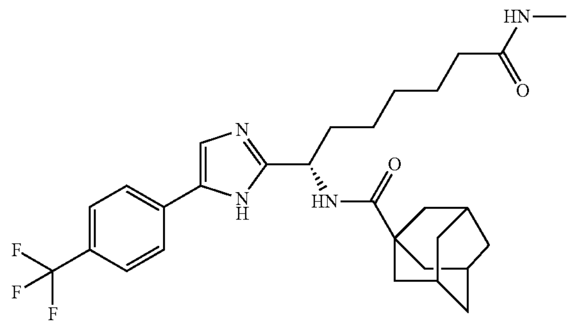 [SMILES: CNC(=O)CCCCC[C@H](NC(=O)C12CC3CC(CC(C3)C1)C2)c1ncc(-c2ccc(C(F)(F)F)cc2)[nH]1] | 531 | Example 1 |
| 101 | (S)-N-methyl-7-(3-(piperidin-1-yl)propanamido)-7-(5-(4-(trifluoromethyl)phenyl)-1H-imidazol-2-yl)heptanamide | 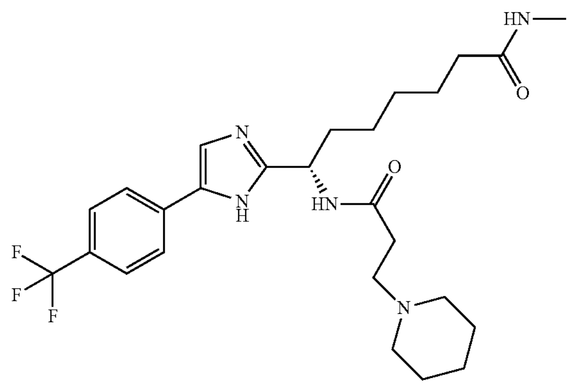 [SMILES: CNC(=O)CCCCC[C@H](NC(=O)CCN1CCCCC1)c1ncc(-c2ccc(C(F)(F)F)cc2)[nH]1] | 508 | Example 1 |
| 102 | (S)-N-(1-(5-(2-methoxyquinolin-3-yl)-1H-imidazol-2-yl)-7-(methylamino)-7-oxoheptyl)-1H-1,2,4-triazole-3-carboxamide | 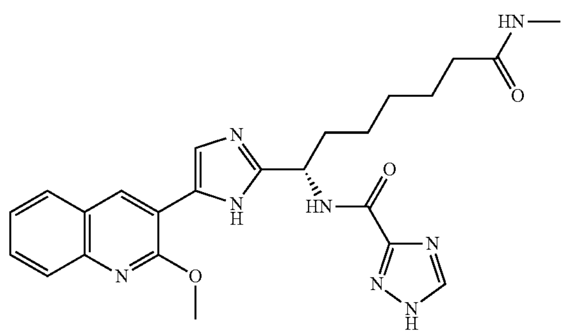 [SMILES: CNC(=O)CCCCC[C@H](NC(=O)c1nc[nH]n1)c1ncc(-c2cc3ccccc3nc2OC)[nH]1] | 477 | Example 2 |
| 103 | 7S)-7-(2-(1H-pyrazol-1-yl)propanamido)-7-(5-(2-methoxyquinolin-3-yl)-1H-imidazol-2-yl)-N-methylheptanamide | 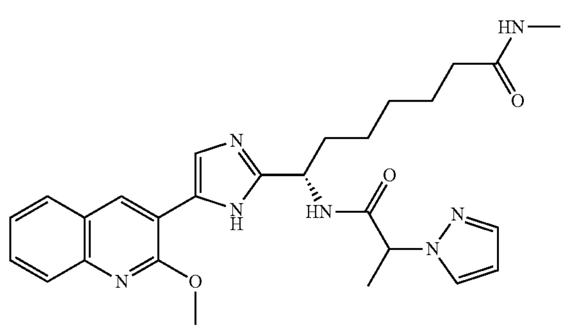 [SMILES: CNC(=O)CCCCC[C@H](NC(=O)C(C)n1cccn1)c1ncc(-c2cc3ccccc3nc2OC)[nH]1] | 504 | Example 2 |

TABLE 1-continued

| Entry | Compound Name | Structure | Molecular Ion [M + H]+ | Procedure |
|---|---|---|---|---|
| 104 | (S)-N-((S)-1-(5-(2-methoxyquinolin-3-yl)-1H-imidazol-2-yl)-7-(methylamino)-7-oxoheptyl)-1-methylpyrrolidine-2-carboxamide | 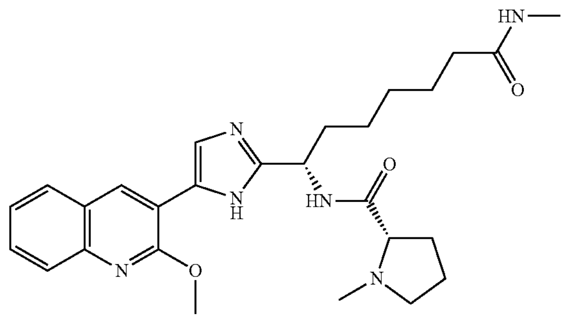 [SMILES: CNC(=O)CCCCC[C@H](NC(=O)[C@@H]1CCCN1C)c1ncc(-c2cc3ccccc3nc2OC)[nH]1] | 493 | Example 2 |
| 105 | (S)-N-(1-(5-(3-methoxyisoquinolin-7-yl)-1H-imidazol-2-yl)-7-(methylamino)-7-oxoheptyl)thiazole-5-carboxamide | 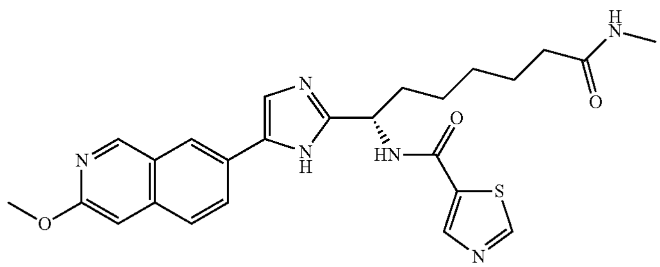 | 493 | Example 4 |
| 106 | (S)-7-(5-(2-methoxyquinolin-3-yl)-1H-imidazol-2-yl)-N-methyl-7-(2-(pyridin-2-yl)acetamido)heptanamide | 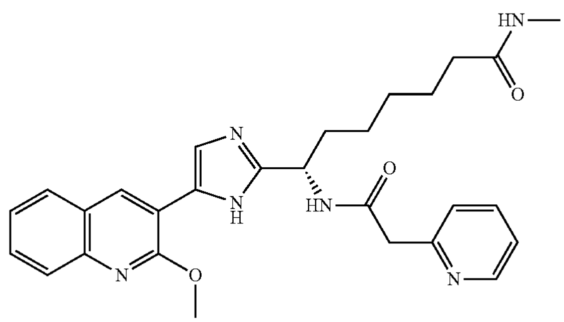 [SMILES: CNC(=O)CCCCC[C@H](NC(=O)Cc1ccccn1)c1ncc(-c2cc3ccccc3nc2OC)[nH]1] | 501 | Example 2 |
| 107 | (S)-N-(1-(5-(2-methoxyquinolin-6-yl)-1H-imidazol-2-yl)-7-(methylamino)-7-oxoheptyl)thiazole-5-carboxamide | 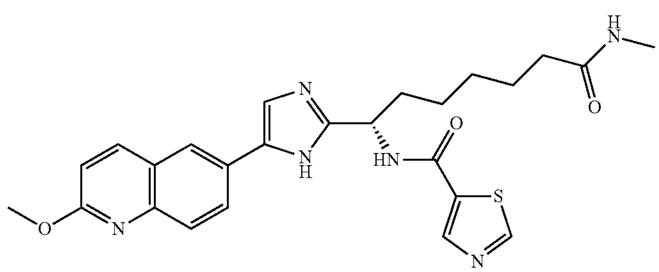 | 493 | Example 4 |
| 108 | (S)-N-(1-(5-([1,1'-biphenyl]-4-yl)-1H-imidazol-2-yl)-7-(methylamino)-7-oxoheptyl)thiazole-5-carboxamide | 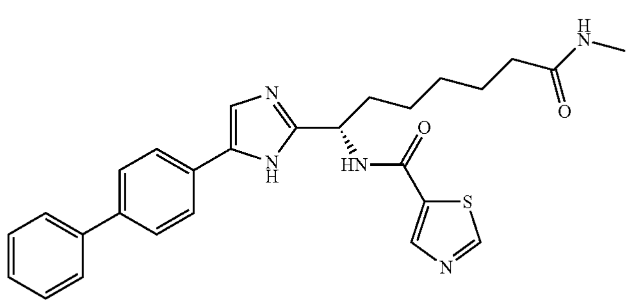 [SMILES: CNC(=O)CCCCC[C@H](NC(=O)c1cncs1)c1ncc(-c2ccc(-c3ccccc3)cc2)[nH]1] | 488 | Example 4 |

TABLE 1-continued

| Entry | Compound Name | Structure | Molecular Ion [M + H]+ | Procedure |
|---|---|---|---|---|
| 109 | (S)-N-(7-(methylamino)-7-oxo-1-(5-(4-(thiophen-2-yl)phenyl)-1H-imidazol-2-yl)heptyl)thiazole-5-carboxamide | 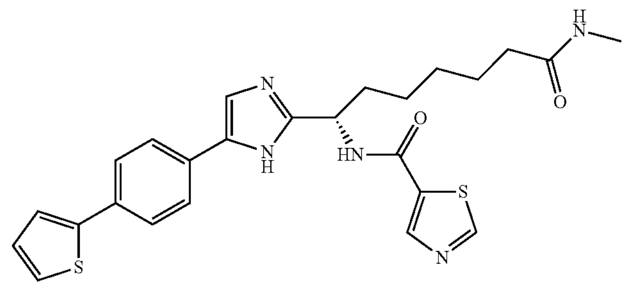 [SMILES: CNC(=O)CCCCC[C@H](NC(=O)c1cncs1)c1ncc(-c2ccc(-c3cccs3)cc2)[nH]1] | 494 | Example 4 |
| 110 | (S)-7-(5-(4-(1H-pyrazol-1-yl)phenyl)-1H-imidazol-2-yl)-N-methyl-7-(2-(quinolin-3-yl)acetamido)heptanamide | 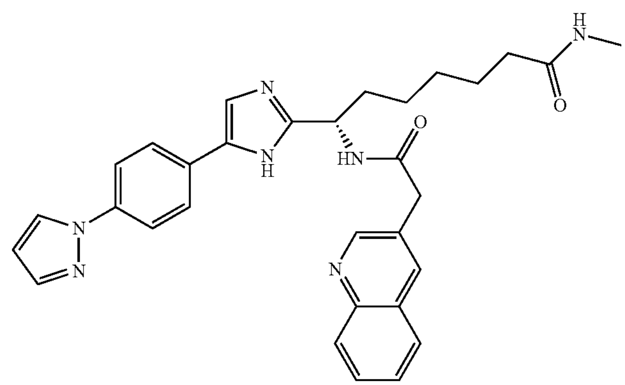 [SMILES: CNC(=O)CCCCC[C@H](NC(=O)Cc1cnc2ccccc2c1)c1ncc(-c2ccc(-n3cccn3)cc2)[nH]1] | 536 | Example 1 |
| 111 | (S)-4-fluoro-N-(1-(5-(isoquinolin-7-yl)-1H-imidazol-2-yl)-7-(methylamino)-7-oxoheptyl)-1-methylpiperidine-4-carboxamide | 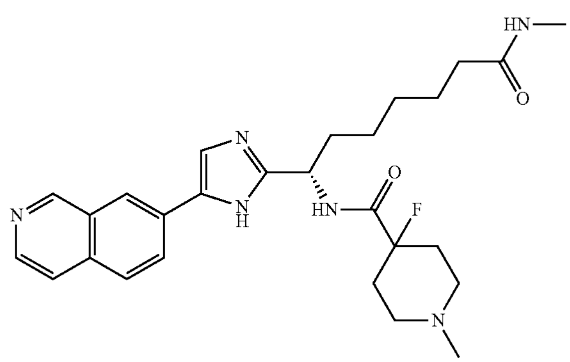 [SMILES: CNC(=O)CCCCC[C@H](NC(=O)C1(F)CCN(C)CC1)c1ncc(-c2ccc3ccncc3c2)[nH]1] | 495 | Example 5 |
| 112 | (S)-N-(1-(5-(1H-benzo[d][1,2,3]triazol-5-yl)-1H-imidazol-2-yl)-7-(methylamino)-7-oxoheptyl)thiazole-5-carboxamide | 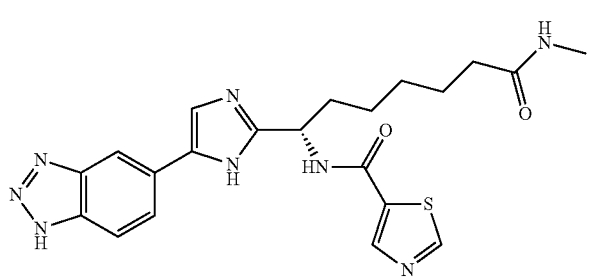 [SMILES: CNC(=O)CCCCC[C@H](NC(=O)c1cncs1)c1ncc(-c2ccc3[nH]nnc3c2)[nH]1] | 453 | Example 4 |

TABLE 1-continued

| Entry | Compound Name | Structure | Molecular Ion [M + H]+ | Procedure |
|---|---|---|---|---|
| 113 | (S)-N-methyl-7-(5-(naphthalen-2-yl)-1H-imidazol-2-yl)-7-(2-(pyrazin-2-yl)acetamido)heptanamide | 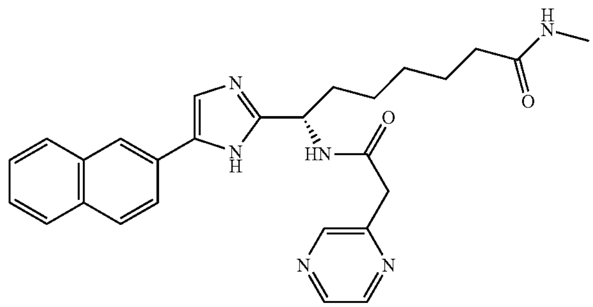 [SMILES: CNC(=O)CCCCC[C@H](NC(=O)Cc1cnccn1)c1ncc(-c2ccc3ccccc3c2)[nH]1] | 471 | Example 1 |
| 114 | (S)-N-(7-(methylamino)-1-(5-(naphthalen-2-yl)-1H-imidazol-2-yl)-7-oxoheptyl)isoquinoline-6-carboxamide | 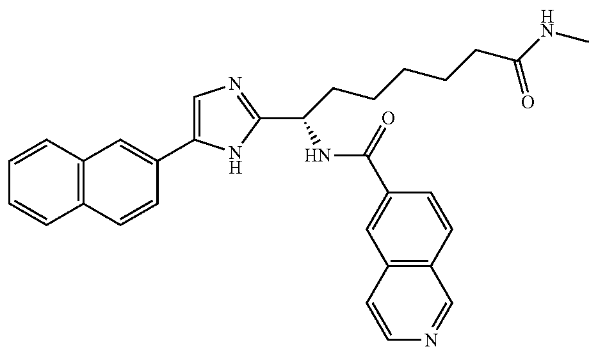 [SMILES: CNC(=O)CCCCC[C@H](NC(=O)c1ccc2cnccc2c1)c1ncc(-c2ccc3ccccc3c2)[nH]1] | 506 | Example 1 |
| 115 | (S)-N-methyl-7-(5-(naphthalen-2-yl)-1H-imidazol-2-yl)-7-(2-(5-oxo-4,5-dihydro-1H-1,2,4-triazol-3-yl)acetamido)heptanamide | 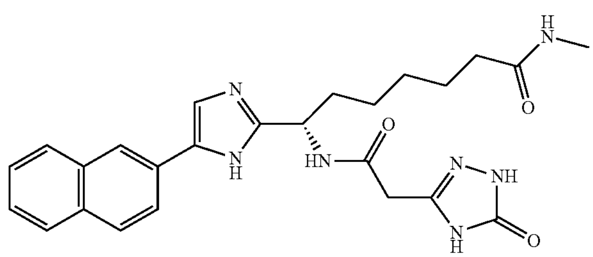 [SMILES: CNC(=O)CCCCC[C@H](NC(=O)Cc1n[nH]c(=O)[nH]1)c1ncc(-c2ccc3ccccc3c2)[nH]1] | 476 | Example 1 |
| 116 | (S)-7-(2-(4H-1,2,4-triazol-4-yl)acetamido)-N-methyl-7-(5-(naphthalen-2-yl)-1H-imidazol-2-yl)heptanamide | 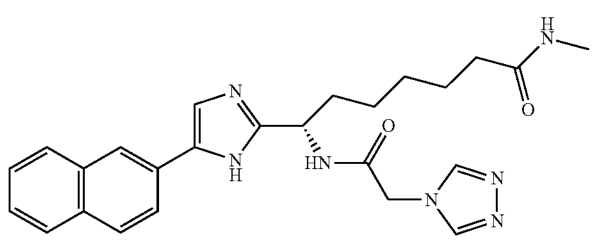 [SMILES: CNC(=O)CCCCC[C@H](NC(=O)Cn1cnnc1)c1ncc(-c2ccc3ccccc3c2)[nH]1] | 460 | Example 1 |
| 117 | (S)-N-(7-(methylamino)-1-(5-(naphthalen-2-yl)-1H-imidazol-2-yl)-7-oxoheptyl)-4-(1H-tetrazol-1-yl)benzamide | 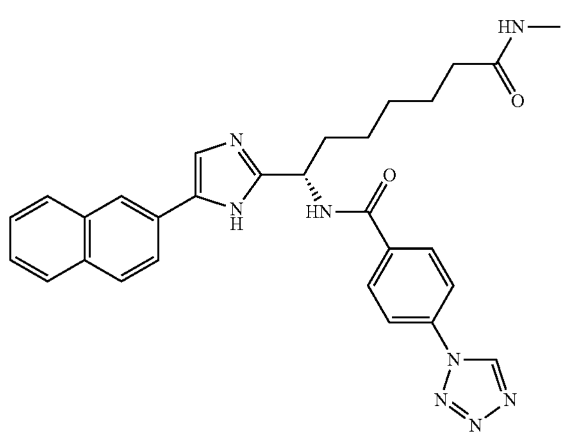 [SMILES: CNC(=O)CCCCC[C@H](NC(=O)c1ccc(-n2cnnn2)cc1)c1ncc(-c2ccc3ccccc3c2)[nH]1] | 523 | Example 1 |

TABLE 1-continued

| Entry | Compound Name | Structure | Molecular Ion [M + H]+ | Procedure |
|---|---|---|---|---|
| 118 | (S)-N-(1-(5-(isoquinolin-7-yl)-1H-imidazol-2-yl)-7-(methylamino)-7-oxoheptyl)-1-methylpiperidine-4-carboxamide | 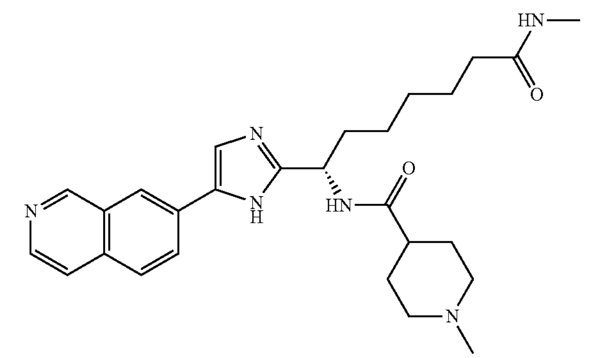 [SMILES: CNC(=O)CCCCC[C@H](NC(=O)C1CCN(C)CC1)c1ncc(-c2ccc3ccncc3c2)[nH]1] | 477 | Example 1 |
| 119 | (S)-7-(5-(isoquinolin-7-yl)-1H-imidazol-2-yl)-N-methyl-7-(2-(3-methyl-1H-pyrazol-1-yl)acetamido)heptanamide | 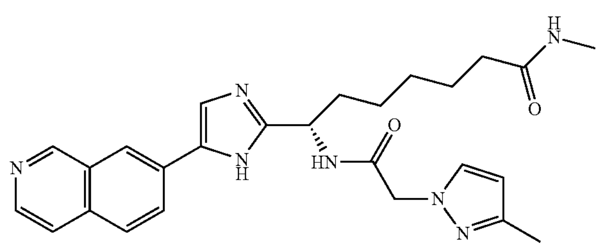 [SMILES: CNC(=O)CCCCC[C@H](NC(=O)Cn1ccc(C)n1)c1ncc(-c2ccc3ccncc3c2)[nH]1] | 474 | Example 1 |
| 120 | (S)-N-(1-(5-(isoquinolin-7-yl)-1H-imidazol-2-yl)-7-(methylamino)-7-oxoheptyl)thiazole-5-carboxamide | 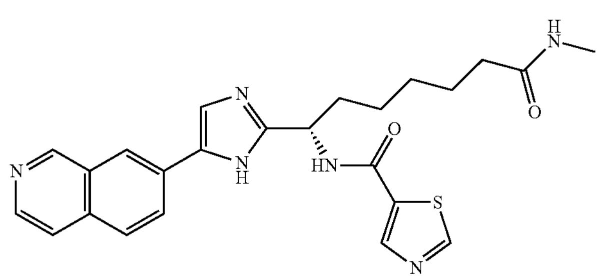 [SMILES: CNC(=O)CCCCC[C@H](NC(=O)c1cncs1)c1ncc(-c2ccc3ccncc3c2)[nH]1] | 463 | Example 1 |
| 121 | N-((S)-1-(5-(isoquinolin-7-yl)-1H-imidazol-2-yl)-7-(methylamino)-7-oxoheptyl)-2-methyltetrahydrofuran-2-carboxamide | 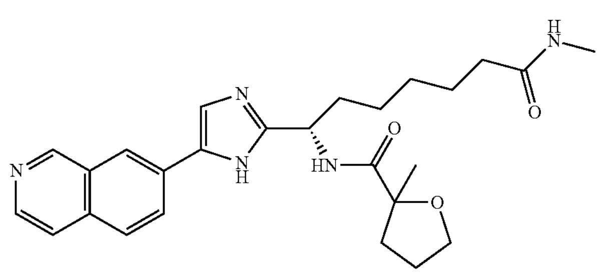 [SMILES: CNC(=O)CCCCC[C@H](NC(=O)C1(C)CCCO1)c1ncc(-c2ccc3ccncc3c2)[nH]1] | 464 | Example 1 |
| 122 | S)-7-(3-(5,7-dimethyl-[1,2,4]triazolo[1,5-a]pyrimidin-6-yl)propanamido)-7-(5-(isoquinolin-7-yl)-1H-imidazol-2-yl)-N-methylheptanamide | 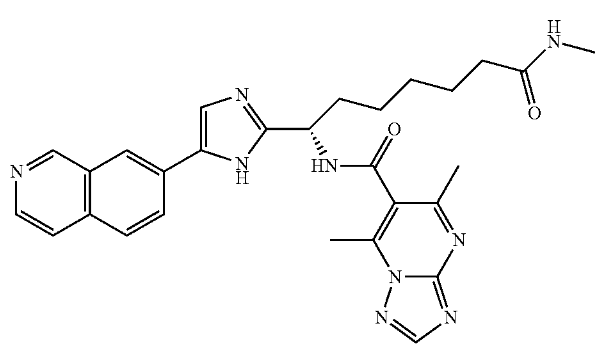 [SMILES: CNC(=O)CCCCC[C@H](NC(=O)c1c(C)nc2ncnn2c1C)c1ncc(-c2ccc3ccncc3c2)[nH]1] | 554 | Example 1 |

TABLE 1-continued

| Entry | Compound Name | Structure | Molecular Ion [M + H]+ | Procedure |
|---|---|---|---|---|
| 123 | 2-methyl-N-((S)-1-(5-(4-(1-methyl-1H-pyrazol-3-yl)phenyl)-1H-imidazol-2-yl)-7-(methylamino)-7-oxoheptyl)tetrahydrofuran-2-carboxamide | 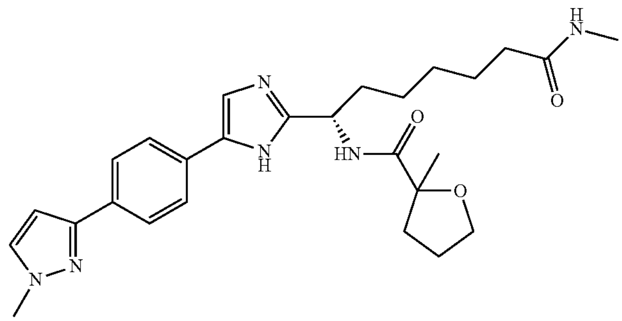 [SMILES: CNC(=O)CCCCC[C@H](NC(=O)C1(C)CCCO1)c1ncc(-c2ccc(-c3ccn(C)n3)cc2)[nH]1] | 493 | Example 1 |
| 124 | (S)-N-(1-(5-(4-(1-methyl-1H-pyrazol-3-yl)phenyl)-1H-imidazol-2-yl)-7-(methylamino)-7-oxoheptyl)-2-(pyrrolidin-1-ylmethyl)thiazole-5-carboxamide | 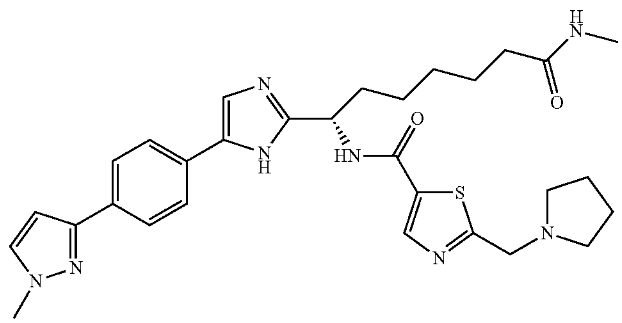 [SMILES: CNC(=O)CCCCC[C@H](NC(=O)c1cnc(CN2CCCC2)s1)c1ncc(-c2ccc(-c3ccn(C)n3)cc2)[nH]1] | 575 | Example 1 |
| 125 | (S)-N-(1-(5-([1,2,4]triazolo[1,5-a]pyridin-7-yl)-1H-imidazol-2-yl)-7-(methylamino)-7-oxoheptyl)thiazole-5-carboxamide | 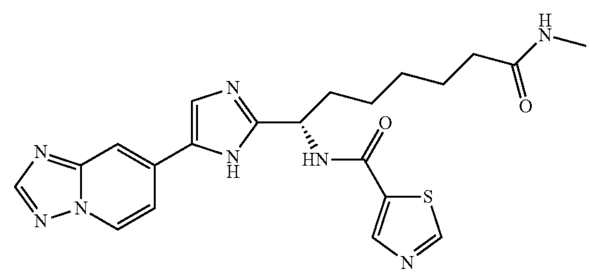 [SMILES: CNC(=O)CCCCC[C@H](NC(=O)c1cncs1)c1ncc(-c2ccn3ncnc3c2)[nH]1] | 453 | Example 4 |
| 126 | (S)-N-(7-(methylamino)-1-(5-(naphthalen-2-yl)-1H-imidazol-2-yl)-7-oxoheptyl)quinuclidine-4-carboxamide | 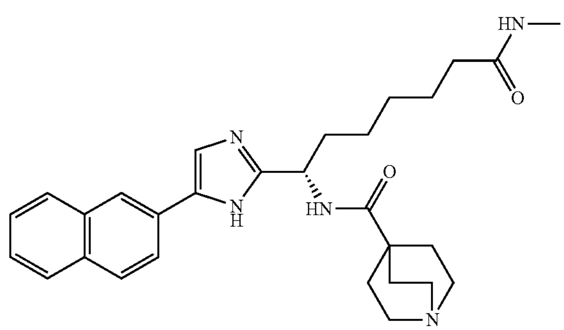 [SMILES: CNC(=O)CCCCC[C@H](NC(=O)C12CCN(CC1)CC2)c1ncc(-c2ccc3ccccc3c2)[nH]1] | 488 | Example 1 |
| 127 | (S)-N-(7-(methylamino)-7-oxo-1-(5-(quinolin-6-yl)-1H-imidazol-2-yl)heptyl)thiazole-5-carboxamide | 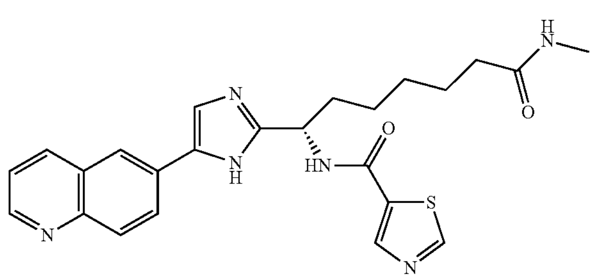 [SMILES: CNC(=O)CCCCC[C@H](NC(=O)c1cncs1)c1ncc(-c2ccc3ncccc3c2)[nH]1] | 463 | Example 5 |

TABLE 1-continued

| Entry | Compound Name | Structure | Molecular Ion [M + H]+ | Procedure |
|---|---|---|---|---|
| 128 | (S)-N-(7-(methylamino)-7-oxo-1-(5-(quinolin-2-yl)-1H-imidazol-2-yl)heptyl)thiazole-5-carboxamide | 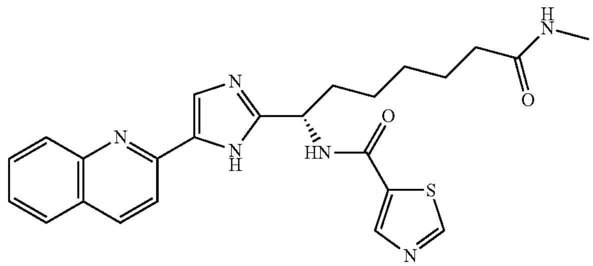 [SMILES: CNC(=O)CCCCC[C@H](NC(=O)c1cncs1)c1ncc(-c2ccc3ccccc3n2)[nH]1] | 463 | Example 5 |
| 129 | (S)-N-(1-(5-(3,4-dichlorophenyl)-1H-imidazol-2-yl)-7-(methylamino)-7-oxoheptyl)thiazole-5-carboxamide | 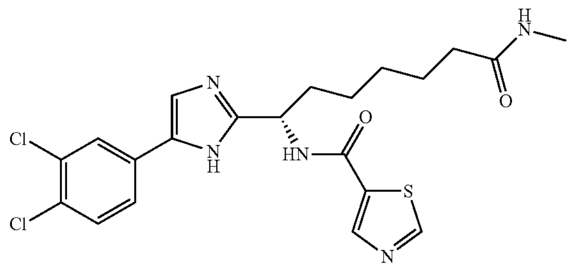 [SMILES: CNC(=O)CCCCC[C@H](NC(=O)c1cncs1)c1ncc(-c2ccc(Cl)c(Cl)c2)[nH]1] | 480, 482 | Example 5 |
| 130 | S)-7-(5-(2-methoxyquinolin-3-yl)-1H-imidazol-2-yl)-N-methyl-7-(3-morpholinopropanamido)heptanamide | 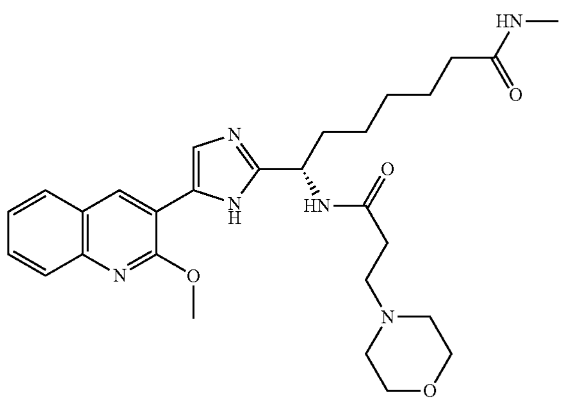 [SMILES: CNC(=O)CCCCC[C@H](NC(=O)CCN1CCOCC1)c1ncc(-c2cc3ccccc3nc2OC)[nH]1] | 523 | Example 1 |
| 131 | (S)-7-(5-(2-methoxyquinolin-3-yl)-1H-imidazol-2-yl)-N-methyl-7-(3-(4-methylpiperazin-1-yl)propanamido)heptanamide | 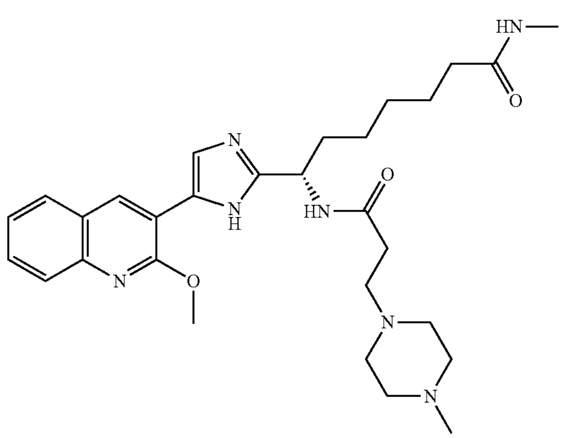 [SMILES: CNC(=O)CCCCC[C@H](NC(=O)CCN1CCN(C)CC1)c1ncc(-c2cc3ccccc3nc2OC)[nH]1] | 536 | Example 1 |

TABLE 1-continued

| Entry | Compound Name | Structure | Molecular Ion [M + H]+ | Procedure |
|---|---|---|---|---|
| 132 | (S)-N-(1-(5-(1-methyl-1H-indol-5-yl)-1H-imidazol-2-yl)-7-(methylamino)-7-oxoheptyl)thiazole-5-carboxamide | 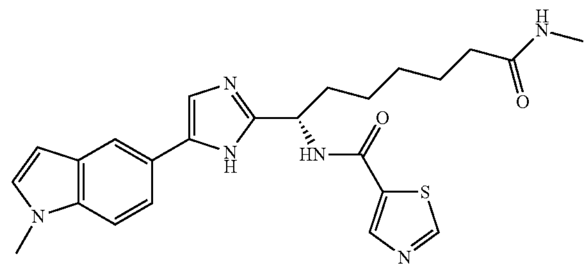 [SMILES: CNC(=O)CCCCC[C@H](NC(=O)c1cncs1)c1ncc(-c2ccc3c(ccn3C)c2)[nH]1] | 465 | Example 4 |
| 133 | (S)-N-(1-(5-(2-methoxyquinolin-3-yl)-1H-imidazol-2-yl)-7-(methylamino)-7-oxoheptyl)-4-methyltetrahydro-2H-pyran-4-carboxamide | 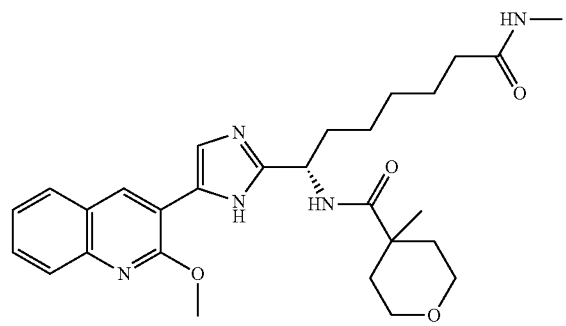 [SMILES: CNC(=O)CCCCC[C@H](NC(=O)C1(C)CCOCC1)c1ncc(-c2cc3ccccc3nc2OC)[nH]1] | 508 | Example 2 |
| 134 | (S)-7-(5-(2-methoxyquinolin-3-yl)-1H-imidazol-2-yl)-N-methyl-7-(3-(1-methyl-1H-pyrazol-4-yl)propanamido)heptanamide | 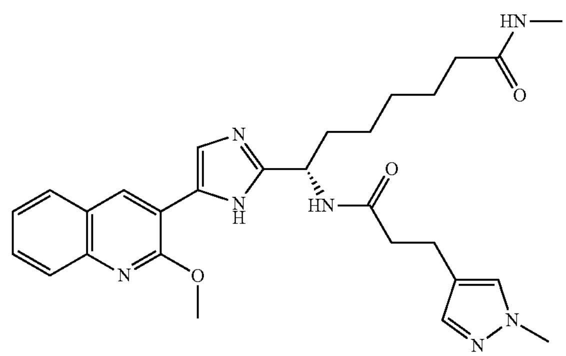 [SMILES: CNC(=O)CCCCC[C@H](NC(=O)CCc1cnn(C)c1)c1ncc(-c2cc3ccccc3nc2OC)[nH]1] | 518 | Example 2 |
| 135 | (S)-N-(1-(5-(2-methoxyquinolin-3-yl)-1H-imidazol-2-yl)-7-(methylamino)-7-oxoheptyl)-1-methyl-1H-pyrazole-3-carboxamide | 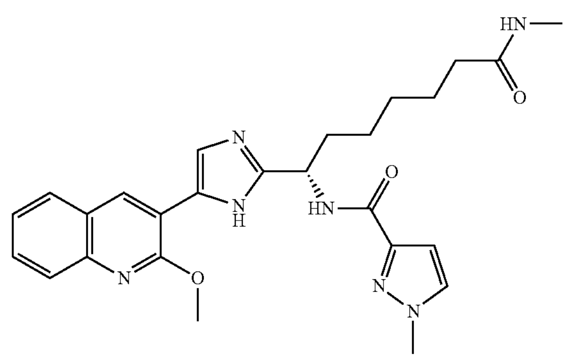 [SMILES: CNC(=O)CCCCC[C@H](NC(=O)c1ccn(C)n1)c1ncc(-c2cc3ccccc3nc2OC)[nH]1] | 490 | Example 2 |
| 136 | (S)-N-(1-(5-(benzofuran-5-yl)-1H-imidazol-2-yl)-7-(methylamino)-7-oxoheptyl)thiazole-5-carboxamide | 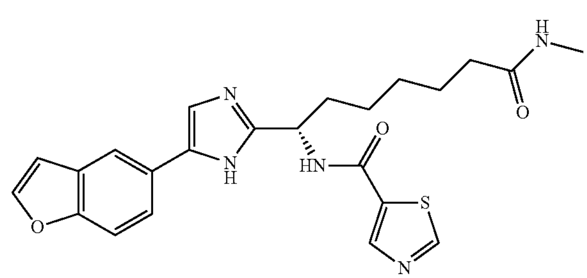 [SMILES: CNC(=O)CCCCC[C@H](NC(=O)c1cncs1)c1ncc(-c2ccc3occc3c2)[nH]1] | 452 | Example 4 |

TABLE 1-continued

| Entry | Compound Name | Structure | Molecular Ion [M + H]+ | Procedure |
|---|---|---|---|---|
| 137 | (S)-N-(1-(5-(1-fluoronaphthalen-2-yl)-1H-imidazol-2-yl)-7-(methylamino)-7-oxoheptyl)thiazole-5-carboxamide | 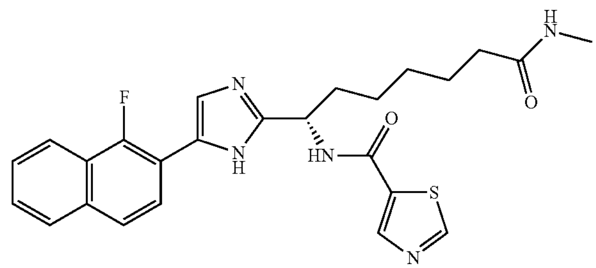 [SMILES: CNC(=O)CCCCC[C@H](NC(=O)c1cncs1)c1ncc(-c2ccc3ccccc3c2F)[nH]1] | 480 | Example 4 |
| 138 | (S)-N-(1-(5-(isoquinolin-6-yl)-1H-imidazol-2-yl)-7-(methylamino)-7-oxoheptyl)thiazole-5-carboxamide | 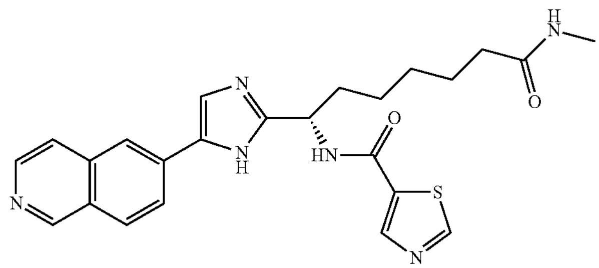 [SMILES: CNC(=O)CCCCC[C@H](NC(=O)c1cncs1)c1ncc(-c2ccc3cnccc3c2)[nH]1] | 463 | Example 4 |
| 139 | (S)-N-(7-(methylamino)-7-oxo-1-(5-(4-(pyridin-2-yl)phenyl)-1H-imidazol-2-yl)heptyl)thiazole-5-carboxamide | 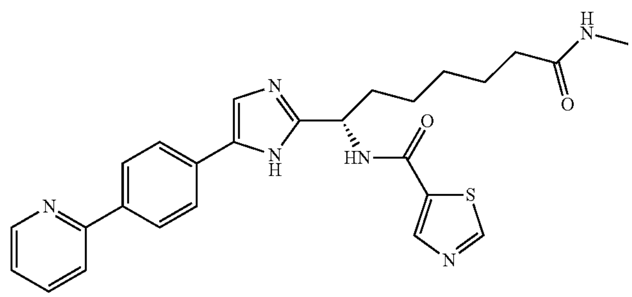 [SMILES: CNC(=O)CCCCC[C@H](NC(=O)c1cncs1)c1ncc(-c2ccc(-c3ccccn3)cc2)[nH]1] | 489 | Example 4 |
| 140 | (S)-N-(1-(5-(1-methyl-2-oxo-1,2-dihydroquinolin-3-yl)-1H-imidazol-2-yl)-7-(methylamino)-7-oxoheptyl)thiazole-5-carboxamide | 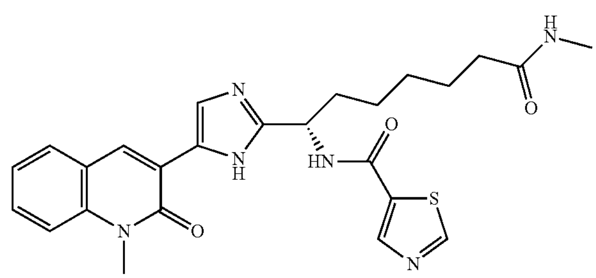 [SMILES: CNC(=O)CCCCC[C@H](NC(=O)c1cncs1)c1ncc(-c2cc3ccccc3n(C)c2=O)[nH]1] | 493 | Example 4 |
| 141 | (S)-N-(1-(5-(4-(1H-pyrazol-1-yl)phenyl)-1H-imidazol-2-yl)-7-(methylamino)-7-oxoheptyl)-2-(pyrrolidin-1-ylmethyl)thiazole-5-carboxamide | 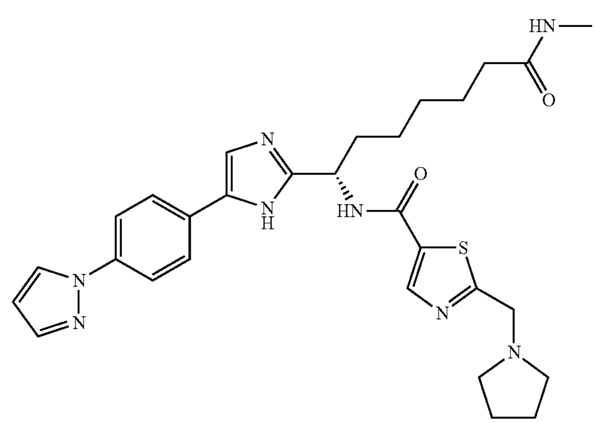 [SMILES: CNC(=O)CCCCC[C@H](NC(=O)c1cnc(CN2CCCC2)s1)c1ncc(-c2ccc(-n3cccn3)cc2)[nH]1] | 561 | Example 1 |

TABLE 1-continued

| Entry | Compound Name | Structure | Molecular Ion [M + H]+ | Procedure |
|---|---|---|---|---|
| 142 | (S)-7-(5-(4-(1H-pyrazol-1-yl)phenyl)-1H-imidazol-2-yl)-7-(3-(benzo[d]thiazol-2-yl)propanamido)-N-methylheptanamide | 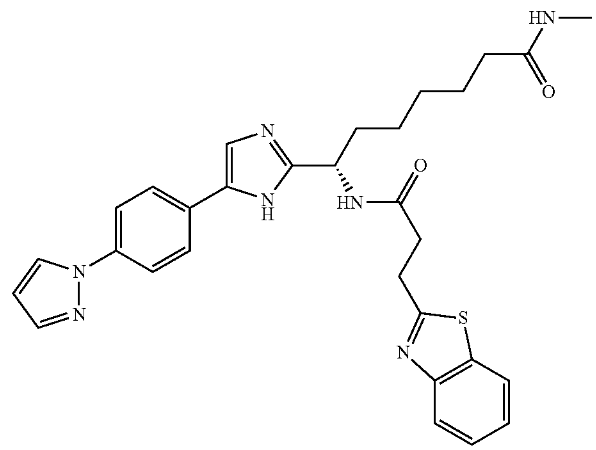 [SMILES: CNC(=O)CCCCC[C@H](NC(=O)CCc1nc2ccccc2s1)c1ncc(-c2ccc(-n3cccn3)cc2)[nH]1] | 556 | Example 1 |
| 143 | (S)-N-(7-(methylamino)-1-(5-(naphthalen-2-yl)-1H-imidazol-2-yl)-7-oxoheptyl)imidazo[1,2-a]pyridine-2-carboxamide | 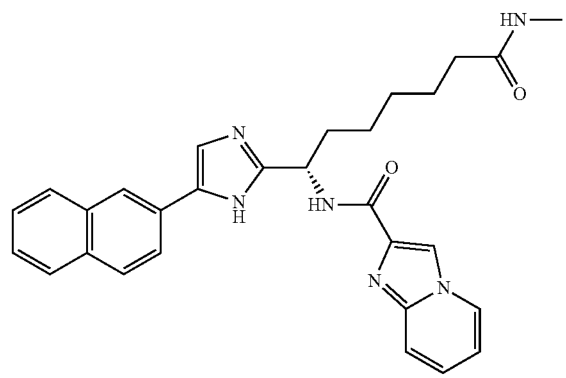 [SMILES: CNC(=O)CCCCC[C@H](NC(=O)c1cn2ccccc2n1)c1ncc(-c2ccc3ccccc3c2)[nH]1] | 495 | Example 1 |
| 144 | 2,2-difluoro-N-((S)-1-(5-(isoquinolin-7-yl)-1H-imidazol-2-yl)-7-(methylamino)-7-oxoheptyl)cyclobutane carboxamide | 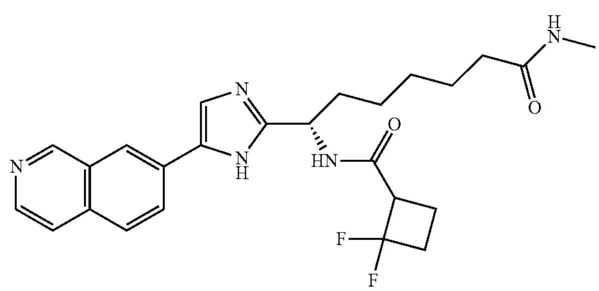 [SMILES: CNC(=O)CCCCC[C@H](NC(=O)C1CCC1(F)F)c1ncc(-c2ccc3ccncc3c2)[nH]1] | 470 | Example 1 |
| 145 | (S)-7-(2-(imidazo[2,1-b]thiazol-3-yl)acetamido)-N-methyl-7-(5-(4-(1-methyl-1H-pyrazol-3-yl)phenyl)-1H-imidazol-2-yl)heptanamide | 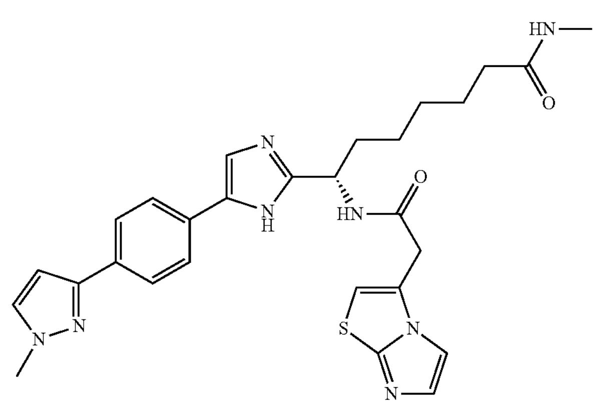 [SMILES: CNC(=O)CCCCC[C@H](NC(=O)Cc1csc2nccn12)c1ncc(-c2ccc(-c3ccn(C)n3)cc2)[nH]1] | 545 | Example 1 |

TABLE 1-continued

| Entry | Compound Name | Structure | Molecular Ion [M + H]+ | Procedure |
|---|---|---|---|---|
| 146 | (S)-N-(1-(5-(benzofuran-7-yl)-1H-imidazol-2-yl)-7-(methylamino)-7-oxoheptyl)thiazole-5-carboxamide | 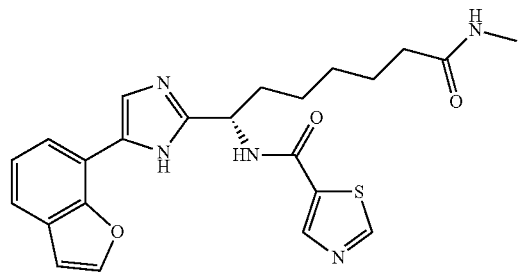 [SMILES: CNC(=O)CCCCC[C@H](NC(=O)c1cncs1)c1ncc(-c2cccc3ccoc23)[nH]1] | 452 | Example 4 |
| 147 | (S)-1-methyl-N-((S)-7-(methylamino)-1-(5-(naphthalen-2-yl)-1H-imidazol-2-yl)-7-oxoheptyl)pyrrolidine-3-carboxamide | 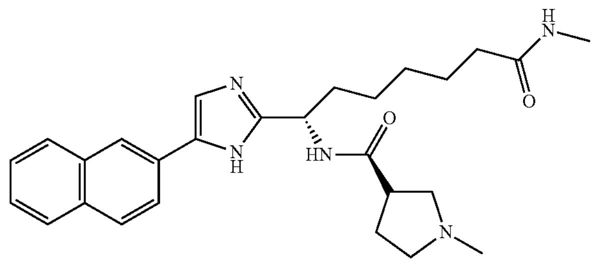 | 462 | Example 1 |
| 148 | (S)-7-(3-(2-ethyl-1H-benzo[d]imidazol-1-yl)propanamido)-N-methyl-7-(5-(naphthalen-2-yl)-1H-imidazol-2-yl)heptanamide | 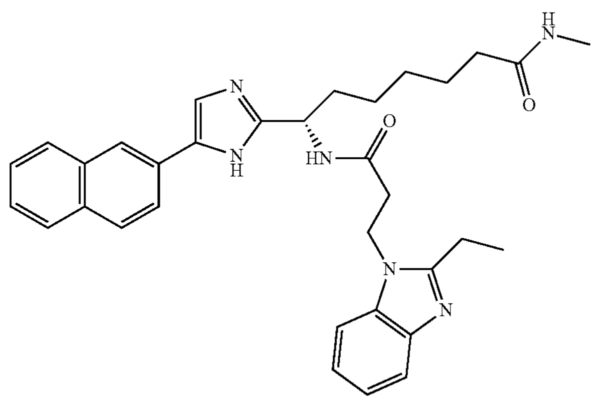 [SMILES: CCc1nc2ccccc2n1CCC(=O)N[C@@H](CCCCCC(=O)NC)c1ncc(-c2ccc3ccccc3c2)[nH]1] | 551 | Example 1 |
| 149 | S)-N-methyl-7-(5-(naphthalen-2-yl)-1H-imidazol-2-yl)-7-(2-(2-oxoquinazolin-1(2H)-yl)acetamido)heptanamide | 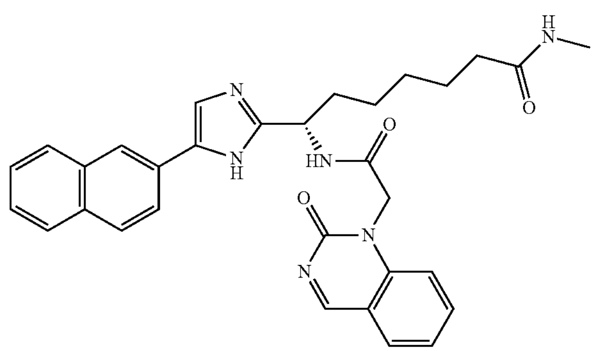 [SMILES: CNC(=O)CCCCC[C@H](NC(=O)Cn1c(=O)ncc2ccccc21)c1ncc(-c2ccc3ccccc3c2)[nH]1] | 537 | Example 1 |
| 150 | (S)-N-(7-(methylamino)-7-oxo-1-(5-(quinolin-6-yl)-1H-imidazol-2-yl)heptyl)quinuclidine-4-carboxamide | 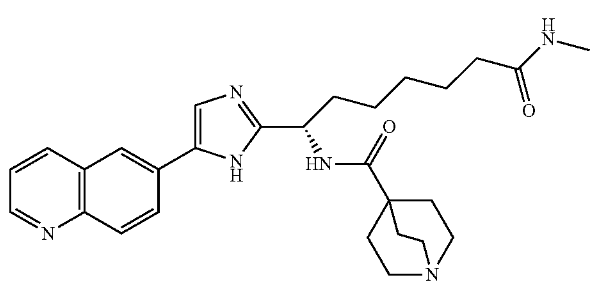 [SMILES: CNC(=O)CCCCC[C@H](NC(=O)C12CCN(CC1)CC2)c1ncc(-c2ccc3ncccc3c2)[nH]1] | 489 | Example 5 |

TABLE 1-continued

| Entry | Compound Name | Structure | Molecular Ion [M + H]+ | Procedure |
|---|---|---|---|---|
| 151 | (S)-N-(1-(5-(6-methoxynaphthalen-2-yl)-1H-imidazol-2-yl)-7-(methylamino)-7-oxoheptyl)quinuclidine-4-carboxamide | 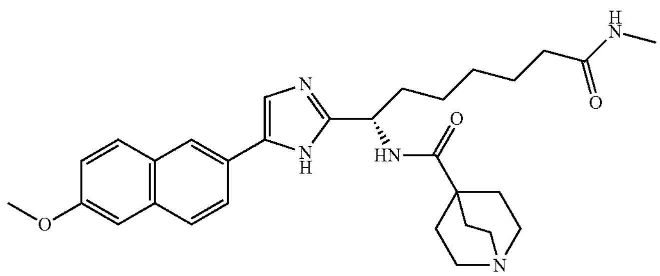 | 518 | Example 5 |
| 152 | (S)-N-(1-(5-(6-fluoronaphthalen-2-yl)-1H-imidazol-2-yl)-7-(methylamino)-7-oxoheptyl)quinuclidine-4-carboxamide | 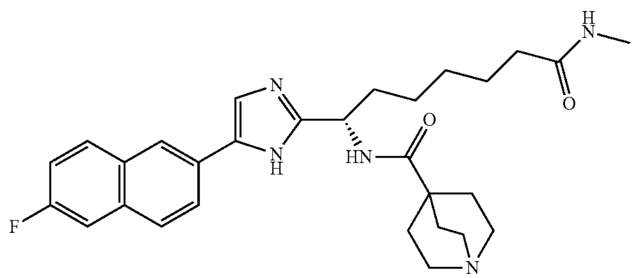 [SMILES: CNC(=O)CCCCC[C@H](NC(=O)C12CCN(CC1)CC2)c1ncc(-c2ccc3cc(F)ccc3c2)[nH]1] | 506 | Example 1 |
| 153 | (S)-7-(2-(6,7-dihydro-5H-thiazolo[3,2-a]pyrimidin-3-yl)acetamido)-7-(5-(isoquinolin-7-yl)-1H-imidazol-2-yl)-N-methylheptanamide | 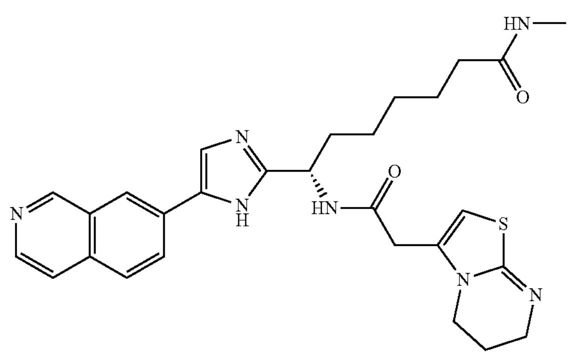 [SMILES: CNC(=O)CCCCC[C@H](NC(=O)CC1=CSC2=NCCCN12)c1ncc(-c2ccc3ccncc3c2)[nH]1] | 532 | Example 1 |
| 154 | (S)-N-(1-(5-(2-methoxyquinolin-3-yl)-1H-imidazol-2-yl)-7-(methylamino)-7-oxoheptyl)-3-(1H-pyrazol-1-yl)benzamide | 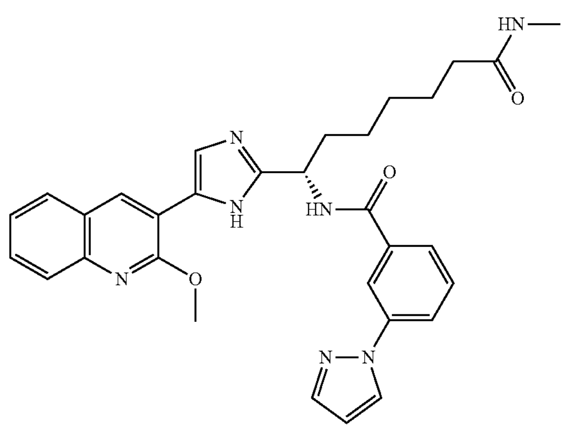 [SMILES: CNC(=O)CCCCC[C@H](NC(=O)c1cccc(-n2cccn2)c1)c1ncc(-c2cc3ccccc3nc2OC)[nH]1] | 552 | Example 2 |

TABLE 1-continued

| Entry | Compound Name | Structure | Molecular Ion [M + H]+ | Procedure |
|---|---|---|---|---|
| 155 | (S)-7-(2-(1H-1,2,3-triazol-1-yl)acetamido)-7-(5-(1H-indazol-5-yl)-1H-imidazol-2-yl)-N-methylheptanamide | 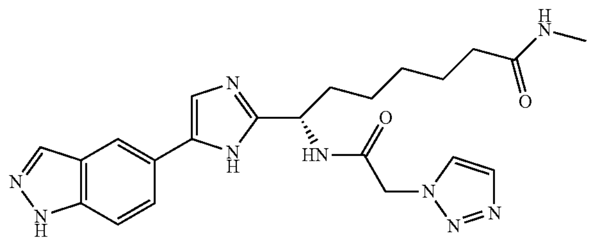 [SMILES: CNC(=O)CCCCC[C@H](NC(=O)Cn1ccnn1)c1ncc(-c2ccc3[nH]ncc3c2)[nH]1] | 450 | Example 5 |
| 156 | (S)-N-(1-(5-(4-(1-methyl-1H-pyrazol-3-yl)phenyl)-1H-imidazol-2-yl)-7-(methylamino)-7-oxoheptyl)thiazole-5-carboxamide | 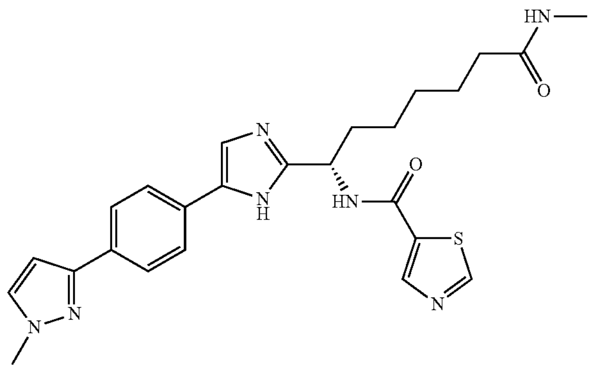 | 492 | Example 4 |
| 157 | (S)-N-(1-(5-(1H-pyrazolo[3,4-b]pyridin-5-yl)-1H-imidazol-2-yl)-7-(methylamino)-7-oxoheptyl)thiazole-5-carboxamide | 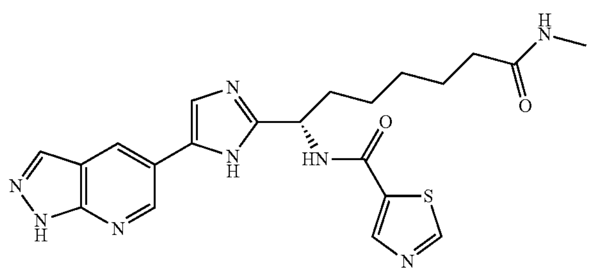 [SMILES: CNC(=O)CCCCC[C@H](NC(=O)c1cncs1)c1ncc(-c2cnc3[nH]ncc3c2)[nH]1] | 453 | Example 4 |
| 158 | (S)-N-(1-(5-(1H-indazol-5-yl)-1H-imidazol-2-yl)-7-(methylamino)-7-oxoheptyl)thiazole-5-carboxamide | 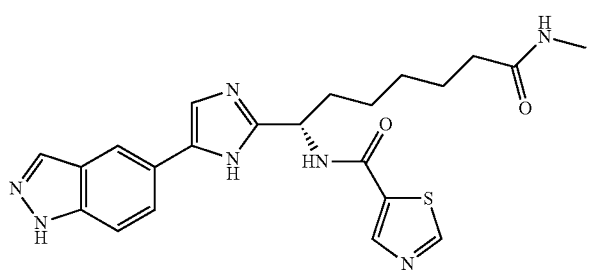 [SMILES: CNC(=O)CCCCC[C@H](NC(=O)c1cncs1)c1ncc(-c2ccc3[nH]ncc3c2)[nH]1] | 452 | Example 4 |
| 159 | (S)-N-(1-(5-(benzo[b]thiophen-5-yl)-1H-imidazol-2-yl)-7-(methylamino)-7-oxoheptyl)thiazole-5-carboxamide | 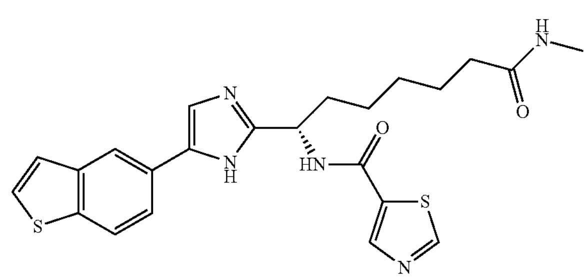 | 468 | Example 4 |

TABLE 1-continued

| Entry | Compound Name | Structure | Molecular Ion [M + H]+ | Procedure |
|---|---|---|---|---|
| 160 | S)-N-(1-(5-(4-(1H-pyrazol-1-yl)phenyl)-1H-imidazol-2-yl)-7-(methylamino)-7-oxoheptyl)-1-methylpiperidine-4-carboxamide | 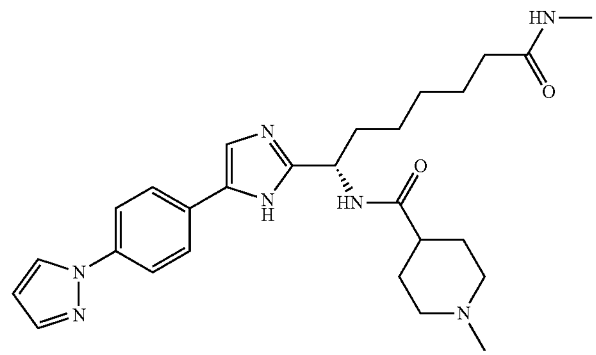 [SMILES: CNC(=O)CCCCC[C@H](NC(=O)C1CCN(C)CC1)c1ncc(-c2ccc(-n3cccn3)cc2)[nH]1] | 492 | Example 1 |
| 161 | (S)-7-(5-(4-(1H-pyrazol-1-yl)phenyl)-1H-imidazol-2-yl)-7-(2-(imidazo[1,2-a]pyridin-3-yl)acetamido)-N-methylheptanamide | 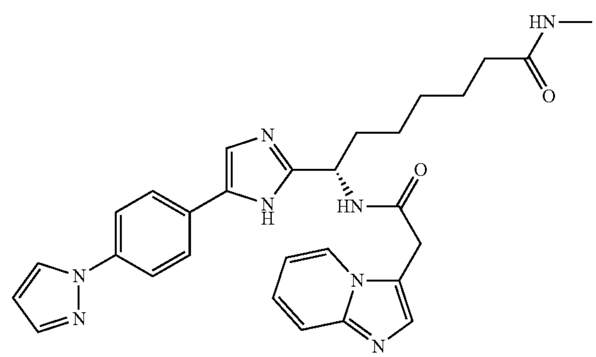 [SMILES: CNC(=O)CCCCC[C@H](NC(=O)Cc1cnc2ccccn12)c1ncc(-c2ccc(-n3cccn3)cc2)[nH]1] | 525 | Example 1 |
| 162 | (S)-N-(7-(methylamino)-1-(5-(naphthalen-2-yl)-1H-imidazol-2-yl)-7-oxoheptyl)imidazo[2,1-b]thiazole-6-carboxamide | 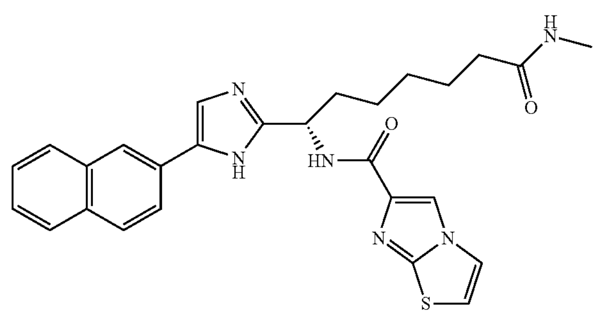 [SMILES: CNC(=O)CCCCC[C@H](NC(=O)c1cn2ccsc2n1)c1ncc(-c2ccc3ccccc3c2)[nH]1] | 501 | Example 1 |
| 163 | (S)-N-methyl-7-(2-(4-methylpiperazin-1-yl)acetamido)-7-(5-(naphthalen-2-yl)-1H-imidazol-2-yl)heptanamide | 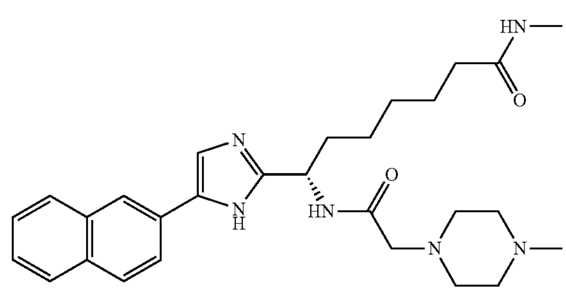 [SMILES: CNC(=O)CCCCC[C@H](NC(=O)CN1CCN(C)CC1)c1ncc(-c2ccc3ccccc3c2)[nH]1] | 491 | Example 1 |

TABLE 1-continued

| Entry | Compound Name | Structure | Molecular Ion [M + H]+ | Procedure |
|---|---|---|---|---|
| 164 | N-((S)-7-(methylamino)-1-(5-(naphthalen-2-yl)-1H-imidazol-2-yl)-7-oxoheptyl)-5-oxopyrrolidine-3-carboxamide | 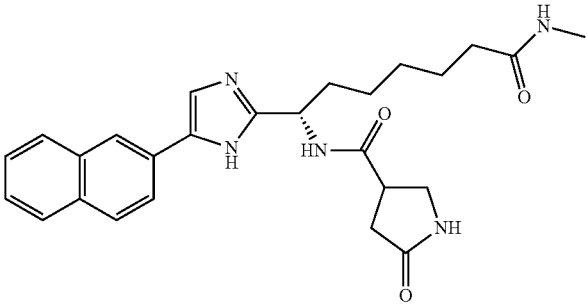 [SMILES: CNC(=O)CCCCC[C@H](NC(=O)C1CNC(=O)C1)c1ncc(-c2ccc3ccccc3c2)[nH]1] | 462 | Example 1 |
| 165 | (S)-7-(5-(isoquinolin-7-yl)-1H-imidazol-2-yl)-N-methyl-7-(3-(5-methyl-4H-1,2,4-triazol-3-yl)propanamido)heptanamide | 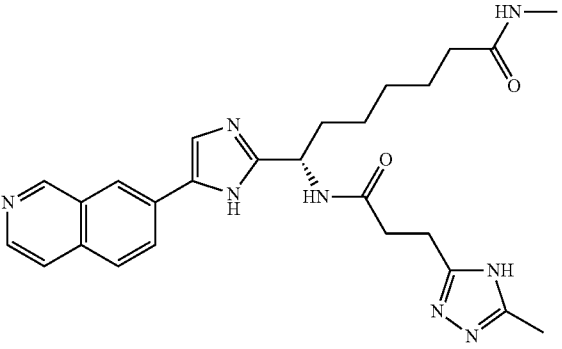 [SMILES: CNC(=O)CCCCC[C@H](NC(=O)CCc1nnc(C)[nH]1)c1ncc(-c2ccc3ccncc3c2)[nH]1] | 489 | Example 1 |
| 166 | (S)-7-(2-(imidazo[2,1-b]thiazol-6-yl)acetamido)-7-(5-(isoquinolin-7-yl)-1H-imidazol-2-yl)-N-methylheptanamide | 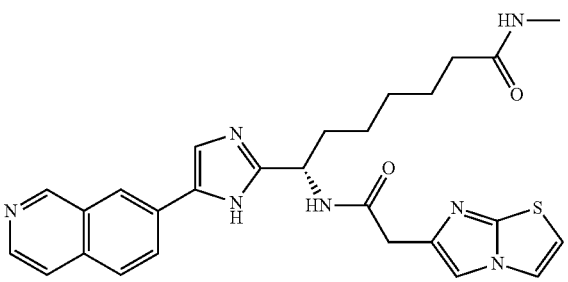 [SMILES: CNC(=O)CCCCC[C@H](NC(=O)Cc1cn2ccsc2n1)c1ncc(-c2ccc3ccncc3c2)[nH]1] | 516 | Example 1 |
| 167 | (S)-7-(2-(2H-indazol-2-yl)acetamido)-N-methyl-7-(5-(4-(1-methyl-1H-pyrazol-3-yl)phenyl)-1H-imidazol-2-yl)heptanamide | 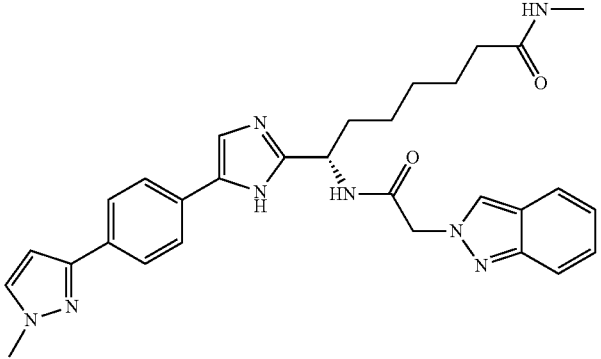 [SMILES: CNC(=O)CCCCC[C@H](NC(=O)Cn1cc2ccccc2n1)c1ncc(-c2ccc(-c3ccn(C)n3)cc2)[nH]1] | 539 | Example 1 |

TABLE 1-continued

| Entry | Compound Name | Structure | Molecular Ion [M + H]+ | Procedure |
|---|---|---|---|---|
| 168 | N-((S)-1-(5-(4-(1-methyl-1H-pyrazol-3-yl)phenyl)-1H-imidazol-2-yl)-7-(methylamino)-7-oxoheptyl)-2-(pyridin-4-yl)cyclopropanecarboxamide | 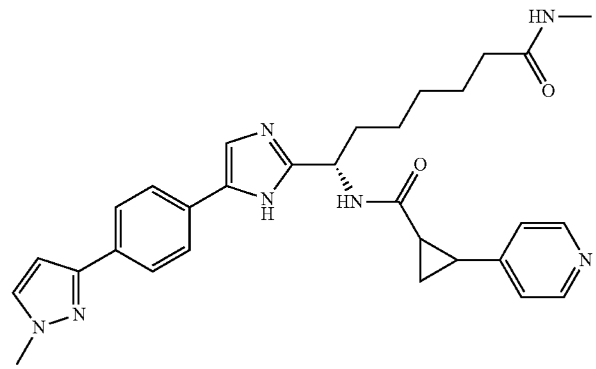 [SMILES: CNC(=O)CCCCC[C@H](NC(=O)C1CC1c1ccncc1)c1ncc(-c2ccc(-c3ccn(C)n3)cc2)[nH]1] | 526 | Example 1 |
| 169 | (S)-N-methyl-7-(2-(3-methyl-1H-pyrazol-1-yl)acetamido)-7-(5-(4-(1-methyl-1H-pyrazol-3-yl)phenyl)-1H-imidazol-2-yl)heptanamide | 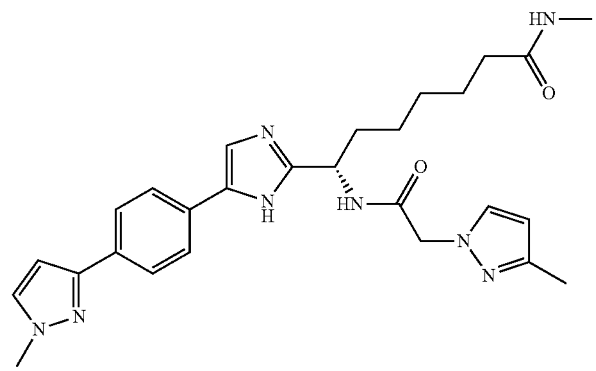 [SMILES: CNC(=O)CCCCC[C@H](NC(=O)Cn1ccc(C)n1)c1ncc(-c2ccc(-c3ccn(C)n3)cc2)[nH]1] | 503 | Example 1 |
| 170 | (S)-N-(1-(5-(4-(1H-pyrazol-1-yl)phenyl)-1H-imidazol-2-yl)-7-(methylamino)-7-oxoheptyl)thiazole-5-carboxamide | 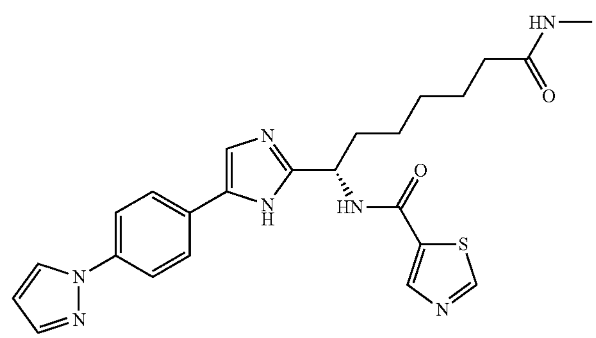 [SMILES: CNC(=O)CCCCC[C@H](NC(=O)c1cncs1)c1ncc(-c2ccc(-n3cccn3)cc2)[nH]1] | 478 | Example 4 |
| 171 | (S)-N-(1-(5-(1H-indol-6-yl)-1H-imidazol-2-yl)-7-(methylamino)-7-oxoheptyl)thiazole-5-carboxamide | 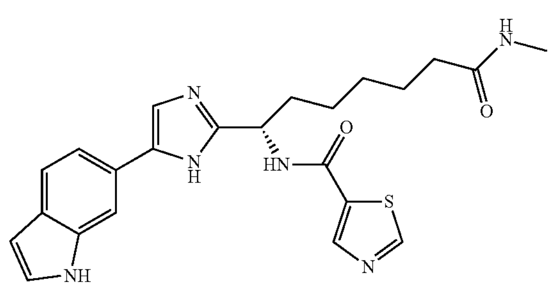 [SMILES: CNC(=O)CCCCC[C@H](NC(=O)c1cncs1)c1ncc(-c2ccc3cc[nH]c3c2)[nH]1] | 451 | Example 4 |

TABLE 1-continued

| Entry | Compound Name | Structure | Molecular Ion [M + H]+ | Procedure |
|---|---|---|---|---|
| 172 | (S)-N-(7-(methylamino)-1-(5-(naphthalen-2-yl)-1H-imidazol-2-yl)-7-oxoheptyl)nicotinamide | 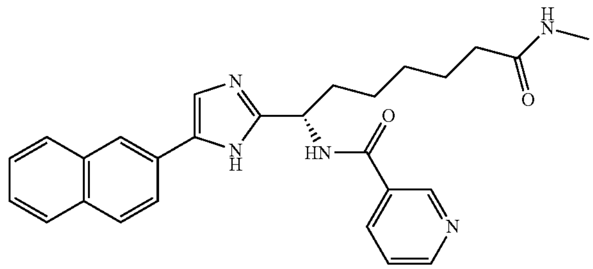 [SMILES: CNC(=O)CCCCC[C@H](NC(=O)c1cccnc1)c1ncc(-c2ccc3ccccc3c2)[nH]1] | 456 | Example 1 |
| 173 | 1-ethyl-N-((S)-7-(methylamino)-1-(5-(naphthalen-2-yl)-1H-imidazol-2-yl)-7-oxoheptyl)piperidine-3-carboxamide | 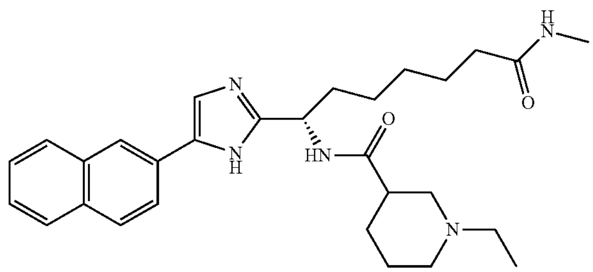 [SMILES: CCN1CCCC(C(=O)N[C@@H](CCCCCC(=O)NC)c2ncc(-c3ccc4ccccc4c3)[nH]2)C1] | 490 | Example 1 |
| 174 | (S)-7-(2-(dimethylamino)acetamido)-7-(5-(2-methoxyquinolin-3-yl)-1H-imidazol-2-yl)-N-methylheptanamide | 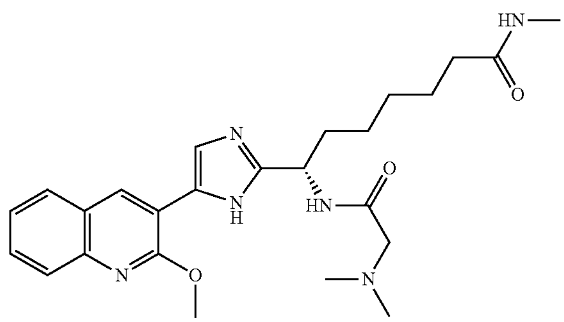 [SMILES: CNC(=O)CCCCC[C@H](NC(=O)CN(C)C)c1ncc(-c2cc3ccccc3nc2OC)[nH]1] | 467 | Example 1 |
| 175 | (S)-7-(3-(1H-1,2,4-triazol-1-yl)propanamido)-7-(5-(2-methoxyquinolin-3-yl)-1H-imidazol-2-yl)-N-methylheptanamide | 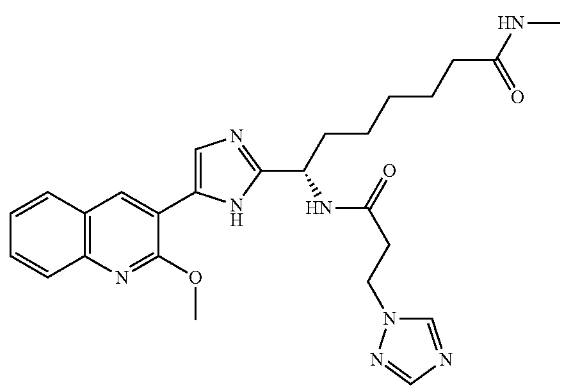 [SMILES: CNC(=O)CCCCC[C@H](NC(=O)CCn1cncn1)c1ncc(-c2cc3ccccc3nc2OC)[nH]1] | 505 | Example 1 |
| 176 | (S)-N-(1-(5-(4-chloro-3-methylphenyl)-1H-imidazol-2-yl)-7-(methylamino)-7-oxoheptyl)quinuclidine-4-carboxamide | 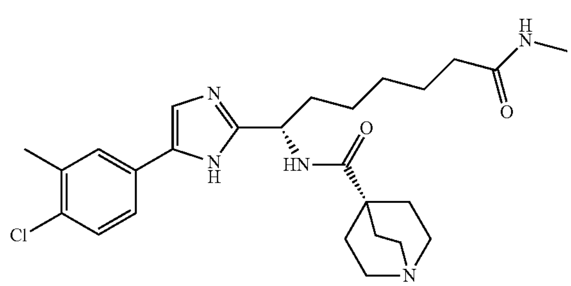 | 484, 486 | Example 5 |

TABLE 1-continued

| Entry | Compound Name | Structure | Molecular Ion [M + H]+ | Procedure |
|---|---|---|---|---|
| 177 | (S)-benzyl (1-(5-(4-(1-methyl-1H-pyrazol-3-yl)phenyl)-1H-imidazol-2-yl)-7-(methylamino)-7-oxoheptyl)carbamate | 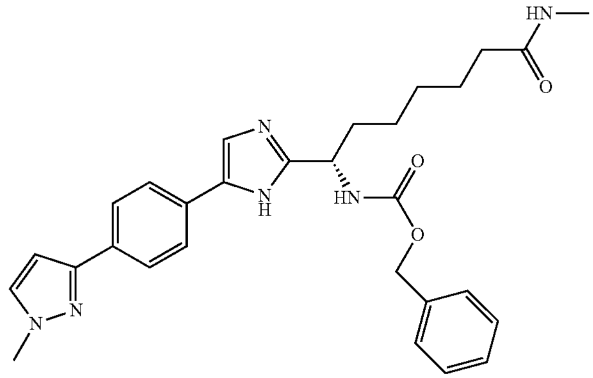 [SMILES: CNC(=O)CCCCC[C@H](NC(=O)OCc1ccccc1)c1ncc(-c2ccc(-c3ccn(C)n3)cc2)[nH]1] | 515 | Example 5 |
| 178 | (S)-4-(2,4-dioxoimidazolidin-1-yl)-N-(1-(5-(2-methoxyquinolin-3-yl)-1H-imidazol-2-yl)-7-(methylamino)-7-oxoheptyl)benzamide | 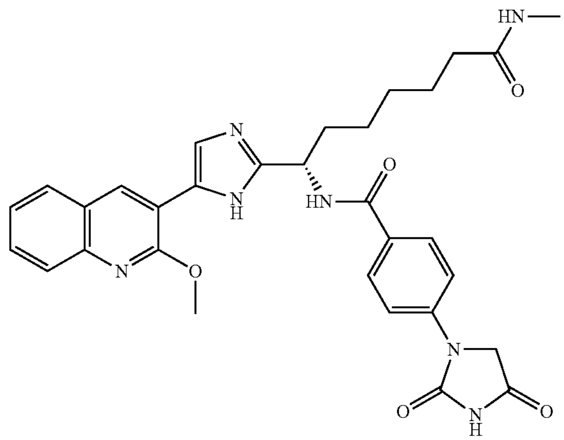 [SMILES: CNC(=O)CCCCC[C@H](NC(=O)c1ccc(N2CC(=O)NC2=O)cc1)c1ncc(-c2cc3ccccc3nc2OC)[nH]1] | 584 | Example 2 |
| 179 | (S)-7-(2-(4H-1,2,4-triazol-4-yl)acetamido)-7-(5-(2-methoxyquinolin-3-yl)-1H-imidazol-2-yl)-N-methylheptanamide | 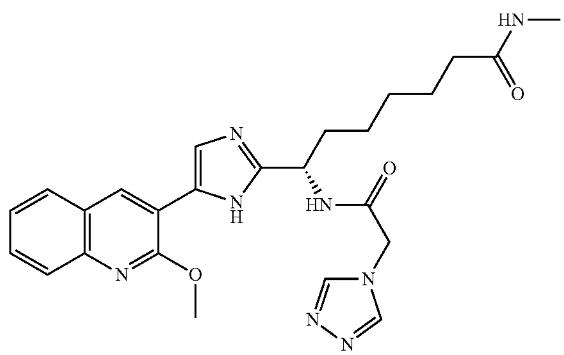 [SMILES: CNC(=O)CCCCC[C@H](NC(=O)Cn1cnnc1)c1ncc(-c2cc3ccccc3nc2OC)[nH]1] | 491 | Example 2 |
| 180 | (S)-7-(5-(2-methoxyquinolin-3-yl)-1H-imidazol-2-yl)-N-methyl-7-(2-(2-phenylthiazol-4-yl)acetamido)heptanamide | 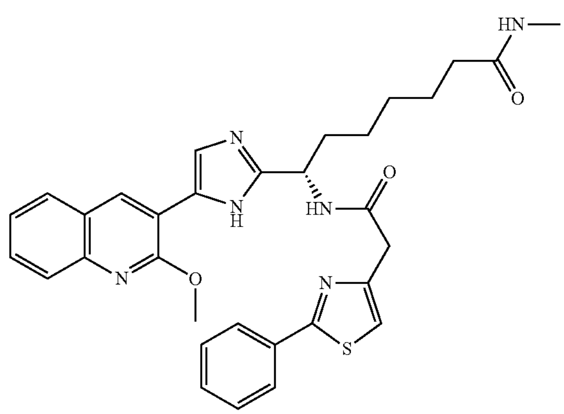 [SMILES: CNC(=O)CCCCC[C@H](NC(=O)Cc1csc(-c2ccccc2)n1)c1ncc(-c2cc3ccccc3nc2OC)[nH]1] | 583 | Example 2 |

TABLE 1-continued

| Entry | Compound Name | Structure | Molecular Ion [M + H]+ | Procedure |
|---|---|---|---|---|
| 181 | (S)-7-(3-(5,7-dimethyl-[1,2,4]triazolo[1,5-a]pyrimidin-6-yl)propanamido)-7-(5-(2-methoxyquinolin-3-yl)-1H-imidazol-2-yl)-N-methylheptanamide | 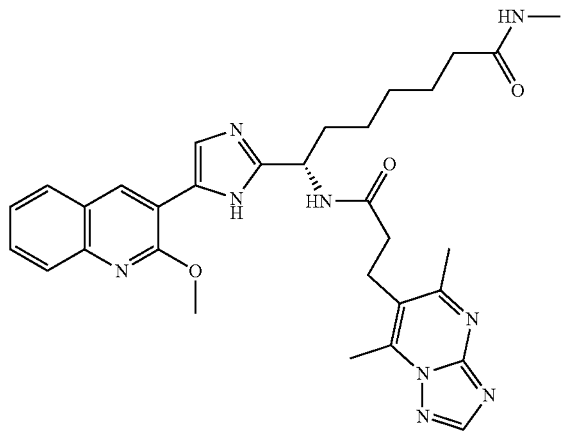 [SMILES: CNC(=O)CCCCC[C@H](NC(=O)CCc1c(C)nc2ncnn2c1C)c1ncc(-c2cc3ccccc3nc2OC)[nH]1] | 584 | Example 2 |
| 182 | N-((S)-1-(5-(2-methoxyquinolin-3-yl)-1H-imidazol-2-yl)-7-(methylamino)-7-oxoheptyl)tetrahydrofuran-2-carboxamide | 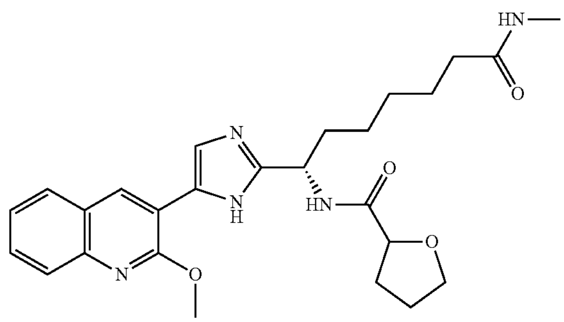 [SMILES: CNC(=O)CCCCC[C@H](NC(=O)C1CCCO1)c1ncc(-c2cc3ccccc3nc2OC)[nH]1] | 480 | Example 2 |
| 183 | (S)-N-(1-(5-(3-(1H-pyrazol-3-yl)phenyl)-1H-imidazol-2-yl)-7-(methylamino)-7-oxoheptyl)thiazole-5-carboxamide | 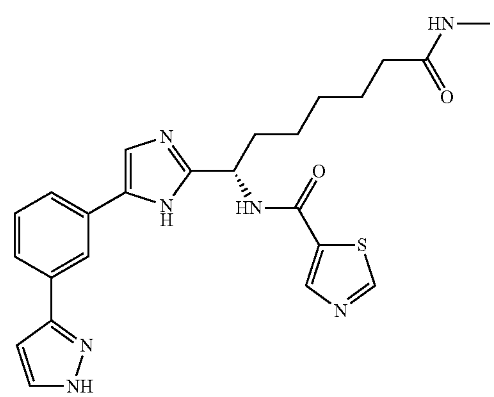 [SMILES: CNC(=O)CCCCC[C@H](NC(=O)c1cncs1)c1ncc(-c2cccc(-c3cc[nH]n3)c2)[nH]1] | 478 | Example 4 |
| 184 | (S)-5-isopropyl-N-(1-(5-(isoquinolin-7-yl)-1H-imidazol-2-yl)-7-(methylamino)-7-oxoheptyl)isoxazole-3-carboxamide | 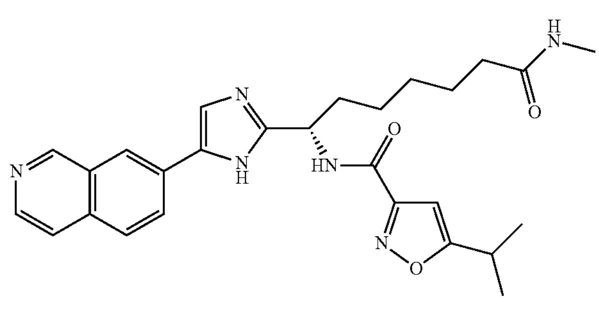 [SMILES: CNC(=O)CCCCC[C@H](NC(=O)c1cc(C(C)C)on1)c1ncc(-c2ccc3ccncc3c2)[nH]1] | 489 | Example 1 |

TABLE 1-continued

| Entry | Compound Name | Structure | Molecular Ion [M + H]+ | Procedure |
|---|---|---|---|---|
| 185 | (S)-N-(7-(methylamino)-7-oxo-1-(5-(3-(trifluoromethyl)isoquinolin-7-yl)-1H-imidazol-2-yl)heptyl)thiazole-5-carboxamide | 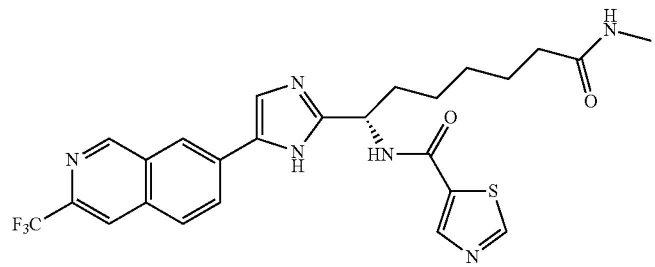 [SMILES: CNC(=O)CCCCC[C@H](NC(=O)c1cncs1)c1ncc(-c2ccc3cc(C(F)(F)F)ncc3c2)[nH]1] | 531 | Example 4 |
| 186 | (S)-N-(1-(5-(1-methyl-1H-indazol-5-yl)-1H-imidazol-2-yl)-7-(methylamino)-7-oxoheptyl)thiazole-5-carboxamide | 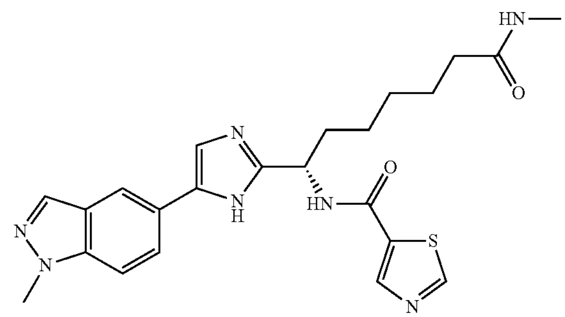 [SMILES: CNC(=O)CCCCC[C@H](NC(=O)c1cncs1)c1ncc(-c2ccc3c(cnn3C)c2)[nH]1] | 466 | Example 4 |
| 187 | (S)-N-(1-(5-(2-methoxy-6-phenylpyridin-3-yl)-1H-imidazol-2-yl)-7-(methylamino)-7-oxoheptyl)thiazole-5-carboxamide | 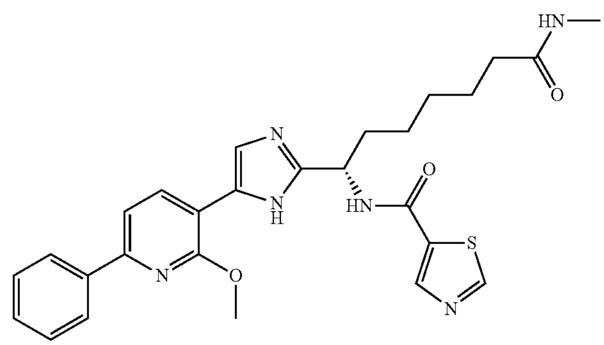 [SMILES: CNC(=O)CCCCC[C@H](NC(=O)c1cncs1)c1ncc(-c2ccc(-c3ccccc3)nc2OC)[nH]1] | 519 | Example 4 |
| 188 | (S)-N-(7-(methylamino)-7-oxo-1-(5-(2-oxo-1,2-dihydroquinolin-3-yl)-1H-imidazol-2-yl)heptyl)thiazole-5-carboxamide | 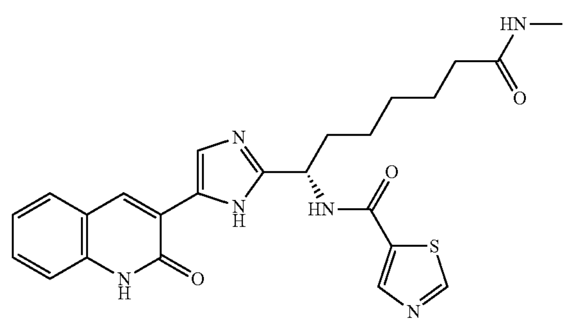 [SMILES: CNC(=O)CCCCC[C@H](NC(=O)c1cncs1)c1ncc(-c2cc3ccccc3[nH]c2=O)[nH]1] | 479 | Example 1 |
| 189 | (S)-N-(1-(5-(6-methoxynaphthalen-2-yl)-1H-imidazol-2-yl)-7-(methylamino)-7-oxoheptyl)thiazole-5-carboxamide | 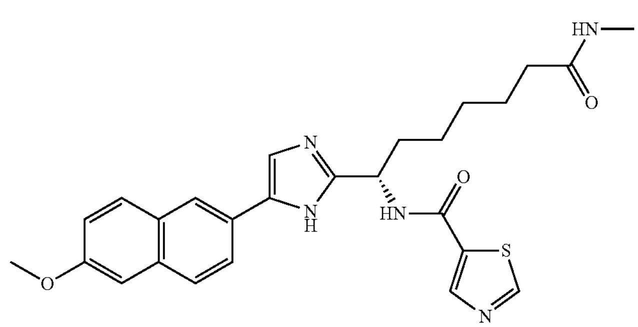 | 492 | Example 4 |

TABLE 1-continued

| Entry | Compound Name | Structure | Molecular Ion [M + H]+ | Procedure |
|---|---|---|---|---|
| 190 | (S)-N-(1-(5-(4-(1H-pyrazol-1-yl)phenyl)-1H-imidazol-2-yl)-7-(methylamino)-7-oxoheptyl)-4-(2,4-dioxoimidazolidin-1-yl)benzamide | 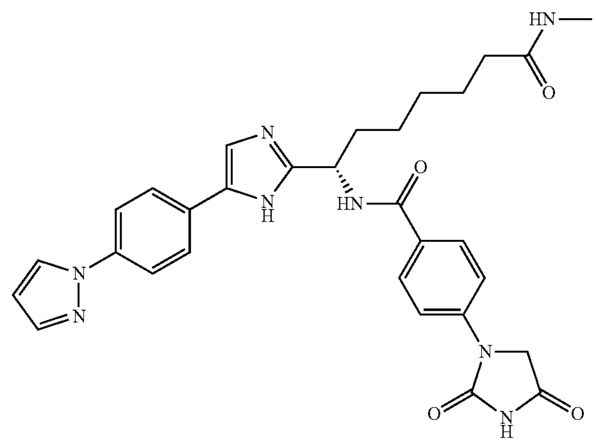 [SMILES: CNC(=O)CCCCC[C@H](NC(=O)c1ccc(N2CC(=O)NC2=O)cc1)c1ncc(-c2ccc(-n3cccn3)cc2)[nH]1] | 569 | Example 1 |
| 191 | (S)-N-(7-(methylamino)-7-oxo-1-(5-(4-(pyridin-3-yl)phenyl)-1H-imidazol-2-yl)heptyl)thiazole-5-carboxamide | 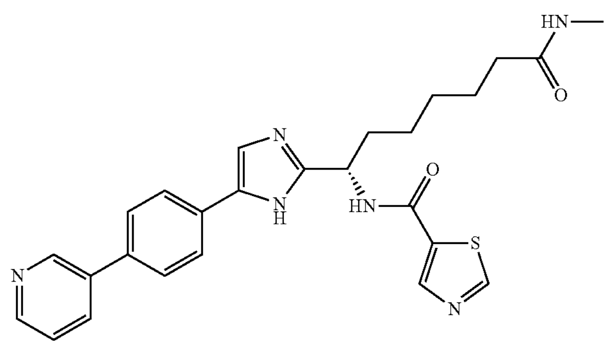 | 489 | Example 4 |
| 192 | (S)-N-(7-(methylamino)-1-(5-(naphthalen-2-yl)-1H-imidazol-2-yl)-7-oxoheptyl)-2-(pyridin-3-yl)thiazole-4-carboxamide | 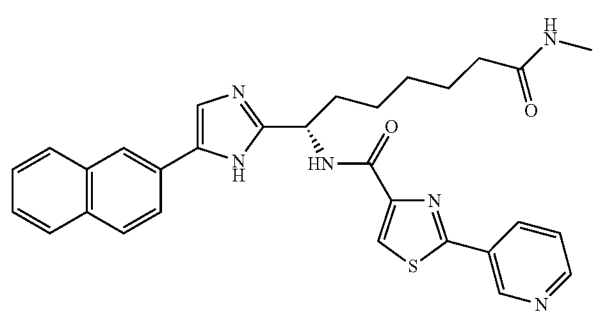 [SMILES: CNC(=O)CCCCC[C@H](NC(=O)c1csc(-c2cccnc2)n1)c1ncc(-c2ccc3ccccc3c2)[nH]1] | 539 | Example 1 |
| 193 | N-((S)-7-(methylamino)-1-(5-(naphthalen-2-yl)-1H-imidazol-2-yl)-7-oxoheptyl)-2-oxo-1,2,3,4-tetrahydroquinoline-4-carboxamide | 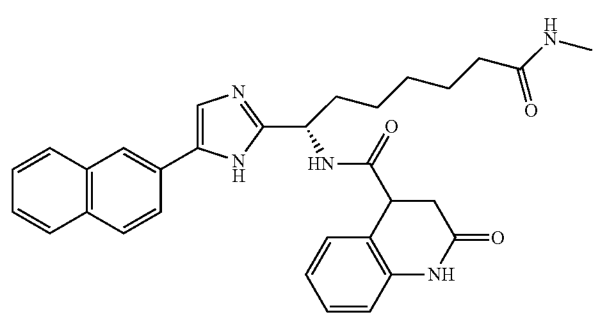 [SMILES: CNC(=O)CCCCC[C@H](NC(=O)C1CC(=O)Nc2ccccc21)c1ncc(-c2ccc3ccccc3c2)[nH]1] | 524 | Example 1 |

TABLE 1-continued

| Entry | Compound Name | Structure | Molecular Ion [M + H]+ | Procedure |
|---|---|---|---|---|
| 194 | (S)-N-methyl-7-(3-(1-methyl-1H-pyrazol-4-yl)propanamido)-7-(5-(naphthalen-2-yl)-1H-imidazol-2-yl)heptanamide | 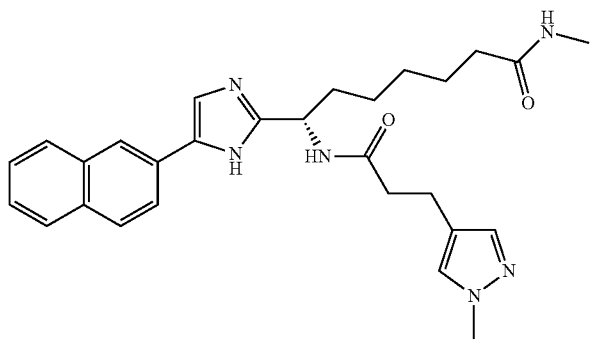 [SMILES: CNC(=O)CCCCC[C@H](NC(=O)CCc1cnn(C)c1)c1ncc(-c2ccc3ccccc3c2)[nH]1] | 487 | Example 1 |
| 195 | (S)-7-(2-(6,7-dihydro-5H-thiazolo[3,2-a]pyrimidin-3-yl)acetamido)-7-(5-(2-methoxyquinolin-3-yl)-1H-imidazol-2-yl)-N-methylheptanamide | 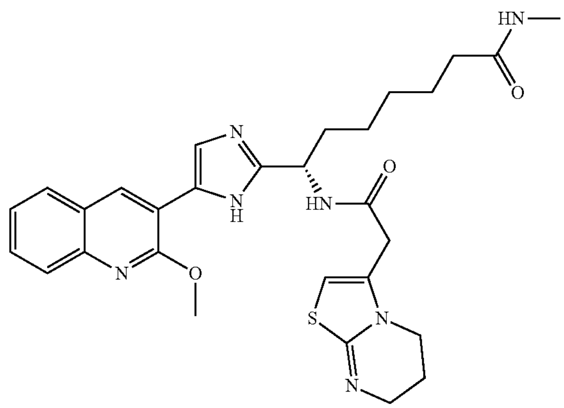 [SMILES: CNC(=O)CCCCC[C@H](NC(=O)CC1=CSC2=NCCCN12)c1ncc(-c2cc3ccccc3nc2OC)[nH]1] | 562 | Example 2 |
| 196 | (S)-7-(2-(6,7-dihydro-5H-thiazolo[3,2-a]pyrimidin-3-yl)acetamido)-N-methyl-7-(5-(naphthalen-2-yl)-1H-imidazol-2-yl)heptanamide | 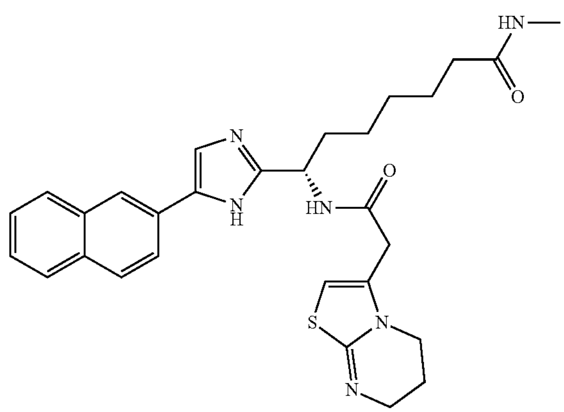 [SMILES: CNC(=O)CCCCC[C@H](NC(=O)CC1=CSC2=NCCCN12)c1ncc(-c2ccc3ccccc3c2)[nH]1] | 531 | Example 1 |
| 197 | (S)-5-methyl-N-(7-(methylamino)-1-(5-(naphthalen-2-yl)-1H-imidazol-2-yl)-7-oxoheptyl)-1,3,4-oxadiazole-2-carboxamide | 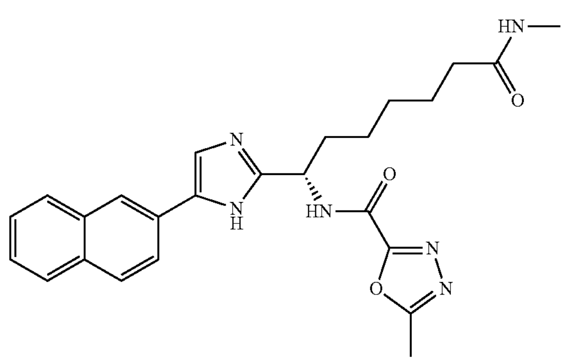 [SMILES: CNC(=O)CCCCC[C@H](NC(=O)c1nnc(C)o1)c1ncc(-c2ccc3ccccc3c2)[nH]1] | 461 | Example 1 |

TABLE 1-continued

| Entry | Compound Name | Molecular Ion [M + H]+ | Procedure |
|---|---|---|---|
| 198 | (S)-N-(7-(methylamino)-7-oxo-1-(5-(2-oxo-1,2-dihydroquinolin-3-yl)-1H-imidazol-2-yl)heptyl)quinuclidine-4-carboxamide | 505 | Example 5 |
| 199 | (S)-N-(7-(methylamino)-7-oxo-1-(5-(5-phenylthiophen-2-yl)-1H-imidazol-2-yl)heptyl)thiazole-5-carboxamide | 494 | Example 4 |
| 200 | (1R,9aR)-N-((S)-1-(5-(isoquinolin-7-yl)-1H-imidazol-2-yl)-7-(methylamino)-7-oxoheptyl)octahydro-1H-quinolizine-1-carboxamide | 517 | Example 1 |
| 201 | (S)-7-(5-(isoquinolin-7-yl)-1H-imidazol-2-yl)-N-methyl-7-(2-(pyrimidin-2-yl)acetamido)heptanamide | 472 | Example 1 |
| 202 | (S)-7-(2-(2H-indazol-2-yl)acetamido)-7-(5-(isoquinolin-7-yl)-1H-imidazol-2-yl)-N-methylheptanamide | 510 | Example 1 |

TABLE 1-continued

| Entry | Compound Name | Structure | Molecular Ion [M + H]+ | Procedure |
|---|---|---|---|---|
| 203 | (S)-N-(1-(5-(4-(1-methyl-1H-pyrazol-3-yl)phenyl)-1H-imidazol-2-yl)-7-(methylamino)-7-oxoheptyl)thiazole-4-carboxamide | 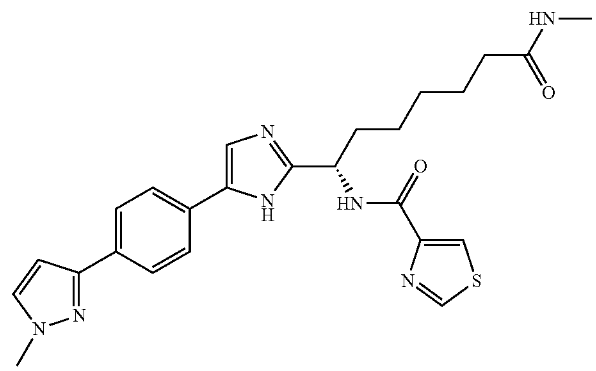 [SMILES: CNC(=O)CCCCC[C@H](NC(=O)c1cscn1)c1ncc(-c2ccc(-c3ccn(C)n3)cc2)[nH]1] | 492 | Example 1 |
| 204 | (S)-N-(1-(5-(4-(1-methyl-1H-pyrazol-3-yl)phenyl)-1H-imidazol-2-yl)-7-(methylamino)-7-oxoheptyl)isothiazole-4-carboxamide | 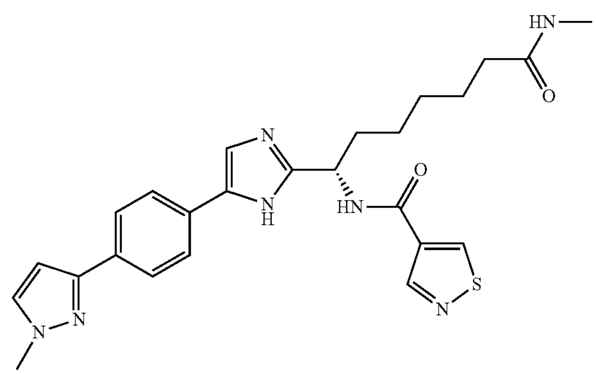 | 492 | Example 1 |
| 205 | (S)-N-methyl-7-(5-(4-(1-methyl-1H-pyrazol-3-yl)phenyl)-1H-imidazol-2-yl)-7-(2-(pyrimidin-2-yl)acetamido)heptanamide | 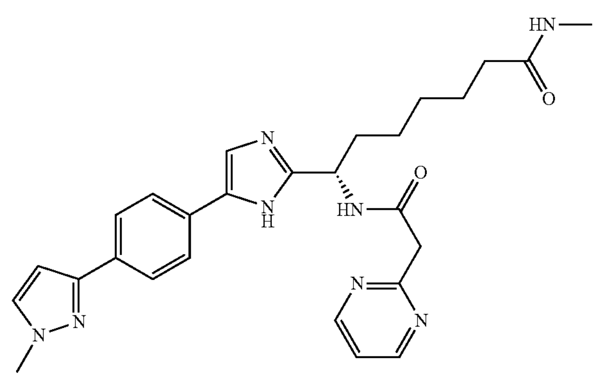 [SMILES: CNC(=O)CCCCC[C@H](NC(=O)Cc1ncccn1)c1ncc(-c2ccc(-c3ccn(C)n3)cc2)[nH]1] | 501 | Example 1 |
| 206 | (S)-N-(1-(5-(3-(1H-pyrazol-1-yl)phenyl)-1H-imidazol-2-yl)-7-(methylamino)-7-oxoheptyl)thiazole-5-carboxamide | 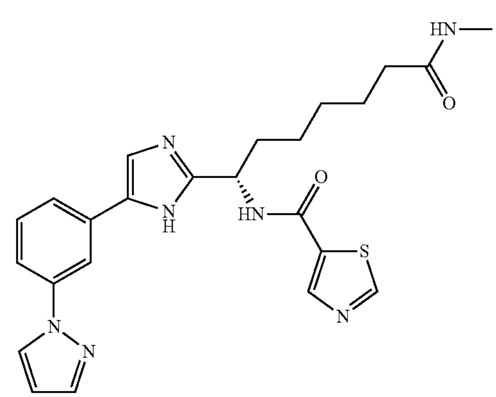 [SMILES: CNC(=O)CCCCC[C@H](NC(=O)c1cncs1)c1ncc(-c2cccc(-n3cccn3)c2)[nH]1] | 478 | Example 4 |

TABLE 1-continued

| Entry | Compound Name | Structure | Molecular Ion [M + H]+ | Procedure |
|---|---|---|---|---|
| 207 | (S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide | 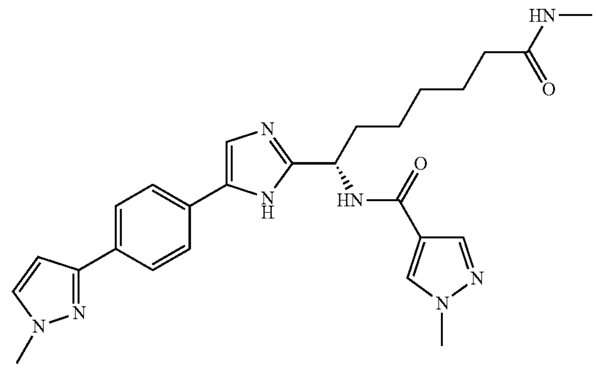 [SMILES: CNC(=O)CCCCC[C@H](NC(=O)c1cnn(C)c1)c1ncc(-c2ccc(-c3ccn(C)n3)cc2)[nH]1] | 489 | Example 5 |
| 208 | (S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-5-carboxamide | 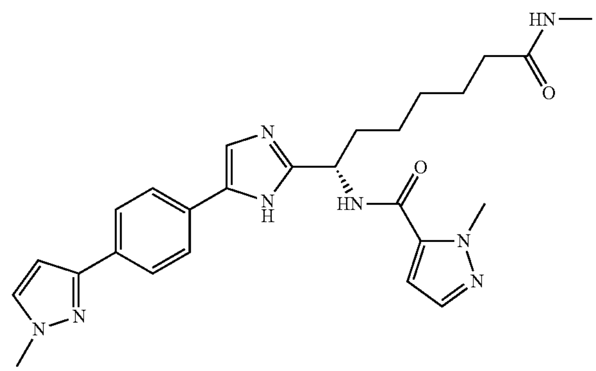 [SMILES: CNC(=O)CCCCC[C@H](NC(=O)c1ccnn1C)c1ncc(-c2ccc(-c3ccn(C)n3)cc2)[nH]1] | 489 | Example 5 |
| 209 | (S)-1-(difluoromethyl)-N-(1-(5-(4-(1-methyl-1H-pyrazol-3-yl)phenyl)-1H-imidazol-2-yl)-7-(methylamino)-7-oxoheptyl)-1H-pyrazole-3-carboxamide | 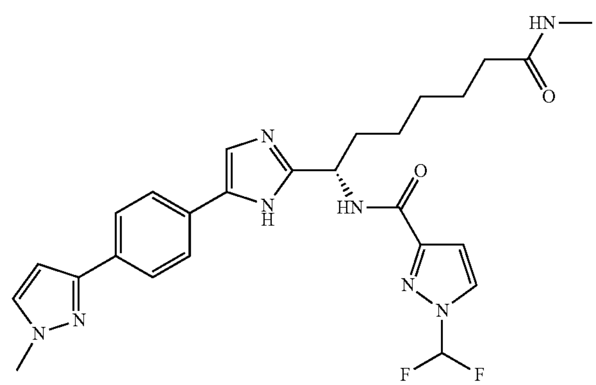 [SMILES: CNC(=O)CCCCC[C@H](NC(=O)c1ccn(C(F)F)n1)c1ncc(-c2ccc(-c3ccn(C)n3)cc2)[nH]1] | 525 | Example 5 |
| 210 | (S)-1,3-dimethyl-N-(1-(5-(4-(1-methyl-1H-pyrazol-3-yl)phenyl)-1H-imidazol-2-yl)-7-(methylamino)-7-oxoheptyl)-1H-pyrazole-5-carboxamide | 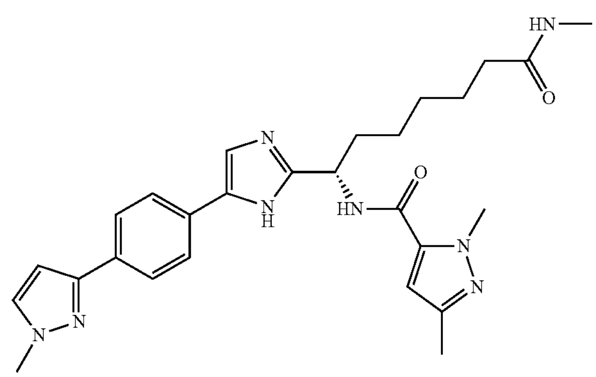 [SMILES: CNC(=O)CCCCC[C@H](NC(=O)c1cc(C)nn1C)c1ncc(-c2ccc(-c3ccn(C)n3)cc2)[nH]1] | 503 | Example 5 |

| Entry | Compound Name | Structure | Molecular Ion [M + H]+ | Procedure |
|---|---|---|---|---|
| 211 | (S)-1,5-dimethyl-N-(1-(5-(4-(1-methyl-1H-pyrazol-3-yl)phenyl)-1H-imidazol-2-yl)-7-(methylamino)-7-oxoheptyl)-1H-pyrazole-3-carboxamide | 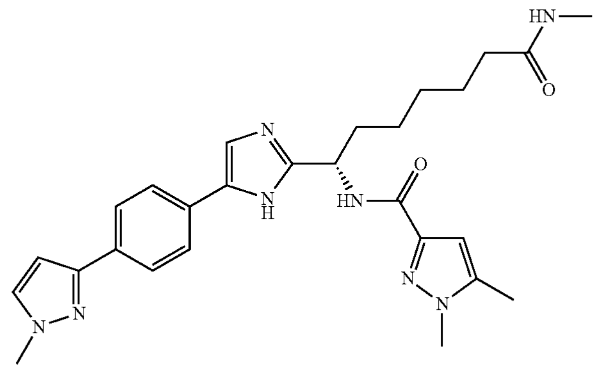 [SMILES: CNC(=O)CCCCC[C@H](NC(=O)c1cc(C)n(C)n1)c1ncc(-c2ccc(-c3ccn(C)n3)cc2)[nH]1] | 503 | Example 5 |
| 212 | (S)-3-(tert-butyl)-1-methyl-N-(1-(5-(4-(1-methyl-1H-pyrazol-3-yl)phenyl)-1H-imidazol-2-yl)-7-(methylamino)-7-oxoheptyl)-1H-pyrazole-5-carboxamide | 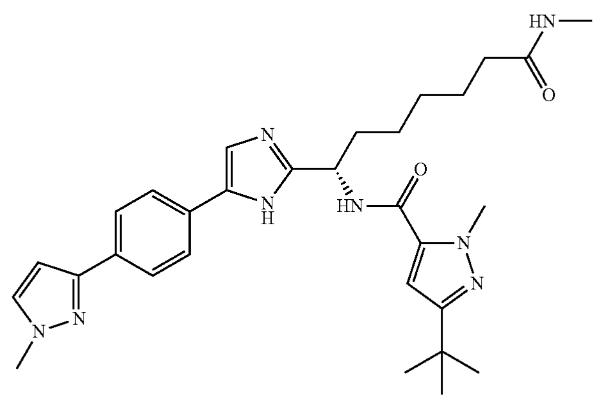 [SMILES: CNC(=O)CCCCC[C@H](NC(=O)c1cc(C(C)(C)C)nn1C)c1ncc(-c2ccc(-c3ccn(C)n3)cc2)[nH]1] | 545 | Example 5 |
| 213 | (S)-N-(7-amino-1-(5-(4-(1-methyl-1H-pyrazol-3-yl)phenyl)-1H-imidazol-2-yl)-7-oxoheptyl)thiazole-5-carboxamide | 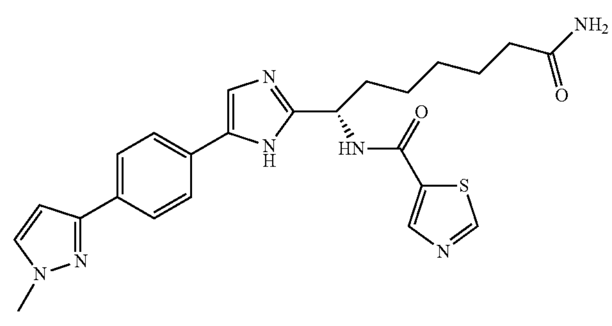 [SMILES: Cn1ccc(-c2ccc(-c3cnc([C@H](CCCCCC(N)=O)NC(=O)c4cncs4)[nH]3)cc2)n1] | 478 | Example 1 |
| 214 | (S)-N-(1-(5-(1-methoxyisoquinolin-7-yl)-1H-imidazol-2-yl)-7-(methylamino)-7-oxoheptyl)thiazole-5-carboxamide | 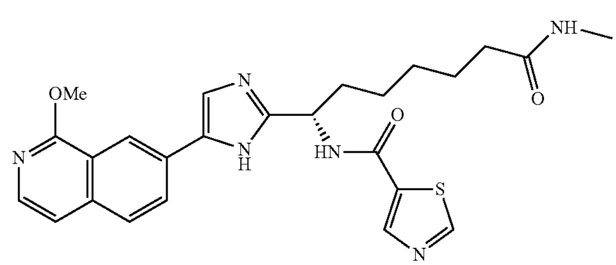 [SMILES: CNC(=O)CCCCC[C@H](NC(=O)c1cncs1)c1ncc(-c2ccc3ccnc(OC)c3c2)[nH]1] | 493 | Example 5 |

TABLE 1-continued

| Entry | Compound Name | Structure | Molecular Ion [M + H]+ | Procedure |
|---|---|---|---|---|
| 215 | (S)-N-(1-(5-(4-(1-methyl-1H-pyrazol-3-yl)phenyl)oxazol-2-yl)-7-(methylamino)-7-oxoheptyl)thiazole-5-carboxamide | 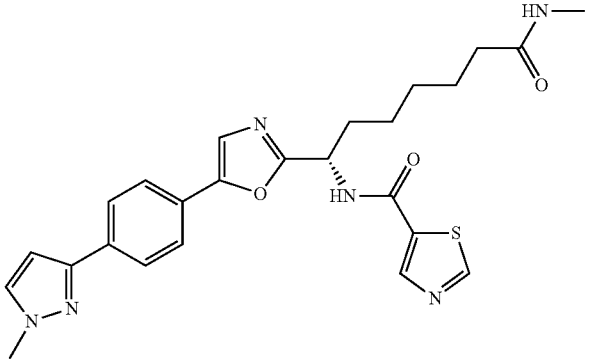 [SMILES: CNC(=O)CCCCC[C@H](NC(=O)c1cncs1)c1ncc(-c2ccc(-c3ccn(C)n3)cc2)o1] | 493 | Example 6 |
| 216 | (S)-1-isopropyl-N-(1-(5-(4-(1-methyl-1H-pyrazol-3-yl)phenyl)oxazol-2-yl)-7-(methylamino)-7-oxoheptyl)-1H-pyrazole-4-carboxamide | 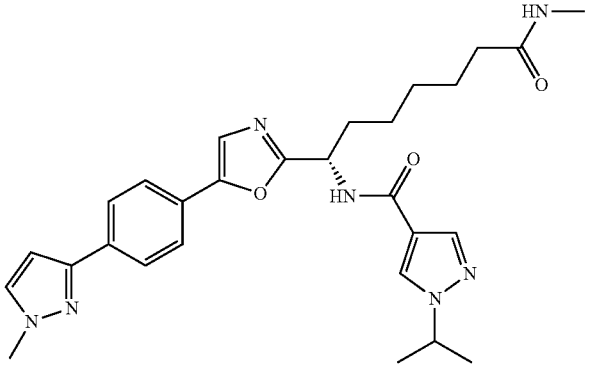 [SMILES: CNC(=O)CCCCC[C@H](NC(=O)c1cnn(C(C)C)c1)c1ncc(-c2ccc(-c3ccn(C)n3)cc2)o1] | 518 | Example 6 |
| 217 | (S)-1-methyl-N-(1-(5-(4-(1-methyl-1H-pyrazol-3-yl)phenyl)oxazol-2-yl)-7-(methylamino)-7-oxoheptyl)-1H-pyrazole-4-carboxamide | 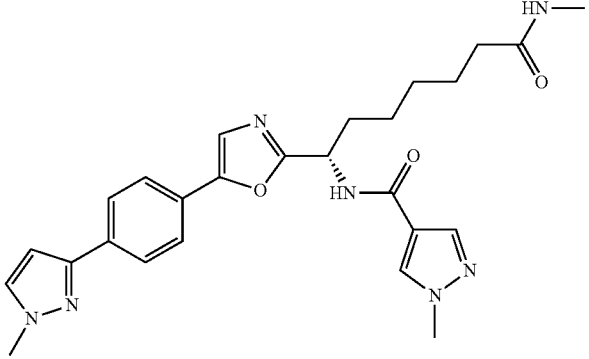 [SMILES: CNC(=O)CCCCC[C@H](NC(=O)c1cnn(C)c1)c1ncc(-c2ccc(-c3ccn(C)n3)cc2)o1] | 490 | Example 6 |
| 218 | (S)-2-methyl-N-(1-(5-(4-(1-methyl-1H-pyrazol-3-yl)phenyl)oxazol-2-yl)-7-(methylamino)-7-oxoheptyl)thiazole-5-carboxamide | 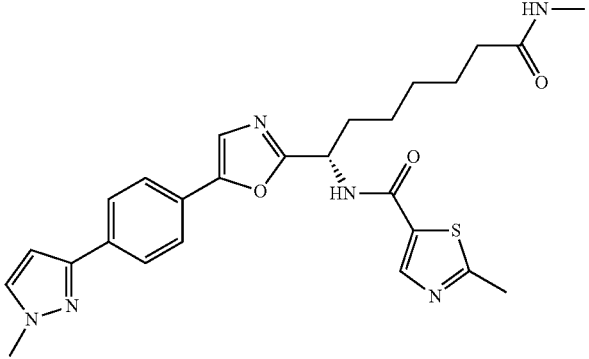 [SMILES: CNC(=O)CCCCC[C@H](NC(=O)c1cnc(C)s1)c1ncc(-c2ccc(-c3ccn(C)n3)cc2)o1] | 507 | Example 6 |

TABLE 1-continued

| Entry | Compound Name | Structure | Molecular Ion [M + H]⁺ | Procedure |
|---|---|---|---|---|
| 219 | (S)-N-(1-(5-(4-(1-methyl-1H-pyrazol-3-yl)phenyl)oxazol-2-yl)-7-(methylamino)-7-oxoheptyl)isothiazole-4-carboxamide | 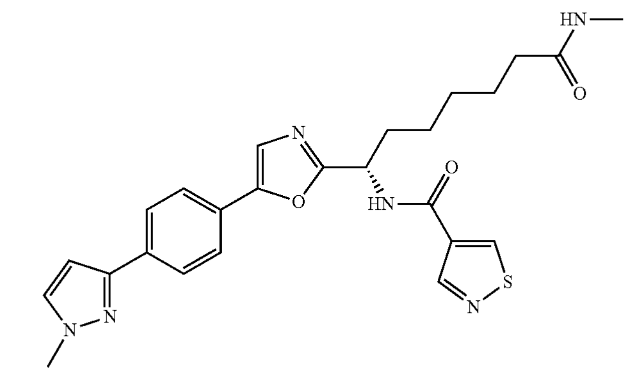 [SMILES: CNC(=O)CCCCC[C@H](NC(=O)c1cnsc1)c1ncc(-c2ccc(-c3ccn(C)n3)cc2)o1] | 493 | Example 6 |
| 220 | (S)-1-isopropyl-N-(1-(5-(3-methoxyisoquinolin-7-yl)-1H-imidazol-2-yl)-7-(methylamino)-7-oxoheptyl)-1H-pyrazole-4-carboxamide | 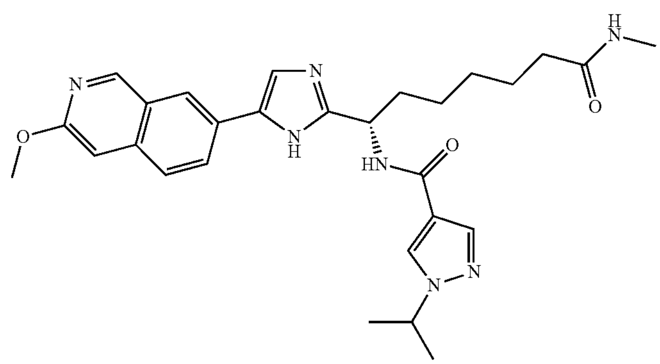 | 518 | Example 4 |
| 221 | (S)-N-(1-(5-(4-(1-methyl-1H-pyrazol-4-yl)phenyl)-1H-imidazol-2-yl)-7-(methylamino)-7-oxoheptyl)thiazole-5-carboxamide | 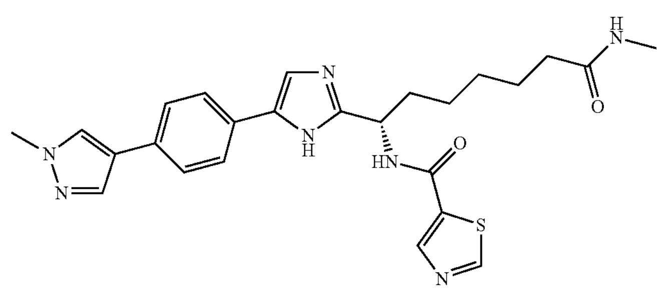 | 492 | Example 5 |
| 222 | (S)-N-(1-(5-(4-(1-methyl-1H-pyrazol-5-yl)phenyl)-1H-imidazol-2-yl)-7-(methylamino)-7-oxoheptyl)thiazole-5-carboxamide | 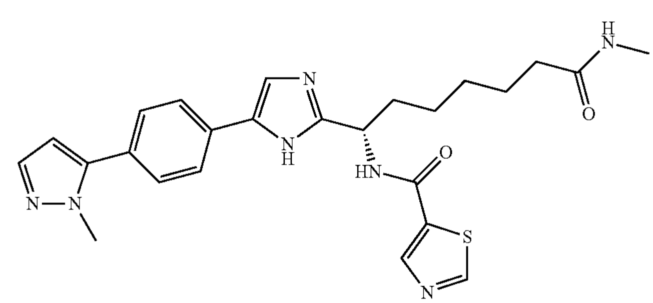 [SMILES: CNC(=O)CCCCC[C@H](NC(=O)c1cncs1)c1ncc(-c2ccc(-c3ccnn3C)cc2)[nH]1] | 492 | Example 5 |

TABLE 1-continued

| Entry | Compound Name | Structure | Molecular Ion [M + H]+ | Procedure |
|---|---|---|---|---|
| 223 | (S)-N-(7-(methylamino)-7-oxo-1-(5-(4-(thiazol-5-yl)phenyl)-1H-imidazol-2-yl)heptyl)thiazole-5-carboxamide | 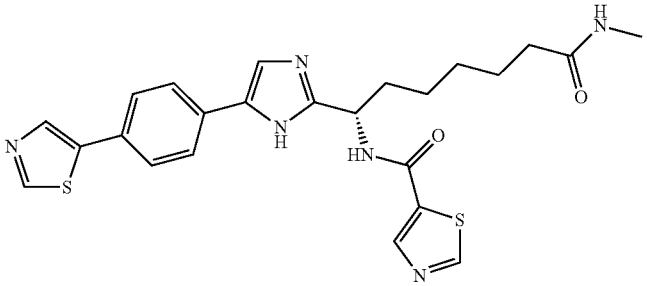 [SMILES: CNC(=O)CCCCC[C@H](NC(=O)c1cncs1)c1ncc(-c2ccc(-c3cncs3)cc2)[nH]1] | 495 | Example 5 |
| 224 | (S)-N-(7-(methylamino)-7-oxo-1-(5-(4-(thiazol-2-yl)phenyl)-1H-imidazol-2-yl)heptyl)thiazole-5-carboxamide | 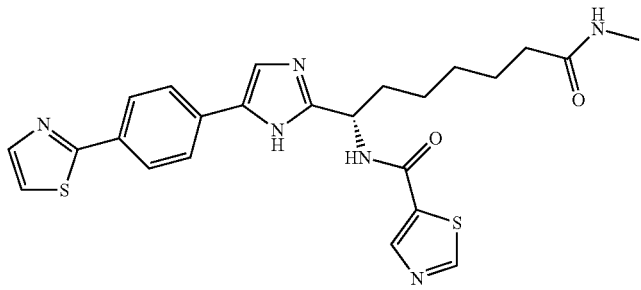 [SMILES: CNC(=O)CCCCC[C@H](NC(=O)c1cncs1)c1ncc(-c2ccc(-c3nccs3)cc2)[nH]1] | 495 | Example 5 |
| 225 | (S)-N-(7-(methylamino)-7-oxo-1-(5-(4-(pyrimidin-2-yl)phenyl)-1H-imidazol-2-yl)heptyl)thiazole-5-carboxamide | 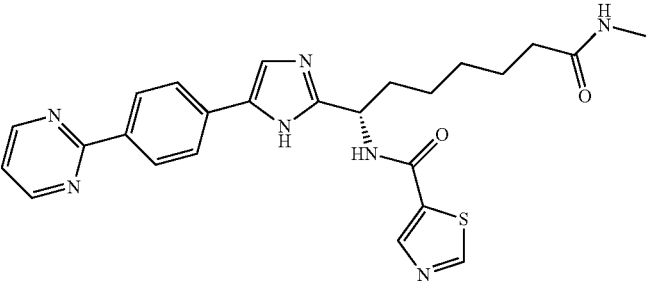 [SMILES: CNC(=O)CCCCC[C@H](NC(=O)c1cncs1)c1ncc(-c2ccc(-c3ncccn3)cc2)[nH]1] | 490 | Example 5 |
| 226 | (S)-N-(7-(methylamino)-7-oxo-1-(5-(4-(thiazol-4-yl)phenyl)-1H-imidazol-2-yl)heptyl)thiazole-5-carboxamide | 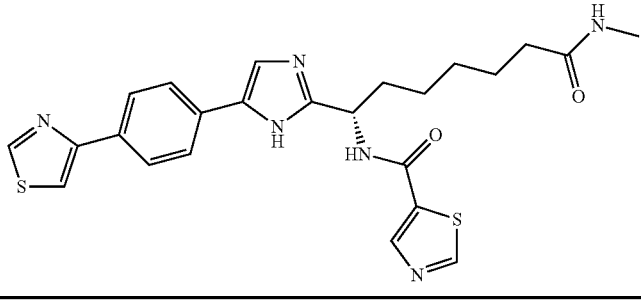 | 495 | Example 5 |

Biology
*Homo sapiens* HDAC1 Inhibition Assay
Overview:

The aim of the assay is to evaluate the inhibition of the deacetylase activity of human HDAC1. To such goal an acetylated substrate is added to the enzyme mix; the resulting enzymatic product is converted to a fluorescent molecule by the addition the enzyme trypsine (developer solution). Fluorescence intensity is inversely proportional to the rate of inhibition of the enzyme (as indicated in the material section below).

Materials:
a) HDAC1 Enzyme

Prepared and purified in-house in large batch quantities by overexpression of C-terminally tagged (Flag epitope) human HDAC1 (NCBI Gene ID: 3065) in mammalian cells (HeLa, cervix adnocarcinoma, ATCC® Number: CCL-2™) b) HDAC Substrate Buffer System Reagents of the HDAC Fluorescent Activity Assay are purchased from Enzo Life Sciences (http://www.enzolifesciences.com/BML-AK500/fluor-de-lys-hdac-fluorometric-activity-assay-kit/) and feature the Fluor-de-Lys™ Substrate/Developer System. The reagents include the proprietary fluorescent substrate as a 50 mM stock solution (KI-104), and the Developer Concentrate (KI-105). Deacetylation of the lysine residue of the Fluor-de-Lys substrate is quantified by measuring the fluorescence (ex 360 nM, em 460 nM) after addition of the proprietary developer.

c) Trichostatin A (TSA) Stock

TSA (Sigma-Aldrich, T8552) is provided as a 10 mM stock solution in 100% dimethylsulfoxide (DMSO).

d) Working Reagents:

Assay Buffer 25 mM Tris/HCl pH 8, 137 mM NaCl, 2.7 mM KCl, 1 mM $MgCl_2$, 0.1 mg/ml BSA Diluted Substrate Solution The commercial 50 mM Fluor-de-Lys substrate (KI-104) is diluted to 150 µM with HDAC Assay Buffer prior to each use. The final concentration in the assay is 20 µM.

Diluted Developer Solution

The commercial 20× Developer Concentrate (KI-105) is diluted 1:167 into HDAC Assay Buffer. 2 µM [final] TSA to this solution increases its ability to stop the reaction.

HDAC1 Working Solution

The HDAC1 enzyme is diluted in assay buffer prior to each use from a fresh aliquot of enzyme.

The final concentration in the assay is 1-2 nM.

Compounds

Test compounds should be prepared in 100% DMSO and transferred to the assay by a nano volume dispenser to reach the appropriate concentration and the appropriate DMSO concentration (0.25%) in the reaction.

Protocol:

The reaction is performed in 384-well microplate in a final volume of 20 µl/well Transfer compounds to the reaction Add 15 µl of HDAC1 enzyme in assay buffer Incubate 10 min at room temperature Start the reaction by adding 5 µl of the 150 µM substrate solution Incubate 1 h at 37° C.

Stop by adding 20 µl of developer plus 4 µM TSA solution (to stop the reaction)

Incubate 10 min at room temperature

Measure the fluorescence at excitation 360 nm and emission 460 nm

Negative controls (0% inhibition) are produced by addition of DMSO to the proper wells.

Positive controls (100% inhibition) are produced by addition of 4 µM TSA to the proper wells.

After result normalization using positive and negative controls, compound potency is determined by fitting the following equation:

$$\% \text{ inh} = Y_{min} + (Y_{max} - Y_{min})/(1+(X/IC50)^{slope})$$

Where:

Ymin=minimum percentage inhibition

Ymax=maximum percentage inhibition

IC50=the concentration of the compound at which 50% inhibition is reached

Slope=the slope of the curve calculated at the IC50

Cell Based HDAC1 Inhibition

Overview:

The aim of the assay is to evaluate the inhibition of the deacetylase activity inside the cells. To such goal a membrane permeable substrate is added to HeLa cells. After the incubation period, cells are lysed and the deacetylated substrate is evaluated using the same principles previously described for the human HDAC1 assay.

Materials:

a) HeLa Cells.

HeLa cells (HeLa, cervix adnocarcinoma, ATCC® Number: CCL-2™) frozen stock are derived from cell cultured in DMEM, glutamine, penicilline, streptomicine and 10% fetal bovine serum (FBS). Stock are frozen in 90% FBD and 10% DMSO.

b) HDAC Substrate Buffer System

Reagents of the HDAC Fluorescent Activity Assay are purchased from Enzo Life Sciences (http://www.enzolifesciences.com/BML-AK500/fluor-de-lys-hdac-fluorometric-activity-assay-kit/) and feature the Fluor-de-Lys™ Substrate/Developer System. The reagents include the proprietary fluorescent substrate as a 50 mM stock solution (KI-104), and the Developer Concentrate (KI-105). Deacetylation of the lysine residue of the Fluor-de-Lys substrate is quantified by measuring the fluorescence (ex 360 nM, em 460 nM) after addition of the proprietary developer.

c) TSA Stock (as Above)

TSA is provided as a 10 mM stock solution in 100% dimethylsulfoxide (DMSO).

d) Compounds

Test compounds should be prepared in 100% DMSO and transferred to the assay by a nano volume dispenser to reach the appropriate concentration and the appropriate DMSO concentration (0.25%) in the reaction.

e) Assay Medium

GIBCO Dulbecco's Mod Eagle Medium without Phenol Red (cat n° 11880) Completed with 10% FCS—fetal bovine serum—, 1% Penicillin-Streptomycin (10 mg/ml) and 1% L-Glutamine 200 mM (100×)

f) Diluted Substrate Solution

The commercial 50 mM Fluor-de-Lys substrate (KI-104) is diluted to 400 uM in Assay Buffer prior to each use.

g) Diluted Stop-Lysis-Developer Solution

The commercial 20× Developer Concentrate (KI-105) is diluted 1:27 0.75× into Assay Buffer containing 3% Igepal-Nonidet NP40 and 4 µM TSA Protocol:

The reaction is performed in 384-well microplate in a final volume of 20 µl/well+10 µl/well of Stop-Lysis-Developer Mix, as following:

seed 10000 HeLa cells/well, from the frozen aliquots, in 15 µl in assay medium and let recover overnight;

transfer compounds to the assay by nano-volume transfer machine in order to reach the desired assay concentration and a final DMSO concentration of 0.25%;

pre-incubate compounds on cells for 30 min;

start the reaction by adding 5 µl of the Diluted Substrate Solution;

stop the reaction after 4 h incubation at 37° C. 5% $CO_2$ by adding 10 µl of Diluted Stop-Lysis-Developer Solution;

incubate 20 min at 37° C.;

after 10 min at RT measure the fluorescence at excitation 360 nm and emission 460 nm Negative controls (0% Effect) are produced by addition of DMSO to the proper wells.

Positive controls (100% Effect) are produced by addition of 4 µM TSA to the proper wells.

After result normalization using positive and negative controls, compound potency is determined by fitting the following equation:

$$\% \text{ inh} = Y_{min} + (Y_{max} - Y_{min})/(1+(X/EC50)^{slope})$$

Where:

Ymin=minimum percentage effect

Ymax=maximum percentage effect

EC50=the concentration of the compound at which 50% effect is reached

Slope=the slope of the curve calculated at the EC50

In Vitro Culture of *P. falciparum* Parasites

Basic culture of *Plasmodium falciparum* 3D7 parasites (Malaria Research and Reference Reagent Resource Center (MR4), MR4 Number: MRA-102).

Starting with a culture with a parasitemia of about 10% (and 5% hematocrit), 0.5 ml of the culture is placed in a fresh 100 mm petri dish with 0.95 ml of fresh erythrocytes (50% hematocrit) and 8.55 ml of culture medium, giving a new starting parasitemia of 0.5%. The petri dish is then incubated at 37° C. in a humidified gas-tight plastic box flushed with a gas mixture consisting of 93% $N_2$, 4% $CO_2$, and 3% $O_2$. The culture medium is changed daily. The supernatant is removed by gently tipping the dish without disturbing the settled cells and aspirating the medium with a Pasteur pipette connected to a vacuum pump. A small amount of the concentrated cells is taken to prepare a blood smear for determination of the parasitemia. Normally, the cultures are split twice a week. If the parasites are growing very slowly then fresh erythrocytes are added to the culture no later than after 7 days. The cultures are then split 1:2 if the parasitemia is lower than 0.5%. To avoid the necessity of daily medium change on weekends, a culture with a 2.5% hematocrit and 0.1-0.2% parasitemia is set up and can be left for 3 days without medium change.

Culture Medium

Standard medium consists of RPMI 1640, supplemented with 25 mM HEPES, 24 mM $NaHCO_3$, 0.36 mM hypoxanthine, 100 µg/ml Neomycin, 5 g/1 Albumax® II, and washed human red blood cells (rbcs) A+.

Isolation of Human Erythrocytes

Normal human blood (A+) is obtained from a local blood bank. 30 ml blood is centrifuged in 50-ml screw-capped tubes at 2000 rpm (800 g) for 10 min. Remove the plasma and the buffy coat and resuspend the red blood cells in 5-10 volumes of RPMI 1640. Wash the cells twice by centrifugation as before, and then resuspend them in an equal volume of RPMI 1640. The erythrocytes are now ready for use and can be stored for a few days at 4° C.

Determination of Parasitemia

The parasitemia (the percentage of infected erythrocytes) is determined by counting a fixed and stained blood smear. Therefore, the culture medium is first removed from a culture and then a drop of settled rbcs is transferred onto a slide. With another clean slide used as a "spreader", touch the drop with it and allow the blood cells to run along its edge. Keeping the spreader at 45°, firmly push it along the slide. Fix the thin film by plunging the slide into methanol for a few seconds. Prepare a staining solution which contains 11 volumes of PBS and 1 volume of Giemsa stock solution. Stain the slides for 15-30 min. Wash the slides for a few seconds under running tap water, and let them dry in a rack. Microscopy is done using oil immersion. The chromatin of the parasites appears purplish-red and the cytoplasm, clear purplish-blue.

*P. falciparum* Growth Inhibition Assay (Pf-LDH)

Compounds of the invention were assessed for in vitro antimalarial activity against a cloroquine sensitive (3D7) strain of the malaria parasite *Plasmodium falciparum*, using a lactate dehydrogenase (PfLDH) assay.

$EC_{50}$ Determination by Pf-LDH Assay 384 plates (where compounds to be tested are dispensed) with 25 µl of parasite inoculum (parasitemia: 0.25%, hematocrit: 2%) are incubated at 37° C. in an atmosphere of 4% $CO_2$, 3% $O_2$, 93% $N_2$. After 72 h of incubation, plates are frozen at −70° C. overnight and thawed at room temperature for at least 4 h. To evaluate PfLDH activity, 70 µl of freshly made reaction mix (143 mM sodium L-lactate, 143 µM 3-acetyl pyridine adenine dinucleotide (APAD), 178.75 µM Nitro Blue tetrazolium chloride (NBT), 286 µg/ml diaphorase (2.83 U/ml), 0.7% Tween 20, 100 mM Tris-HCl pH 8.0) is dispensed using a Multidrop Combi dispenser. Plates are shaken to ensure mixing and absorbance at 650 nM is monitored in a plate reader after 10 min of incubation at room temperature.

Negative controls (0% Effect) are produced by addition of DMSO to the proper wells.

Positive controls (100% Effect) are produced by addition of 150 nM Artemisinin (Sigma-Aldrich, 361593)

After result normalization using positive and negative controls, compound potency is determined by fitting the following equation:

$$\% \text{ inh} = Y\text{min} + (Y\text{max} - Y\text{min})/(1+(X/EC50)^{\text{slope}}))$$

Where:
Ymin=minimum percentage effect
Ymax=maximum percentage effect
EC50=the concentration of the compound at which 50% effect is reached
Slope=the slope of the curve calculated at the EC50

Histone Hyperacetylation and Immunodetection of Altered Histone Modifications Assay The effect of test compounds on histone acetylation status was determined by incubating *Plasmodium falciparum* 3D7 infected erythrocytes or HeLa cells with different concentrations of drugs or vehicle (0.01% DMSO) alone. Infected erythrocytes were collected at 14-16 hours post treatment and lysed in saponin (0.15%). The isolated parasites were washed three times with PBS and resuspended directly in SDS sample buffer. HeLa cell were collected at 14-16 hours post treatment and resuspended directly in SDS sample buffer. Samples were thereafter incubated at 100° C. for 10 min and centrifuged at 16,000 g for 10 min. Supernatants were analyzed by 12% SDS-PAGE and transferred onto PVDF (Immun-Blot PVDF Membrane for Protein Blotting, BIORAD, Cat: No 162-0177) membranes. Western Blot were performed on membrane stripes with antibody directed against histone 4 acetylated lysine 8 (H4K8Ac, Millipore 07-328) and antibody against actin (Sigma, A2066). Horseradish peroxidase conjugated secondary antibodies and an enhanced chemiluminescence kit were used according to manufacturer's instructions (GE Healthcare).

Results

The in vitro antimalarial activities of the exemplified compounds were determined in the PfLDH assay described above. Compounds of the invention are capable of killing and/or inhibiting the growth of the parasites in cultures of infected erythrocytes. To evaluate the compounds selective toxicity against *plasmodium* parasites versus human cell lines, compounds were tested in the HDAC HeLa Cell based assay. Selectivity was calculated as the ratio between the activity measured in the HDAC HeLa Cell based assay and the activity measured in the Pf-LDH assay. The mammalian (human) anti-HDAC activity of the exemplified compounds was also measured using the enzymatic assay, as described above. By virtue of the inherently weaker activities that are commonly measured in a cell based setting than in biochemical assays it will be apparent that selectivities calculated as described above take on increased relevance in cases where the antiparasitic activity in the Pf-LDH cell based assay is stronger than activity in the hHDAC biochemical assay. Results are reported in the following Table 2.

TABLE 2

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 1 | (S)-N-methyl-7-(5-(naphthalen-2-yl)-1H-imidazol-2-yl)-7-(2-(piperidin-1-yl)acetamido)heptanamide | 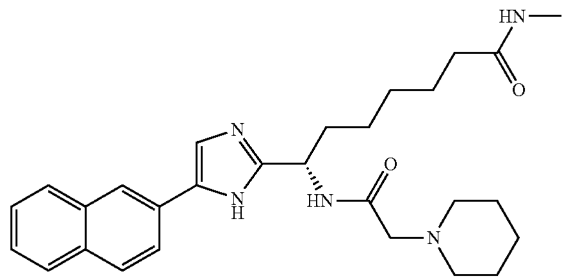 [SMILES: CNC(=O)CCCCC[C@H](NC(=O)CN1CCCCC1)c1ncc(-c2ccc3ccccc3c2)[nH]1] | B | B | C | 3.8 |
| 2 | (S)-N-(7-(methylamino)-1-(5-(naphthalen-2-yl)-1H-imidazol-2-yl)-7-oxoheptyl)-5,6,7,8-tetrahydro-1,8-naphthyridine-4-carboxamide | 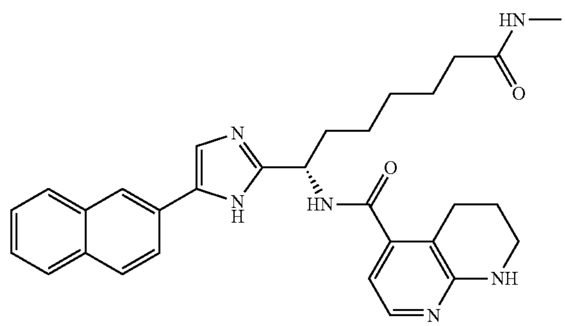 [SMILES: CNC(=O)CCCCC[C@H](NC(=O)c1ccnc2c1CCCN2)c1ncc(-c2ccc3ccccc3c2)[nH]1] | B | B | C | 4.0 |
| 3 | (S)-N-methyl-7-(5-(naphthalen-2-yl)-1H-imidazol-2-yl)-7-(3-nitrophenylsulfonamido)heptanamide | 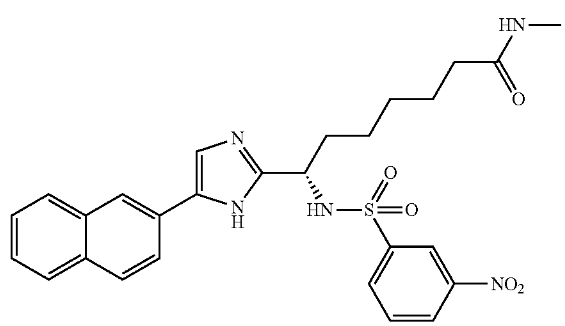 [SMILES: CNC(=O)CCCCC[C@H](NS(=O)(=O)c1cccc([N+](=O)[O-])c1)c1ncc(-c2ccc3ccccc3c2)[nH]1] | A | A | B | 7.0 |
| 4 | (S)-1-methyl-N-((S)-7-(methylamino)-1-(5-(naphthalen-2-yl)-1H-imidazol-2-yl)-7-oxoheptyl)pyrrolidine-3-carboxamide | 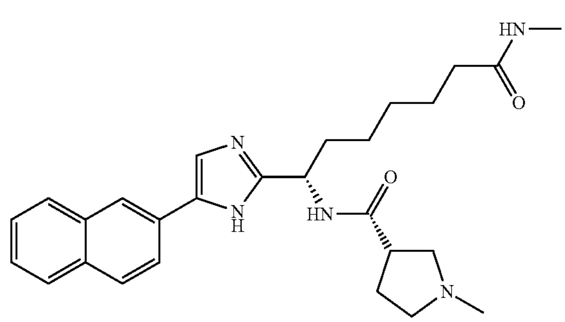 | B | A | C | 6.8 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 5 | (S)-1-methyl-N-(7-(methylamino)-1-(5-(naphthalen-2-yl)-1H-imidazol-2-yl)-7-oxo-heptyl)piperidine-4-carboxamide | 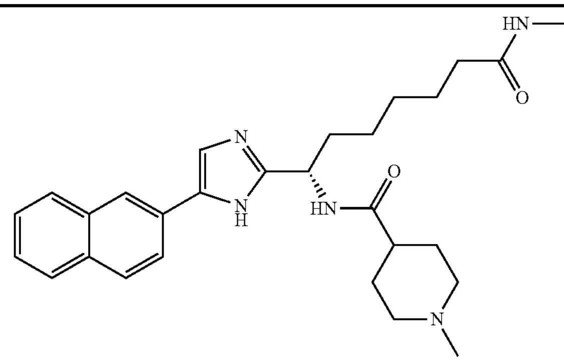 | B | A | C | 5.1 |
| 6 | (S)-7-(2-(1H-1,2,3-triazol-1-yl)acetamido)-7-(5-(2-methoxyquinolin-3-yl)-1H-imidazol-2-yl)-N-methylheptanamide | 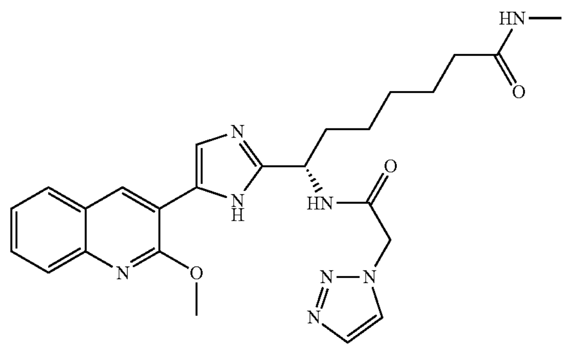 [SMILES: CNC(=O)CCCCC[C@H](NC(=O)Cn1ccnn1)c1ncc(-c2cc3ccccc3nc2OC)[nH]1] | B | B | C | 3.8 |
| 7 | (S)-7-(2-(1H-benzo[d][1,2,3]triazol-1-yl)acetamido)-7-(5-(2-methoxyquinolin-3-yl)-1H-imidazol-2-yl)-N-methylheptanamide | 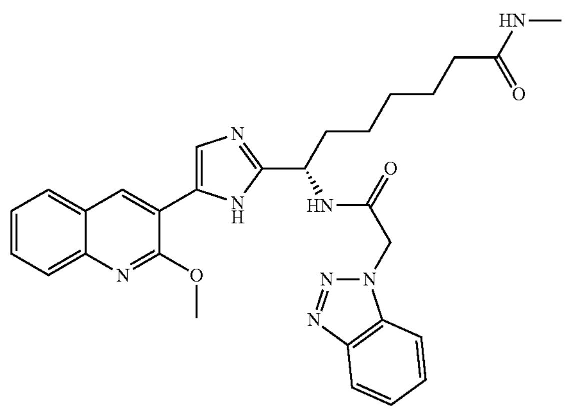 [SMILES: CNC(=O)CCCCC[C@H](NC(=O)Cn1nnc2ccccc21)c1ncc(-c2cc3ccccc3nc2OC)[nH]1] | B | A | B | 2.0 |
| 8 | (S)-7-(3-(2-ethyl-1H-benzo[d]imidazol-1-yl)propanamido)-7-(5-(2-methoxyquinolin-3-yl)-1H-imidazol-2-yl)-N-methylheptanamide | 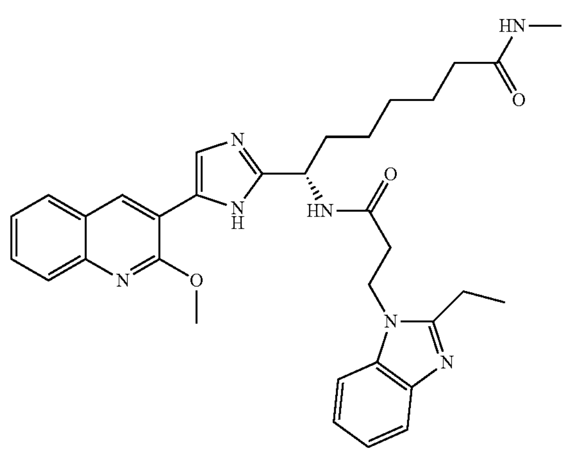 [SMILES: CCc1nc2ccccc2n1CCC(=O)N[C@@H](CCCCCC(=O)NC)c1ncc(-c2cc3ccccc3nc2OC)[nH]1] | B | A | B | 2.6 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 9 | (S)-N-(1-(5-(2-methoxyquinolin-3-yl)-1H-imidazol-2-yl)-7-(methylamino)-7-oxoheptyl)-1,3-dimethyl-1H-pyrazole-5-carboxamide | 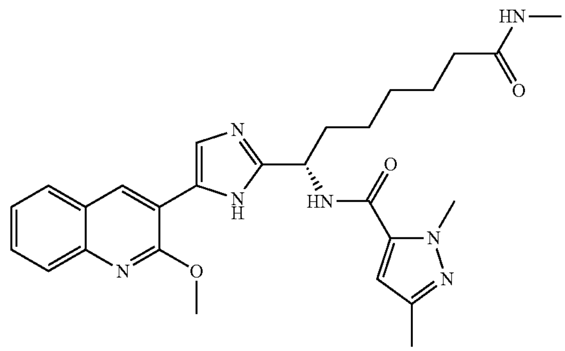 [SMILES: CNC(=O)CCCCC[C@H](NC(=O)c1cc(C)nn1C)c1ncc(-c2cc3ccccc3nc2OC)[nH]1] | B | A | B | 4.1 |
| 10 | S)-N-(7-(methylamino)-7-oxo-1-(5-(quinolin-7-yl)-1H-imidazol-2-yl)heptyl)thiazole-5-carboxamide | 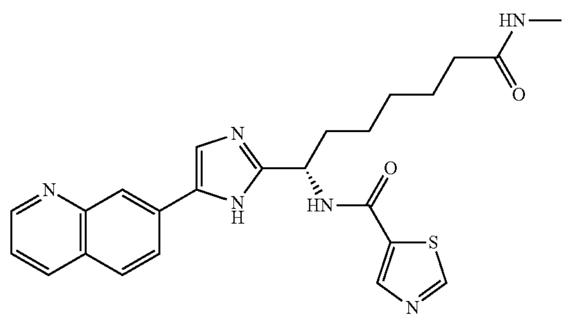 [SMILES: CNC(=O)CCCCC[C@H](NC(=O)c1cncs1)c1ncc(-c2ccc3cccnc3c2)[nH]1] | B | C | C | 6.6 |
| 11 | (S)-7-(2-(1H-1,2,4-triazol-1-yl)acetamido)-7-(5-(4-(1H-pyrazol-1-yl)phenyl)-1H-imidazol-2-yl)-N-methylheptanamide | 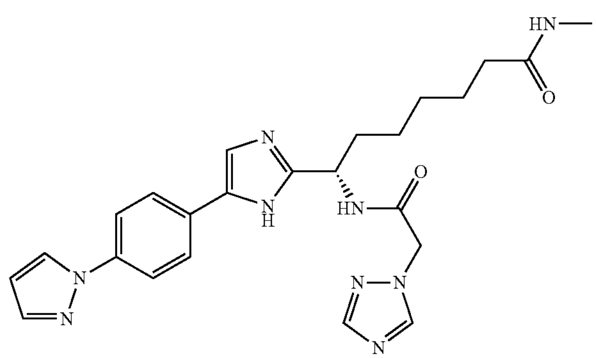 [SMILES: CNC(=O)CCCCC[C@H](NC(=O)Cn1cncn1)c1ncc(-c2ccc(-n3cccn3)cc2)[nH]1] | C | C | C | 3.0 |
| 12 | (S)-N-(1-(5-(4-(1H-pyrazol-1-yl)phenyl)-1H-imidazol-2-yl)-7-(methylamino)-7-oxoheptyl)isothiazole-4-carboxamide | 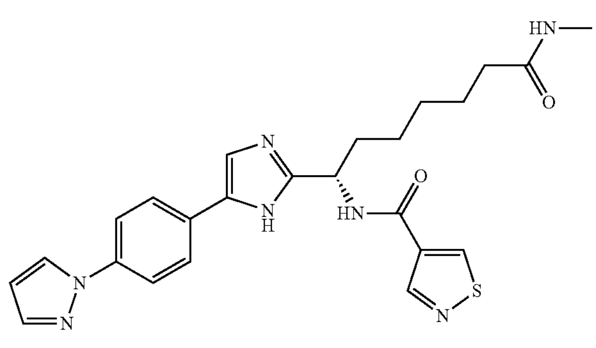 [SMILES: CNC(=O)CCCCC[C@H](NC(=O)c1cnsc1)c1ncc(-c2ccc(-n3cccn3)cc2)[nH]1] | B | B | C | 24 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 13 | (S)-2,3-dimethyl-N-(7-(methylamino)-1-(5-(naphthalen-2-yl)-1H-imidazol-2-yl)-7-oxo-heptyl)quinoxaline-5-carboxamide | 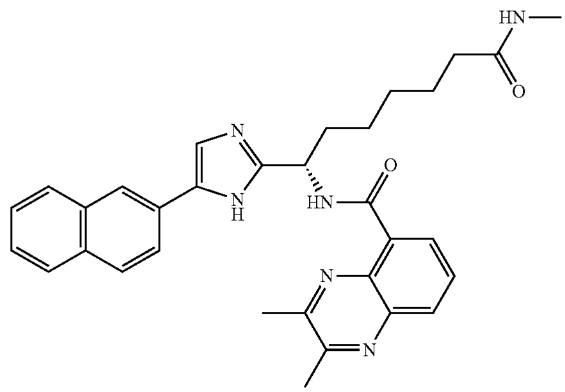 [SMILES: CNC(=O)CCCCC[C@H](NC(=O)c1cccc2nc(C)c(C)nc12)c1ncc(-c2ccc3ccccc3c2)[nH]1] | B | B | C | 3.5 |
| 14 | (S)-N-(l-(5-(3-methoxyquinolin-7-yl)-1H-imidazol-2-yl)-7-(methylamino)-7-oxoheptyl)thiazole-5-carboxamide | 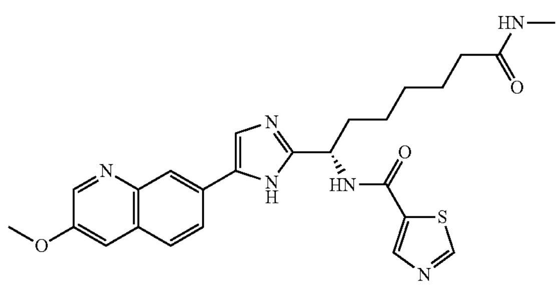 | B | B | C | 12.4 |
| 15 | (S)-7-(2-(imidazo[1,2-a]pyridin-3-yl)acetamido)-7-(5-(isoquinolin-7-yl)-1H-imidazol-2-yl)-N-methylheptanamide | 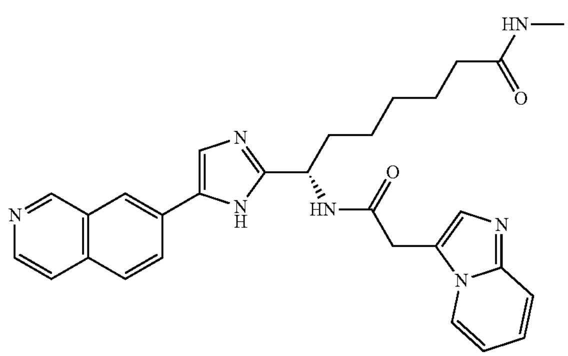 [SMILES: CNC(=O)CCCCC[C@H](NC(=O)Cc1cnc2ccccn12)c1ncc(-c2ccc3ccncc3c2)[nH]1] | B | A | C | 5.0 |
| 16 | (S)-N-(1-(5-(4-(1-methyl-1H-pyrazol-3-yl)phenyl)-1H-imidazol-2-yl)-7-(methylamino)-7-oxoheptyl)isothiazole-5-carboxamide | 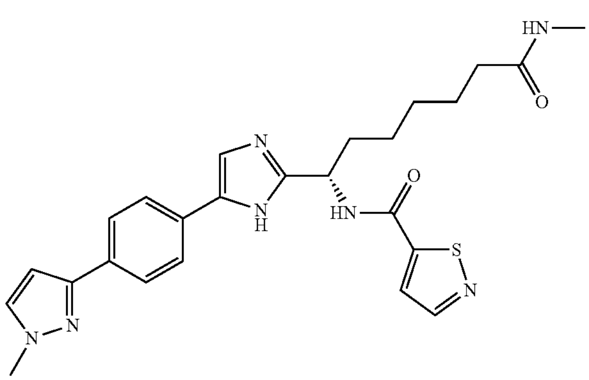 [SMILES: CNC(=O)CCCCC[C@H](NC(=O)c1ccns1)c1ncc(-c2ccc(-c3ccn(C)n3)cc2)[nH]1] | A | B | C | 16.6 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 17 | (S)-2-methyl-N-(1-(5-(4-(1-methyl-1H-pyrazol-3-yl)phenyl)-1H-imidazol-2-yl)-7-(methylamino)-7-oxoheptyl)thiazole-5-carboxamide | 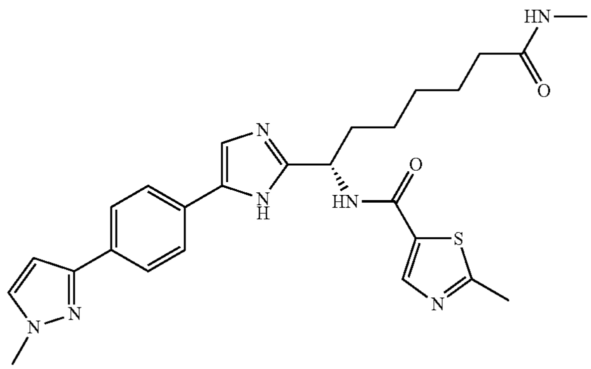 [SMILES: CNC(=O)CCCCC[C@H](NC(=O)c1cnc(C)s1)c1ncc(-c2ccc(-c3ccn(C)n3)cc2)[nH]1] | A | B | C | 22.0 |
| 18 | (S)-1-methyl-N-(7-(methylamino)-7-oxo-1-(5-(2-oxo-1,2-dihydroquinolin-3-yl)-1H-imidazol-2-yl)heptyl)azetidine-3-carboxamide | 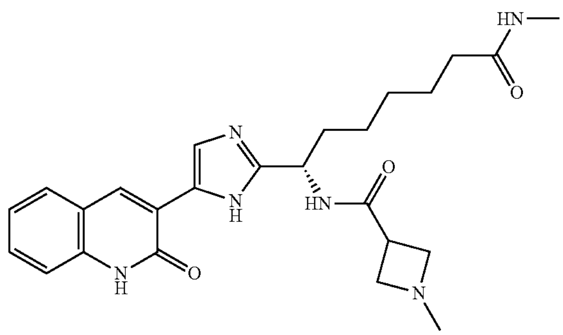 [SMILES: CNC(=O)CCCCC[C@H](NC(=O)C1CN(C)C1)c1ncc(-c2cc3ccccc3[nH]c2=O)[nH]1] | C | B | C | 4.5 |
| 19 | (S)-N-(7-(methylamino)-7-oxo-1-(5-(2-(trifluoromethyl)quinolin-6-yl)-1H-imidazol-2-yl)heptyl)thiazole-5-carboxamide | 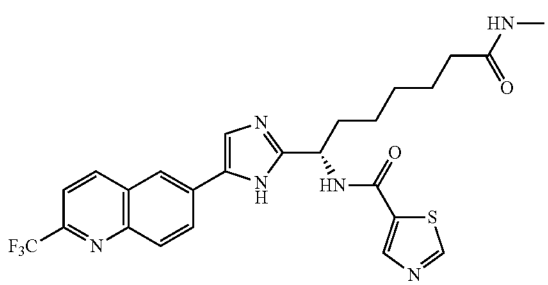 [SMILES: CNC(=O)CCCCC[C@H](NC(=O)c1cncs1)c1ncc(-c2ccc3nc(C(F)(F)F)ccc3c2)[nH]1] | B | B | C | 6.5 |
| 20 | (S)-N-methyl-7-(5-(naphthalen-2-yl)-1H-imidazol-2-yl)-7-(2-(5-(pyrrolidin-1-yl)-2H-tetrazol-2-yl)acetamido)heptanamide | 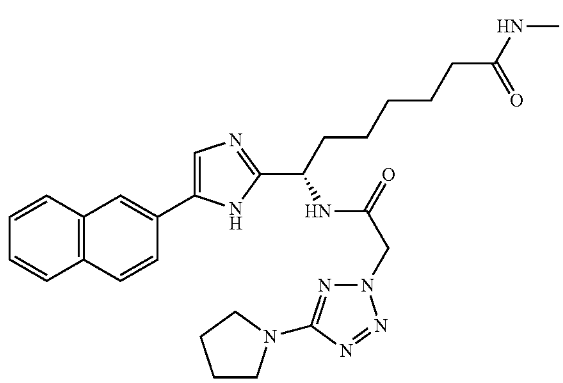 [SMILES: CNC(=O)CCCCC[C@H](NC(=O)Cn1nnc(N2CCCC2)n1)c1ncc(-c2ccc3ccccc3c2)[nH]1] | B | A | C | 6.2 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 21 | (S)-N-methyl-7-(5-(naphthalen-2-yl)-1H-imidazol-2-yl)-7-(2-phenylacetamido)heptanamide | 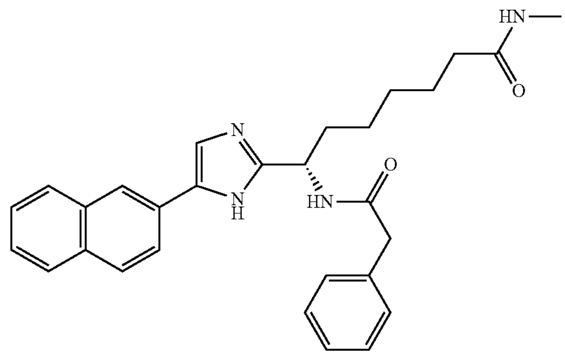 [SMILES: CNC(=O)CCCCC[C@H](NC(=O)Cc1ccccc1)c1ncc(-c2ccc3ccccc3c2)[nH]1] | B | A | B | 2.4 |
| 22 | (S)-7-(2-([1,2,4]triazolo[1,5-a]pyrimidin-6-yl)acetamido)-N-methyl-7-(5-(naphthalen-2-yl)-1H-imidazol-2-yl)heptanamide | 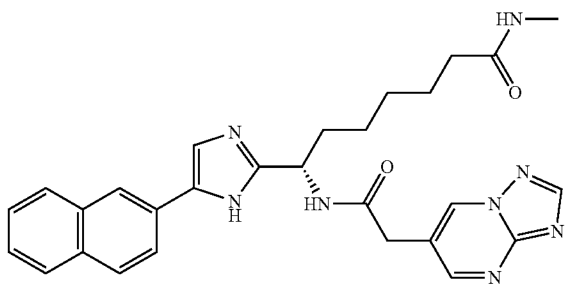 [SMILES: CNC(=O)CCCCC[C@H](NC(=O)Cc1cnc2ncnn2c1)c1ncc(-c2ccc3ccccc3c2)[nH]1] | A | A | C | 18.8 |
| 23 | (S)-N-methyl-7-(2-morpholinoacetamido)-7-(5-(naphthalen-2-yl)-1H-imidazol-2-yl)heptanamide | 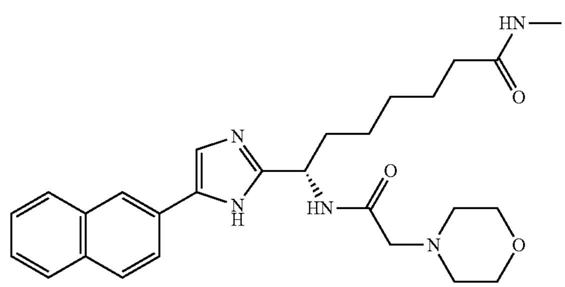 [SMILES: CNC(=O)CCCCC[C@H](NC(=O)CN1CCOCC1)c1ncc(-c2ccc3ccccc3c2)[nH]1] | B | B | C | 2.0 |
| 24 | (S)-N-(1-(5-(1H-indol-5-yl)-1H-imidazol-2-yl)-7-(methylamino)-7-oxoheptyl)thiazole-5-carboxamide | 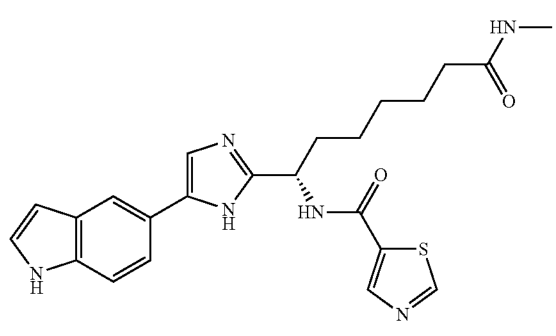 [SMILES: CNC(=O)CCCCC[C@H](NC(=O)c1cncs1)c1ncc(-c2ccc3[nH]ccc3c2)[nH]1] | A | B | C | 19.0 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 25 | (S)-N-(1-(5-(5-ethoxynaphthalen-2-yl)-1H-imidazol-2-yl)-7-(methylamino)-7-oxoheptyl)thiazole-5-carboxamide | 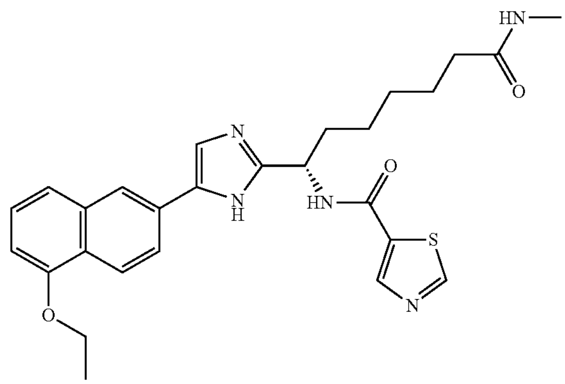 [SMILES: CCOc1cccc2cc(-c3cnc([C@H](CCCCCC(=O)NC)NC(=O)c4cncs4)[nH]3)ccc12] | A | B | C | 14.0 |
| 26 | S)-1-methyl-N-(7-(methylamino)-1-(5-(naphthalen-2-yl)-1H-imidazol-2-yl)-7-oxoheptyl)azetidine-3-carboxamide | 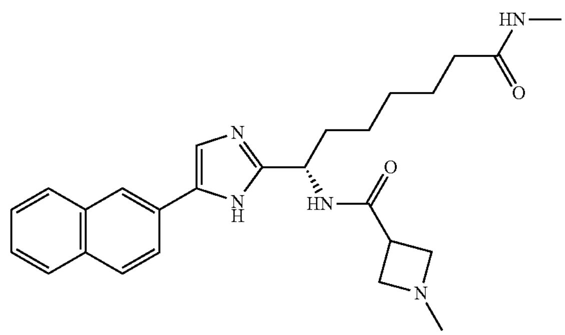 [SMILES: CNC(=O)CCCCC[C@H](NC(=O)C1CN(C)C1)c1ncc(-c2ccc3ccccc3c2)[nH]1] | B | A | C | 2.2 |
| 27 | (S)-7-(3-(1H-imidazol-1-yl)propanamido)-7-(5-(2-methoxyquinolin-3-yl)-1H-imidazol-2-yl)-N-methylheptanamide | 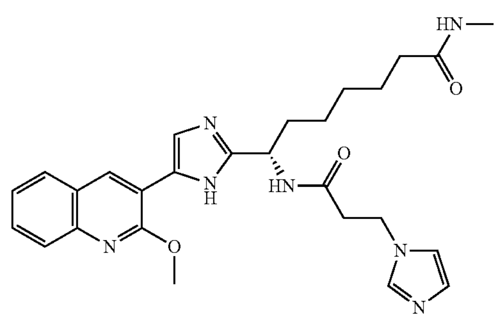 [SMILES: CNC(=O)CCCCC[C@H](NC(=O)CCn1ccnc1)c1ncc(-c2cc3ccccc3nc2OC)[nH]1] | B | B | C | 2.6 |
| 28 | (S)-7-(3-(2-ethyl-1H-benzo[d]imidazol-1-yl)propanamido)-N-methyl-7-(5-(4-(trifluoromethyl)phenyl)-1H-imidazol-2-yl)heptanamide | 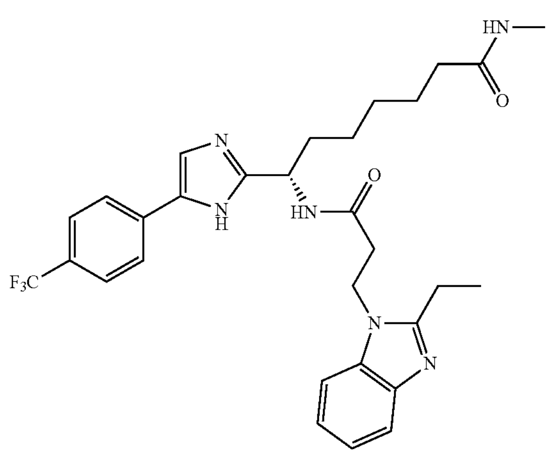 [SMILES: CCc1nc2ccccc2n1CCC(=O)N[C@@H](CCCCCC(=O)NC)c1ncc(-c2ccc(C(F)(F)F)cc2)[nH]1] | B | A | C | 7.3 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 29 | (S)-N-(7-(methylamino)-7-oxo-1-(5-(4-(pyridin-4-yl)phenyl)-1H-imidazol-2-yl)heptyl)thiazole-5-carboxamide | 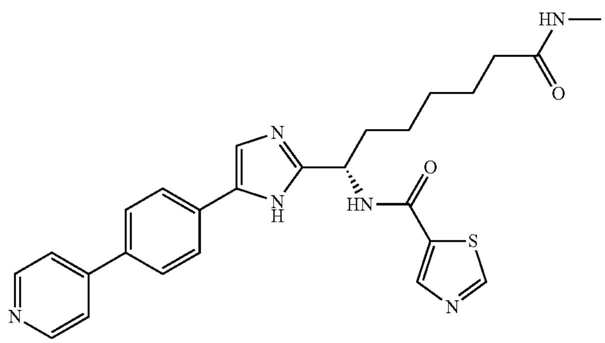 [SMILES: CNC(=O)CCCCC[C@H](NC(=O)c1cncs1)c1ncc(-c2ccc(-c3ccncc3)cc2)[nH]1] | B | B | C | 4.0 |
| 30 | (S)-N-(1-(5-(2-methoxyquinolin-3-yl)-1H-imidazol-2-yl)-7-(methylamino)-7-oxoheptyl)-2-(pyridin-3-yl)thiazole-4-carboxamide | 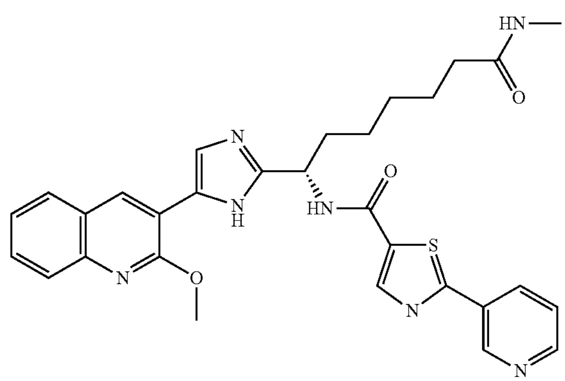 | B | C | C | 5.9 |
| 31 | (S)-N-(1-(5-(2-methoxyquinolin-3-yl)-1H-imidazol-2-yl)-7-(methylamino)-7-oxoheptyl)-5-methyl-1,3,4-thiadiazole-2-carboxamide | 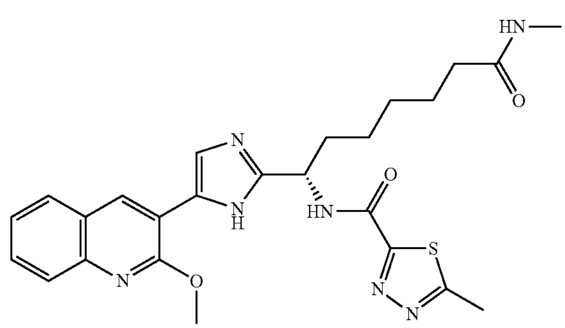 [SMILES: CNC(=O)CCCCC[C@H](NC(=O)c1nnc(C)s1)c1ncc(-c2cc3ccccc3nc2OC)[nH]1] | B | A | B | 1.4 |
| 32 | (7S)-7-(2-(3-(dimethylamino)pyrrolidin-1-yl)acetamido)-7-(5-(2-methoxyquinolin-3-yl)-1H-imidazol-2-yl)-N-methylheptanamide | 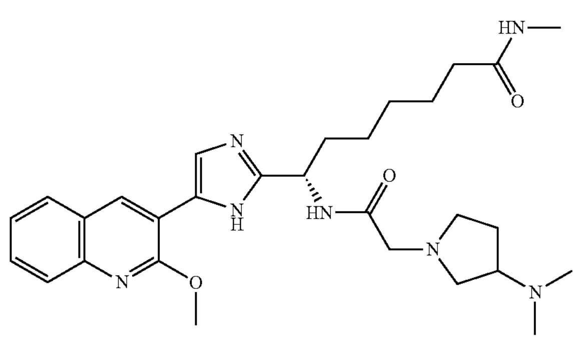 [SMILES: CNC(=O)CCCCC[C@H](NC(=O)CN1CCC(N(C)C)C1)c1ncc(-c2cc3ccccc3nc2OC)[nH]1] | C | A | C | 3.1 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 33 | N-((S)-1-(5-(2-methoxyquinolin-3-yl)-1H-imidazol-2-yl)-7-(methylamino)-7-oxoheptyl)-1-methylpiperidine-3-carboxamide | 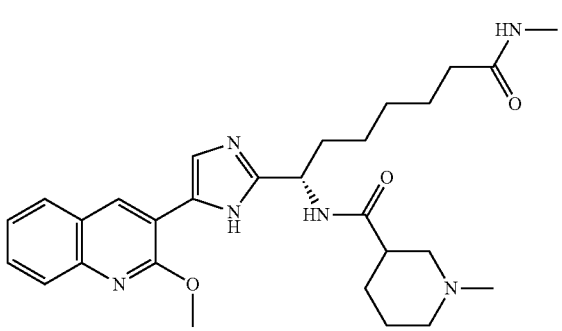 [SMILES: CNC(=O)CCCCC[C@H](NC(=O)C1CCCN(C)C1)c1ncc(-c2cc3ccccc3nc2OC)[nH]1] | B | A | B | 1.2 |
| 34 | (S)-N-(1-(5-(1H-indazol-5-yl)-1H-imidazol-2-yl)-7-(methylamino)-7-oxoheptyl)isothiazole-4-carboxamide | 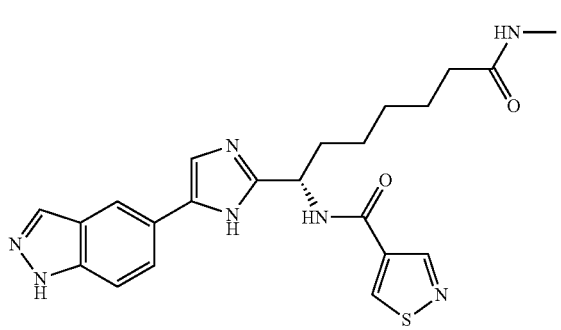 [SMILES: CNC(=O)CCCCC[C@H](NC(=O)c1cnsc1)c1ncc(-c2ccc3[nH]ncc3c2)[nH]1] | B | B | C | 12.2 |
| 35 | (S)-N-(1-(5-(3-(aminomethyl)phenyl)-1H-imidazol-2-yl)-7-(methylamino)-7-oxoheptyl)thiazole-5-carboxamide | 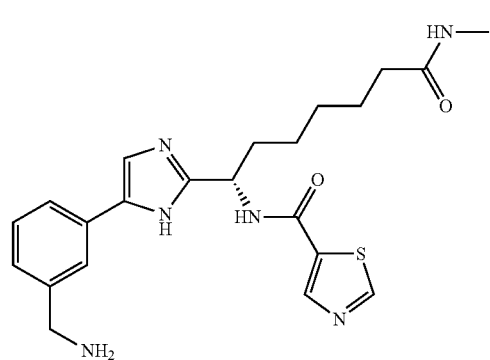 | A | B | C | 27.8 |
| 36 | (S)-N-(7-(methylamino)-7-oxo-1-(5-(quinolin-3-yl)-1H-imidazol-2-yl)heptyl)thiazole-5-carboxamide | 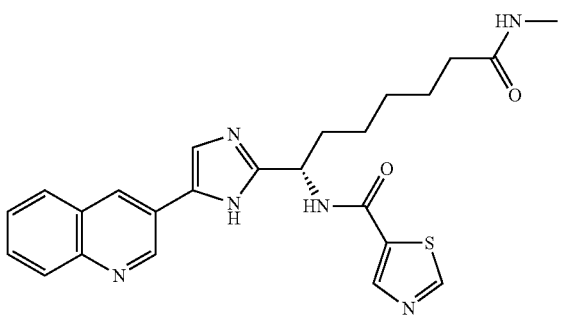 [SMILES: CNC(=O)CCCCC[C@H](NC(=O)c1cncs1)c1ncc(-c2cnc3ccccc3c2)[nH]1] | A | B | C | 13.6 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 37 | (S)-benzyl(1-(5-(4-(1H-pyrazol-3-yl)phenyl)-1H-imidazol-2-yl)-7-(methylamino)-7-oxoheptyl)carbamate | 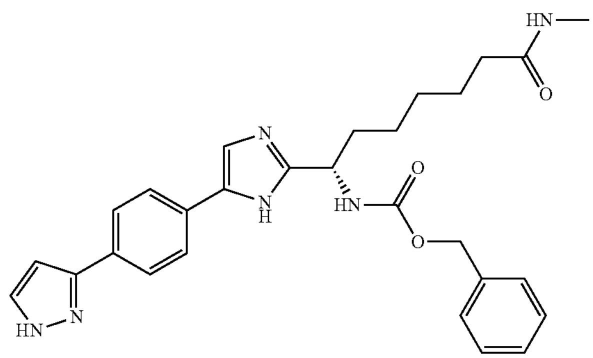 [SMILES: CNC(=O)CCCCC[C@H](NC(=O)OCc1ccccc1)c1ncc(-c2ccc(-c3cc[nH]n3)cc2)[nH]1] | B | A | C | 6.7 |
| 38 | (S)-7-(5-(4-(1H-pyrazol-1-yl)phenyl)-1H-imidazol-2-yl)-7-(3-(5,7-dimethyl-[1,2,4]triazolo[1,5-a]pyrimidin-6-yl)propanamido)-N-methylheptanamide | 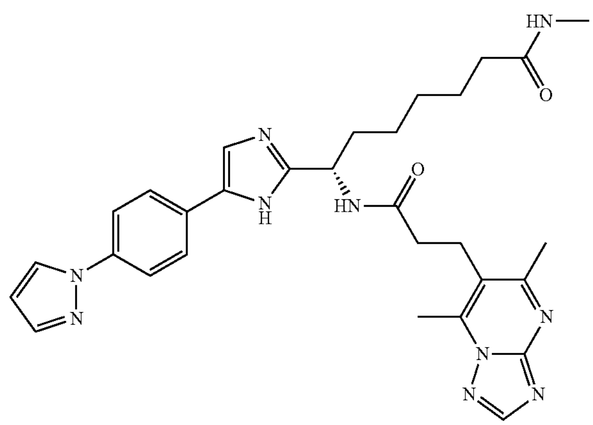 [SMILES: CNC(=O)CCCCC[C@H](NC(=O)CCc1c(C)nc2ncnn2c1C)c1ncc(-c2ccc(-n3cccn3)cc2)[nH]1] | B | B | C | 12.9 |
| 39 | (S)-7-(5-(4-(1H-pyrazol-1-yl)phenyl)-1H-imidazol-2-yl)-7-(2-(6,7-dihydro-5H-thiazolo[3,2-a]pyrimidin-3-yl)acetamido)-N-methylheptanamide | 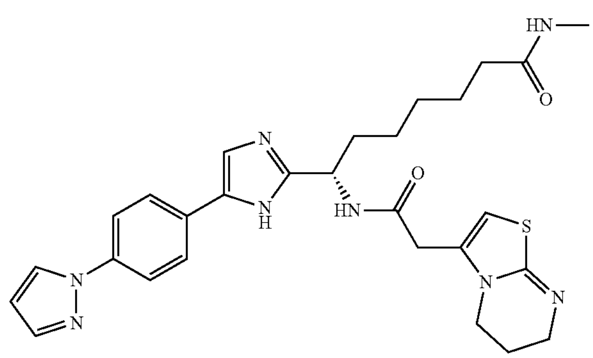 [SMILES: CNC(=O)CCCCC[C@H](NC(=O)CC1=CSC2=NCCCN12)c1ncc(-c2ccc(-n3cccn3)cc2)[nH]1] | B | B | C | 8.8 |
| 40 | (S)-4-methyl-N-(7-(methylamino)-1-(5-(naphthalen-2-yl)-1H-imidazol-2-yl)-7-oxoheptyl)tetrahydro-2H-pyran-4-carboxamide | 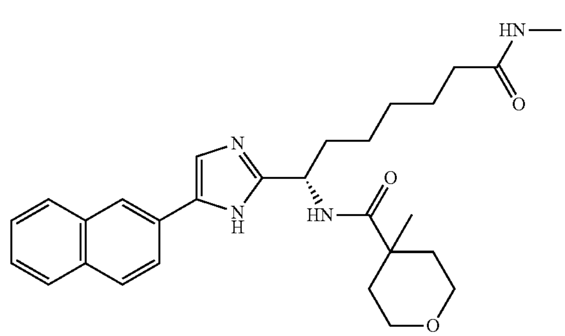 [SMILES: CNC(=O)CCCCC[C@H](NC(=O)C1(C)CCOCC1)c1ncc(-c2ccc3ccccc3c2)[nH]1] | B | B | C | 12.0 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 41 | (S)-4-(2,4-dioxoimidazolidin-1-yl)-N-(7-(methylamino)-1-(5-(naphthalen-2-yl)-1H-imidazol-2-yl)-7-oxo-heptyl)benzamide | 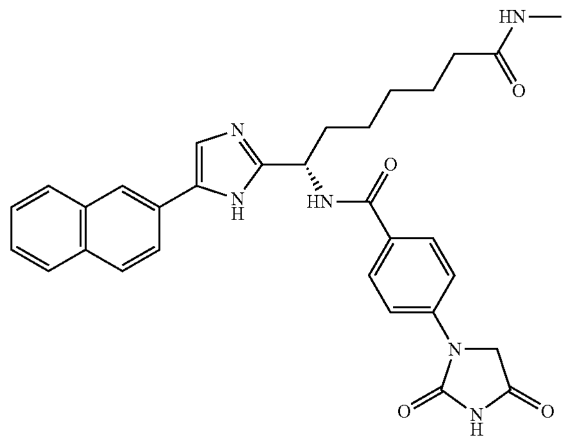 [SMILES: CNC(=O)CCCCC[C@H](NC(=O)c1ccc(N2CC(=O)NC2=O)cc1)c1ncc(-c2ccc3ccccc3c2)[nH]1] | A | B | C | 14.7 |
| 42 | (S)-3-(3,5-dimethyl-1H-pyrazol-1-yl)-N-(7-(methylamino)-1-(5-(naphthalen-2-yl)-1H-imidazol-2-yl)-7-oxo-heptyl)benzamide | 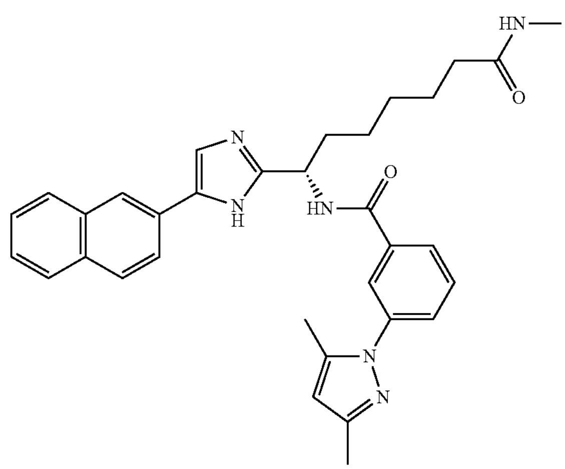 [SMILES: CNC(=O)CCCCC[C@H](NC(=O)c1cccc(-n2nc(C)cc2C)c1)c1ncc(-c2ccc3ccccc3c2)[nH]1] | B | B | C | 5.5 |
| 43 | (S)-N-(7-(methylamino)-1-(5-(naphthalen-2-yl)-1H-imidazol-2-yl)-7-oxoheptyl)-[1,2,4]triazolo[1,5-a]pyrimidine-2-carboxamide | 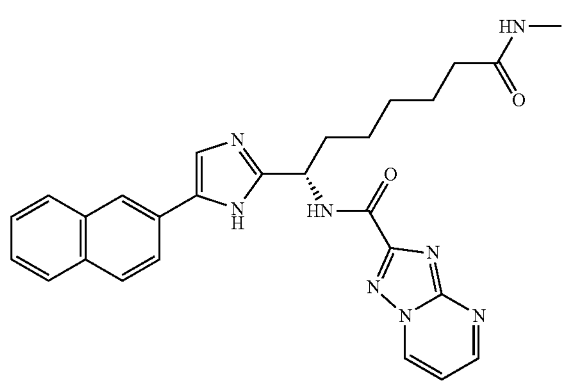 [SMILES: CNC(=O)CCCCC[C@H](NC(=O)c1nc2ncccn2n1)c1ncc(-c2ccc3ccccc3c2)[nH]1] | C | B | C | 4.0 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 44 | (S)-7-(2-(1H-benzo[d]imidazol-1-yl)acetamido)-N-methyl-7-(5-(naphthalen-2-yl)-1H-imidazol-2-yl)heptanamide | 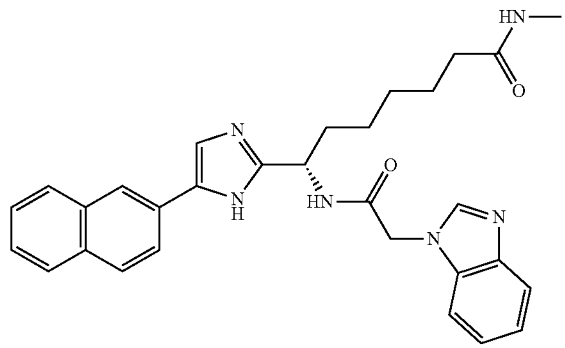 [SMILES: CNC(=O)CCCCC[C@H](NC(=O)Cn1cnc2ccccc21)c1ncc(-c2ccc3ccccc3c2)[nH]1] | B | A | C | 5.8 |
| 45 | (S)-N-(7-(methylamino)-1-(5-(naphthalen-2-yl)-1H-imidazol-2-yl)-7-oxoheptyl)-1,2,5-thiadiazole-3-carboxamide | 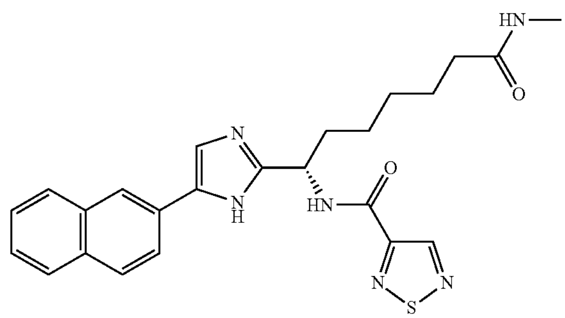 [SMILES: CNC(=O)CCCCC[C@H](NC(=O)c1cnsn1)c1ncc(-c2ccc3ccccc3c2)[nH]1] | C | B | C | 5.0 |
| 46 | (S)-N-(1-(5-(isoquinolin-7-yl)-1H-imidazol-2-yl)-7-(methylamino)-7-oxoheptyl)isothiazole-4-carboxamide | 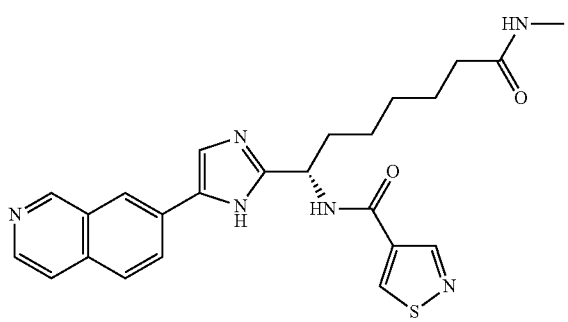 [SMILES: CNC(=O)CCCCC[C@H](NC(=O)c1cnsc1)c1ncc(-c2ccc3ccncc3c2)[nH]1] | A | A | B | 10.6 |
| 47 | (S)-N-(1-(5-(isoquinolin-7-yl)-1H-imidazol-2-yl)-7-(methylamino)-7-oxoheptyl)thiazole-4-carboxamide | 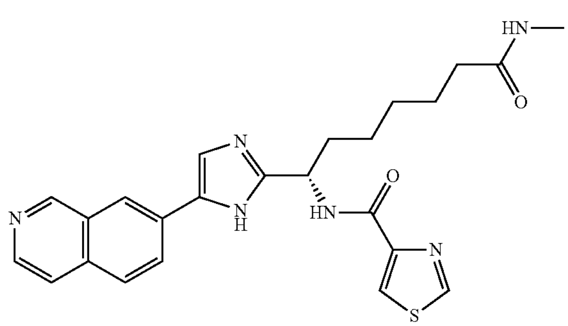 [SMILES: CNC(=O)CCCCC[C@H](NC(=O)c1cscn1)c1ncc(-c2ccc3ccncc3c2)[nH]1] | B | C | C | 6.8 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 48 | N-((S)-1-(5-(isoquinolin-7-yl)-1H-imidazol-2-yl)-7-(methylamino)-7-oxoheptyl)-2-(pyridin-4-yl)cyclopropane-carboxamide | 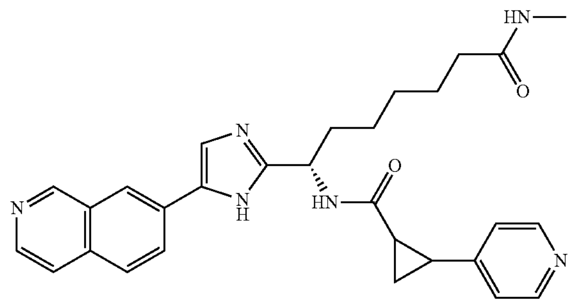 [SMILES: CNC(=O)CCCCC[C@H](NC(=O)C1CC1c1ccncc1)c1ncc(-c2ccc3ccncc3c2)[nH]1] | B | B | C | 9.4 |
| 49 | (S)-N-(1-(5-(isoquinolin-7-yl)-1H-imidazol-2-yl)-7-(methylamino)-7-oxoheptyl)-2-methylthiazole-5-carboxamide | 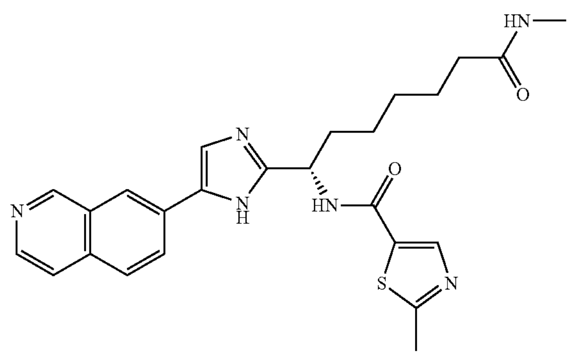 [SMILES: CNC(=O)CCCCC[C@H](NC(=O)c1cnc(C)s1)c1ncc(-c2ccc3ccncc3c2)[nH]1] | A | A | B | 9.7 |
| 50 | (S)-1-isopropyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide | 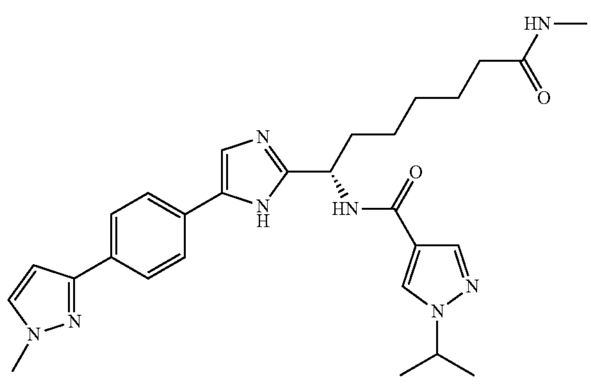 [SMILES: CNC(=O)CCCCC[C@H](NC(=O)c1cnn(C(C)C)c1)c1ncc(-c2ccc(-c3ccn(C)n3)cc2)[nH]1] | A | B | C | 38.8 |
| 51 | (S)-N-(1-(5-(benzo[b]thiophen-2-yl)-1H-imidazol-2-yl)-7-(methylamino)-7-oxoheptyl)thiazole-5-carboxamide | 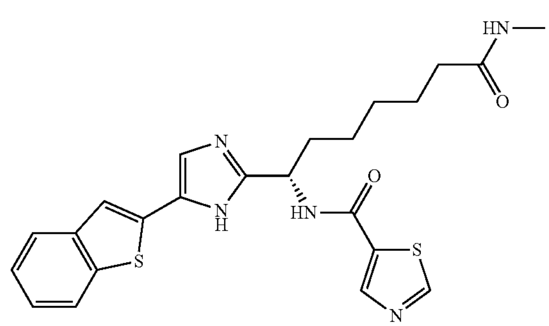 [SMILES: CNC(=O)CCCCC[C@H](NC(=O)c1cncs1)c1ncc(-c2cc3ccccc3s2)[nH]1] | B | B | C | 4.1 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 52 | (S)-N-(1-(5-(4-cyanophenyl)-1H-imidazol-2-yl)-7-(methylamino)-7-oxoheptyl)thiazole-5-carboxamide | 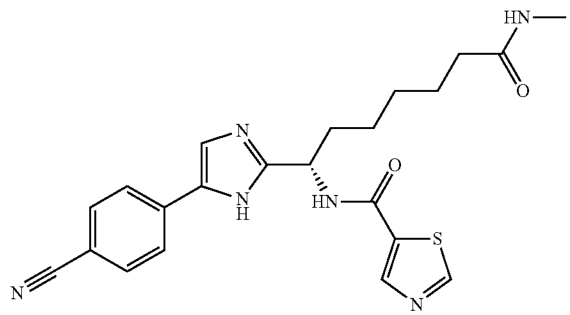 [SMILES: CNC(=O)CCCCC[C@H](NC(=O)c1cncs1)c1ncc(-c2ccc(C#N)cc2)[nH]1] | C | B | C | 2.7 |
| 53 | (S)-N-(1-(5-(4-acetamidophenyl)-1H-imidazol-2-yl)-7-(methylamino)-7-oxoheptyl)thiazole-5-carboxamide | 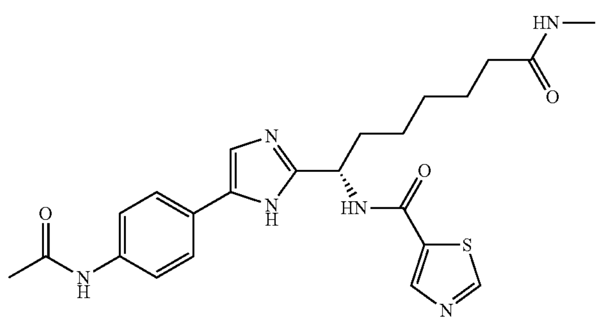 [SMILES: CNC(=O)CCCCC[C@H](NC(=O)c1cncs1)c1ncc(-c2ccc(NC(C)=O)cc2)[nH]1] | B | B | C | 15.0 |
| 54 | (S)-N-(1-(5-(5-methoxy-1H-indol-2-yl)-1H-imidazol-2-yl)-7-(methylamino)-7-oxoheptyl)thiazole-5-carboxamide | 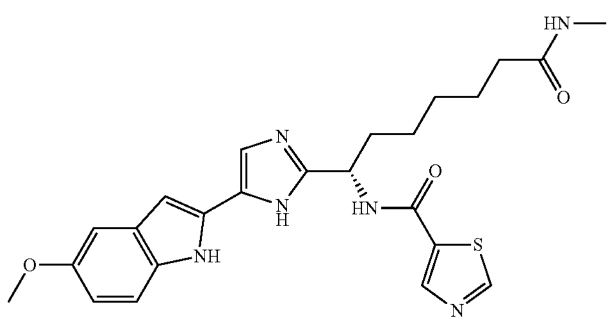 | B | B | C | 8.7 |
| 55 | (S)-N-(7-amino-1-(5-(2-methoxyquinolin-3-yl)oxazol-2-yl)-7-oxoheptyl)quinuclidine-4-carboxamide | 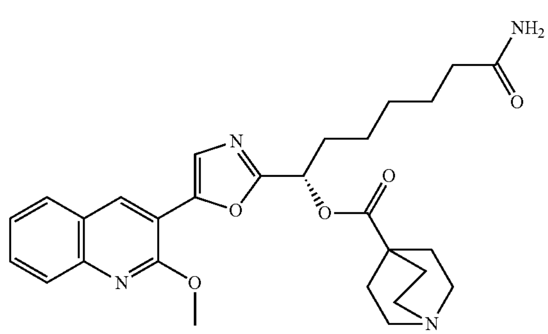 [SMILES: COc1nc2ccccc2cc1-c1cnc([C@H](CCCCCC(N)=O)OC(=O)C23CCN(CC2)CC3)o1] | B | A | B | 2.4 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 56 | (S)-N-(1-(5-(2-methoxyquinolin-3-yl)oxazol-2-yl)-7-(methylamino)-7-oxo-heptyl)quinuclidine-4-carboxamide | 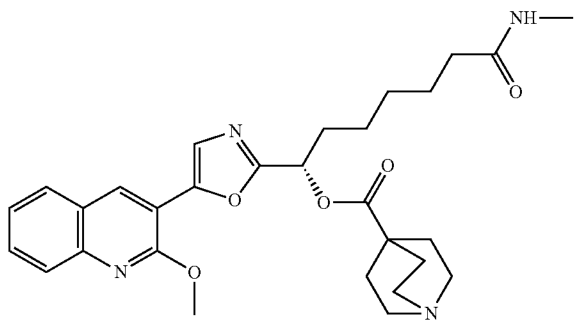 [SMILES: CNC(=O)CCCCC[C@H](OC(=O)C12CCN(CC1)CC2)c1ncc(-c2cc3ccccc3nc2OC)o1] | B | A | C | 3.3 |
| 57 | (S)-N-(1-(5-(4-chloro-2-methoxyphenyl)-1H-imidazol-2-yl)-7-(methylamino)-7-oxoheptyl)thiazole-5-carboxamide | 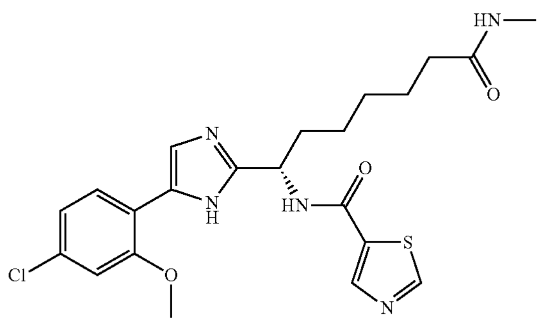 [SMILES: CNC(=O)CCCCC[C@H](NC(=O)c1cncs1)c1ncc(-c2ccc(Cl)cc2OC)[nH]1] | B | B | C | 2.6 |
| 58 | (S)-7-(2-(1H-1,2,3-triazol-1-yl)acetamido)-7-(5-(isoquinolin-7-yl)-1H-imidazol-2-yl)-N-methylheptanamide | 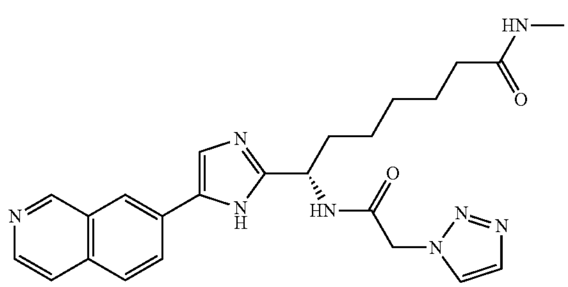 [SMILES: CNC(=O)CCCCC[C@H](NC(=O)Cn1ccnn1)c1ncc(-c2ccc3ccncc3c2)[nH]1] | B | B | C | 7.9 |
| 59 | (S)-N-(1-(5-(4-(5-methyl-1H-pyrazol-3-yl)phenyl)-1H-imidazol-2-yl)-7-(methylamino)-7-oxoheptyl)thiazole-5-carboxamide | 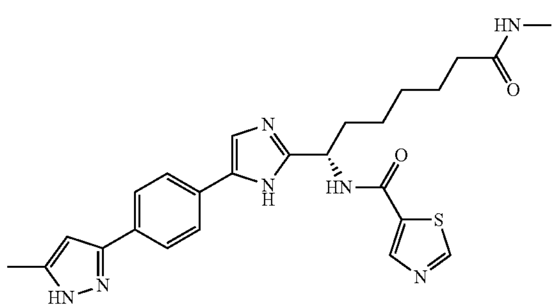 | B | B | C | 17.2 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 60 | (S)-N-(1-(5-(4-(aminomethyl)phenyl)-1H-imidazol-2-yl)-7-(methylamino)-7-oxoheptyl)thiazole-5-carboxamide | 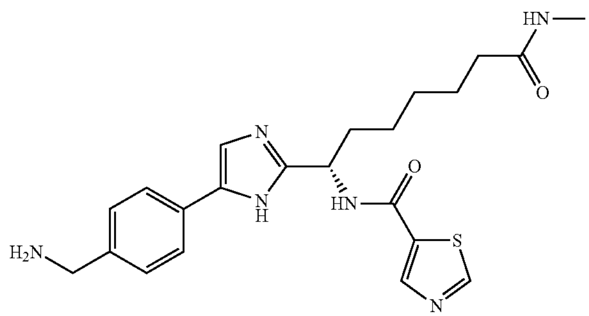 [SMILES: CNC(=O)CCCCC[C@H](NC(=O)c1cncs1)c1ncc(-c2ccc(CN)cc2)[nH]1] | C | B | C | 4.0 |
| 61 | N-((S)-1-(5-(4-(1H-pyrazol-1-yl)phenyl)-1H-imidazol-2-yl)-7-(methylamino)-7-oxoheptyl)-2-oxo-1,2,3,4-tetrahydroquinoline-4-carboxamide | 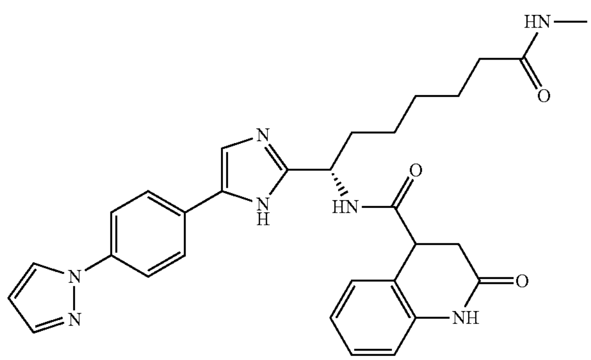 [SMILES: CNC(=O)CCCCC[C@H](NC(=O)C1CC(=O)Nc2ccccc21)c1ncc(-c2ccc(-n3cccn3)cc2)[nH]1] | B | B | C | 8.1 |
| 62 | (S)-7-(2-(1H-1,2,3-triazol-1-yl)acetamido)-7-(5-(4-(1H-pyrazol-1-yl)phenyl)-1H-imidazol-2-yl)-N-methylheptanamide | 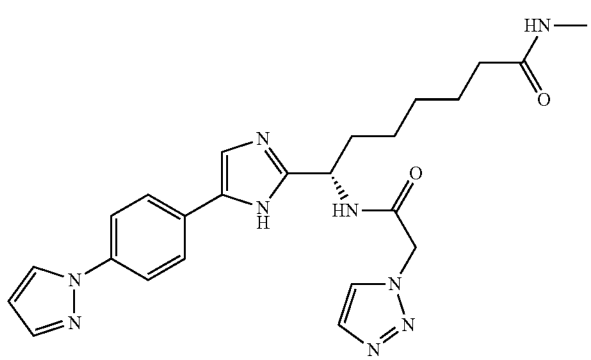 [SMILES: CNC(=O)CCCCC[C@H](NC(=O)Cn1ccnn1)c1ncc(-c2ccc(-n3cccn3)cc2)[nH]1] | C | C | C | 2.5 |
| 63 | (S)-N-methyl-7-(5-(naphthalen-2-yl)-1H-imidazol-2-yl)-7-(2-(4-phenylthiazol-2-yl)acetamido)heptanamide | 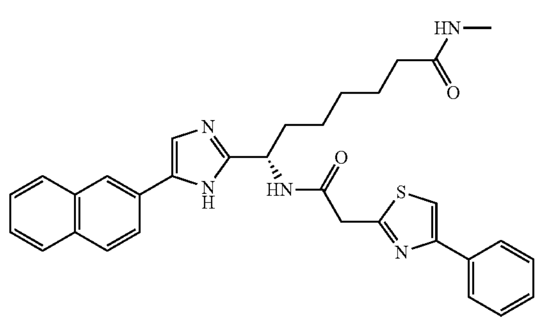 [SMILES: CNC(=O)CCCCC[C@H](NC(=O)Cc1nc(-c2ccccc2)cs1)c1ncc(-c2ccc3ccccc3c2)[nH]1] | B | B | C | 3.8 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 64 | (S)-N-(7-(methylamino)-1-(5-(naphthalen-2-yl)-1H-imidazol-2-yl)-7-oxoheptyl)-3-morpholino-benzamide | 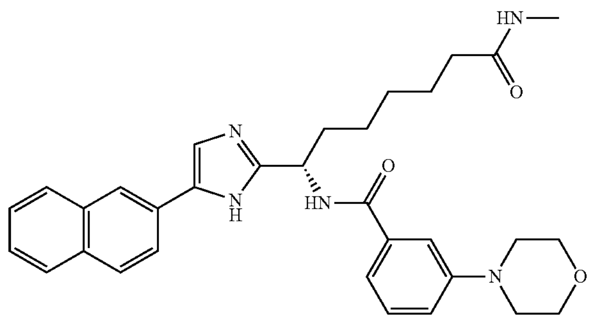 [SMILES: CNC(=O)CCCCC[C@H](NC(=O)c1cccc(N2CCOCC2)c1)c1ncc(-c2ccc3ccccc3c2)[nH]1] | B | C | C | 3.8 |
| 65 | (S)-N-(1-(5-(isoquinolin-7-yl)-1H-imidazol-2-yl)-7-(methylamino)-7-oxoheptyl)-2-(pyrrolidin-1-ylmethyl)thiazole-5-carboxamide | 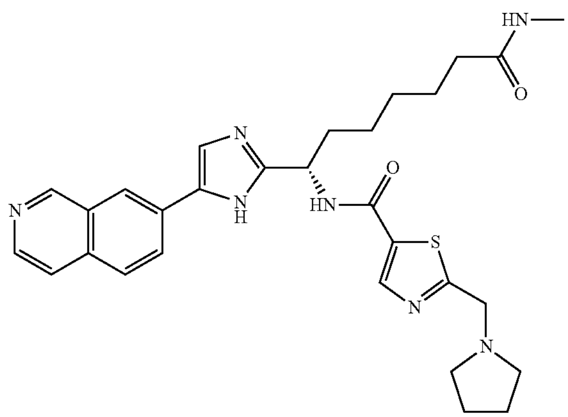 [SMILES: CNC(=O)CCCCC[C@H](NC(=O)c1cnc(CN2CCCC2)s1)c1ncc(-c2ccc3ccncc3c2)[nH]1] | A | A | B | 6.1 |
| 66 | (S)-7-(5-(isoquinolin-7-yl)-1H-imidazol-2-yl)-N-methyl-7-(2-(pyrrolidin-1-yl)acetamido)heptanamide | 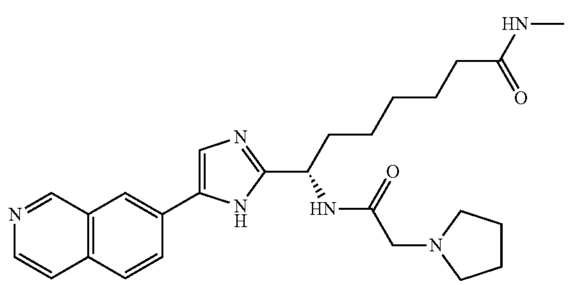 [SMILES: CNC(=O)CCCCC[C@H](NC(=O)CN1CCCC1)c1ncc(-c2ccc3ccncc3c2)[nH]1] | C | B | C | 3.1 |
| 67 | (S)-N-(1-(5-(isoquinolin-7-yl)-1H-imidazol-2-yl)-7-(methylamino)-7-oxoheptyl)isothiazole-5-carboxamide | 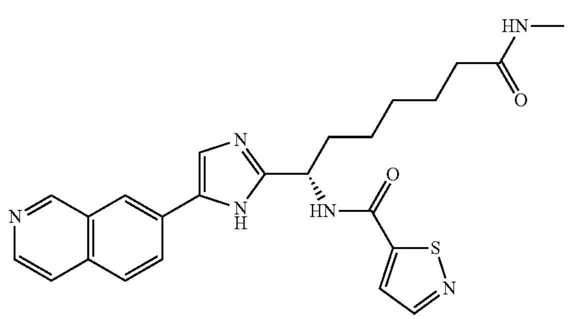 [SMILES: CNC(=O)CCCCC[C@H](NC(=O)c1ccns1)c1ncc(-c2ccc3ccncc3c2)[nH]1] | A | A | B | 7.6 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 68 | (S)-7-(5-(isoquinolin-7-yl)-1H-imidazol-2-yl)-N-methyl-7-(2-(4-methylthiazol-2-yl)acetamido)heptanamide | 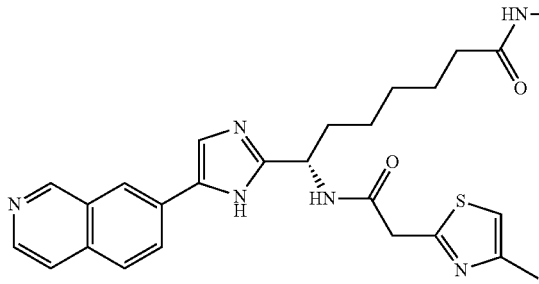 | C | B | C | 3.9 |
| 69 | (S)-7-(2-(1H-1,2,3-triazol-1-yl)acetamido)-N-methyl-7-(5-(4-(1-methyl-1H-pyrazol-3-yl)phenyl)-1H-imidazol-2-yl)heptanamide | 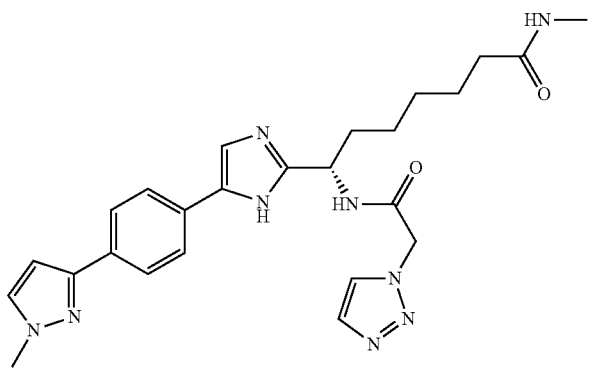 [SMILES: CNC(=O)CCCCC[C@H](NC(=O)Cn1ccnn1)c1ncc(-c2ccc(-c3ccn(C)n3)cc2)[nH]1] | C | C | C | 5.0 |
| 70 | (S)-7-(2-(5-methoxy-2-methyl-1H-indol-3-yl)acetamido)-7-(5-(naphthalen-2-yl)-4H-1,2,4-triazol-3-yl)heptanamide | 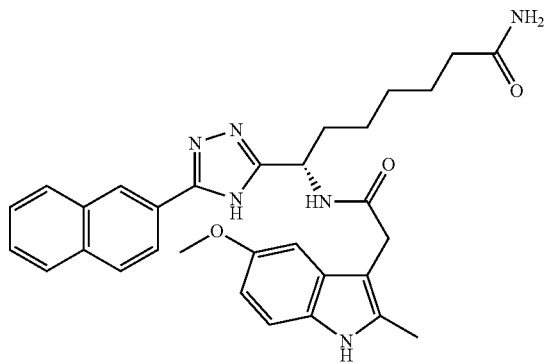 [SMILES: COc1ccc2[nH]c(C)c(CC(=O)N[C@@H](CCCCCC(N)=O)c3nnc(-c4ccc5ccccc5c4)[nH]3)c2c1] | A | A | B | 2.6 |
| 71 | (S)-N-(1-(5-(2-methoxyquinolin-3-yl)oxazol-2-yl)-7-(methylamino)-7-oxoheptyl)-1-methylazetidine-3-carboxamide | 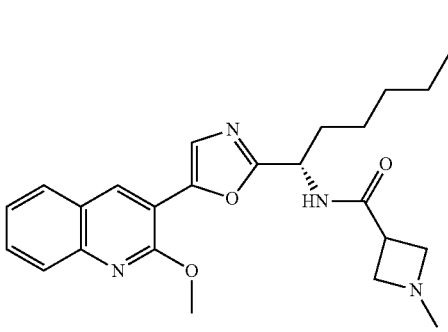 | A | A | B | 2.6 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 72 | (S)-benzyl (7-(methylamino)-1-(5-(naphthalen-2-yl)-1H-imidazol-2-yl)-7-oxo-heptyl)carbamate | 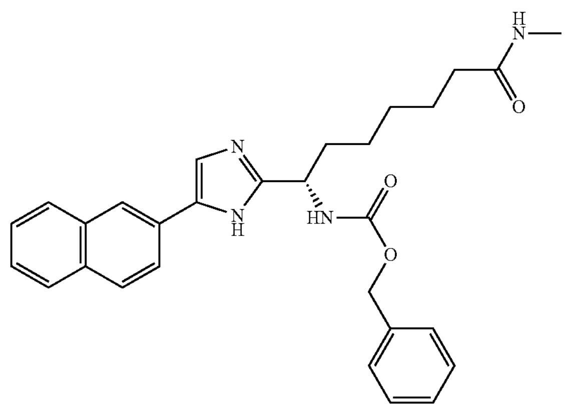 [SMILES: CNC(=O)CCCCC[C@H](NC(=O)OCc1ccccc1)c1ncc(-c2ccc3ccccc3c2)[nH]1] | B | A | B | 2.4 |
| 73 | (S)-5-methoxy-N-(7-(methylamino)-1-(5-(naphthalen-2-yl)-1H-imidazol-2-yl)-7-oxoheptyl)-1H-indole-2-carboxamide | 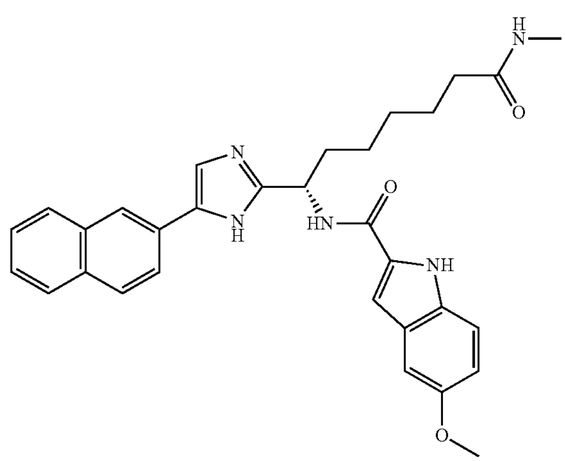 [SMILES: CNC(=O)CCCCC[C@H](NC(=O)c1cc2cc(OC)ccc2[nH]1)c1ncc(-c2ccc3ccccc3c2)[nH]1] | B | B | C | 14.8 |
| 74 | (S)-N-methyl-7-(5-(naphthalen-2-yl)-1H-imidazol-2-yl)-7-(2-(2-oxo-benzo[d]oxazol-3(2H)-yl)acetamido)heptanamide | 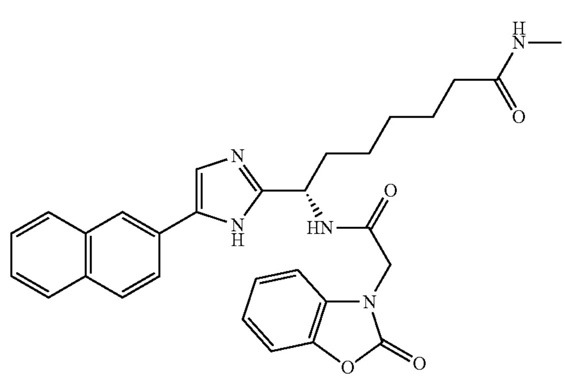 [SMILES: CNC(=O)CCCCC[C@H](NC(=O)Cn1c(=O)oc2ccccc21)c1ncc(-c2ccc3ccccc3c2)[nH]1] | B | A | B | 3.1 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 75 | (S)-7-(2-(5-methoxy-2-methyl-1H-indol-3-yl)acetamido)-N-methyl-7-(5-(naphthalen-2-yl)-1H-imidazol-2-yl)heptanamide | 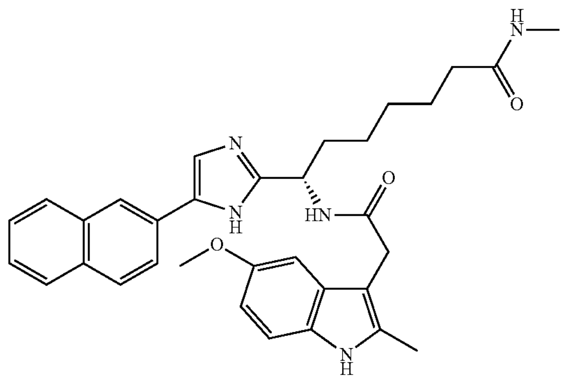 [SMILES: CNC(=O)CCCCC[C@H](NC(=O)Cc1c(C)[nH]c2ccc(OC)cc12)c1ncc(-c2ccc3ccccc3c2)[nH]1] | A | A | A | 2.1 |
| 76 | (S)-7-(5-(2-methoxyquinolin-3-yl)-1H-imidazol-2-yl)-N-methyl-7-(2-(pyrazin-2-yl)acetamido)heptanamide | 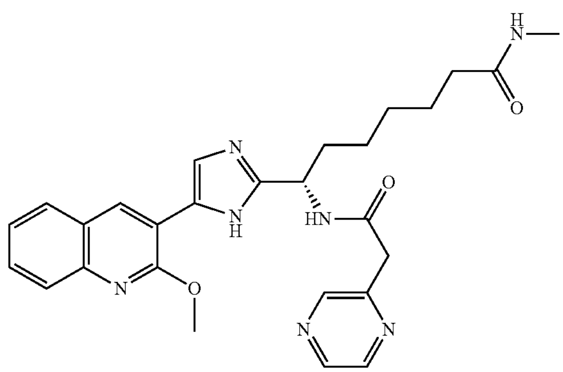 [SMILES: CNC(=O)CCCCC[C@H](NC(=O)Cc1cnccn1)c1ncc(-c2cc3ccccc3nc2OC)[nH]1] | B | B | C | 6.9 |
| 77 | (S)-N-(1-(5-(2-methoxyquinolin-3-yl)-1H-imidazol-2-yl)-7-(methylamino)-7-oxoheptyl)-5-methyl-1,3,4-oxadiazole-2-carboxamide | 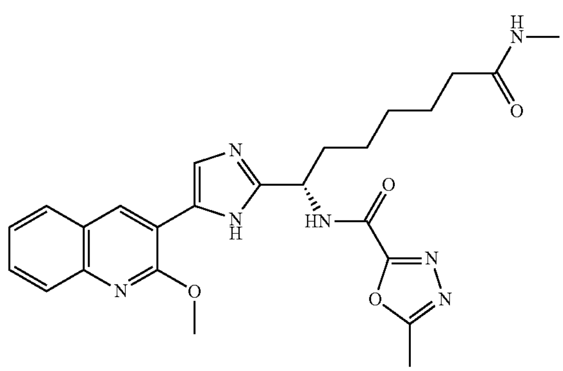 [SMILES: CNC(=O)CCCCC[C@H](NC(=O)c1nnc(C)o1)c1ncc(-c2cc3ccccc3nc2OC)[nH]1] | B | B | C | 3.0 |
| 78 | (S)-N-(1-(5-(4-((dimethylamino)methyl)phenyl)-1H-imidazol-2-yl)-7-(methylamino)-7-oxoheptyl)thiazole-5-carboxamide | 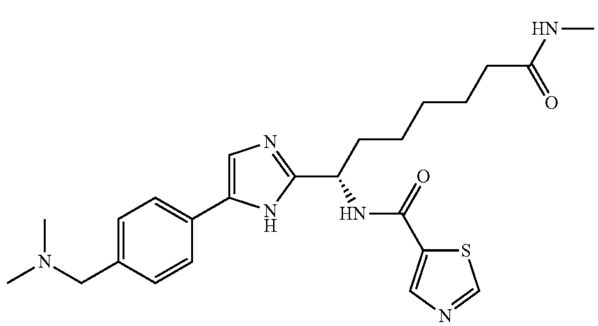 | C | B | C | 4.2 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 79 | (S)-N-(1-(5-(2,3-dihydro-benzo[b][1,4]dioxin-5-yl)-1H-imidazol-2-yl)-7-(methylamino)-7-oxohceptyl)thiazole-5-carboxamide | 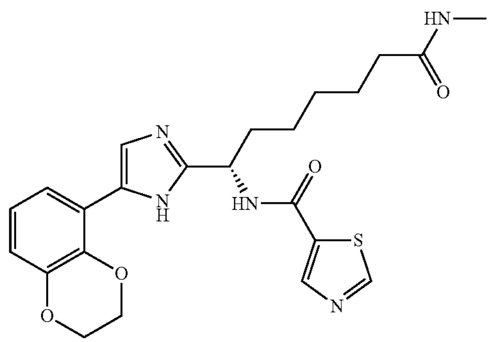 [SMILES: CNC(=O)CCCCC[C@H](NC(=O)c1cncs1)c1ncc(-c2cccc3c2OCCO3)[nH]1] | C | B | C | 5.0 |
| 80 | (S)-N-(1-(5-(2-chloroquinolin-3-yl)-1H-imidazol-2-yl)-7-(methylamino)-7-oxoheptyl)thiazole-5-carboxamide | 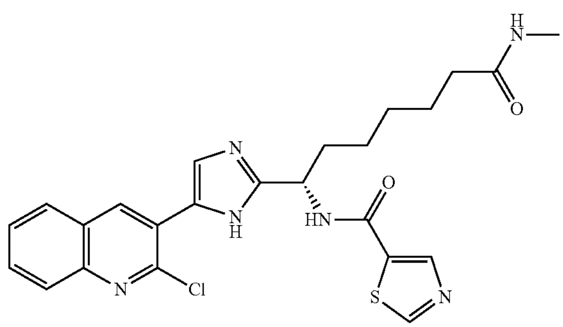 [SMILES: CNC(=O)CCCCC[C@H](NC(=O)c1cncs1)c1ncc(-c2cc3ccccc3nc2Cl)[nH]1] | B | B | C | 6.4 |
| 81 | (S)-N-(1-(5-(4-(3,5-dimethyl-1H-pyrazol-1-yl)phenyl)-1H-imidazol-2-yl)-7-(methylamino)-7-oxoheptyl)thiazole-5-carboxamide | 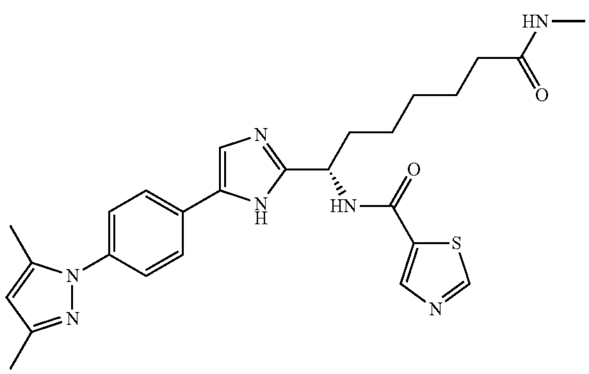 [SMILES: CNC(=O)CCCCC[C@H](NC(=O)c1cncs1)c1ncc(-c2ccc(-n3nc(C)cc3C)cc2)[nH]1] | C | C | C | 3.0 |
| 82 | (S)-5-methyl-N-(7-(methylamino)-1-(5-(naphthalen-2-yl)-1H-imidazol-2-yl)-7-oxoheptyl)-1-phenyl-1H-pyrazole-3-carboxamide | 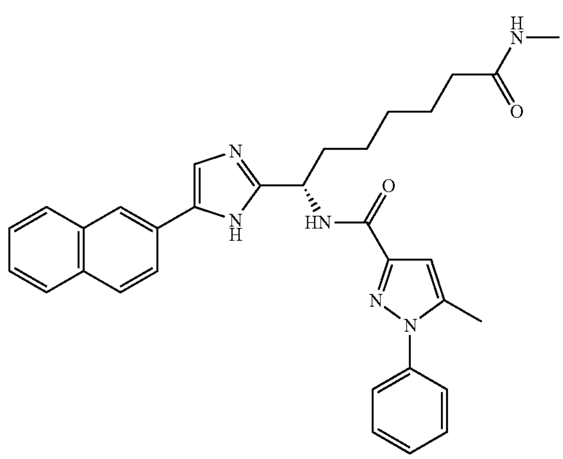 [SMILES: CNC(=O)CCCCC[C@H](NC(=O)c1cc(C)n(-c2ccccc2)n1)c1ncc(-c2ccc3ccccc3c2)[nH]1] | C | C | C | 3.8 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 83 | (S)-N-(7-(methylamino)-1-(5-(naphthalen-2-yl)-1H-imidazol-2-yl)-7-oxoheptyl)-6-(1H-pyrrol-1-yl)nicotinamide | 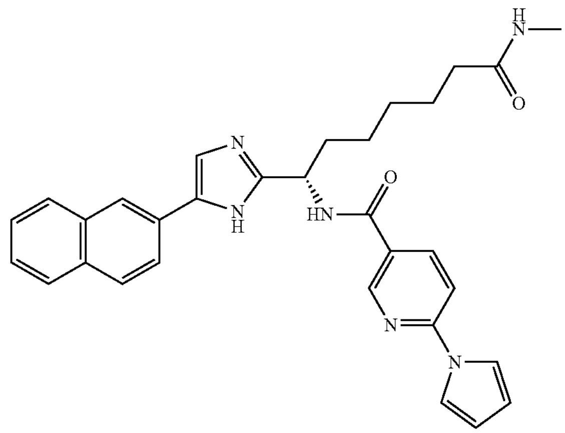 [SMILES: CNC(=O)CCCCC[C@H](NC(=O)c1ccc(-n2cccc2)nc1)c1ncc(-c2ccc3ccccc3c2)[nH]1] | B | B | C | 8.6 |
| 84 | (S)-5-methyl-N-(7-(methylamino)-1-(5-(naphthalen-2-yl)-1H-imidazol-2-yl)-7-oxoheptyl)-1,3,4-thiadiazole-2-carboxamide | 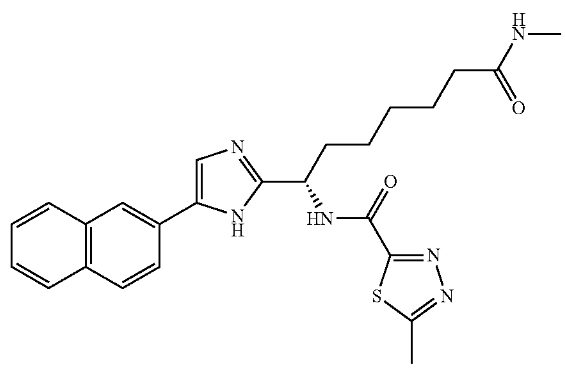 [SMILES: CNC(=O)CCCCC[C@H](NC(=O)c1nnc(C)s1)c1ncc(-c2ccc3ccccc3c2)[nH]1] | C | B | C | 2.5 |
| 85 | (7S)-7-(2-(1H-pyrazol-1-yl)propanamido)-N-methyl-7-(5-(naphthalen-2-yl)-1H-imidazol-2-yl)heptanamide | 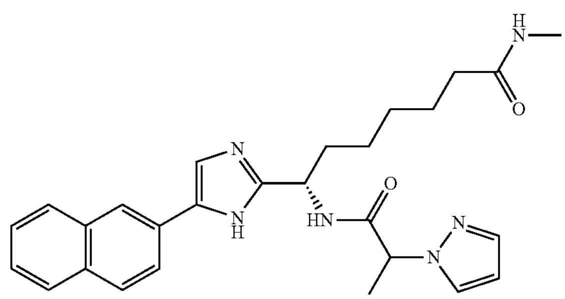 [SMILES: CNC(=O)CCCCC[C@H](NC(=O)C(C)n1cccn1)c1ncc(-c2ccc3ccccc3c2)[nH]1] | B | B | C | 7.9 |
| 86 | (S)-3-(furan-2-yl)-N-(7-(methylamino)-1-(5-(naphthalen-2-yl)-1H-imidazol-2-yl)-7-oxoheptyl)-1H-pyrazole-5-carboxamide | 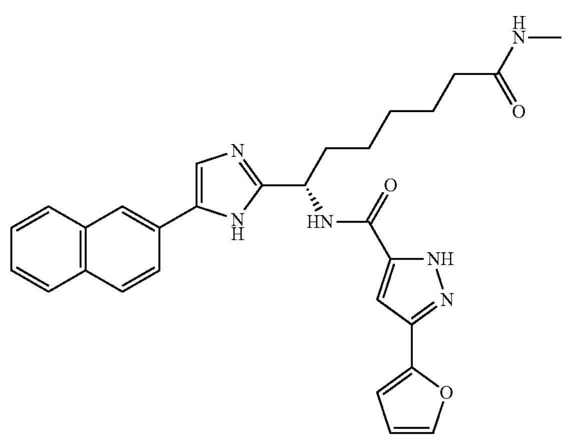 [SMILES: CNC(=O)CCCCC[C@H](NC(=O)c1cc(-c2ccco2)n[nH]1)c1ncc(-c2ccc3ccccc3c2)[nH]1] | B | B | C | 8.3 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 87 | (S)-N-(7-(methylamino)-1-(5-(naphthalen-2-yl)-1H-imidazol-2-yl)-7-oxoheptyl)-2-(1H-tetrazol-1-yl)benzamide | 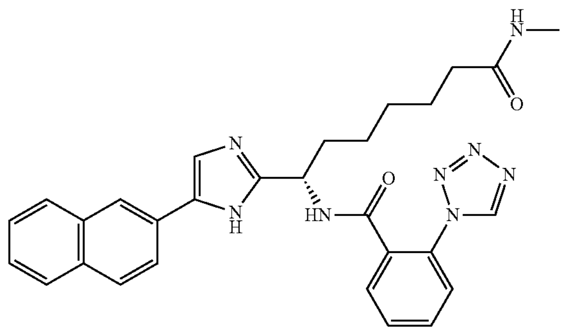 [SMILES: CNC(=O)CCCCC[C@H](NC(=O)c1ccccc1-n1cnnn1)c1ncc(-c2ccc3ccccc3c2)[nH]1] | B | B | C | 7.3 |
| 88 | (S)-N-(7-(methylamino)-1-(5-(naphthalen-2-yl)-1H-imidazol-2-yl)-7-oxo-heptyl)quinoxaline-5-carboxamide | 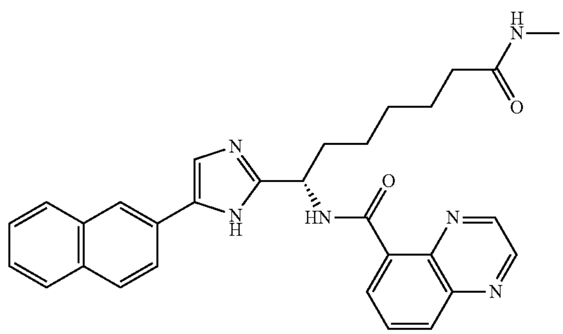 [SMILES: CNC(=O)CCCCC[C@H](NC(=O)c1cccc2nccnc12)c1ncc(-c2ccc3ccccc3c2)[nH]1] | C | C | C | 3.4 |
| 89 | (S)-7-(2-(1H-1,2,4-triazol-1-yl)acetamido)-7-(5-(isoquinolin-7-yl)-1H-imidazol-2-yl)-N-methylheptanamide | 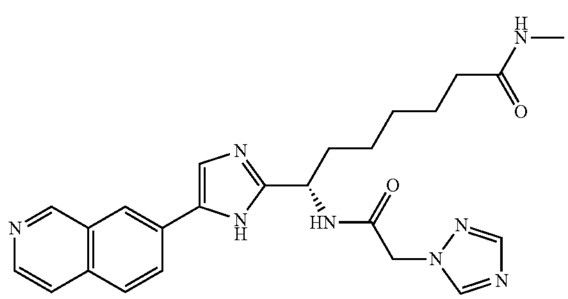 [SMILES: CNC(=O)CCCCC[C@H](NC(=O)Cn1cncn1)c1ncc(-c2ccc3ccncc3c2)[nH]1] | B | B | C | 8.2 |
| 90 | (S)-1-isopropyl-N-(1-(5-(isoquinolin-7-yl)-1H-imidazol-2-yl)-7-(methylamino)-7-oxoheptyl)-1H-pyrazole-4-carboxamide | 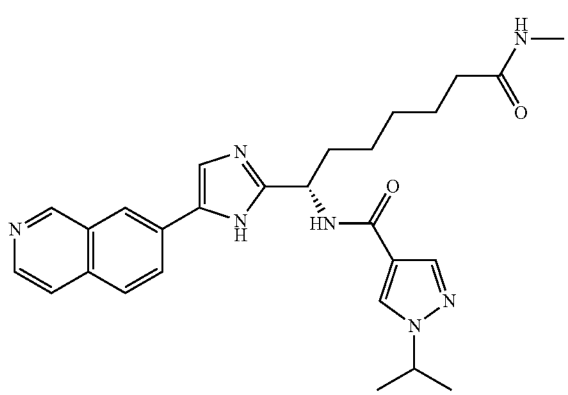 [SMILES: CNC(=O)CCCCC[C@H](NC(=O)c1cnn(C(C)C)c1)c1ncc(-c2ccc3ccncc3c2)[nH]1] | A | A | B | 8.7 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 91 | 2,2-difluoro-N-((S)-1-(5-(4-(1-methyl-1H-pyrazol-3-yl)phenyl)-1H-imidazol-2-yl)-7-(methylamino)-7-oxo-heptyl)cyclobutane-carboxamide | 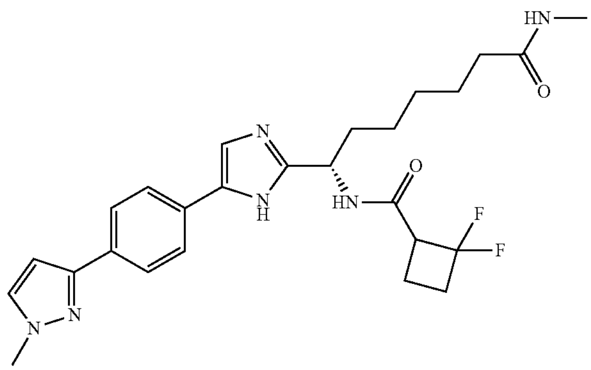 [SMILES: CNC(=O)CCCCC[C@H](NC(=O)C1CCC1(F)F)c1ncc(-c2ccc(-c3ccn(C)n3)cc2)[nH]1] | C | C | C | 3.7 |
| 92 | (S)-7-(2-(6,7-dihydro-5H-thiazolo[3,2-a]pyrimidin-3-yl)acetamido)-N-methyl-7-(5-(4-(1-methyl-1H-pyrazol-3-yl)phenyl)-1H-imidazol-2-yl)heptanamide | 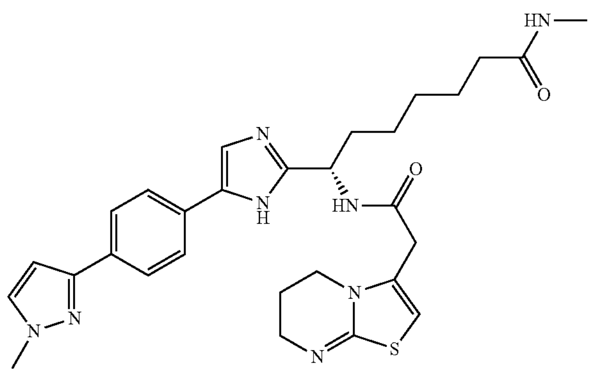 [SMILES: CNC(=O)CCCCC[C@H](NC(=O)CC1=CSC2=NCCCN12)c1ncc(-c2ccc(-c3ccn(C)n3)cc2)[nH]1] | C | B | C | 4.0 |
| 93 | (S)-benzyl (1-(5-(isoquinolin-7-yl)-1H-imidazol-2-yl)-7-(methylamino)-7-oxoheptyl)carbamate | 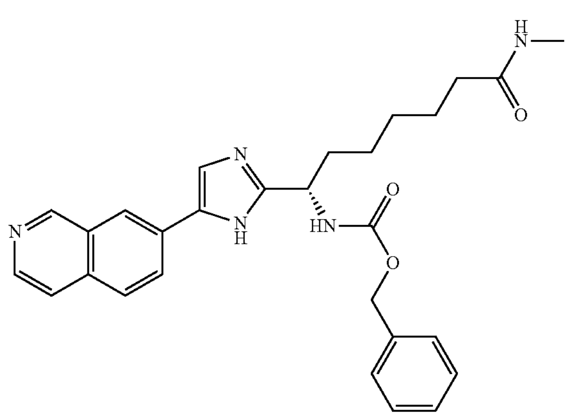 [SMILES: CNC(=O)CCCCC[C@H](NC(=O)OCc1ccccc1)c1ncc(-c2ccc3ccncc3c2)[nH]1] | A | A | C | 11.8 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 94 | (S)-7-(3-(2-ethyl-1H-benzo[d]imidazol-1-yl)propanamido)-N-methyl-7-(5-(naphthalen-2-yl)-1,3,4-oxadiazol-2-yl)heptanamide | 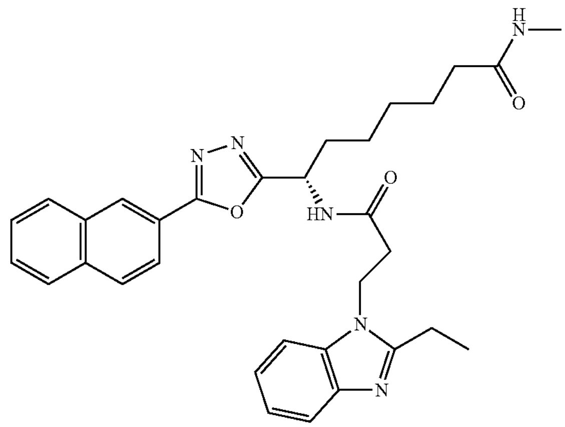 [SMILES: CCc1nc2ccccc2n1CCC(=O)N[C@@H](CCCCCC(=O)NC)c1nnc(-c2ccc3ccccc3c2)o1] | B | B | C | 9.9 |
| 95 | (S)-N-(7-(methylamino)-1-(5-(naphthalen-2-yl)-1H-imidazol-2-yl)-7-oxo-heptyl)thiazole-5-carboxamide | 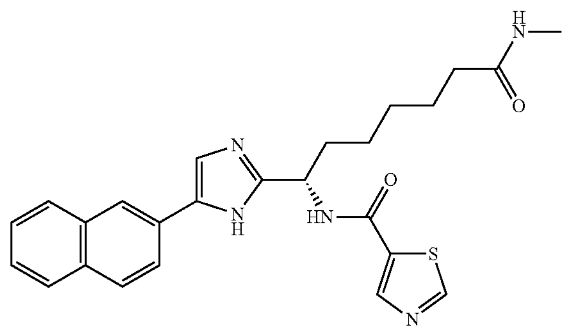 [SMILES: CNC(=O)CCCCC[C@H](NC(=O)c1cncs1)c1ncc(-c2ccc3ccccc3c2)[nH]1] | A | A | B | 5.6 |
| 96 | (S)-7-(2-(5-methoxy-2-methyl-1H-indol-3-yl)acetamido)-7-(5-(naphthalen-2-yl)-1H-imidazol-2-yl)heptanamide | 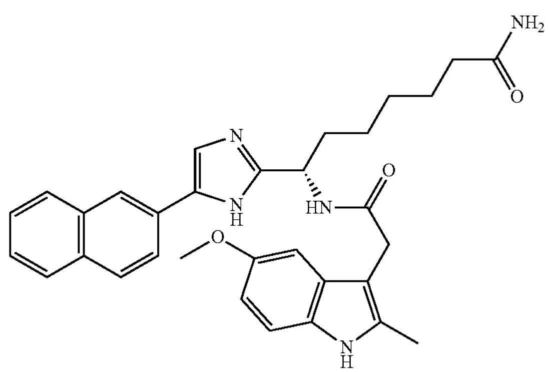 [SMILES: COc1ccc2[nH]c(C)c(CC(=O)N[C@@H](CCCCCC(N)=O)c3ncc(-c4ccc5ccccc5c4)[nH]3)c2c1] | A | A | A | 8.9 |
| 97 | (S)-N-(1-(5-(3-methoxynaphthalen-2-yl)-1H-imidazol-2-yl)-7-(methylamino)-7-oxoheptyl)thiazole-5-carboxamide | 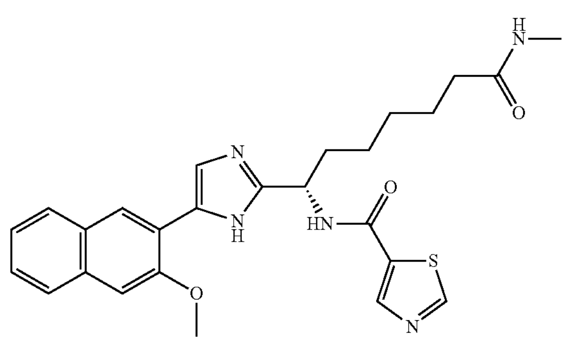 [SMILES: CNC(=O)CCCCC[C@H](NC(=O)c1cncs1)c1ncc(-c2cc3ccccc3cc2OC)[nH]1] | A | A | A | 2.9 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 98 | (S)-N-(1-(5-(2-methoxyquinolin-3-yl)-1H-imidazol-2-yl)-7-(methylamino)-7-oxoheptyl)-1-methylazetidine-3-carboxamide | 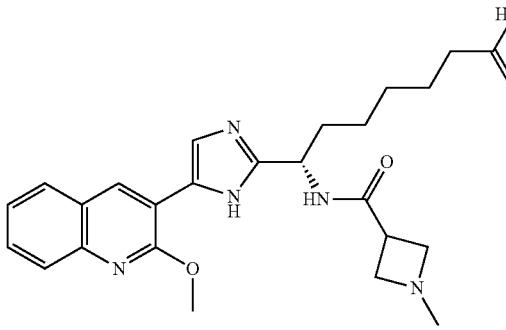 | B | B | C | 3.0 |
| 99 | (S)-7-(5-(2-methoxyquinolin-3-yl)-1H-imidazol-2-yl)-N-methyl-7-(3-(piperidin-1-yl)propanamido)heptanamide | 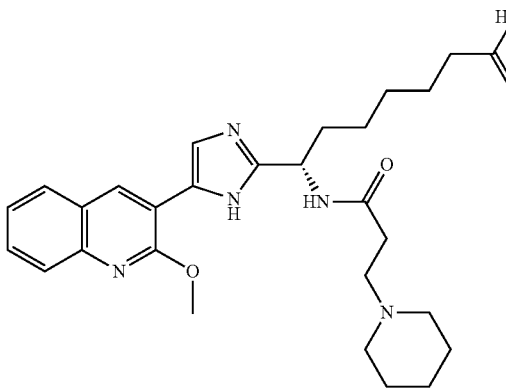 | B | A | B | 3.1 |
| 100 | (1r,3R,5S)-N-((S)-7-(methylamino)-7-oxo-1-(5-(4-(trifluoromethyl)phenyl)-1H-imidazol-2-yl)heptyl)adamantane-1-carboxamide | 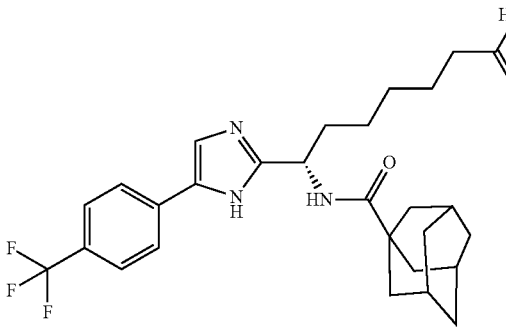 | B | C | C | 9.1 |
| 101 | (S)-N-methyl-7-(3-(piperidin-1-yl)propanamido)-7-(5-(4-(trifluoromethyl)phenyl)-1H-imidazol-2-yl)heptanamide | 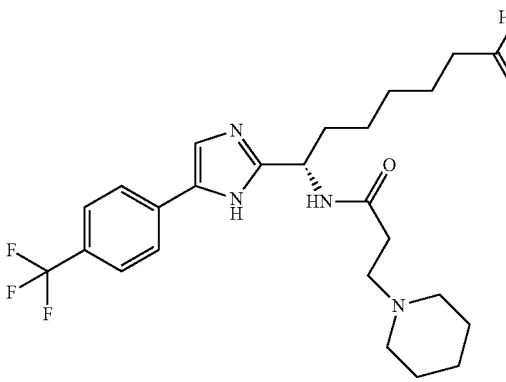 | B | C | C | 3.2 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 102 | (S)-N-(1-(5-(2-methoxyquinolin-3-yl)-1H-imidazol-2-yl)-7-(methylamino)-7-oxoheptyl)-1H-1,2,4-triazole-3-carboxamide | 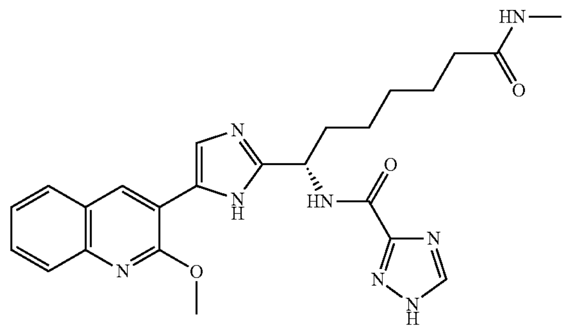 [SMILES: CNC(=O)CCCCC[C@H](NC(=O)c1nc[nH]n1)c1ncc(-c2cc3ccccc3nc2OC)[nH]1] | C | C | C | 2.6 |
| 103 | 7S)-7-(2-(1H-pyrazol-1-yl)propanamido)-7-(5-(2-methoxyquinolin-3-yl)-1H-imidazol-2-yl)-N-methylheptanamide | 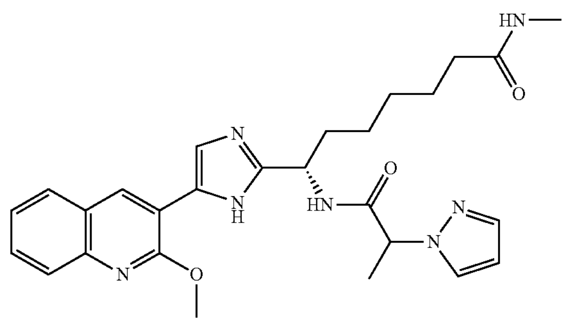 [SMILES: CNC(=O)CCCCC[C@H](NC(=O)C(C)n1cccn1)c1ncc(-c2cc3ccccc3nc2OC)[nH]1] | B | C | C | 9.3 |
| 104 | (S)-N-((S)-1-(5-(2-methoxyquinolin-3-yl)-1H-imidazol-2-yl)-7-(methylamino)-7-oxoheptyl)-1-methylpyrrolidine-2-carboxamide | 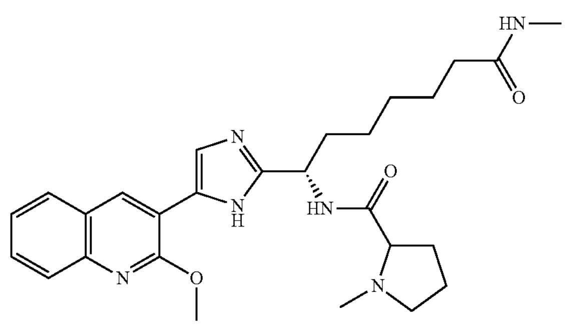 | C | C | C | 2.5 |
| 105 | (S)-N-(1-(5-(3-methoxyisoquinolin-7-yl)-1H-imidazol-2-yl)-7-(methylamino)-7-oxoheptyl)thiazole-5-carboxamide | 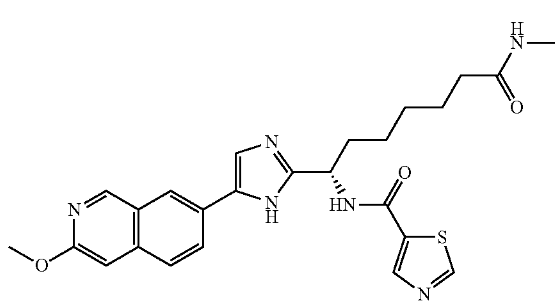 | A | A | B | 13.9 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 106 | (S)-7-(5-(2-methoxyquinolin-3-yl)-1H-imidazol-2-yl)-N-methyl-7-(2-(pyridin-2-yl)acetamido)heptanamide | 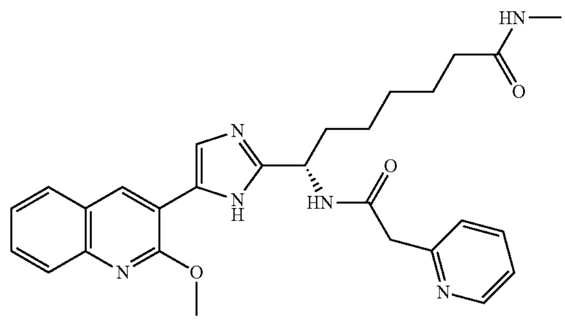 [SMILES: CNC(=O)CCCCC[C@H](NC(=O)Cc1ccccn1)c1ncc(-c2cc3ccccc3nc2OC)[nH]1] | C | B | C | 2.0 |
| 107 | (S)-N-(1-(5-(2-methoxyquinolin-6-yl)-1H-imidazol-2-yl)-7-(methylamino)-7-oxoheptyl)thiazole-5-carboxamide | 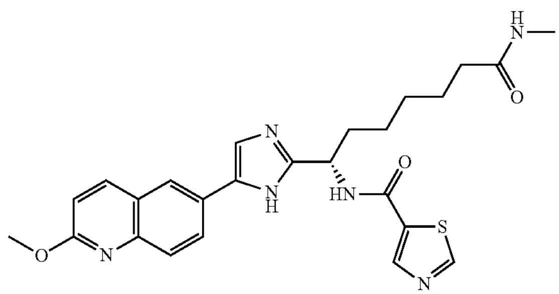 | A | A | B | 3.0 |
| 108 | (S)-N-(1-(5-([1,1'-biphenyl]-4-yl)-1H-imidazol-2-yl)-7-(methylamino)-7-oxoheptyl)thiazole-5-carboxamide | 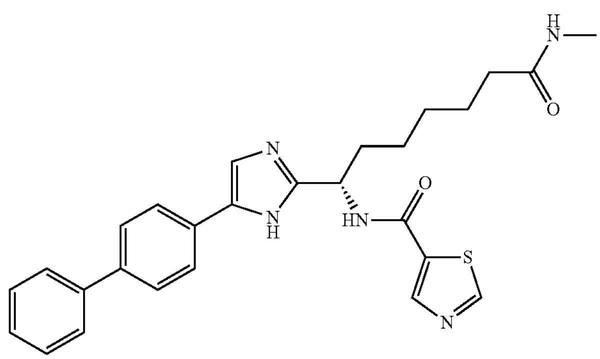 | C | C | C | 3.5 |
| 109 | (S)-N-(7-(methylamino)-7-oxo-1-(5-(4-(thiophen-2-yl)phenyl)-1H-imidazol-2-yl)heptyl)thiazole-5-carboxamide | 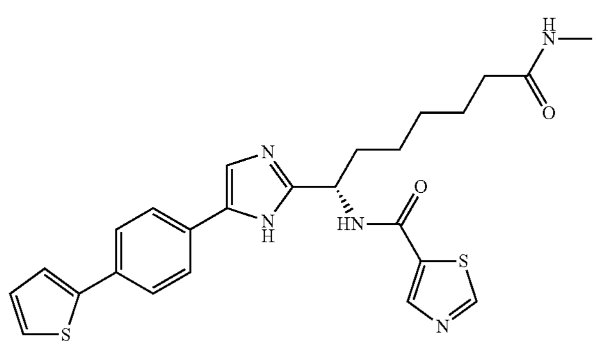 [SMILES: CNC(=O)CCCCC[C@H](NC(=O)c1cncs1)c1ncc(-c2ccc(-c3cccs3)cc2)[nH]1] | B | B | C | 4.0 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 110 | (S)-7-(5-(4-(1H-pyrazol-1-yl)phenyl)-1H-imidazol-2-yl)-N-methyl-7-(2-(quinolin-3-yl)acetamido)heptanamide | 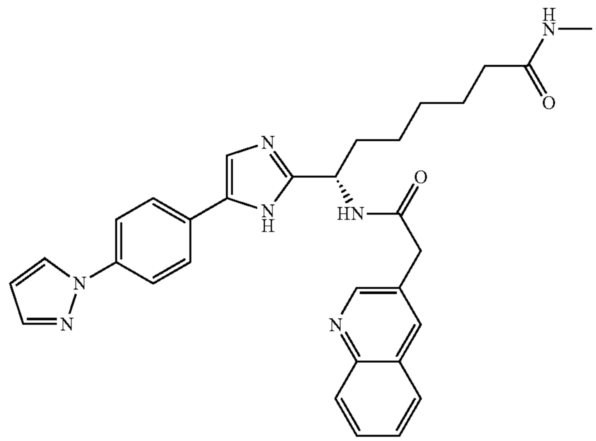 [SMILES: CNC(=O)CCCCC[C@H](NC(=O)Cc1cnc2ccccc2c1)c1ncc(-c2ccc(-n3cccn3)cc2)[nH]1] | B | A | B | 6.7 |
| 111 | (S)-4-fluoro-N-(1-(5-(isoquinolin-7-yl)-1H-imidazol-2-yl)-7-(methylamino)-7-oxoheptyl)-1-methylpiperidine-4-carboxamide | 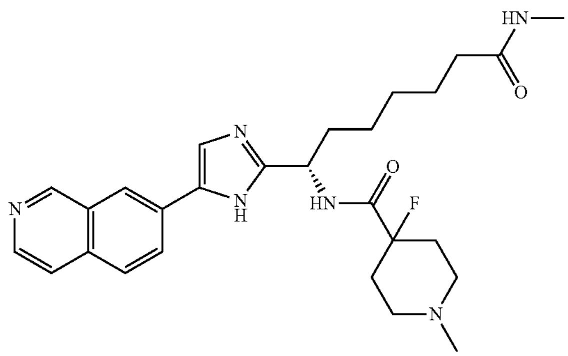 [SMILES: CNC(=O)CCCCC[C@H](NC(=O)C1(F)CCN(C)CC1)c1ncc(-c2ccc3ccncc3c2)[nH]1] | C | B | C | 4.9 |
| 112 | (S)-N-(1-(5-(1H-benzo[d][1,2,3]triazol-5-yl)-1H-imidazol-2-yl)-7-(methylamino)-7-oxoheptyl)thiazole-5-carboxamide | 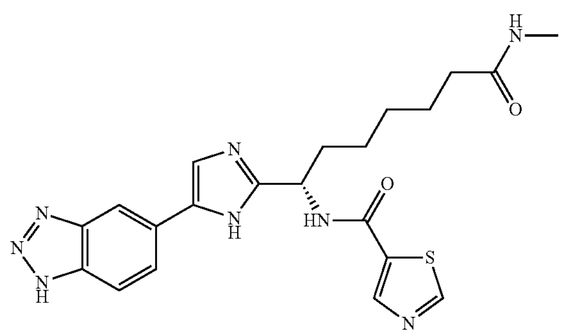 [SMILES: CNC(=O)CCCCC[C@H](NC(=O)c1cncs1)c1ncc(-c2ccc3[nH]nnc3c2)[nH]1] | C | C | C | 2.5 |
| 113 | (S)-N-methyl-7-(5-(naphthalen-2-yl)-1H-imidazol-2-yl)-7-(2-(pyrazin-2-yl)acetamido)heptanamide | 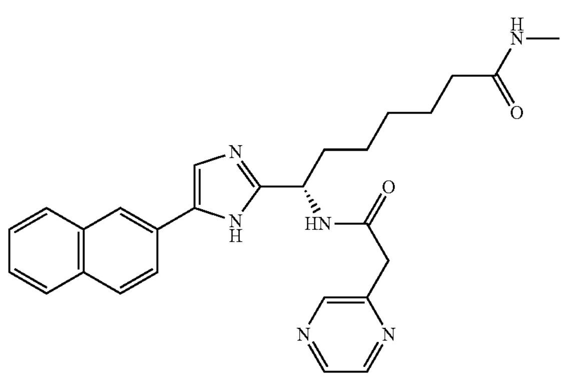 [SMILES: CNC(=O)CCCCC[C@H](NC(=O)Cc1cnccn1)c1ncc(-c2ccc3ccccc3c2)[nH]1] | B | B | C | 12.0 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 114 | (S)-N-(7-(methylamino)-1-(5-(naphthalen-2-yl)-1H-imidazol-2-yl)-7-oxo-heptyl)isoquinoline-6-carboxamide | 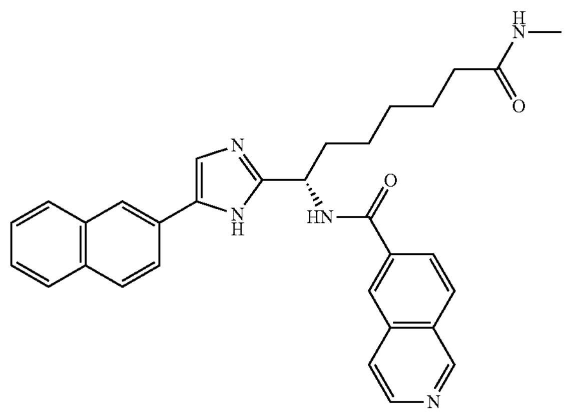 [SMILES: CNC(=O)CCCCC[C@H](NC(=O)c1ccc2cnccc2c1)c1ncc(-c2ccc3ccccc3c2)[nH]1] | B | B | C | 6.8 |
| 115 | (S)-N-methyl-7-(5-(naphthalen-2-yl)-1H-imidazol-2-yl)-7-(2-(5-oxo-4,5-dihydro-1H-1,2,4-triazol-3-yl)aceta-mido)heptanamide | 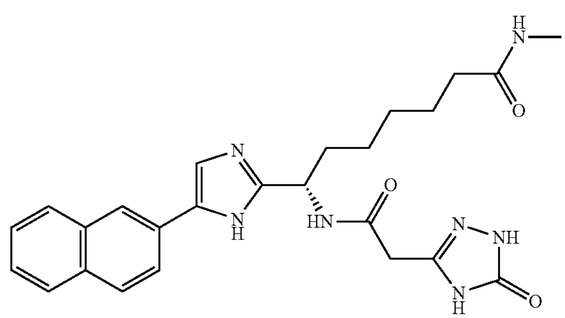 [SMILES: CNC(=O)CCCCC[C@H](NC(=O)Cc1n[nH]c(=O)[nH]1)c1ncc(-c2ccc3ccccc3c2)[nH]1] | B | B | C | 6.8 |
| 116 | (S)-7-(2-(4H-1,2,4-triazol-4-yl)acetamido)-N-methyl-7-(5-(naphthalen-2-yl)-1H-imidazol-2-yl)heptanamide | 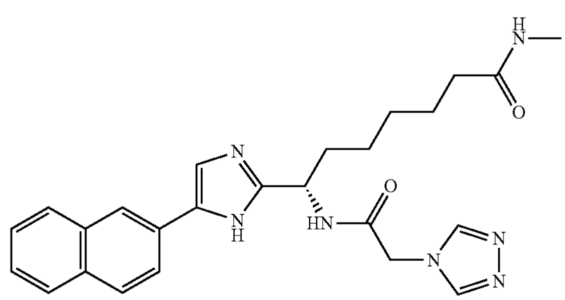 [SMILES: CNC(=O)CCCCC[C@H](NC(=O)Cn1cnnc1)c1ncc(-c2ccc3ccccc3c2)[nH]1] | B | B | C | 10.2 |
| 117 | (S)-N-(7-(methylamino)-1-(5-(naphthalen-2-yl)-1H-imidazol-2-yl)-7-oxoheptyl)-4-(1H-tetrazol-1-yl)benzamide | 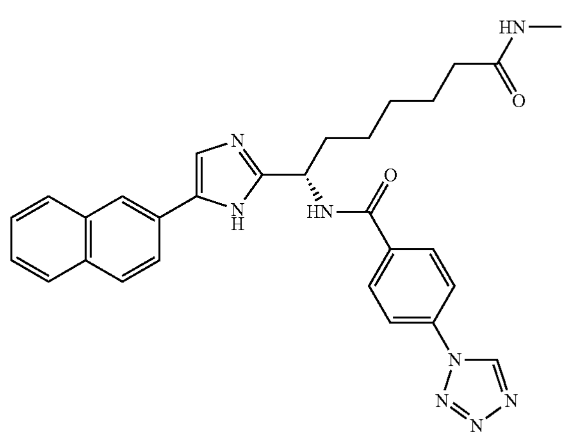 [SMILES: CNC(=O)CCCCC[C@H](NC(=O)c1ccc(-n2cnnn2)cc1)c1ncc(-c2ccc3ccccc3c2)[nH]1] | B | B | C | 7.7 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 118 | (S)-N-(1-(5-(isoquinolin-7-yl)-1H-imidazol-2-yl)-7-(methylamino)-7-oxoheptyl)-1-methylpiperidine-4-carboxamide | 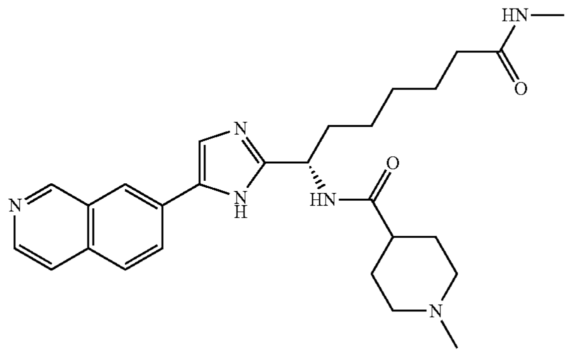 [SMILES: CNC(=O)CCCCC[C@H](NC(=O)C1CCN(C)CC1)c1ncc(-c2ccc3ccncc3c2)[nH]1] | B | B | C | 4.4 |
| 119 | (S)-7-(5-(isoquinolin-7-yl)-1H-imidazol-2-yl)-N-methyl-7-(2-(3-methyl-1H-pyrazol-1-yl)acetamido)heptanamide | 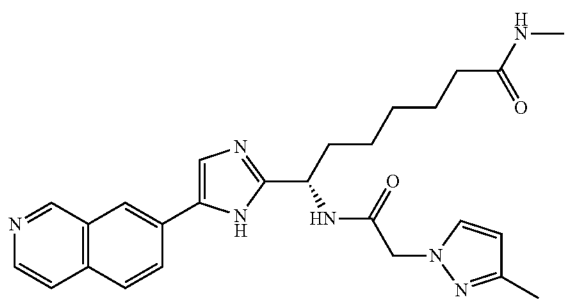 [SMILES: CNC(=O)CCCCC[C@H](NC(=O)Cn1ccc(C)n1)c1ncc(-c2ccc3ccncc3c2)[nH]1] | B | B | C | 6.4 |
| 120 | (S)-N-(7-(methylamino)-7-oxo-1-(5-(4-(pyrimidin-2-yl)phenyl)-1H-imidazol-2-yl)heptyl)thiazole-5-carboxamide | 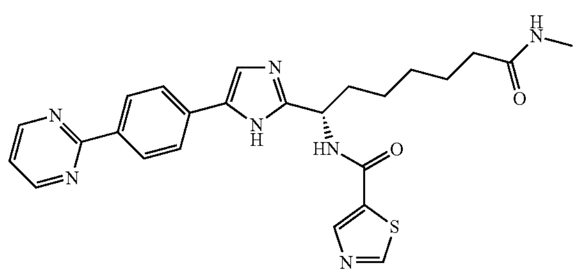 [SMILES: CNC(=O)CCCCC[C@H](NC(=O)c1cncs1)c1ncc(-c2ccc(-c3ncccn3)cc2)[nH]1] | B | B | C | 10.9 |
| 121 | N-((S)-1-(5-(isoquinolin-7-yl)-1H-imidazol-2-yl)-7-(methylamino)-7-oxoheptyl)-2-methyltetrahydrofuran-2-carboxamide | 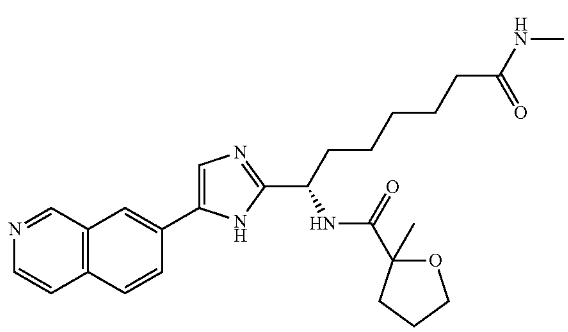 [SMILES: CNC(=O)CCCCC[C@H](NC(=O)C1(C)CCCO1)c1ncc(-c2ccc3ccncc3c2)[nH]1] | C | C | C | 2.0 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 122 | S)-7-(3-(5,7-dimethyl-[1,2,4]triazolo[1,5-a]pyrimidin-6-yl)propanamido)-7-(5-(isoquinolin-7-yl)-1H-imidazol-2-yl)-N-methylheptanamide | 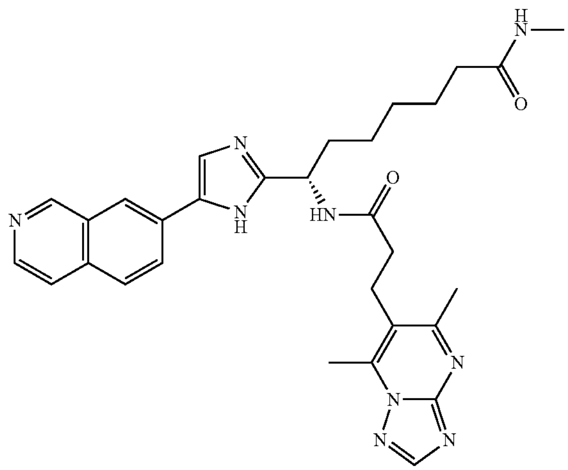 [SMILES: CNC(=O)CCCCC[C@H](NC(=O)CCc1c(C)nc2ncnn2c1C)c1ncc(-c2ccc3ccncc3c2)[nH]1] | A | A | B | 8.1 |
| 123 | 2-methyl-N-((S)-1-(5-(4-(1-methyl-1H-pyrazol-3-yl)phenyl)-1H-imidazol-2-yl)-7-(methylamino)-7-oxoheptyl)tetrahydrofuran-2-carboxamide | 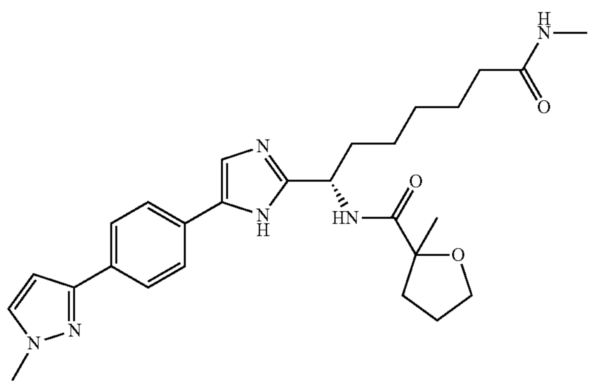 [SMILES: CNC(=O)CCCCC[C@H](NC(=O)C1(C)CCCO1)c1ncc(-c2ccc(-c3ccn(C)n3)cc2)[nH]1] | C | C | C | 2.0 |
| 124 | (S)-N-(1-(5-(4-(1-methyl-1H-pyrazol-3-yl)phenyl)-1H-imidazol-2-yl)-7-(methylamino)-7-oxoheptyl)-2-(pyrrolidin-1-ylmethyl)thiazole-5-carboxamide | 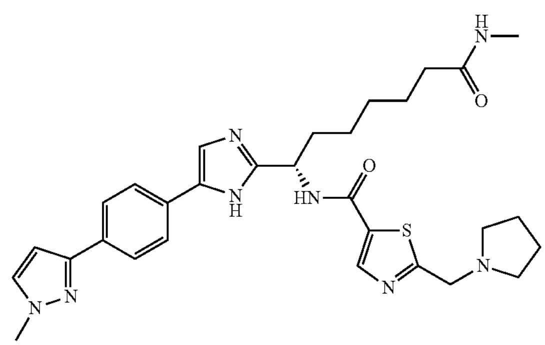 [SMILES: CNC(=O)CCCCC[C@H](NC(=O)c1cnc(CN2CCCC2)s1)c1ncc(-c2ccc(-c3ccn(C)n3)cc2)[nH]1] | A | B | C | 11.7 |
| 125 | (S)-N-(1-(5-([1,2,4]triazolo[1,5-a]pyridin-7-yl)-1H-imidazol-2-yl)-7-(methylamino)-7-oxoheptyl)thiazole-5-carboxamide | 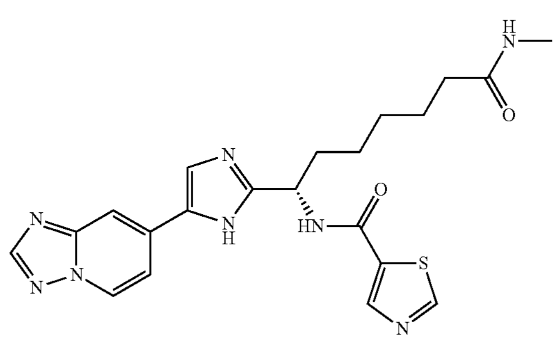 [SMILES: CNC(=O)CCCCC[C@H](NC(=O)c1cncs1)c1ncc(-c2ccn3ncnc3c2)[nH]1] | C | C | C | 5.0 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 126 | (S)-N-(7-(methylamino)-1-(5-(naphthalen-2-yl)-1H-imidazol-2-yl)-7-oxo-heptyl)quinuclidine-4-carboxamide | 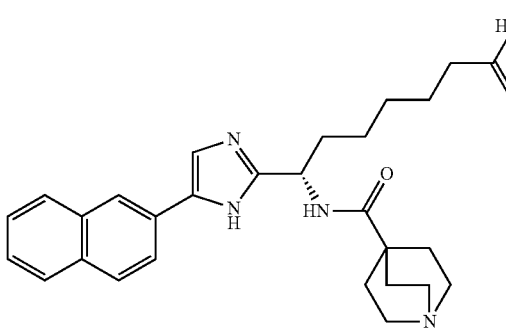 | A | A | B | 12.2 |
| 127 | (S)-N-(7-(methylamino)-7-oxo-1-(5-(quinolin-6-yl)-1H-imidazol-2-yl)heptyl)thiazole-5-carboxamide | 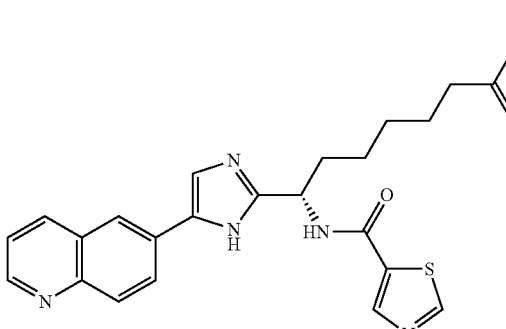 | A | B | C | 19.2 |
| 128 | (S)-N-(7-(methylamino)-7-oxo-1-(5-(quinolin-2-yl)-1H-imidazol-2-yl)heptyl)thiazole-5-carboxamide | 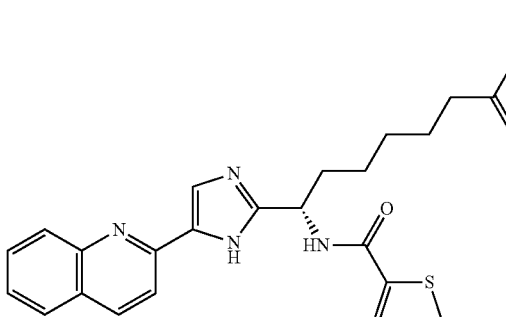 | B | C | C | 6.2 |
| 129 | (S)-N-(1-(5-(3,4-dichlorophenyl)-1H-imidazol-2-yl)-7-(methylamino)-7-oxoheptyl)thiazole-5-carboxamide | 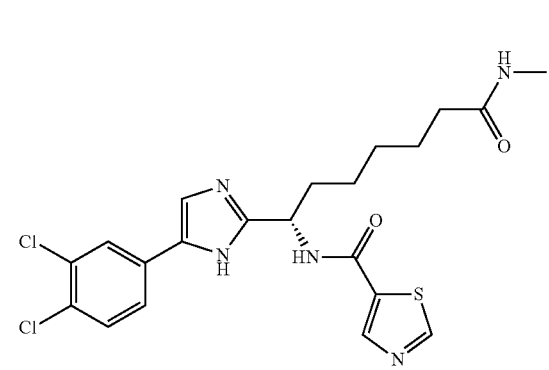 [SMILES: CNC(=O)CCCCC[C@H](NC(=O)c1cncs1)c1ncc(-c2ccc(Cl)c(Cl)c2)[nH]1] | C | C | C | 4.0 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 130 | S)-7-(5-(2-methoxyquinolin-3-yl)-1H-imidazol-2-yl)-N-methyl-7-(3-morpholino-propana-mido)heptanamide | 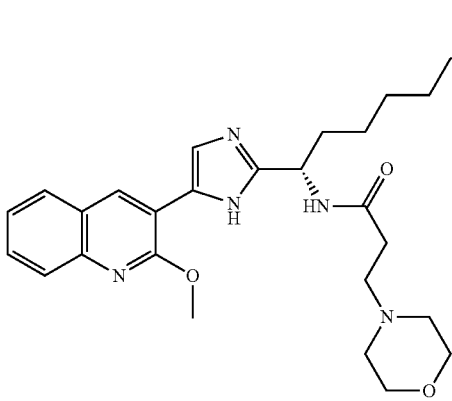 | B | C | C | 4.0 |
| 131 | (S)-7-(5-(2-methoxyquinolin-3-yl)-1H-imidazol-2-yl)-N-methyl-7-(3-(4-methylpiperazin-1-yl)propana-mido)heptanamide | 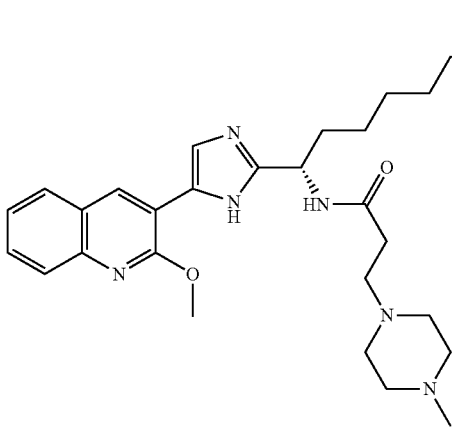 | B | A | C | 4.4 |
| 132 | (S)-N-(1-(5-(1-methyl-1H-indol-5-yl)-1H-imidazol-2-yl)-7-(methylamino)-7-oxoheptyl)thiazole-5-carboxamide | 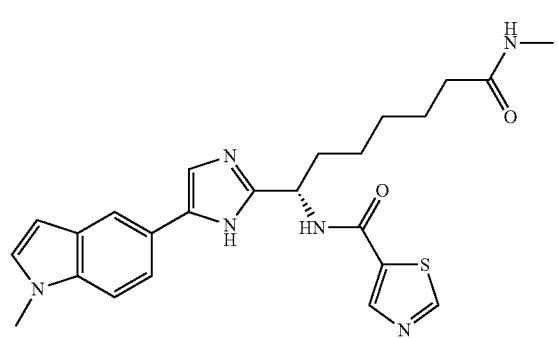 [SMILES: CNC(=O)CCCCC[C@H](NC(=O)c1cncs1)c1ncc(-c2ccc3c(ccn3C)c2)[nH]1] | A | A | B | 4.5 |
| 133 | (S)-N-(1-(5-(2-methoxyquinolin-3-yl)-1H-imidazol-2-yl)-7-(methylamino)-7-oxoheptyl)-4-methyltetrahydro-2H-pyran-4-carboxamide | 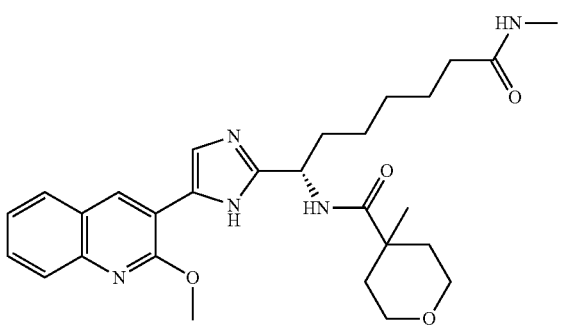 [SMILES: CNC(=O)CCCCC[C@H](NC(=O)C1(C)CCOCC1)c1ncc(-c2cc3ccccc3nc2OC)[nH]1] | B | B | C | 10.3 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 134 | (S)-7-(5-(2-methoxyquinolin-3-yl)-1H-imidazol-2-yl)-N-methyl-7-(3-(1-methyl-1H-pyrazol-4-yl)propanamido)heptanamide | 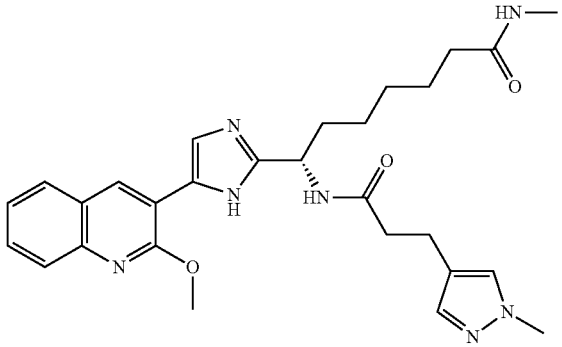 [SMILES: CNC(=O)CCCCC[C@H](NC(=O)CCc1cnn(C)c1)c1ncc(-c2cc3ccccc3nc2OC)[nH]1] | B | C | C | 10.1 |
| 135 | (S)-N-(1-(5-(2-methoxyquinolin-3-yl)-1H-imidazol-2-yl)-7-(methylamino)-7-oxoheptyl)-1-methyl-1H-pyrazole-3-carboxamide | 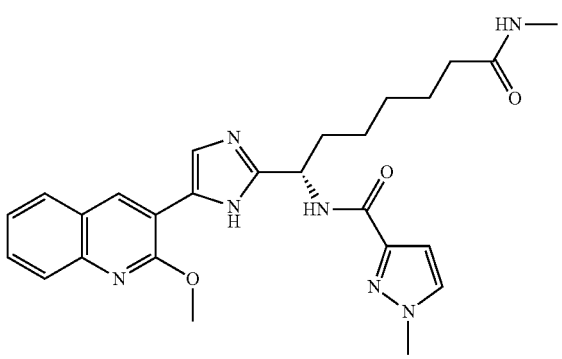 [SMILES: CNC(=O)CCCCC[C@H](NC(=O)c1ccn(C)n1)c1ncc(-c2cc3ccccc3nc2OC)[nH]1] | B | C | C | 5.8 |
| 136 | (S)-N-(1-(5-(benzofuran-5-yl)-1H-imidazol-2-yl)-7-(methylamino)-7-oxoheptyl)thiazole-5-carboxamide | 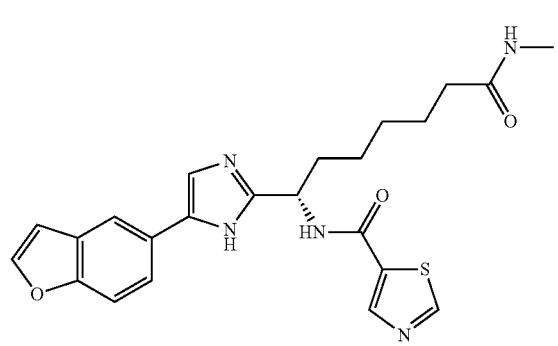 [SMILES: CNC(=O)CCCCC[C@H](NC(=O)c1cncs1)c1ncc(-c2ccc3occc3c2)[nH]1] | C | C | C | 5.0 |
| 137 | (S)-N-(1-(5-(1-fluoronaphthalen-2-yl)-1H-imidazol-2-yl)-7-(methylamino)-7-oxoheptyl)thiazole-5-carboxamide | 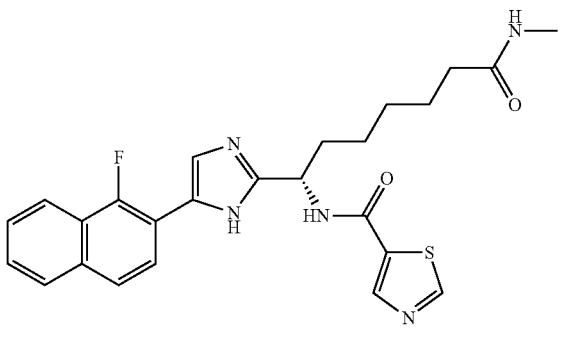 [SMILES: CNC(=O)CCCCC[C@H](NC(=O)c1cncs1)c1ncc(-c2ccc3ccccc3c2F)[nH]1] | C | C | C | 2.4 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 138 | (S)-N-(1-(5-(isoquinolin-6-yl)-1H-imidazol-2-yl)-7-(methylamino)-7-oxoheptyl)thiazole-5-carboxamide | 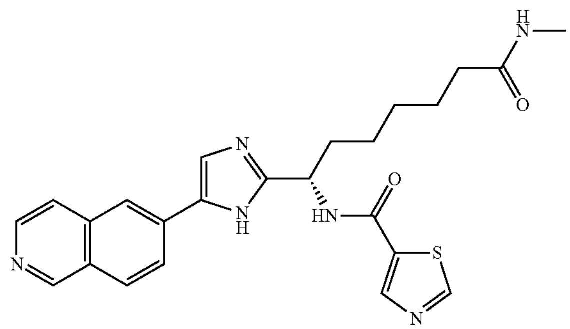 | A | B | B | 3.6 |
| 139 | (S)-N-(7-(methylamino)-7-oxo-1-(5-(4-(pyridin-2-yl)phenyl)-1H-imidazol-2-yl)heptyl)thiazole-5-carboxamide | 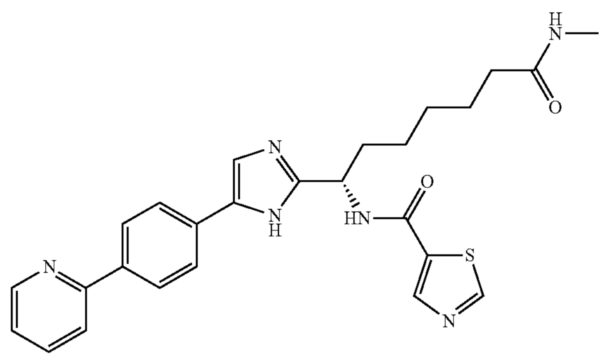 [SMILES: CNC(=O)CCCCC[C@H](NC(=O)c1cncs1)c1ncc(-c2ccc(-c3ccccn3)cc2)[nH]1] | B | B | C | 9.2 |
| 140 | (S)-N-(1-(5-(1-methyl-2-oxo-1,2-dihydroquinolin-3-yl)-1H-imidazol-2-yl)-7-(methylamino)-7-oxoheptyl)thiazole-5-carboxamide | 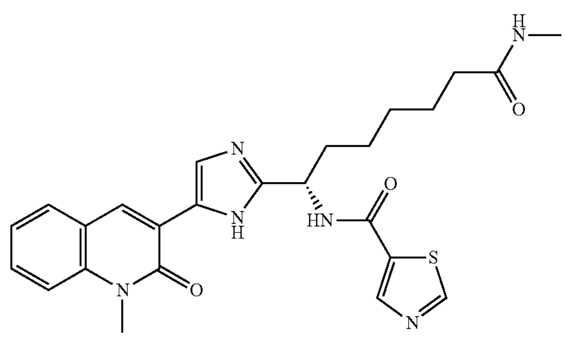 [SMILES: CNC(=O)CCCCC[C@H](NC(=O)c1cncs1)c1ncc(-c2cc3ccccc3n(C)c2=O)[nH]1] | B | B | C | 18.3 |
| 141 | (S)-N-(1-(5-(4-(1H-pyrazol-1-yl)phenyl)-1H-imidazol-2-yl)-7-(methylamino)-7-oxoheptyl)-2-(pyrrolidin-1-ylmethyl)thiazole-5-carboxamide | 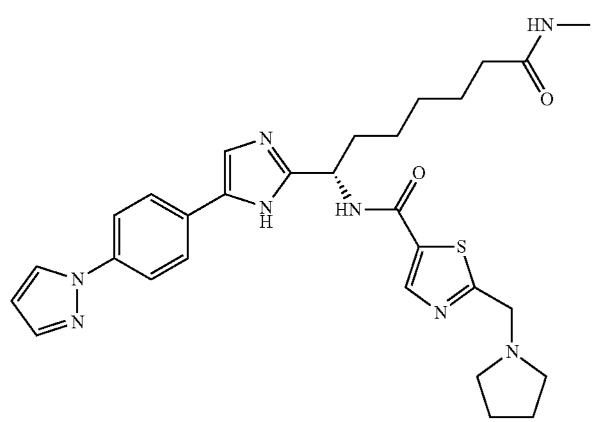 [SMILES: CNC(=O)CCCCC[C@H](NC(=O)c1cnc(CN2CCCC2)s1)c1ncc(-c2ccc(-n3cccn3)cc2)[nH]1] | B | B | C | 9.4 |

TABLE 2-continued

| Entry | Compound Name | Structure | Pf-LDH EC$_{50}$ $^a$ | hHDAC IC$_{50}$ $^a$ | HDAC HeLa Cell Based IC$_{50}$ $^a$ | Selectivity Index$^b$ |
|---|---|---|---|---|---|---|
| 142 | (S)-7-(5-(4-(1H-pyrazol-1-yl)phenyl)-1H-imidazol-2-yl)-7-(3-(benzo[d]thiazol-2-yl)propanamido)-N-methylheptanamide | 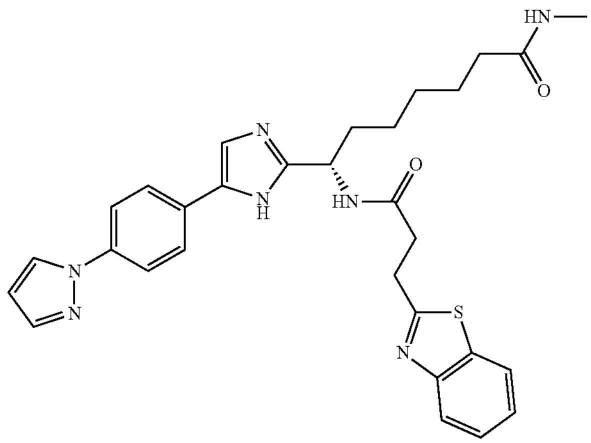 [SMILES: CNC(=O)CCCCC[C@H](NC(=O)CCc1nc2ccccc2s1)c1ncc(-c2ccc(-n3cccn3)cc2)[nH]1] | B | B | C | 5.8 |
| 143 | (S)-N-(1-(5-(isoquinolin-7-yl)-1H-imidazol-2-yl)-7-(methylamino)-7-oxoheptyl)thiazole-5-carboxamide | 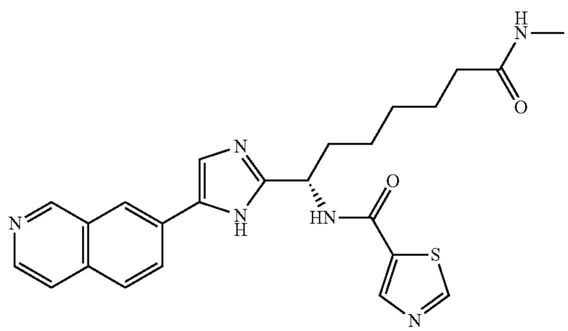 [SMILES: CNC(=O)CCCCC[C@H](NC(=O)c1cncs1)c1ncc(-c2ccc3ccncc3c2)[nH]1] | A | A | B | 17.5 |
| 144 | (S)-N-(7-(methylamino)-1-(5-(naphthalen-2-yl)-1H-imidazol-2-yl)-7-oxo-heptyl)imidazo[1,2-a]pyridine-2-carboxamide | 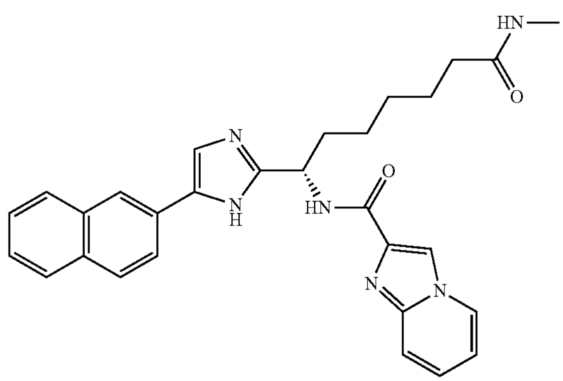 [SMILES: CNC(=O)CCCCC[C@H](NC(=O)c1cn2ccccc2n1)c1ncc(-c2ccc3ccccc3c2)[nH]1] | C | C | C | 4.0 |
| 145 | 2,2-difluoro-N-((S)-1-(5-(isoquinolin-7-yl)-1H-imidazol-2-yl)-7-(methylamino)-7-oxo-heptyl)cyclobutane-carboxamide | 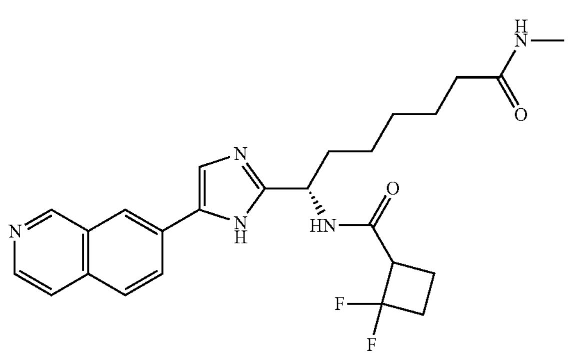 [SMILES: CNC(=O)CCCCC[C@H](NC(=O)C1CCC1(F)F)c1ncc(-c2ccc3ccncc3c2)[nH]1] | B | B | C | 11.6 |

TABLE 2-continued

| Entry | Compound Name | Structure | Pf-LDH EC$_{50}$ [a] | hHDAC IC$_{50}$ [a] | HDAC HeLa Cell Based IC$_{50}$ [a] | Selectivity Index[b] |
|---|---|---|---|---|---|---|
| 146 | (S)-7-(2-(imidazo[2,1-b]thiazol-3-yl)acetamido)-N-methyl-7-(5-(4-(1-methyl-1H-pyrazol-3-yl)phenyl)-1H-imidazol-2-yl)heptanamide | 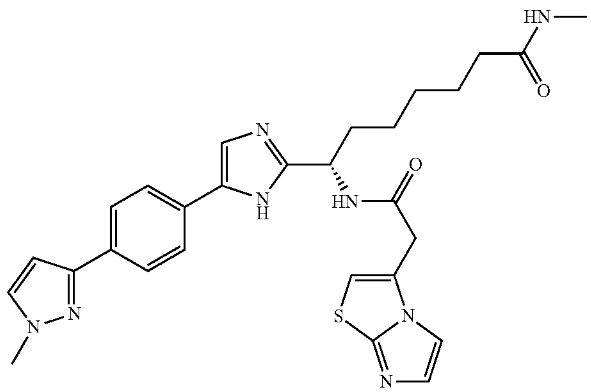 [SMILES: CNC(=O)CCCCC[C@H](NC(=O)Cc1csc2nccn12)c1ncc(-c2ccc(-c3ccn(C)n3)cc2)[nH]1] | B | B | C | 6.5 |
| 147 | (S)-N-(1-(5-(benzofuran-7-yl)-1H-imidazol-2-yl)-7-(methylamino)-7-oxoheptyl)thiazole-5-carboxamide | 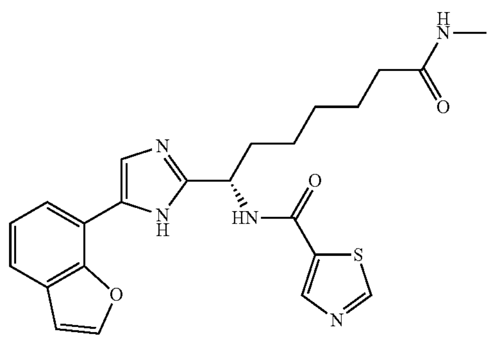 [SMILES: CNC(=O)CCCCC[C@H](NC(=O)c1cncs1)c1ncc(-c2cccc3ccoc23)[nH]1] | B | B | C | 4.9 |
| 148 | (S)-7-(2-(5-methoxy-2-methyl-1H-indol-3-yl)acetamido)-N-methyl-7-(5-(naphthalen-2-yl)-4H-1,2,4-triazol-3-yl)heptanamide | 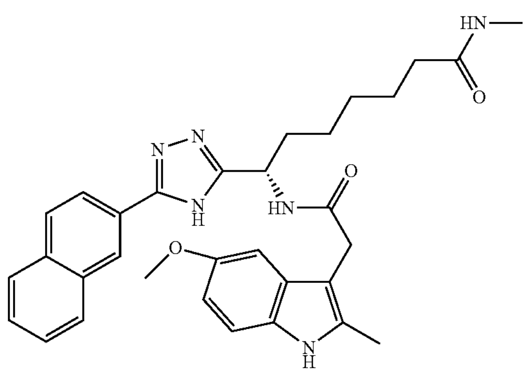 [SMILES: CNC(=O)CCCCC[C@H](NC(=O)Cc1c(C)[nH]c2ccc(OC)cc12)c1nnc(-c2ccc3ccccc3c2)[nH]1] | A | A | C | 11.0 |
| 149 | (S)-1-methyl-N-((S)-7-(methylamino)-1-(5-(naphthalen-2-yl)-1H-imidazol-2-yl)-7-oxoheptyl)pyrrolidine-3-carboxamide | 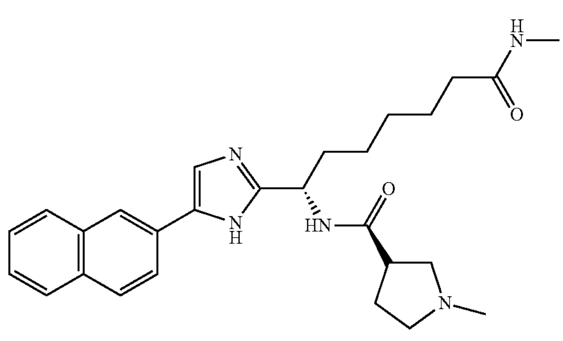 | B | B | C | 4.1 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 150 | (S)-7-(3-(2-ethyl-1H-benzo[d]imidazol-1-yl)propanamido)-N-methyl-7-(5-(naphthalen-2-yl)-1H-imidazol-2-yl)heptanamide | 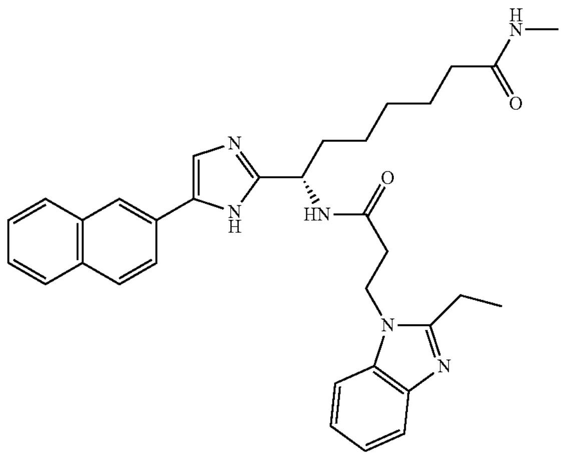 [SMILES: CCc1nc2ccccc2n1CCC(=O)N[C@@H](CCCCCC(=O)NC)c1ncc(-c2ccc3ccccc3c2)[nH]1] | A | A | A | 7.6 |
| 151 | (S)-N-methyl-7-(5-(naphthalen-2-yl)-1H-imidazol-2-yl)-7-(2-(2-oxoquinazolin-1(2H)-yl)acetamido)heptanamide | 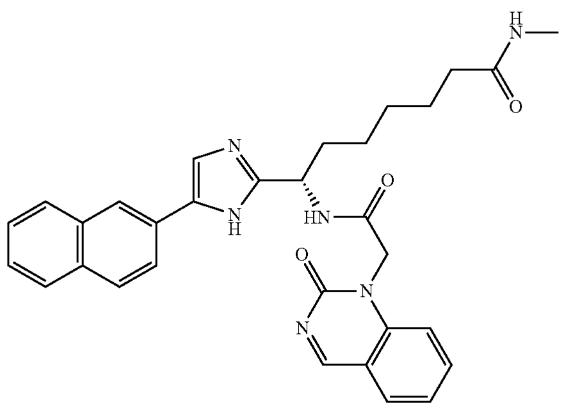 [SMILES: CNC(=O)CCCCC[C@H](NC(=O)Cn1c(=O)ncc2ccccc21)c1ncc(-c2ccc3ccccc3c2)[nH]1] | B | A | B | 2.0 |
| 152 | S)-N-(7-(methylamino)-7-oxo-1-(5-(quinolin-6-yl)-1H-imidazol-2-yl)heptyl)quinuclidine-4-carboxamide | 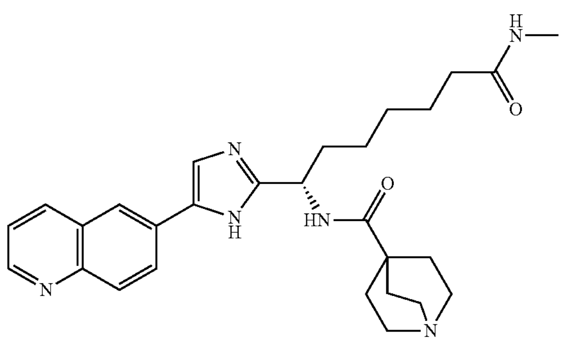 [SMILES: CNC(=O)CCCCC[C@H](NC(=O)C12CCN(CC1)CC2)c1ncc(-c2ccc3ncccc3c2)[nH]1] | B | A | C | 3.6 |
| 153 | (S)-N-(1-(5-(6-methoxynaphthalen-2-yl)-1H-imidazol-2-yl)-7-(methylamino)-7-oxoheptyl)quinuclidine-4-carboxamide | 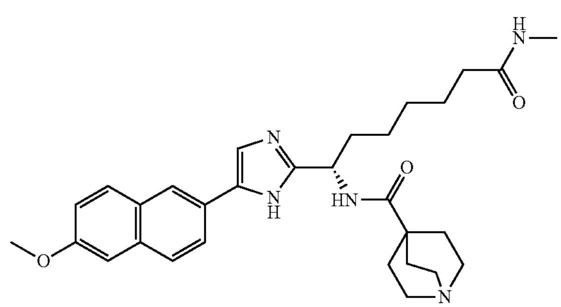 | A | A | B | 8.4 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 154 | (S)-N-(1-(5-(6-fluoronaphthalen-2-yl)-1H-imidazol-2-yl)-7-(methylamino)-7-oxo-heptyl)quinuclidine-4-carboxamide | 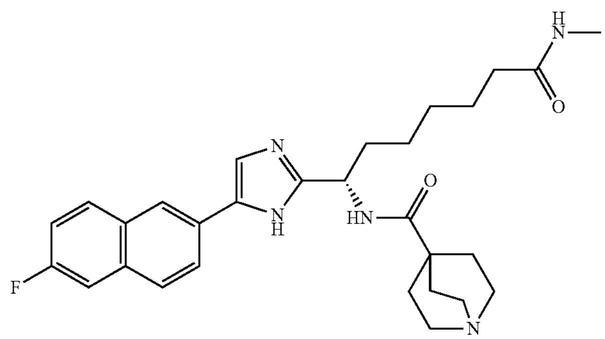 [SMILES: CNC(=O)CCCCC[C@H](NC(=O)C12CCN(CC1)CC2)c1ncc(-c2ccc3cc(F)ccc3c2)[nH]1] | A | A | C | 6.6 |
| 155 | (S)-7-(2-(6,7-dihydro-5H-thiazolo[3,2-a]pyrimidin-3-yl)acetamido)-7-(5-(isoquinolin-7-yl)-1H-imidazol-2-yl)-N-methyl-heptanamide | 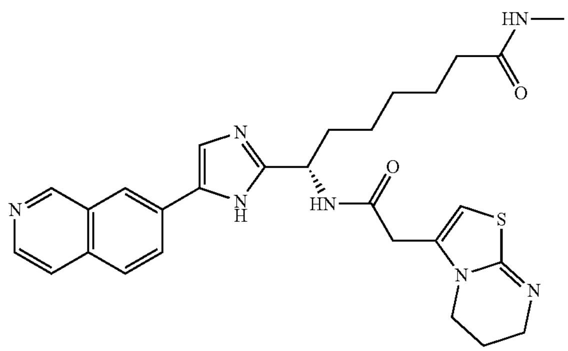 [SMILES: CNC(=O)CCCCC[C@H](NC(=O)CC1=CSC2=NCCCN12)c1ncc(-c2ccc3ccncc3c2)[nH]1] | B | B | C | 5.0 |
| 156 | (S)-N-(1-(5-(2-methoxyquinolin-3-yl)-1H-imidazol-2-yl)-7-(methylamino)-7-oxoheptyl)-3-(1H-pyrazol-1-yl)benzamide | 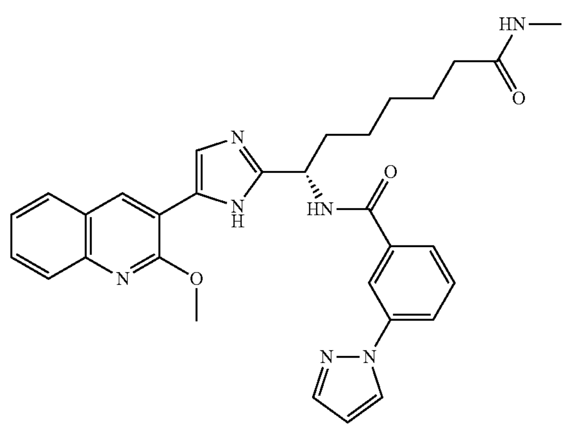 [SMILES: CNC(=O)CCCCC[C@H](NC(=O)c1cccc(-n2cccn2)c1)c1ncc(-c2cc3ccccc3nc2OC)[nH]1] | B | C | C | 5.4 |
| 157 | (S)-7-(2-(1H-1,2,3-triazol-1-yl)acetamido)-7-(5-(1H-indazol-5-yl)-1H-imidazol-2-yl)-N-methyl-heptanamide | 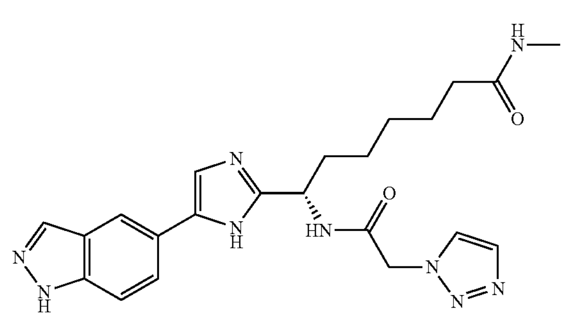 [SMILES: CNC(=O)CCCCC[C@H](NC(=O)Cn1ccnn1)c1ncc(-c2ccc3[nH]ncc3c2)[nH]1] | C | C | C | 3.5 |

TABLE 2-continued

| Entry | Compound Name | Structure | Pf-LDH EC$_{50}$ [a] | hHDAC IC$_{50}$ [a] | HDAC HeLa Cell Based IC$_{50}$ [a] | Selectivity Index[b] |
|---|---|---|---|---|---|---|
| 158 | (S)-N-(1-(5-(4-(1-methyl-1H-pyrazol-3-yl)phenyl)-1H-imidazol-2-yl)-7-(methylamino)-7-oxoheptyl)thiazole-5-carboxamide | 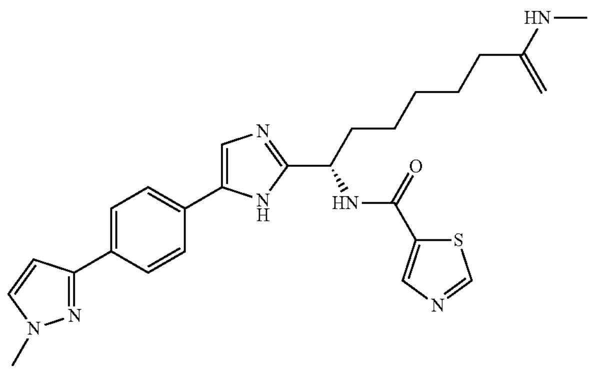 [SMILES: C=C(CCCCC[C@H](NC(=O)c1cncs1)c1ncc(-c2ccc(-c3ccn(C)n3)cc2)[nH]1)NC] | A | B | C | 27.2 |
| 159 | (S)-N-(1-(5-(1H-pyrazolo[3,4-b]pyridin-5-yl)-1H-imidazol-2-yl)-7-(methylamino)-7-oxoheptyl)thiazole-5-carboxamide | 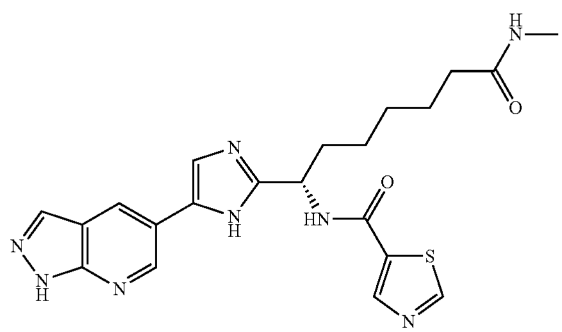 [SMILES: CNC(=O)CCCCC[C@H](NC(=O)c1cncs1)c1ncc(-c2cnc3[nH]ncc3c2)[nH]1] | C | C | C | 2.5 |
| 160 | (S)-N-(1-(5-(1H-indazol-5-yl)-1H-imidazol-2-yl)-7-(methylamino)-7-oxoheptyl)thiazole-5-carboxamide | 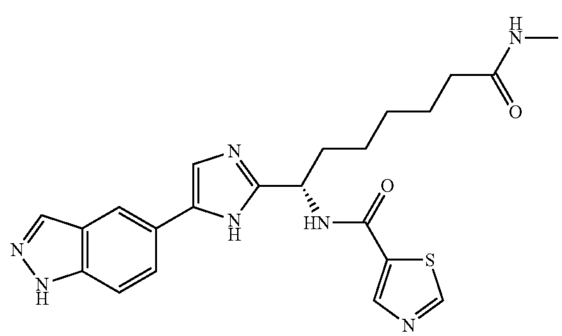 | A | B | C | 12.2 |
| 161 | (S)-N-(1-(5-(benzo[b]thiophen-5-yl)-1H-imidazol-2-yl)-7-(methylamino)-7-oxoheptyl)thiazole-5-carboxamide | 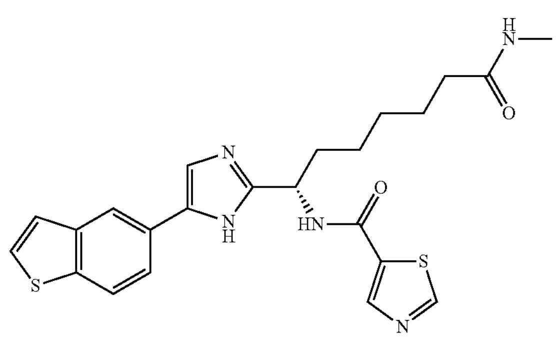 [SMILES: CNC(=O)CCCCC[C@H](NC(=O)c1cncs1)c1ncc(-c2ccc3sccc3c2)[nH]1] | B | B | C | 6.0 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 162 | S)-N-(1-(5-(4-(1H-pyrazol-1-yl)phenyl)-1H-imidazol-2-yl)-7-(methylamino)-7-oxoheptyl)-1-methylpiperidine-4-carboxamide | 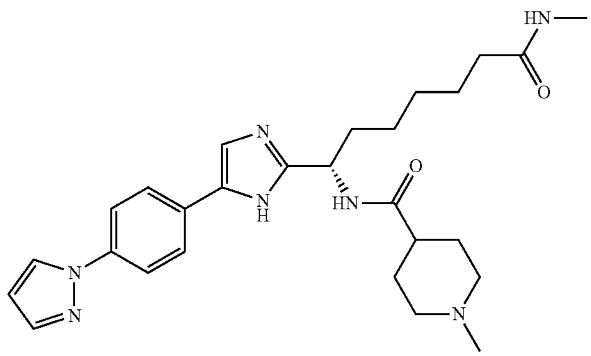 [SMILES: CNC(=O)CCCCC[C@H](NC(=O)C1CCN(C)CC1)c1ncc(-c2ccc(-n3cccn3)cc2)[nH]1] | C | C | C | 2.3 |
| 163 | (S)-7-(5-(4-(1H-pyrazol-1-yl)phenyl)-1H-imidazol-2-yl)-7-(2-(imidazo[1,2-a]pyridin-3-yl)acetamido)-N-methylheptanamide | 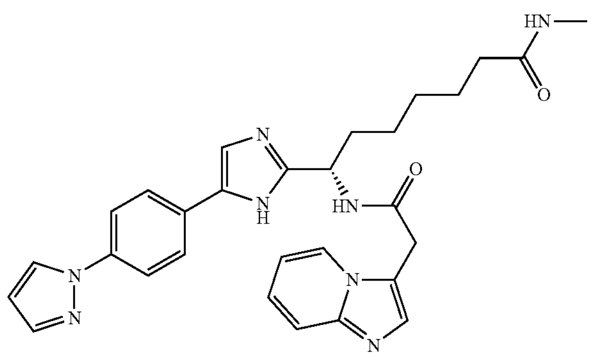 [SMILES: CNC(=O)CCCCC[C@H](NC(=O)Cc1cnc2ccccn12)c1ncc(-c2ccc(-n3cccn3)cc2)[nH]1] | B | B | C | 12.0 |
| 164 | (S)-N-(7-(methylamino)-1-(5-(naphthalen-2-yl)-1H-imidazol-2-yl)-7-oxoheptyl)imidazo[2,1-b]thiazole-6-carboxamide | 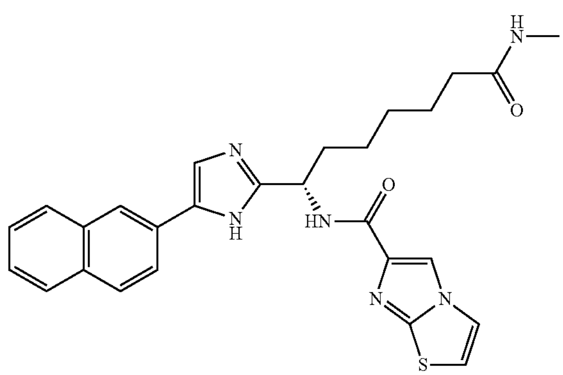 [SMILES: CNC(=O)CCCCC[C@H](NC(=O)c1cn2ccsc2n1)c1ncc(-c2ccc3ccccc3c2)[nH]1] | C | C | C | 3.8 |
| 165 | (S)-N-methyl-7-(2-(4-methylpiperazin-1-yl)acetamido)-7-(5-(naphthalen-2-yl)-1H-imidazol-2-yl)heptanamide | 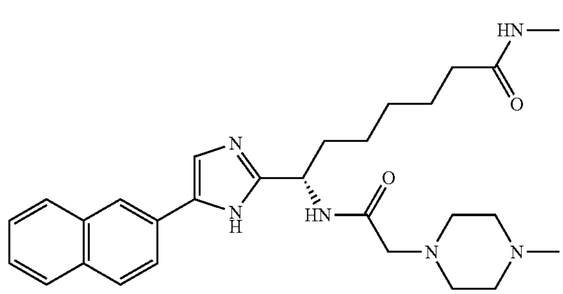 | C | B | C | 3.2 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 166 | N-((S)-7-(methylamino)-1-(5-(naphthalen-2-yl)-1H-imidazol-2-yl)-7-oxoheptyl)-5-oxopyrrolidine-3-carboxamide | 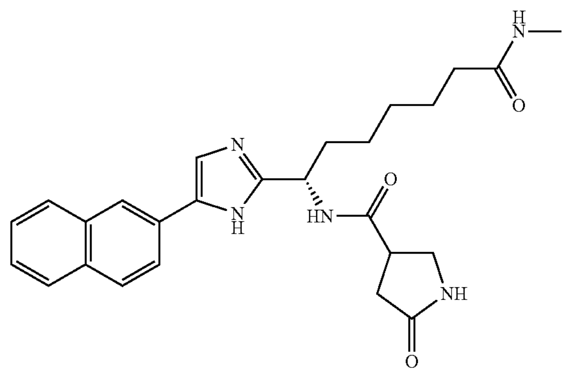 [SMILES: CNC(=O)CCCCC[C@H](NC(=O)C1CNC(=O)C1)c1ncc(-c2ccc3ccccc3c2)[nH]1] | B | B | C | 12.0 |
| 167 | (S)-7-(5-(isoquinolin-7-yl)-1H-imidazol-2-yl)-N-methyl-7-(3-(5-methyl-4H-1,2,4-triazol-3-yl)propanamido)heptanamide | 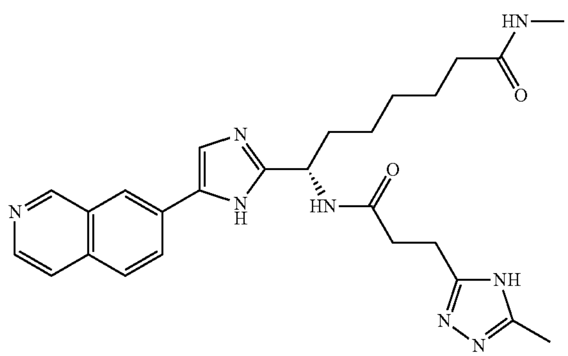 [SMILES: CNC(=O)CCCCC[C@H](NC(=O)CCc1nnc(C)[nH]1)c1ncc(-c2ccc3ccncc3c2)[nH]1] | B | B | C | 6.6 |
| 168 | (S)-7-(2-(imidazo[2,1-b]thiazol-6-yl)acetamido)-7-(5-(isoquinolin-7-yl)-1H-imidazol-2-yl)-N-methyl-heptanamide | 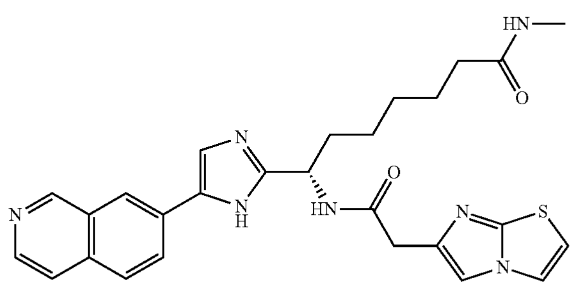 [SMILES: CNC(=O)CCCCC[C@H](NC(=O)Cc1cn2ccsc2n1)c1ncc(-c2ccc3ccncc3c2)[nH]1] | B | B | C | 7.1 |
| 169 | (S)-7-(2-(2H-indazol-2-yl)acetamido)-N-methyl-7-(5-(4-(1-methyl-1H-pyrazol-3-yl)phenyl)-1H-imidazol-2-yl)heptanamide | 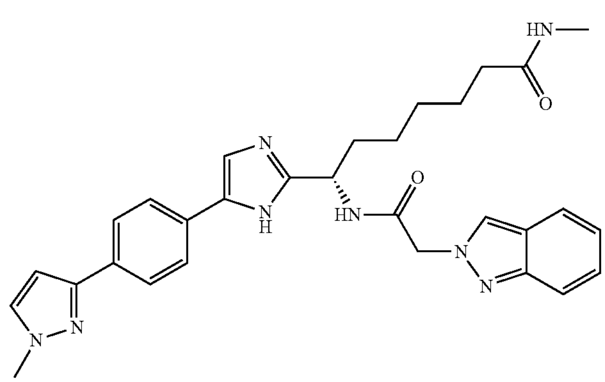 [SMILES: CNC(=O)CCCCC[C@H](NC(=O)Cn1cc2ccccc2n1)c1ncc(-c2ccc(-c3ccn(C)n3)cc2)[nH]1] | B | A | B | 3.1 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 170 | N-((S)-1-(5-(4-(1-methyl-1H-pyrazol-3-yl)phenyl)-1H-imidazol-2-yl)-7-(methylamino)-7-oxoheptyl)-2-(pyridin-4-yl)cyclopropanecarboxamide | 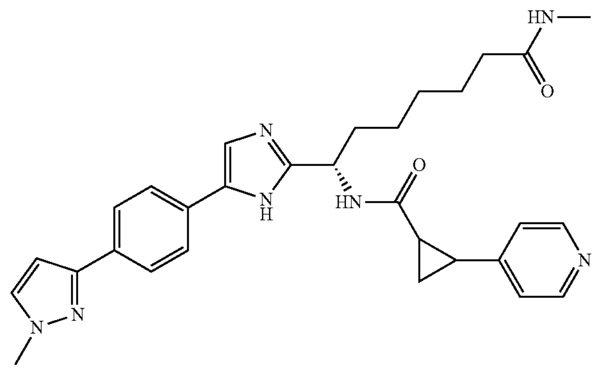 [SMILES: CNC(=O)CCCCC[C@H](NC(=O)C1CC1c1ccncc1)c1ncc(-c2ccc(-c3ccn(C)n3)cc2)[nH]1] | B | B | C | 10.3 |
| 171 | (S)-N-methyl-7-(2-(3-methyl-1H-pyrazol-1-yl)acetamido)-7-(5-(4-(1-methyl-1H-pyrazol-3-yl)phenyl)-1H-imidazol-2-yl)heptanamide | 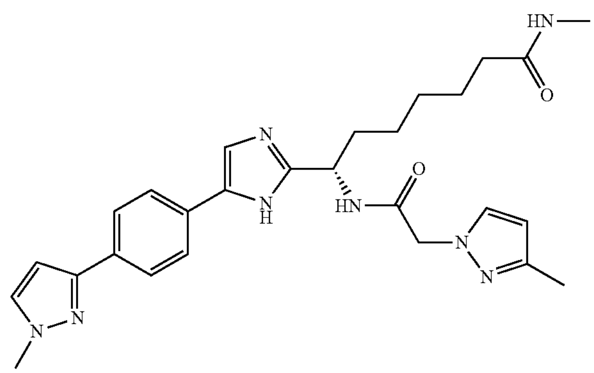 [SMILES: CNC(=O)CCCCC[C@H](NC(=O)Cn1ccc(C)n1)c1ncc(-c2ccc(-c3ccn(C)n3)cc2)[nH]1] | C | C | C | 3.2 |
| 172 | (S)-N-(1-(5-(4-(1H-pyrazol-1-yl)phenyl)-1H-imidazol-2-yl)-7-(methylamino)-7-oxoheptyl)thiazole-5-carboxamide | 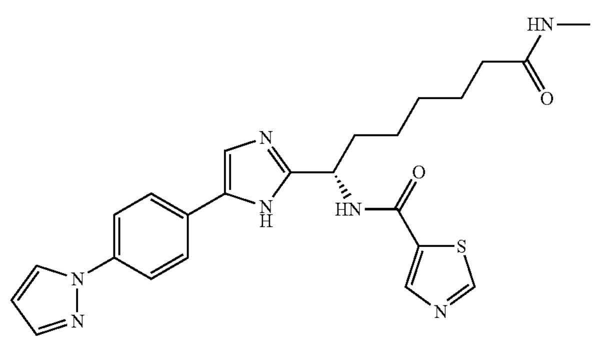 [SMILES: CNC(=O)CCCCC[C@H](NC(=O)c1cncs1)c1ncc(-c2ccc(-n3cccn3)cc2)[nH]1] | A | B | C | 23.0 |
| 173 | (S)-N-(1-(5-(1H-indol-6-yl)-1H-imidazol-2-yl)-7-(methylamino)-7-oxoheptyl)thiazole-5-carboxamide | 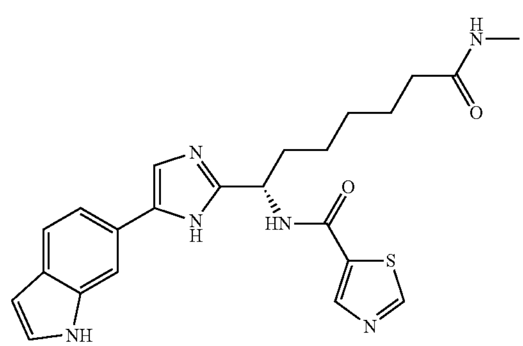 [SMILES: CNC(=O)CCCCC[C@H](NC(=O)c1cncs1)c1ncc(-c2ccc3cc[nH]c3c2)[nH]1] | B | B | C | 6.3 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 174 | (S)-7-(2-(5-methoxy-2-methyl-1H-indol-3-yl)acetamido)-7-(5-(naphthalen-2-yl)-1,3,4-oxadiazol-2-yl)heptanamide | 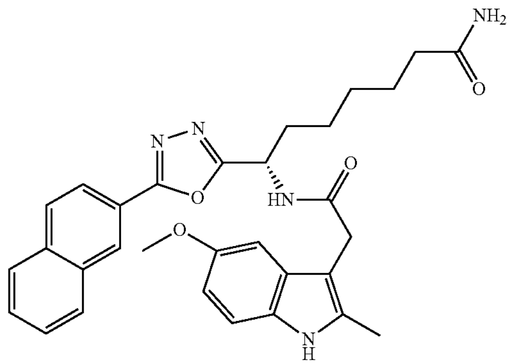 [SMILES: COc1ccc2[nH]c(C)c(CC(=O)N[C@@H](CCCCCC(N)=O)c3nnc(-c4ccc5ccccc5c4)o3)c2c1] | B | A | C | 7.2 |
| 175 | (S)-N-(7-(methylamino)-1-(5-(naphthalen-2-yl)-1H-imidazol-2-yl)-7-oxo-heptyl)nicotinamide | 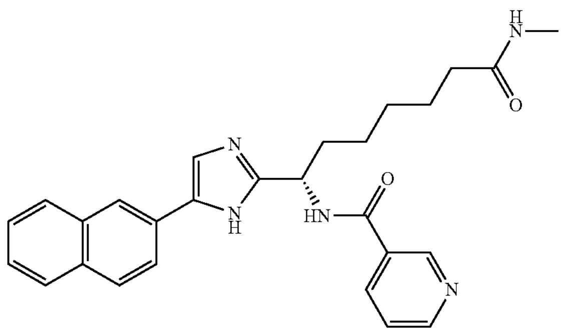 [SMILES: CNC(=O)CCCCC[C@H](NC(=O)c1cccnc1)c1ncc(-c2ccc3ccccc3c2)[nH]1] | A | A | B | 4.0 |
| 176 | 1-ethyl-N-((S)-7-(methylamino)-1-(5-(naphthalen-2-yl)-1H-imidazol-2-yl)-7-oxo-heptyl)piperidine-3-carboxamide | 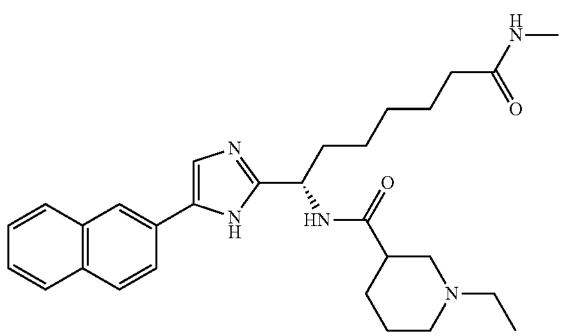 [SMILES: CCN1CCCC(C(=O)N[C@@H](CCCCCC(=O)NC)c2ncc(-c3ccc4ccccc4c3)[nH]2)C1] | B | A | C | 4.8 |
| 177 | (S)-N-(1-(5-(2-methoxyquinolin-3-yl)-1H-imidazol-2-yl)-7-(methylamino)-7-oxo-heptyl)quinuclidine-4-carboxamide | 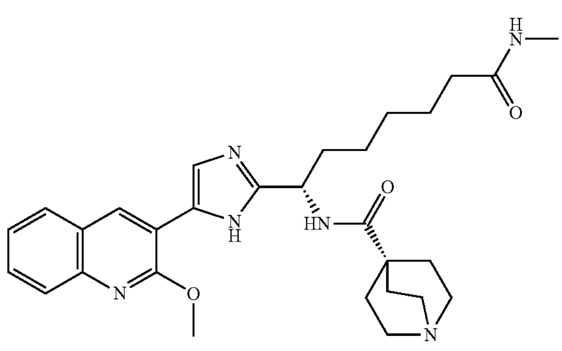 | A | A | B | 5.0 |

TABLE 2-continued

| Entry | Compound Name | Structure | Pf-LDH EC$_{50}$ [a] | hHDAC IC$_{50}$ [a] | HDAC HeLa Cell Based IC$_{50}$ [a] | Selectivity Index[b] |
|---|---|---|---|---|---|---|
| 178 | (S)-N-(1-(5-(2-methoxyquinolin-3-yl)-1H-imidazol-2-yl)-7-(methylamino)-7-oxoheptyl)thiazole-5-carboxamide | 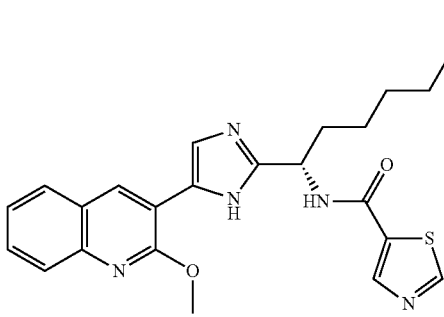 | A | A | A | 2.0 |
| 179 | (S)-7-(2-(dimethylamino)acetamido)-7-(5-(2-methoxyquinolin-3-yl)-1H-imidazol-2-yl)-N-methylheptanamide | 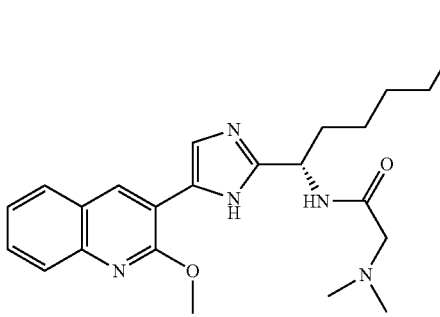 | C | B | C | 2.0 |
| 180 | (S)-7-(3-(1H-1,2,4-triazol-1-yl)propanamido)-7-(5-(2-methoxyquinolin-3-yl)-1H-imidazol-2-yl)-N-methyl-heptanamide | 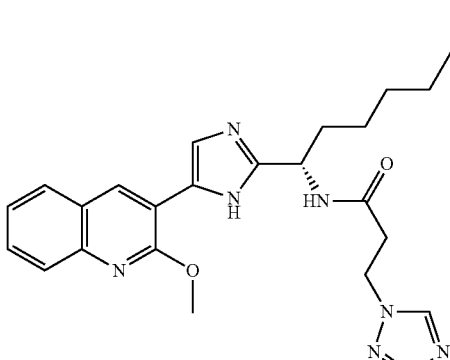 | B | B | C | 5.0 |
| 181 | (S)-N-(1-(5-(4-chloro-3-methylphenyl)-1H-imidazol-2-yl)-7-(methylamino)-7-oxo-heptyl)quinuclidine-4-carboxamide | 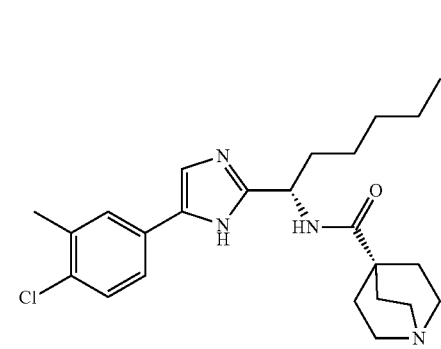 | C | B | C | 3.1 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 182 | (S)-benzyl(1-(5-(4-(1-methyl-1H-pyrazol-3-yl)phenyl)-1H-imidazol-2-yl)-7-(methylamino)-7-oxoheptyl)carbamate | 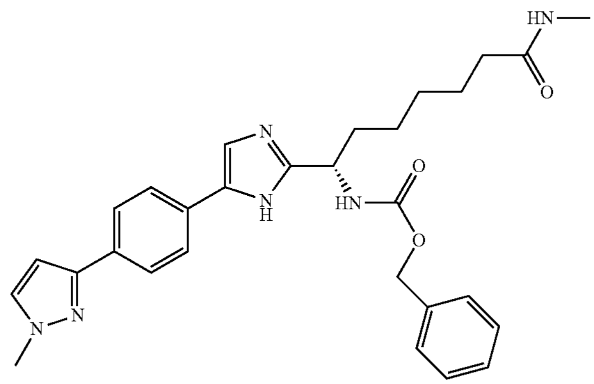 [SMILES: CNC(=O)CCCCC[C@H](NC(=O)OCc1ccccc1)c1ncc(-c2ccc(-c3ccn(C)n3)cc2)[nH]1] | B | B | C | 8.7 |
| 183 | (S)-4-(2,4-dioxoimidazolidin-1-yl)-N-(1-(5-(2-methoxyquinolin-3-yl)-1H-imidazol-2-yl)-7-(methylamino)-7-oxoheptyl)benzamide | 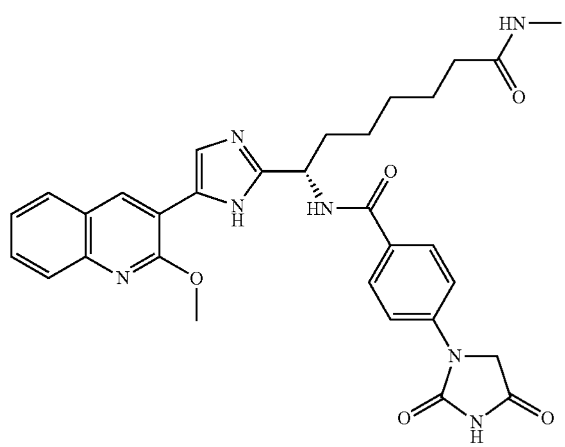 [SMILES: CNC(=O)CCCCC[C@H](NC(=O)c1ccc(N2CC(=O)NC2=O)cc1)c1ncc(-c2cc3ccccc3nc2OC)[nH]1] | B | B | C | 6.0 |
| 184 | (S)-7-(2-(4H-1,2,4-triazol-4-yl)acetamido)-7-(5-(2-methoxyquinolin-3-yl)-1H-imidazol-2-yl)-N-methylheptanamide | 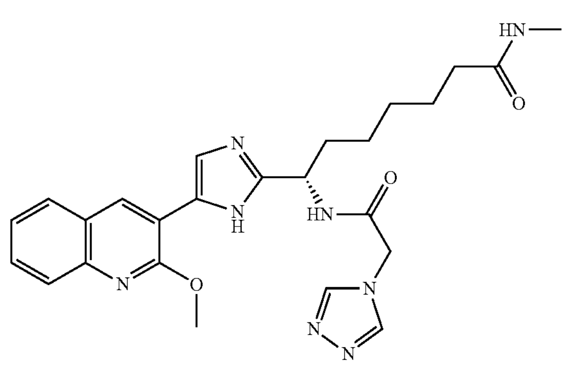 [SMILES: CNC(=O)CCCCC[C@H](NC(=O)Cn1cnnc1)c1ncc(-c2cc3ccccc3nc2OC)[nH]1] | B | B | C | 11.0 |

TABLE 2-continued

| Entry | Compound Name | Structure | Pf-LDH EC$_{50}$ $^a$ | hHDAC IC$_{50}$ $^a$ | HDAC HeLa Cell Based IC$_{50}$ $^a$ | Selectivity Index$^b$ |
|---|---|---|---|---|---|---|
| 185 | (S)-7-(5-(2-methoxyquinolin-3-yl)-1H-imidazol-2-yl)-N-methyl-7-(2-(2-phenylthiazol-4-yl)acetamido)heptanamide | 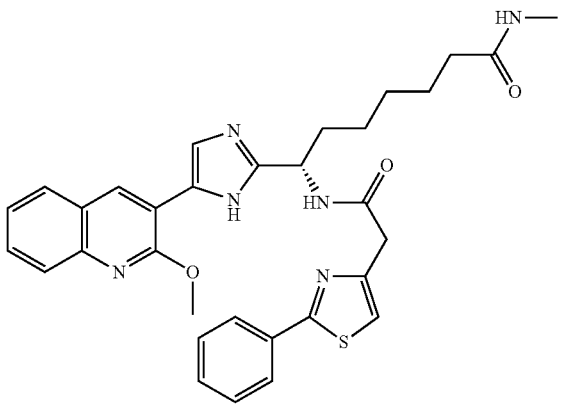 [SMILES: CNC(=O)CCCCC[C@H](NC(=O)Cc1csc(-c2ccccc2)n1)c1ncc(-c2cc3ccccc3nc2OC)[nH]1] | B | B | C | 2.6 |
| 186 | (S)-7-(3-(5,7-dimethyl-[1,2,4]triazolo[1,5-a]pyrimidin-6-yl)propanamido)-7-(5-(2-methoxyquinolin-3-yl)-1H-imidazol-2-yl)-N-methylheptanamide | 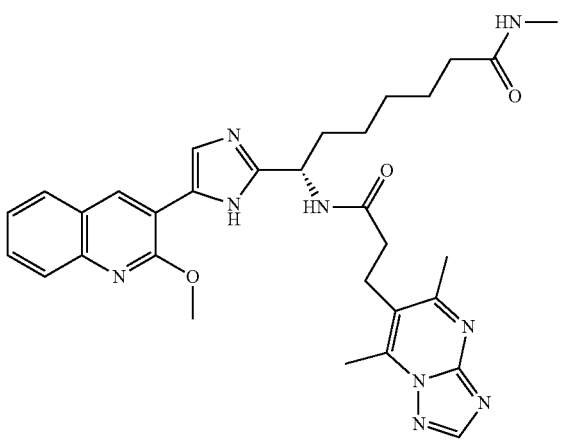 [SMILES: CNC(=O)CCCCC[C@H](NC(=O)CCc1c(C)nc2ncnn2c1C)c1ncc(-c2cc3ccccc3nc2OC)[nH]1] | A | A | B | 14.0 |
| 187 | N-((S)-1-(5-(2-methoxyquinolin-3-yl)-1H-imidazol-2-yl)-7-(methylamino)-7-oxoheptyl)tetrahydrofuran-2-carboxamide | 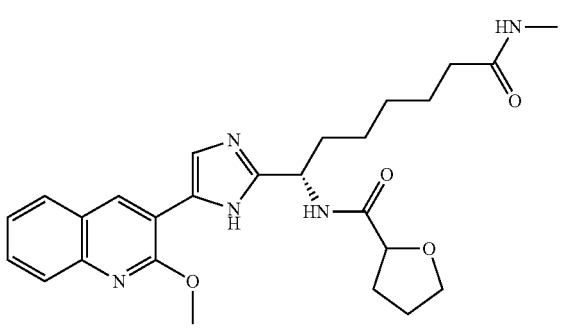 [SMILES: CNC(=O)CCCCC[C@H](NC(=O)C1CCCO1)c1ncc(-c2cc3ccccc3nc2OC)[nH]1] | C | C | C | 2.7 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 188 | (S)-N-(1-(5-(3-(1H-pyrazol-3-yl)phenyl)-1H-imidazol-2-yl)-7-(methylamino)-7-oxoheptyl)thiazole-5-carboxamide | 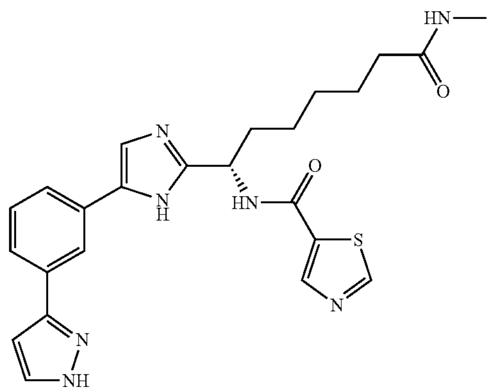 [SMILES: CNC(=O)CCCCC[C@H](NC(=O)c1cncs1)c1ncc(-c2cccc(-c3cc[nH]n3)c2)[nH]1] | B | C | C | 15.6 |
| 189 | (S)-5-isopropyl-N-(1-(5-(isoquinolin-7-yl)-1H-imidazol-2-yl)-7-(methylamino)-7-oxoheptyl)isoxazole-3-carboxamide | 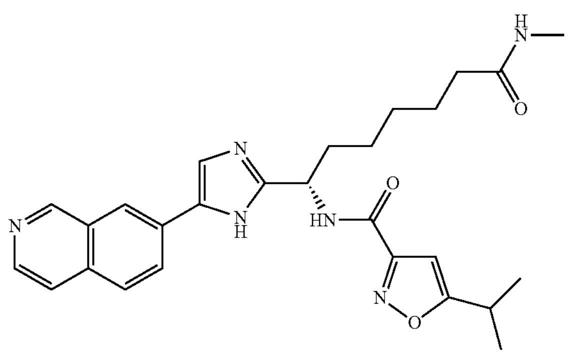 [SMILES: CNC(=O)CCCCC[C@H](NC(=O)c1cc(C(C)C)on1)c1ncc(-c2ccc3ccncc3c2)[nH]1] | B | B | C | 7.7 |
| 190 | (S)-N-(7-(methylamino)-7-oxo-1-(5-(3-(trifluoromethyl)isoquinolin-7-yl)-1H-imidazol-2-yl)heptyl)thiazole-5-carboxamide | 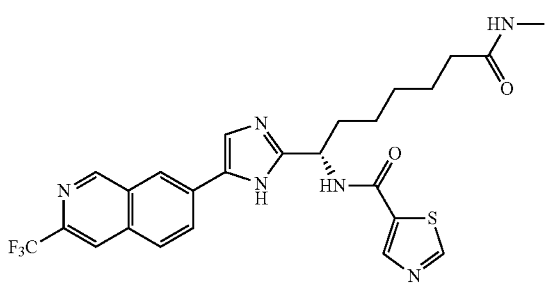 [SMILES: CNC(=O)CCCCC[C@H](NC(=O)c1cncs1)c1ncc(-c2ccc3cc(C(F)(F)F)ncc3c2)[nH]1] | A | A | B | 16.3 |
| 191 | (S)-N-(1-(5-(1-methyl-1H-indazol-5-yl)-1H-imidazol-2-yl)-7-(methylamino)-7-oxoheptyl)thiazole-5-carboxamide | 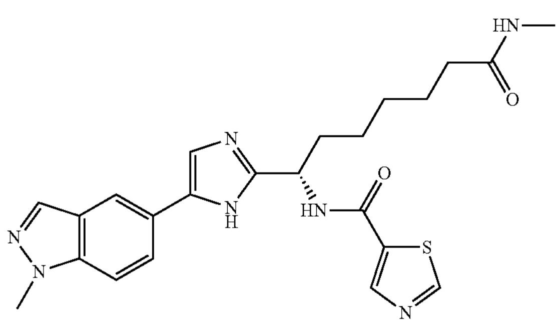 [SMILES: CNC(=O)CCCCC[C@H](NC(=O)c1cncs1)c1ncc(-c2ccc3c(cnn3C)c2)[nH]1] | A | B | B | 14.0 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 192 | (S)-N-(1-(5-(2-methoxy-6-phenylpyridin-3-yl)-1H-imidazol-2-yl)-7-(methylamino)-7-oxoheptyl)thiazole-5-carboxamide | 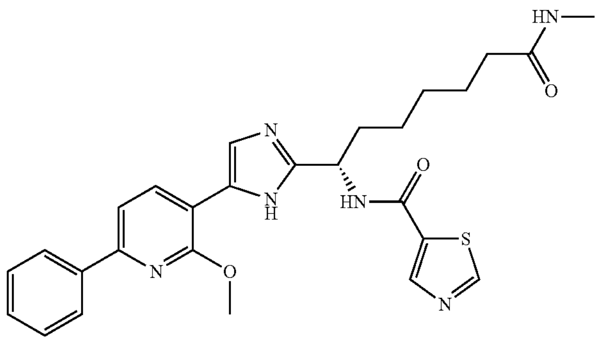 [SMILES: CNC(=O)CCCCC[C@H](NC(=O)c1cncs1)c1ncc(-c2ccc(-c3ccccc3)nc2OC)[nH]1] | B | C | C | 5.6 |
| 193 | (S)-N-(7-(methylamino)-7-oxo-1-(5-(2-oxo-1,2-dihydroquinolin-3-yl)-1H-imidazol-2-yl)heptyl)thiazole-5-carboxamide | 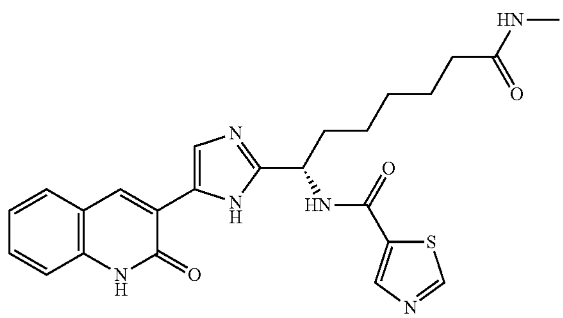 [SMILES: CNC(=O)CCCCC[C@H](NC(=O)c1cncs1)c1ncc(-c2cc3ccccc3[nH]c2=O)[nH]1] | A | A | C | 54.3 |
| 194 | (S)-N-(1-(5-(6-methoxynaphthalen-2-yl)-1H-imidazol-2-yl)-7-(methylamino)-7-oxoheptyl)thiazole-5-carboxamide | 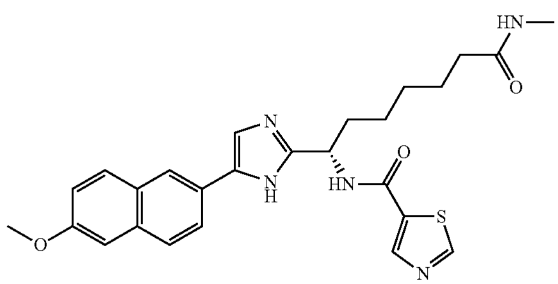 | A | A | B | 3.0 |
| 195 | (S)-N-(1-(5-(4-(1H-pyrazol-1-yl)phenyl)-1H-imidazol-2-yl)-7-(methylamino)-7-oxoheptyl)-4-(2,4-dioxoimidazolidin-1-yl)benzamide | 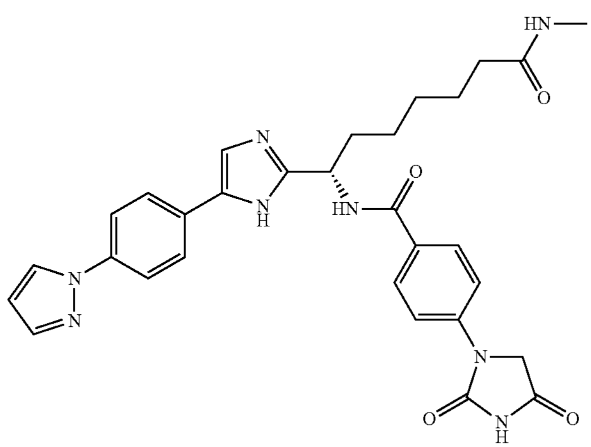 [SMILES: CNC(=O)CCCCC[C@H](NC(=O)c1ccc(N2CC(=O)NC2=O)cc1)c1ncc(-c2ccc(-n3cccn3)cc2)[nH]1] | B | C | C | 16.1 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 196 | (S)-N-(7-(methylamino)-7-oxo-1-(5-(4-(pyridin-3-yl)phenyl)-1H-imidazol-2-yl)heptyl)thiazole-5-carboxamide | 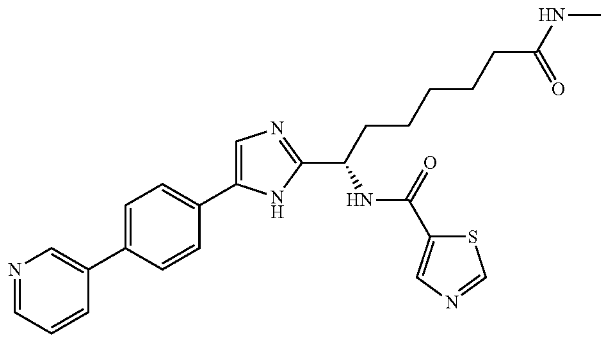 [SMILES: CNC(=O)CCCCC[C@H](NC(=O)c1cncs1)c1ncc(-c2ccc(-c3cccnc3)cc2)[nH]1] | B | B | C | 18.0 |
| 197 | (S)-N-(7-(methylamino)-1-(5-(naphthalen-2-yl)-1H-imidazol-2-yl)-7-oxoheptyl)-2-(pyridin-3-yl)thiazole-4-carboxamide | 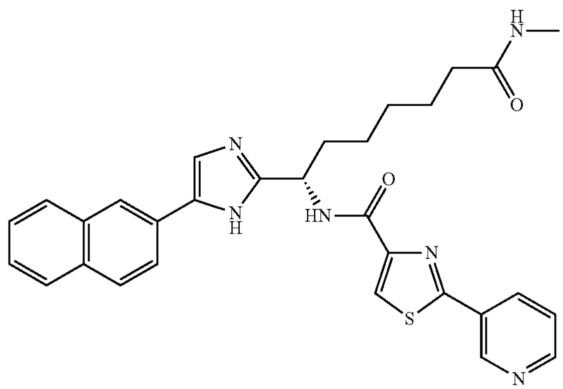 [SMILES: CNC(=O)CCCCC[C@H](NC(=O)c1csc(-c2cccnc2)n1)c1ncc(-c2ccc3ccccc3c2)[nH]1] | B | C | C | 6.6 |
| 198 | N-((S)-7-(methylamino)-1-(5-(naphthalen-2-yl)-1H-imidazol-2-yl)-7-oxoheptyl)-2-oxo-1,2,3,4-tetrahydroquinoline-4-carboxamide | 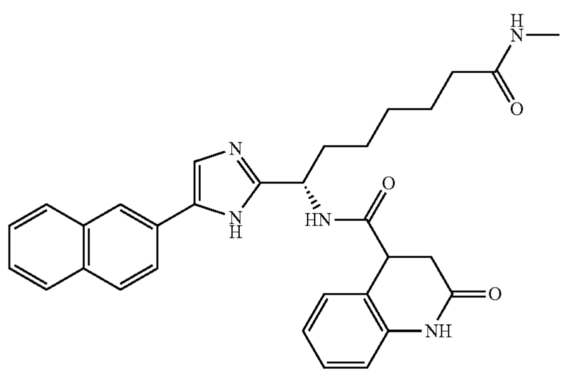 [SMILES: CNC(=O)CCCCC[C@H](NC(=O)C1CC(=O)Nc2ccccc21)c1ncc(-c2ccc3ccccc3c2)[nH]1] | A | B | C | 16.0 |
| 199 | (S)-N-methyl-7-(3-(1-methyl-1H-pyrazol-4-yl)propanamido)-7-(5-(naphthalen-2-yl)-1H-imidazol-2-yl)heptanamide | 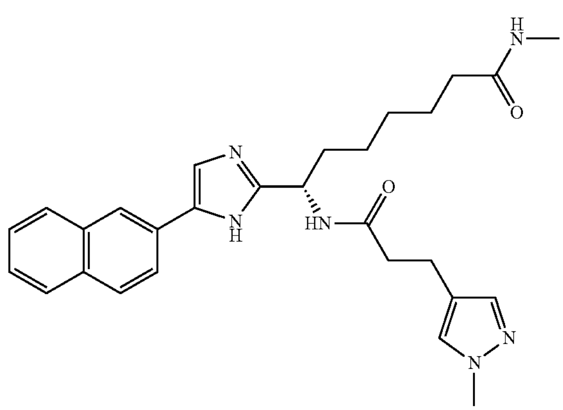 [SMILES: CNC(=O)CCCCC[C@H](NC(=O)CCc1cnn(C)c1)c1ncc(-c2ccc3ccccc3c2)[nH]1] | B | A | C | 7.0 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 200 | (S)-7-(2-(5-methoxy-2-methyl-1H-indol-3-yl)acetamido)-N-methyl-7-(5-(naphthalen-2-yl)-1,3,4-oxadiazol-2-yl)heptanamide | 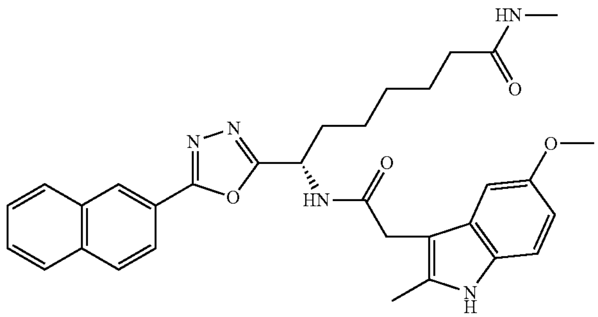 [SMILES: CNC(=O)CCCCC[C@H](NC(=O)Cc1c(C)[nH]c2ccc(OC)cc12)c1nnc(-c2ccc3ccccc3c2)o1] | B | A | C | 13.5 |
| 201 | (S)-7-(2-(6,7-dihydro-5H-thiazolo[3,2-a]pyrimidin-3-yl)acetamido)-7-(5-(2-methoxyquinolin-3-yl)-1H-imidazol-2-yl)-N-methylheptanamide | 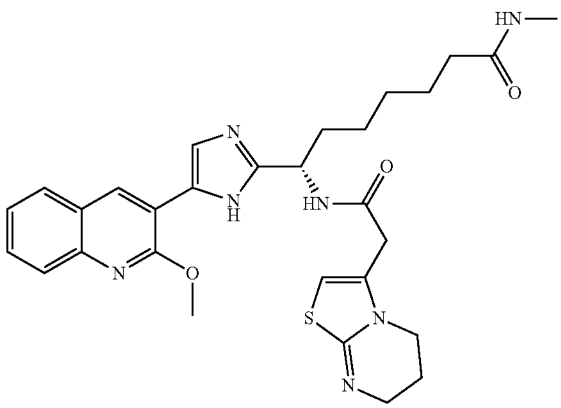 [SMILES: CNC(=O)CCCCC[C@H](NC(=O)CC1=CSC2=NCCCN12)c1ncc(-c2cc3ccccc3nc2OC)[nH]1] | A | B | C | 5.6 |
| 202 | (S)-7-(2-(6,7-dihydro-5H-thiazolo[3,2-a]pyrimidin-3-yl)acetamido)-N-methyl-7-(5-(naphthalen-2-yl)-1H-imidazol-2-yl)heptanamide | 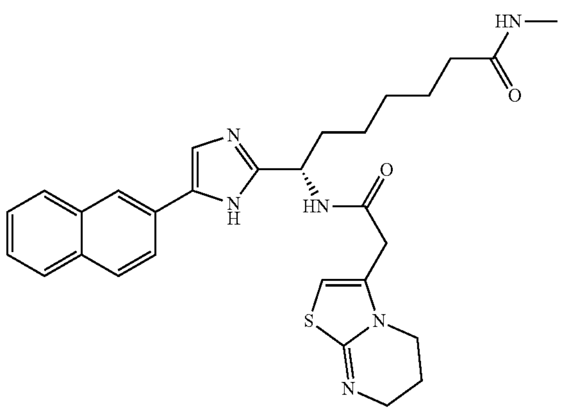 [SMILES: CNC(=O)CCCCC[C@H](NC(=O)CC1=CSC2=NCCCN12)c1ncc(-c2ccc3ccccc3c2)[nH]1] | A | B | C | 17.7 |
| 203 | (S)-5-methyl-N-(7-(methylamino)-1-(5-(naphthalen-2-yl)-1H-imidazol-2-yl)-7-oxoheptyl)-1,3,4-oxadiazole-2-carboxamide | 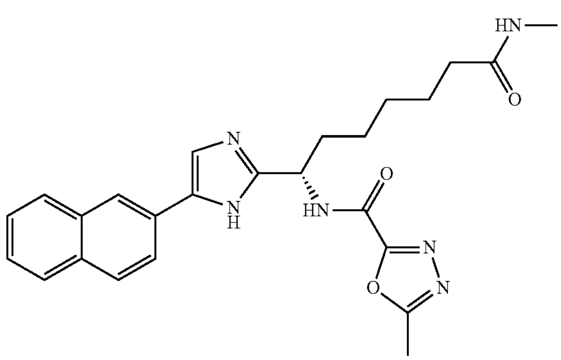 [SMILES: CNC(=O)CCCCC[C@H](NC(=O)c1nnc(C)o1)c1ncc(-c2ccc3ccccc3c2)[nH]1] | B | C | C | 4.8 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 204 | (S)-N-(7-(methylamino)-7-oxo-1-(5-(2-oxo-1,2-dihydroquinolin-3-yl)-1H-imidazol-2-yl)heptyl)quinuclidine-4-carboxamide | 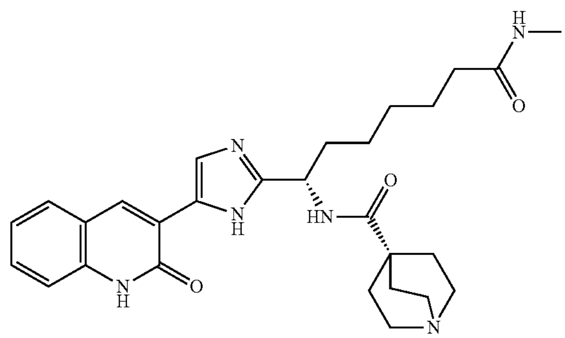 | C | B | C | 4.0 |
| 205 | (S)-N-(7-(methylamino)-7-oxo-1-(5-(5-phenylthiophen-2-yl)-1H-imidazol-2-yl)heptyl)thiazole-5-carboxamide | 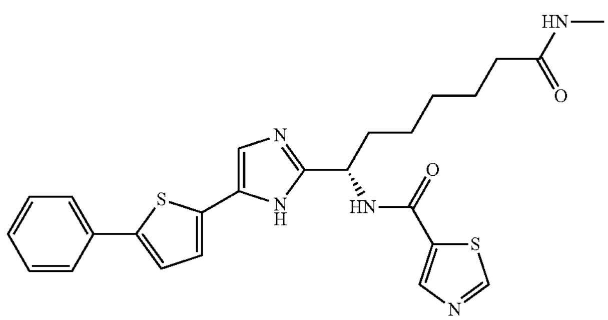 [SMILES: CNC(=O)CCCCC[C@H](NC(=O)c1cncs1)c1ncc(-c2ccc(-c3ccccc3)s2)[nH]1] | B | B | C | 9.2 |
| 206 | (1R,9aR)-N-((S)-1-(5-(isoquinolin-7-yl)-1H-imidazol-2-yl)-7-(methylamino)-7-oxoheptyl)octahydro-1H-quinolizine-1-carboxamide | 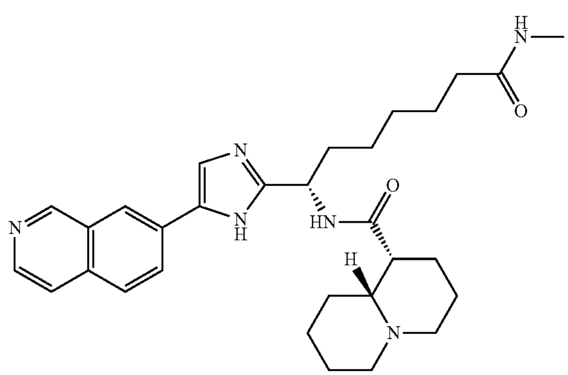 [SMILES: CNC(=O)CCCCC[C@H](NC(=O)[C@@H]1CCCN2CCCC[C@H]12)c1ncc(-c2ccc3ccncc3c2)[nH]1] | B | B | C | 5.5 |
| 207 | (S)-7-(5-(isoquinolin-7-yl)-1H-imidazol-2-yl)-N-methyl-7-(2-(pyrimidin-2-yl)acetamido)heptanamide | 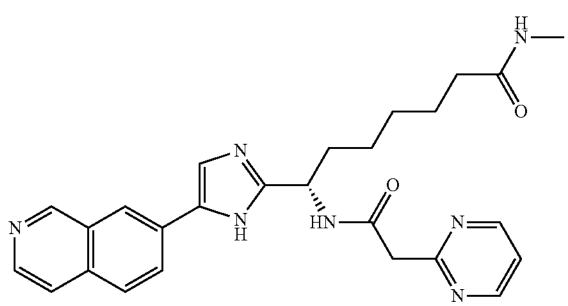 [SMILES: CNC(=O)CCCCC[C@H](NC(=O)Cc1ncccn1)c1ncc(-c2ccc3ccncc3c2)[nH]1] | B | C | C | 7.4 |

TABLE 2-continued

| Entry | Compound Name | Structure | Pf-LDH EC$_{50}$[a] | hHDAC IC$_{50}$[a] | HDAC HeLa Cell Based IC$_{50}$[a] | Selectivity Index[b] |
|---|---|---|---|---|---|---|
| 208 | (S)-7-(2-(2H-indazol-2-yl)acetamido)-7-(5-(isoquinolin-7-yl)-1H-imidazol-2-yl)-N-methyl-heptanamide | 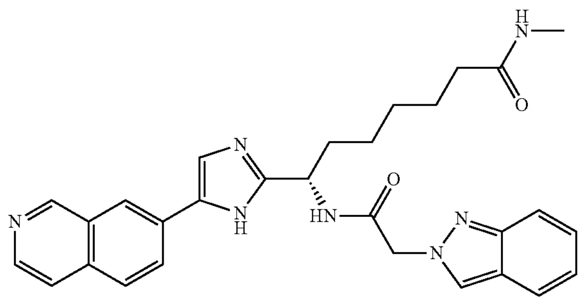 [SMILES: CNC(=O)CCCCC[C@H](NC(=O)Cn1cc2ccccc2n1)c1ncc(-c2ccc3ccncc3c2)[nH]1] | A | A | C | 9.8 |
| 209 | (S)-N-(1-(5-(4-(1-methyl-1H-pyrazol-3-yl)phenyl)-1H-imidazol-2-yl)-7-(methylamino)-7-oxoheptyl)thiazole-4-carboxamide | 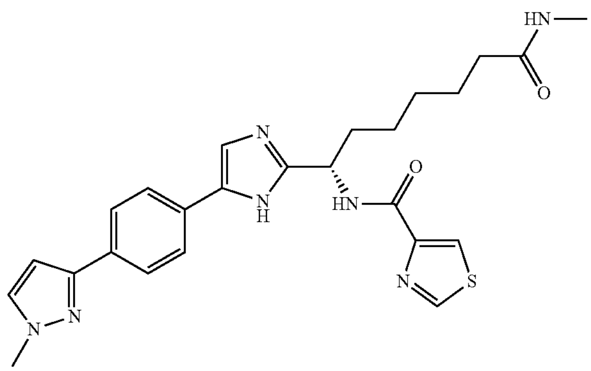 [SMILES: CNC(=O)CCCCC[C@H](NC(=O)c1cscn1)c1ncc(-c2ccc(-c3ccn(C)n3)cc2)[nH]1] | C | C | C | 3.1 |
| 210 | (S)-N-(1-(5-(4-(1-methyl-1H-pyrazol-3-yl)phenyl)-1H-imidazol-2-yl)-7-(methylamino)-7-oxoheptyl)isothiazole-4-carboxamide | 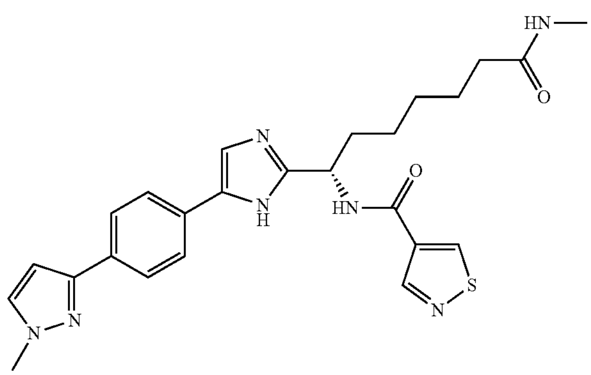 [SMILES: CNC(=O)CCCCC[C@H](NC(=O)c1cnsc1)c1ncc(-c2ccc(-c3ccn(C)n3)cc2)[nH]1] | A | B | C | 22.2 |
| 211 | (S)-N-methyl-7-(5-(4-(1-methyl-1H-pyrazol-3-yl)phenyl)-1H-imidazol-2-yl)-7-(2-(pyrimidin-2-yl)acetamido)heptanamide | 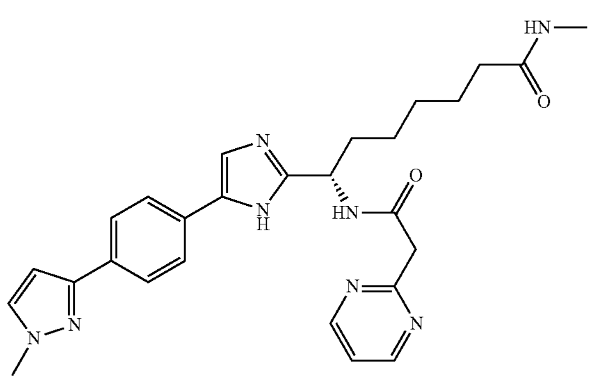 [SMILES: CNC(=O)CCCCC[C@H](NC(=O)Cc1ncccn1)c1ncc(-c2ccc(-c3ccn(C)n3)cc2)[nH]1] | C | C | C | 3.6 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 212 | (S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide | 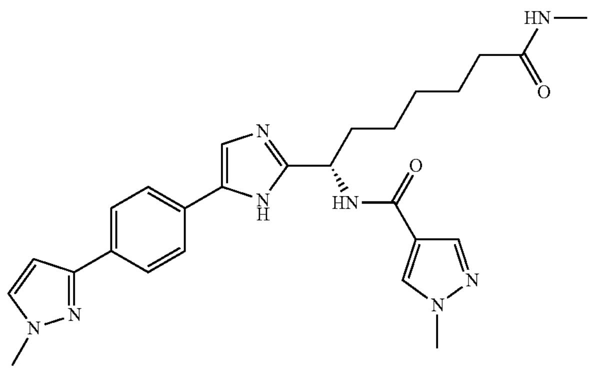 [SMILES: CNC(=O)CCCCC[C@H](NC(=O)c1cnn(C)c1)c1ncc(-c2ccc(-c3ccn(C)n3)cc2)[nH]1] | A | B | C | 35.5 |
| 213 | (S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-5-carboxamide | 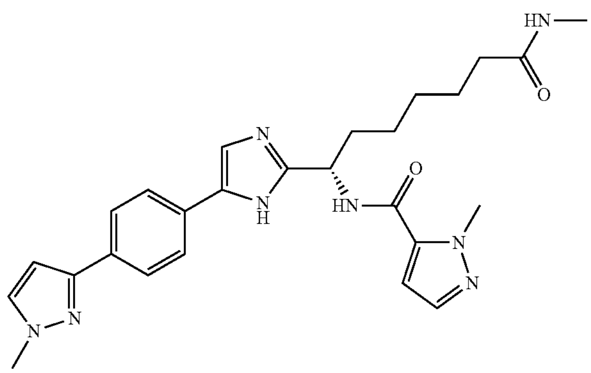 [SMILES: CNC(=O)CCCCC[C@H](NC(=O)c1ccnn1C)c1ncc(-c2ccc(-c3ccn(C)n3)cc2)[nH]1] | B | C | C | 15.0 |
| 214 | (S)-1-(difluoromethyl)-N-(1-(5-(4-(1-methyl-1H-pyrazol-3-yl)phenyl)-1H-imidazol-2-yl)-7-(methylamino)-7-oxoheptyl)-1H-pyrazole-3-carboxamide | 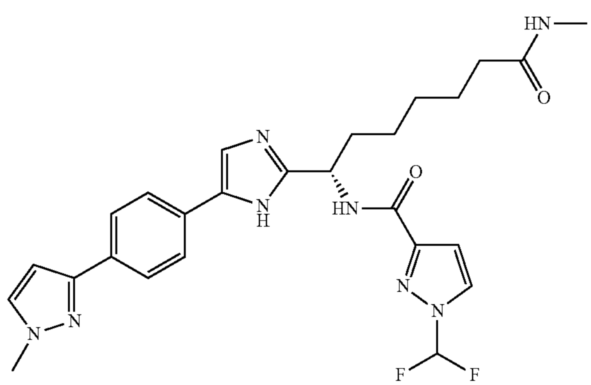 [SMILES: CNC(=O)CCCCC[C@H](NC(=O)c1ccn(C(F)F)n1)c1ncc(-c2ccc(-c3ccn(C)n3)cc2)[nH]1] | B | C | C | 6.8 |
| 215 | (S)-1,3-dimethyl-N-(1-(5-(4-(1-methyl-1H-pyrazol-3-yl)phenyl)-1H-imidazol-2-yl)-7-(methylamino)-7-oxoheptyl)-1H-pyrazole-5-carboxamide | 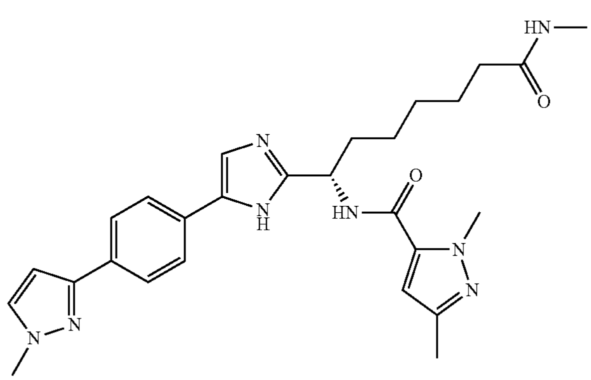 [SMILES: CNC(=O)CCCCC[C@H](NC(=O)c1cc(C)nn1C)c1ncc(-c2ccc(-c3ccn(C)n3)cc2)[nH]1] | B | C | C | 14.1 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 216 | (S)-1,5-dimethyl-N-(1-(5-(4-(1-methyl-1H-pyrazol-3-yl)phenyl)-1H-imidazol-2-yl)-7-(methylamino)-7-oxoheptyl)-1H-pyrazole-3-carboxamide | 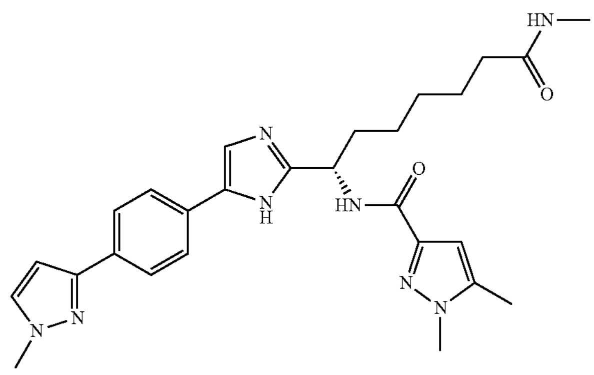 [SMILES: CNC(=O)CCCCC[C@H](NC(=O)c1cc(C)n(C)n1)c1ncc(-c2ccc(-c3ccn(C)n3)cc2)[nH]1] | B | C | C | 7.6 |
| 217 | (S)-3-(tert-butyl)-1-methyl-N-(1-(5-(4-(1-methyl-1H-pyrazol-3-yl)phenyl)-1H-imidazol-2-yl)-7-(methylamino)-7-oxoheptyl)-1H-pyrazole-5-carboxamide | 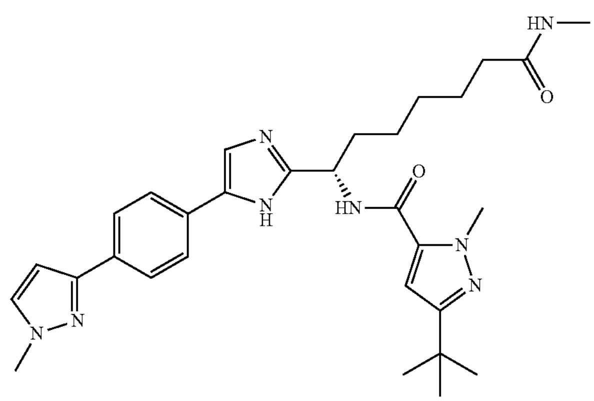 [SMILES: CNC(=O)CCCCC[C@H](NC(=O)c1cc(C(C)(C)C)nn1C)c1ncc(-c2ccc(-c3ccn(C)n3)cc2)[nH]1] | B | B | C | 20.1 |
| 218 | (S)-N-(7-amino-1-(5-(4-(1-methyl-1H-pyrazol-3-yl)phenyl)-1H-imidazol-2-yl)-7-oxoheptyl)thiazole-5-carboxamide | 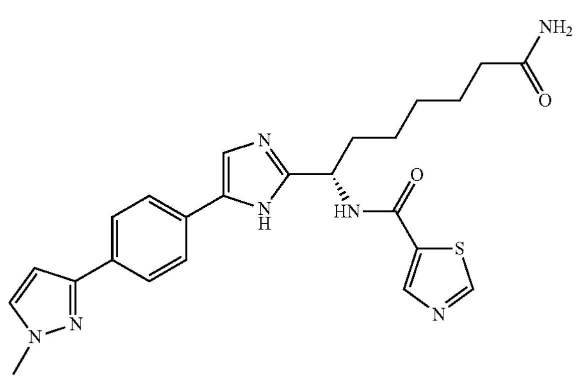 [SMILES: Cn1ccc(-c2ccc(-c3cnc([C@H](CCCCCC(N)=O)NC(=O)c4cncs4)[nH]3)cc2)n1] | A | A | B | 26.8 |
| 219 | (S)-N-(1-(5-(1-methoxyisoquinolin-7-yl)-1H-imidazol-2-yl)-7-(methylamino)-7-oxoheptyl)thiazole-5-carboxamide | 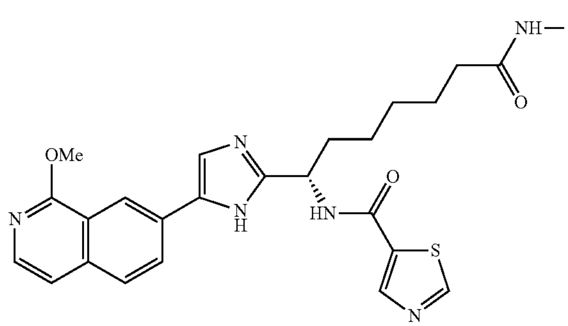 [SMILES: CNC(=O)CCCCC[C@H](NC(=O)c1cncs1)c1ncc(-c2ccc3ccnc(OC)c3c2)[nH]1] | B | B | C | 6.9 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 220 | (S)-7-(5-(2-methoxyquinolin-3-yl)-1H-imidazol-2-yl)-N-methyl-7-(4-cyanophenyl-sulfonamido)heptanamide | 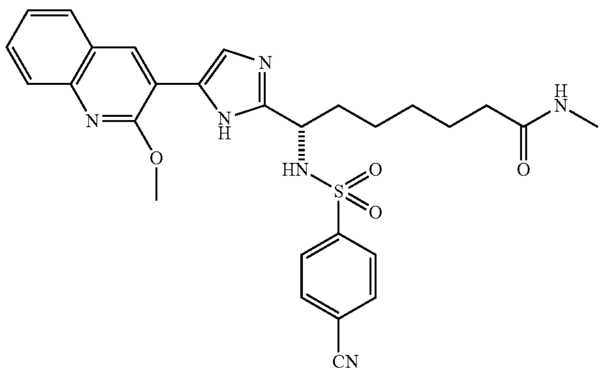 [SMILES: CNC(=O)CCCCC[C@H](NS(=O)(=O)c1ccc(C#N)cc1)c1ncc(-c2cc3ccccc3nc2OC)[nH]1] | A | A | B | 8.1 |
| 221 | (S)-N-(1-(5-(4-(1H-pyrazol-5-yl)phenyl)-1H-imidazol-2-yl)-7-(methylamino)-7-oxoheptyl)thiazole-5-carboxamide | 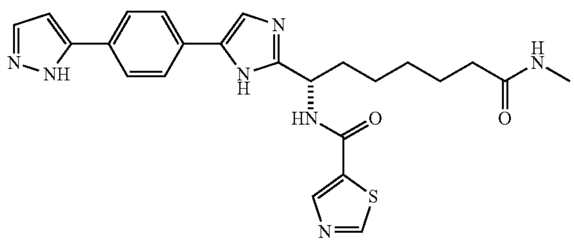 [SMILES: CNC(=O)CCCCC[C@H](NC(=O)c1cncs1)c1ncc(-c2ccc(-c3ccn[nH]3)cc2)[nH]1] | A | B | C | 37 |
| 222 | (S)-N-(1-(5-(4-(1-methyl-1H-pyrazol-3-yl)phenyl)oxazol-2-yl)-7-(methylamino)-7-oxoheptyl)thiazole-5-carboxamide | 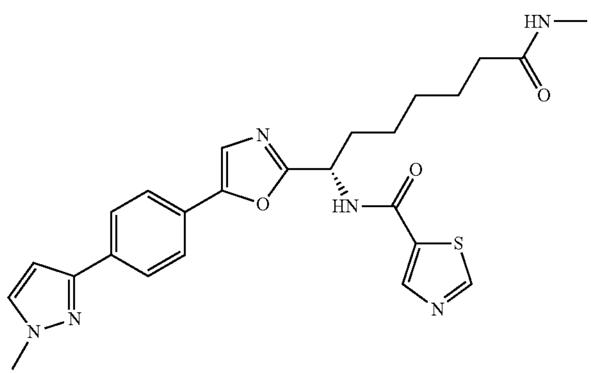 [SMILES: CNC(=O)CCCCC[C@H](NC(=O)c1cncs1)c1ncc(-c2ccc(-c3ccn(C)n3)cc2)o1] | B | C | C | 26.8 |
| 223 | (S)-1-isopropyl-N-(1-(5-(4-(1-methyl-1H-pyrazol-3-yl)phenyl)oxazol-2-yl)-7-(methylamino)-7-oxoheptyl)-1H-pyrazole-4-carboxamide | 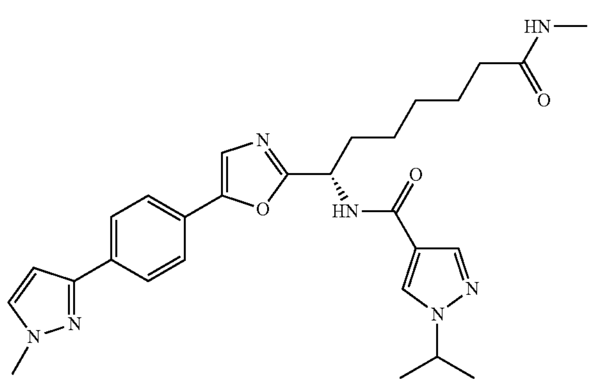 [SMILES: CNC(=O)CCCCC[C@H](NC(=O)c1cnn(C(C)C)c1)c1ncc(-c2ccc(-c3ccn(C)n3)cc2)o1] | B | C | C | 8.8 |

TABLE 2-continued

| Entry | Compound Name | Structure | Pf-LDH EC$_{50}$$^a$ | hHDAC IC$_{50}$$^a$ | HDAC HeLa Cell Based IC$_{50}$$^a$ | Selectivity Index$^b$ |
|---|---|---|---|---|---|---|
| 224 | (S)-1-methyl-N-(1-(5-(4-(1-methyl-1H-pyrazol-3-yl)phenyl)oxazol-2-yl)-7-(methylamino)-7-oxoheptyl)-1H-pyrazole-4-carboxamide | 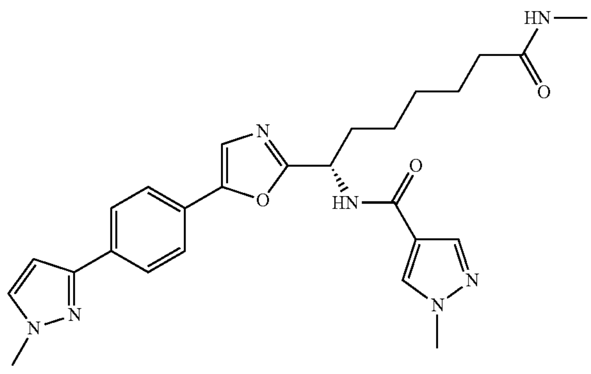 [SMILES: CNC(=O)CCCCC[C@H](NC(=O)c1cnn(C)c1)c1ncc(-c2ccc(-c3ccn(C)n3)cc2)o1] | B | C | C | 5.0 |
| 225 | (S)-2-methyl-N-(1-(5-(4-(1-methyl-1H-pyrazol-3-yl)phenyl)oxazol-2-yl)-7-(methylamino)-7-oxoheptyl)thiazole-5-carboxamide | 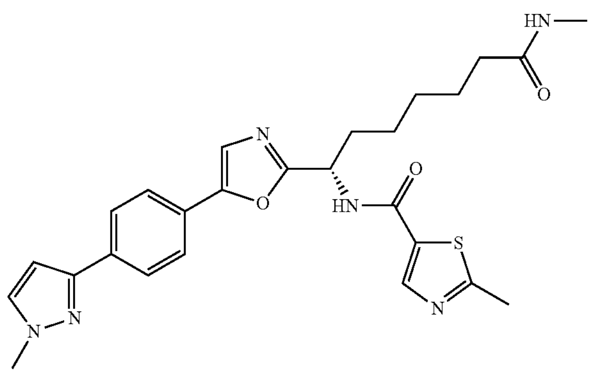 [SMILES: CNC(=O)CCCCC[C@H](NC(=O)c1cnc(C)s1)c1ncc(-c2ccc(-c3ccn(C)n3)cc2)o1] | B | C | C | 20.5 |
| 226 | (S)-N-(1-(5-(4-(1-methyl-1H-pyrazol-3-yl)phenyl)oxazol-2-yl)-7-(methylamino)-7-oxoheptyl)isothiazole-4-carboxamide | 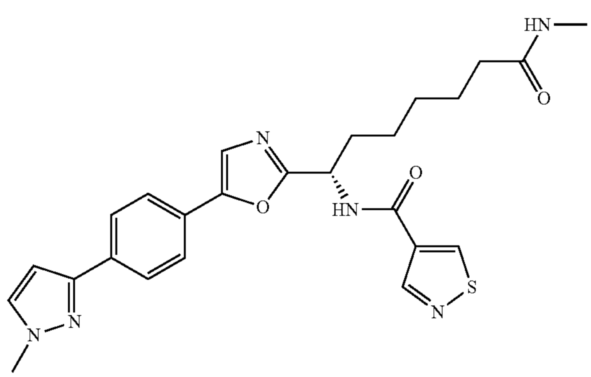 [SMILES: CNC(=O)CCCCC[C@H](NC(=O)c1cnsc1)c1ncc(-c2ccc(-c3ccn(C)n3)cc2)o1] | B | C | C | 3.8 |
| 227 | (S)-1-isopropyl-N-(1-(5-(3-methoxyisoquinolin-7-yl)-1H-imidazol-2-yl)-7-(methylamino)-7-oxoheptyl)-1H-pyrazole-4-carboxamide | 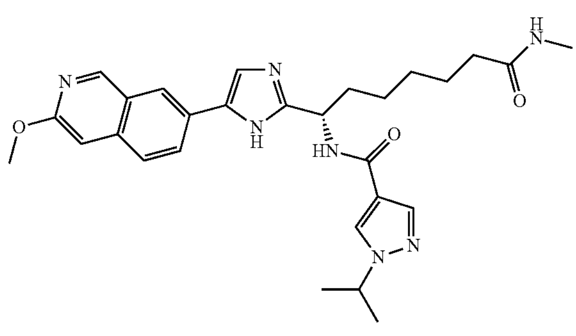 | A | A | B | 23.5 |

TABLE 2-continued

| Entry | Compound Name | Structure | Pf-LDH EC$_{50}$ $^a$ | hHDAC IC$_{50}$ $^a$ | HDAC HeLa Cell Based IC$_{50}$ $^a$ | Selectivity Index$^b$ |
|---|---|---|---|---|---|---|
| 228 | (S)-N-(1-(5-(4-(1-methyl-1H-pyrazol-4-yl)phenyl)-1H-imidazol-2-yl)-7-(methylamino)-7-oxoheptyl)thiazole-5-carboxamide | 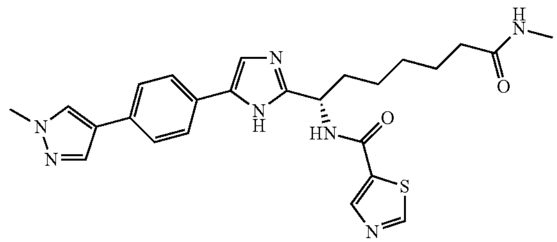 | B | C | C | 6.7 |
| 229 | (S)-N-(1-(5-(4-(1-methyl-1H-pyrazol-5-yl)phenyl)-1H-imidazol-2-yl)-7-(methylamino)-7-oxoheptyl)thiazole-5-carboxamide | 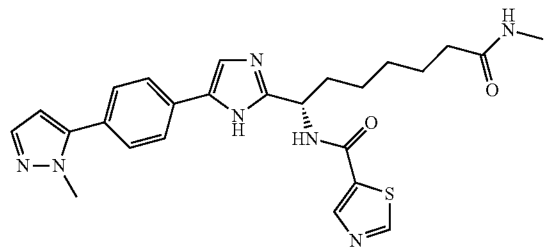 [SMILES: CNC(=O)CCCCC[C@H](NC(=O)c1cncs1)c1ncc(-c2ccc(-c3ccnn3C)cc2)[nH]1] | B | C | C | 5.6 |
| 230 | (S)-N-(7-(methylamino)-7-oxo-1-(5-(4-(thiazol-5-yl)phenyl)-1H-imidazol-2-yl)heptyl)thiazole-5-carboxamide | 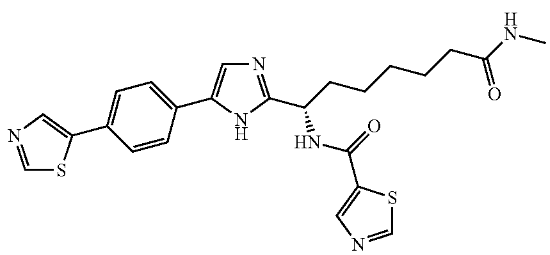 [SMILES: CNC(=O)CCCCC[C@H](NC(=O)c1cncs1)c1ncc(-c2ccc(-c3cncs3)cc2)[nH]1] | B | B | C | 3.6 |
| 231 | (S)-N-(7-(methylamino)-7-oxo-1-(5-(4-(thiazol-2-yl)phenyl)-1H-imidazol-2-yl)heptyl)thiazole-5-carboxamide | 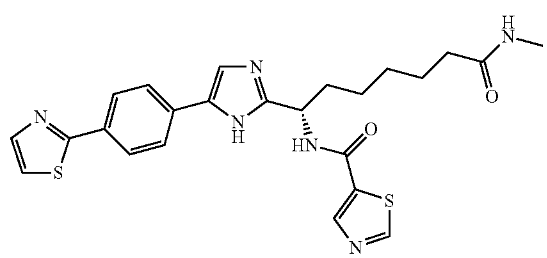 [SMILES: CNC(=O)CCCCC[C@H](NC(=O)c1cncs1)c1ncc(-c2ccc(-c3nccs3)cc2)[nH]1] | A | B | C | 10.6 |
| 232 | (S)-N-(7-(methylamino)-7-oxo-1-(5-(4-(thiazol-4-yl)phenyl)-1H-imidazol-2-yl)heptyl)thiazole-5-carboxamide | 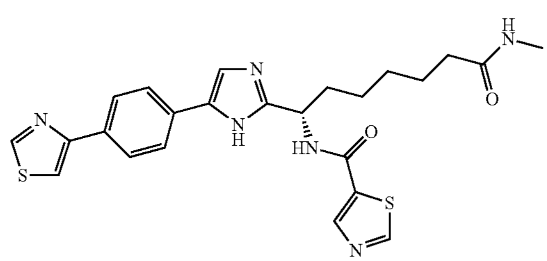 [SMILES: CNC(=O)CCCCC[C@H](NC(=O)c1cncs1)c1ncc(-c2ccc(-c3cscn3)cc2)[nH]1] | A | B | C | 14.2 |

$^a$ A: <1 µM; B: 1 µM-5 µM; C: >5 µM;
$^b$ Selectivity Index = HDAC HeLa Cell Based IC$_{50}$ (µM)/Pf-LDH EC$_{50}$ (µM)

The data reported in Table 2 demonstrate that compounds of the invention are potent HDAC inhibitors that selectively suppress the growth of Plasmodium falciparum at concentrations that are invariably lower than the concentrations required for the inhibition of the growth of mammalian cells. Compounds of the invention show low (Selectivity Index 1-2), moderate (Selectivity Index 2-5), good (Selectivity Index 5-10) or high parasite specific selectivity (Selectivity Index>10). Less than 1% of the compounds of the invention show low selectivity, 37% show moderate selectivity, 35% show good selectivity and more than 26% show high selectivity. The selective profile is supported by the fact that the most selective inhibitors are invariably more potent in the antiparasitic Pf-LDH cell based assay than they are against the isolated hHDAC enzyme.

Figure 2:
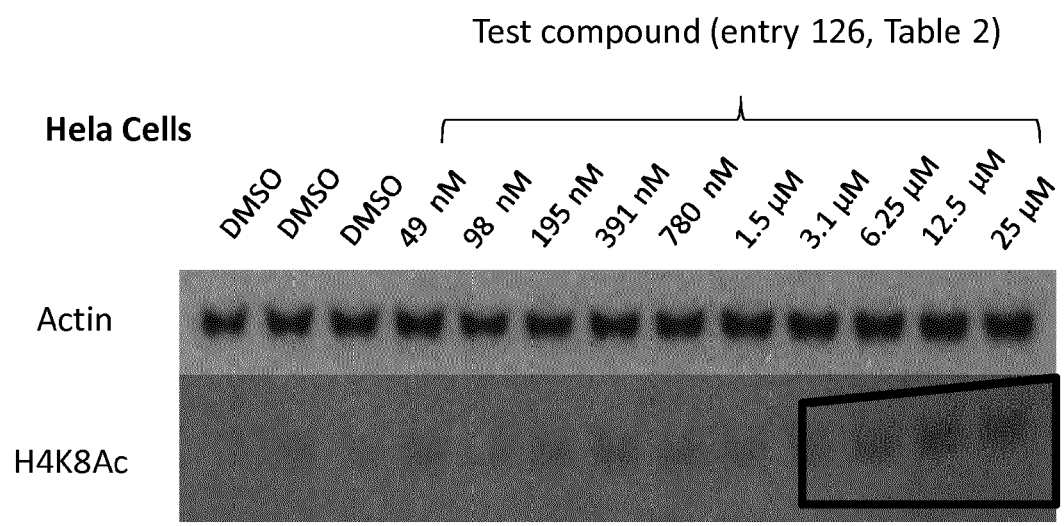
FIG. 2. Hyperacetylation of HeLa's histones. HeLa cells were incubated in vitro for 14-16 hours with increasing concentrations (49 nM to 25 uM) of compound (S)-N-(7-(methylamino)-1-(5-(naphthalen-2-yl)-1H-imidazol-2-yl)-7-oxoheptyl)quinuclidine-4-carboxamide (Table 2, entry 126) or were treated with vehicle (0.01% DMSO). Beta-actin was used as loading control (see materials and methods). H4K8Ac: antibody directed against acetylated lysine 8 of histone 4.

The experiment shown in FIG. 1 (A) demonstrates that after treatment with compound (S)-N-(7-(methylamino)-1-(5-(naphthalen-2-yl)-1H-imidazol-2-yl)-7-oxoheptyl)quinuclidine-4-carboxamide (entry 126, Table 2) an increase in acetylated histone-H4 compared to DMSO control was detected in *P. falciparum* 3D7 infected erythrocytes using anti-(tetra)acetyl H4 antibodies. The altered acetylation profile observed after treatment with the compound of the invention occurred at concentrations above the compounds expected $EC_{50}$ (Pf-LDH $EC_{50}$=293 nM±76 (n=11)) to approximately 10 fold the $EC_{50}$ (3 μM). No change in histone acetylation was observed in HeLa cells within the same concentration range (FIG. 2), with hyperacetylation only becoming apparent above the compounds $EC_{50}$ in HeLa cells (4 μM). FIG. 1 (B) shows the effects of compound D9 (entry 221, Table 2; Example 4) on the hyperacetylation assay. For this compound, the estimated $EC_{50}$ is 350 nM in the hyperacetylation assay, while no change was observed in HeLa cells up to 10 μM (data not shown). These findings demonstrate that the compounds of the invention are selective parasitic HDAC inhibitors, thus endowed with selective antimalarial activity.

CONCLUSIONS

Compounds of the present invention are selective parasitic HDAC inhibitors characterized by an amide moiety as a zinc binding group. The structural properties of these compounds enhance their antimalarial activity and this is clearly demonstrated to result from HDAC inhibition as a mechanism of action. Blockade of parasite HDACs results directly in parasite death, and is clearly distinct from an anti-inflammatory effect in mammals that can result from inhibition of mammalian HDACs. It is apparent from the selective profile of the compounds of this invention that they are outwith the scope for the treatment of diseases induced by endogenous or parasitic factors wherein damage is induced by autoimmune inflammatory response. As shown by the data reported in Table 2, many of the compounds disclosed herein are potent inhibitors of the *Plasmodium falciparum* parasite, with $EC_{50}$ values in the low to sub-micromolar range. Worthy of specific note is the fact that the measured activity of the compounds of the invention in the Pf-LDH growth inhibition assay is invariably higher than the activity measured in the mammalian HDAC HeLa Cell based assay and hHDAC biochemical assay. This trend supports the assertion that the instant compounds are over an order of magnitude selectively cytotoxic to parasites, in particular to *Plasmodium falciparum*.

The invention claimed is:
1. A compound selected from the group consisting of:
(S)-N-(1-(5-(6-methoxynaphthalen-2-yl)-1H-imidazol-2-yl)-7-(methylamino)-7-oxoheptyl)quinuclidine-4-carboxamide;
(S)-N-(1-(5-(6-fluoronaphthalen-2-yl)-1H-imidazol-2-yl)-7-(methylamino)-7-oxoheptyl)quinuclidine-4-carboxamide;
(S)-N-(1-(5-(3-(aminomethyl)phenyl)-1H-imidazol-2-yl)-7-(methylamino)-7-oxoheptyl)thiazole-5-carboxamide;
(S)-N-(1-(5-(2-methoxyquinolin-3-yl)-1H-imidazol-2-yl)-7-(methylamino)-7-oxoheptyl)quinuclidine-4-carboxamide;
(S)-N-(1-(5-(2-methoxyquinolin-3-yl)-1H-imidazol-2-yl)-7-(methylamino)-7-oxoheptyl)thiazole-5-carboxamide;
(S)-7-(5-(2-methoxyquinolin-3-yl)-1H-imidazol-2-yl)-N-methyl-7-(4-cyanophenylsulfonamido)heptanamide;
(S)-N-(1-(5-(4-(1H-pyrazol-5-yl)phenyl)-1H-imidazol-2-yl)-7-(methylamino)-7-oxoheptyl)thiazole-5-carboxamide;
(S)-N-(7-(methylamino)-7-oxo-1-(5-(quinolin-6-yl)-1H-imidazol-2-yl)heptyl)thiazole-5-carboxamide;
(S)-N-(1-(5-(1H-indol-5-yl)-1H-imidazol-2-yl)-7-(methylamino)-7-oxoheptyl)thiazole-5-carboxamide;
(S)-N-(7-(methylamino)-7-oxo-1-(5-(2-oxo-1,2-dihydroquinolin-3-yl)-1H-imidazol-2-yl)heptyl)thiazole-5-carboxamide;
(S)-N-(7-(methylamino)-7-oxo-1-(5-(quinolin-3-yl)-1H-imidazol-2-yl)heptyl)thiazole-5-carboxamide;
(S)-N-(1-(5-(4-(1H-pyrazol-1-yl)phenyl)-1H-imidazol-2-yl)-7-(methylamino)-7-oxoheptyl)thiazole-5-carboxamide;
(S)-N-(1-(5-(1H-indazol-5-yl)-1H-imidazol-2-yl)-7-(methylamino)-7-oxoheptyl)thiazole-5-carboxamide;
(S)-N-(1-(5-(isoquinolin-7-yl)-1H-imidazol-2-yl)-7-(methylamino)-7-oxoheptyl)thiazole-5-carboxamide;
(S)-N-(1-(5-(4-(1-methyl-1H-pyrazol-3-yl)phenyl)-1H-imidazol-2-yl)-7-(methylamino)-7-oxoheptyl)thiazole-5-carboxamide;
(S)-N-(1-(5-(isoquinolin-7-yl)-1H-imidazol-2-yl)-7-(methylamino)-7-oxoheptyl)isothiazole-4-carboxamide;
(S)-N-(7-(methylamino)-7-oxo-1-(5-(3-(trifluoromethyl)isoquinolin-7-yl)-1H-imidazol-2-yl)heptyl)thiazole-5-carboxamide;
(S)-N-(1-(5-(3-methoxyisoquinolin-7-yl)-1H-imidazol-2-yl)-7-(methylamino)-7-oxoheptyl)thiazole-5-carboxamide;
(S)-N-(1-(5-(isoquinolin-7-yl)-1H-imidazol-2-yl)-7-(methylamino)-7-oxoheptyl)isothiazole-5-carboxamide;
(S)-1-isopropyl-N-(1-(5-(isoquinolin-7-yl)-1H-imidazol-2-yl)-7-(methylamino)-7-oxoheptyl)-1H-pyrazole-4-carboxamide;
(S)-N-(1-(5-(isoquinolin-7-yl)-1H-imidazol-2-yl)-7-(methylamino)-7-oxoheptyl)-2-methylthiazole-5-carboxamide;
(S)-N-(1-(5-(4-(1-methyl-1H-pyrazol-3-yl)phenyl)-1H-imidazol-2-yl)-7-(methylamino)-7-oxoheptyl)isothiazole-5-carboxamide;
(S)-1-isopropyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide;
(S)-2-methyl-N-(1-(5-(4-(1-methyl-1H-pyrazol-3-yl)phenyl)-1H-imidazol-2-yl)-7-(methylamino)-7-oxoheptyl)thiazole-5-carboxamide;
(S)-N-(1-(5-(4-(1-methyl-1H-pyrazol-3-yl)phenyl)-1H-imidazol-2-yl)-7-(methylamino)-7-oxoheptyl)isothiazole-4-carboxamide;
(S)-N-(1-(5-(4-(1-methyl-1H-pyrazol-3-yl)phenyl)-1H-imidazol-2-yl)-7-(methylamino)-7-oxoheptyl)-2-(pyrrolidin-1-ylmethyl)thiazole-5-carboxamide;
(S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide;
(S)-1-isopropyl-N-(1-(5-(3-methoxyisoquinolin-7-yl)-1H-imidazol-2-yl)-7-(methylamino)-7-oxoheptyl)-1H-pyrazole-4-carboxamide;
(S)-N-(7-(methylamino)-7-oxo-1-(5-(4-(thiazol-2-yl)phenyl)-1H-imidazol-2-yl)heptyl)thiazole-5-carboxamide;
(S)-N-(7-(methylamino)-7-oxo-1-(5-(4-(thiazol-4-yl)phenyl)-1H-imidazol-2-yl)heptyl)thiazole-5-carboxamide;
and pharmaceutically acceptable salts, tautomers, stereoisomers thereof.

2. A method of treating a parasitic disease, comprising administering an effective amount of the compound to a mammal in need thereof, wherein the compound selected from the group consisting of:
- (S)-N-(1-(5-(6 methoxynaphthalen-2-yl)-1H-imidazol-2-yl)-7-(methylamino)-7-oxoheptyl)quinuclidine-4-carboxamide;
- (S)-N-(1-(5-(6 fluoronaphthalen-2-yl)-1H-imidazol-2-yl)-7-(methylamino)-7-oxoheptyl)quinuclidine-4-carboxamide;
- (S)-N-(1-(5-(3-(aminomethyl)phenyl)-1H-imidazol-2-yl)-7-(methylamino)-7-oxoheptyl)thiazole-5-carboxamide;
- (S)-N-(1-(5-(2-methoxyquinolin-3-yl)-1H-imidazol-2-yl)-7-(methylamino)-7-oxoheptyl)quinuclidine-4-carboxamide;
- (S)-N-(1-(5-(2-methoxyquinolin-3-yl)-1H-imidazol-2-yl)-7-(methylamino)-7-oxoheptyl)thiazole-5-carboxamide;
- (S)-7-(5-(2-methoxyquinolin-3-yl)-1H-imidazol-2-yl)-N-methyl-7-(4-cyanophenylsulfonamido)heptanamide;
- (S)-N-(1-(5-(4-(1H pyrazol-5-yl)phenyl)-1H-imidazol-2-yl)-7-(methylamino)-7-oxoheptyl)thiazole-5-carboxamide;
- (S)-N-(7-(methylamino)-7-oxo-1-(5-(quinolin-6-yl)-1H-imidazol-2-yl)heptyl)thiazole-5-carboxamide;
- (S)-N-(1-(5-(1H-indol-5-yl)-1H-imidazol-2-yl)-7-(methylamino)-7-oxoheptyl)thiazole-5-carboxamide;
- (S)-N-(7-(methylamino)-7-oxo-1-(5-(2-oxo-1,2-dihydroquinolin-3-yl)-1H-imidazol-2-yl)heptyl)thiazole-5-carboxamide;
- (S)-N-(7-(methylamino)-7-oxo-1-(5-(quinolin-3-yl)-1H-imidazol-2-yl)heptyl)thiazole-5-carboxamide;
- (S)-N-(1-(5-(4-(1H pyrazol-1-yl)phenyl)-1H-imidazol-2-yl)-7-(methylamino)-7-oxoheptyl)thiazole-5-carboxamide;
- (S)-N-(1-(5-(1H-indazol-5-yl)-1H-imidazol-2-yl)-7-(methylamino)-7-oxoheptyl)thiazole-5-carboxamide;
- (S)-N-(1-(5-(isoquinolin-7-yl)-1H-imidazol-2-yl)-7-(methylamino)-7-oxoheptyl)thiazole-5-carboxamide;
- (S)-N-(1-(5-(4-(1-methyl-1H-pyrazol-3-yl)phenyl)-1H-imidazol-2-yl)-7-(methylamino)-7-oxoheptyl)thiazole-5-carboxamide;
- (S)-N-(1-(5-(isoquinolin-7-yl)-1H-imidazol-2-yl)-7-(methylamino)-7-oxoheptyl)isothiazole-4-carboxamide;
- (S)-N-(7-(methylamino)-7-oxo-1-(5-(3-(trifluoromethyl)isoquinolin-7-yl)-1H-imidazol-2-yl)heptyl)thiazole-5-carboxamide;
- (S)-N-(1-(5-(3 methoxyisoquinolin-7-yl)-1H-imidazol-2-yl)-7-(methylamino)-7-oxoheptyl)thiazole-5-carboxamide;
- (S)-N-(1-(5-(isoquinolin-7-yl)-1H-imidazol-2-yl)-7-(methylamino)-7-oxoheptyl)isothiazole-5-carboxamide;
- (S)-1-isopropyl-N-(1-(5-(isoquinolin-7-yl)-1H-imidazol-2-yl)-7-(methylamino)-7-oxoheptyl)-1H-pyrazole-4-carboxamide;
- (S)-N-(1-(5-(isoquinolin-7-yl)-1H-imidazol-2-yl)-7-(methylamino)-7-oxoheptyl)-2-methylthiazole-5-carboxamide;
- (S)-N-(1-(5-(4-(1-methyl-1H-pyrazol-3-yl)phenyl)-1H-imidazol-2-yl)-7-(methylamino)-7-oxoheptyl)isothiazole-5-carboxamide;
- (S)-1-isopropyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide;
- (S)-2-methyl-N-(1-(5-(4-(1-methyl-1H-pyrazol-3-yl)phenyl)-1H-imidazol-2-yl)-7-(methylamino)-7-oxoheptyl)thiazole-5-carboxamide;
- (S)-N-(1-(5-(4-(1-methyl-1H-pyrazol-3-yl)phenyl)-1H-imidazol-2-yl)-7-(methylamino)-7-oxoheptyl)isothiazole-4-carboxamide;
- (S)-N-(1-(5-(4-(1-methyl-1H-pyrazol-3-yl)phenyl)-1H-imidazol-2-yl)-7-(methylamino)-7-oxoheptyl)-2-(pyrrolidin-1-ylmethyl)thiazole-5-carboxamide;
- (S)-1-methyl N (1-(5-(4-(1-methyl-1H-pyrazol-3-yl)phenyl)-1H-imidazol-2-yl)-7-(methylamino)-7-oxoheptyl)-1H-pyrazole-4-carboxamide;
- (S)-1-isopropyl N (1-(5-(3 methoxyisoquinolin-7-yl)-1H-imidazol-2-yl)-7-(methylamino)-7-oxoheptyl)-1H-pyrazole-4-carboxamide;
- (S)-N-(7-(methylamino)-7-oxo-1-(5-(4-(thiazol-2-yl)phenyl)-1H-imidazol-2-yl)heptyl)thiazole-5-carboxamide;
- (S)-N-(7-(methylamino)-7-oxo-1-(5-(4-(thiazol-4-yl)phenyl)-1H-imidazol-2-yl)heptyl)thiazole-5-carboxamide;

and pharmaceutically acceptable salts, tautomers, stereoisomers thereof.

3. The method according to claim 2, wherein the parasitic disease is selected from the group consisting of malaria, leishmaniasis, trypanosomiasis, toxoplasmosis and schistosomiasis.

4. The method according to claim 3, wherein the parasitic disease is malaria.

5. The method according to claim 4, wherein malaria is caused by parasites *Plasmodium falciparum* or *Plasmodium vivax*.

6. The method according to claim 5, wherein the compound exhibits selective toxicity for said parasites with respect to host cells.

7. The method according to claim 5, wherein the compound exhibits selective killing and/or growth-inhibiting activity for said parasites with respect to a host mammal.

8. A pharmaceutical composition comprising an effective amount of one or more compounds, alone or in combination with other active compounds, and at least one pharmaceutically acceptable excipient, for use in the treatment of parasitic diseases wherein the compound is selected from the group consisting of:
- (S)-N-(1-(5-(6 methoxynaphthalen-2-yl)-1H-imidazol-2-yl)-7-(methylamino)-7-oxoheptyl)quinuclidine-4-carboxamide;
- (S)-N-(1-(5-(6 fluoronaphthalen-2-yl)-1H-imidazol-2-yl)-7-(methylamino)-7-oxoheptyl)quinuclidine-4-carboxamide;
- (S)-N-(1-(5-(3-(aminomethyl)phenyl)-1H-imidazol-2-yl)-7-(methylamino)-7-oxoheptyl)thiazole-5-carboxamide;
- (S)-N-(1-(5-(2-methoxyquinolin-3-yl)-1H-imidazol-2-yl)-7-(methylamino)-7-oxoheptyl)quinuclidine-4-carboxamide;
- (S)-N-(1-(5-(2-methoxyquinolin-3-yl)-1H-imidazol-2-yl)-7-(methylamino)-7-oxoheptyl)thiazole-5-carboxamide;
- (S)-7-(5-(2-methoxyquinolin-3-yl)-1H-imidazol-2-yl)-N-methyl-7-(4-cyanophenylsulfonamido)heptanamide;
- (S)-N-(1-(5-(4-(1H pyrazol-5-yl)phenyl)-1H-imidazol-2-yl)-7-(methylamino)-7-oxoheptyl)thiazole-5-carboxamide;
- (S)-N-(7-(methylamino)-7-oxo-1-(5-(quinolin-6-yl)-1H-imidazol-2-yl)heptyl)thiazole-5-carboxamide;
- (S)-N-(1-(5-(1H-indol-5-yl)-1H-imidazol-2-yl)-7-(methylamino)-7-oxoheptyl)thiazole-5-carboxamide;

(S)-N-(7-(methylamino)-7-oxo-1-(5-(2-oxo-1,2-dihydro-quinolin-3-yl)-1H-imidazol-2-yl)heptyl)thiazole-5-carboxamide;

(S)-N-(7-(methylamino)-7-oxo-1-(5-(quinolin-3-yl)-1H-imidazol-2-yl)heptyl)thiazole-5-carboxamide;

(S)-N-(1-(5-(4-(1H pyrazol-1-yl)phenyl)-1H-imidazol-2-yl)-7-(methylamino)-7-oxoheptyl)thiazole-5-carboxamide;

(S)-N-(1-(5-(1H-indazol-5-yl)-1H-imidazol-2-yl)-7-(methylamino)-7-oxoheptyl)thiazole-5-carboxamide;

(S)-N-(1-(5-(isoquinolin-7-yl)-1H-imidazol-2-yl)-7-(methylamino)-7-oxoheptyl)thiazole-5-carboxamide;

(S)-N-(1-(5-(4-(1-methyl-1H-pyrazol-3-yl)phenyl)-1H-imidazol-2-yl)-7-(methylamino)-7-oxoheptyl)thiazole-5-carboxamide;

(S)-N-(1-(5-(isoquinolin-7-yl)-1H-imidazol-2-yl)-7-(methylamino)-7-oxoheptyl)isothiazole-4-carboxamide;

(S)-N-(7-(methylamino)-7-oxo-1-(5-(3-(trifluoromethyl)isoquinolin-7-yl)-1H-imidazol-2-yl)heptyl)thiazole-5-carboxamide;

(S)-N-(1-(5-(3 methoxyisoquinolin-7-yl)-1H-imidazol-2-yl)-7-(methylamino)-7-oxoheptyl)thiazole-5-carboxamide;

(S)-N-(1-(5-(isoquinolin-7-yl)-1H-imidazol-2-yl)-7-(methylamino)-7-oxoheptyl)isothiazole-5-carboxamide;

(S)-1-isopropyl-N-(1-(5-(isoquinolin-7-yl)-1H-imidazol-2-yl)-7-(methylamino)-7-oxoheptyl)-1H-pyrazole-4-carboxamide;

(S)-N-(1-(5-(isoquinolin-7-yl)-1H-imidazol-2-yl)-7-(methylamino)-7-oxoheptyl)-2-methylthiazole-5-carboxamide;

(S)-N-(1-(5-(4-(1-methyl-1H-pyrazol-3-yl)phenyl)-1H-imidazol-2-yl)-7-(methylamino)-7-oxoheptyl)isothiazole-5-carboxamide;

(S)-1-isopropyl N (1-(5-(4-(1-methyl-1H-pyrazol-3-yl)phenyl)-1H-imidazol-2-yl)-7-(methylamino)-7-oxoheptyl)-1H-pyrazole-4-carboxamide;

(S)-2-methyl N (1-(5-(4-(1-methyl-1H-pyrazol-3-yl)phenyl)-1H-imidazol-2-yl)-7-(methylamino)-7-oxoheptyl)thiazole-5-carboxamide;

(S)-N-(1-(5-(4-(1-methyl-1H-pyrazol-3-yl)phenyl)-1H-imidazol-2-yl)-7-(methylamino)-7-oxoheptyl)isothiazole-4-carboxamide;

(S)-N-(1-(5-(4-(1-methyl-1H-pyrazol-3-yl)phenyl)-1H-imidazol-2-yl)-7-(methylamino)-7-oxoheptyl)-2-(pyrrolidin-1-ylmethyl)thiazole-5-carboxamide;

(S)-1-methyl-N-(1-(5-(4-(1-methyl-1H-pyrazol-3-yl)phenyl)-1H-imidazol-2-yl)-7-(methylamino)-7-oxoheptyl)-1H-pyrazole-4-carboxamide;

(S)-1-isopropyl-N-(1-(5-(3 methoxyisoquinolin-7-yl)-1H-imidazol-2-yl)-7-(methylamino)-7-oxoheptyl)-1H-pyrazole-4-carboxamide;

(S)-N-(7-(methylamino)-7-oxo-1-(5-(4-(thiazol-2-yl)phenyl)-1H-imidazol-2-yl)heptyl)thiazole-5-carboxamide;

(S)-N-(7-(methylamino)-7-oxo-1-(5-(4-(thiazol-4-yl)phenyl)-1H-imidazol-2-yl)heptyl)thiazole-5-carboxamide;

and pharmaceutically acceptable salts, tautomers, stereoisomers thereof.

9. A method of treating a parasitic disease, comprising administering the pharmaceutical composition according to claim 8, to a mammal in need thereof.

* * * * *